US011236131B2

(12) United States Patent
Cobbold et al.

(10) Patent No.: US 11,236,131 B2
(45) Date of Patent: Feb. 1, 2022

(54) RE-DIRECTED IMMUNOTHERAPY

(71) Applicant: The University of Birmingham, Birmingham (GB)

(72) Inventors: Mark Cobbold, Winchester, MA (US); David Millar, Winchester, MA (US)

(73) Assignee: The University of Birmingham, Birmingham (GB)

( * ) Notice: Subject to any disclaimer, the term of this patent is extended or adjusted under 35 U.S.C. 154(b) by 83 days.

(21) Appl. No.: 16/366,240

(22) Filed: Mar. 27, 2019

(65) Prior Publication Data

US 2019/0270779 A1 Sep. 5, 2019

Related U.S. Application Data

(63) Continuation of application No. 14/972,059, filed on Dec. 16, 2015, now Pat. No. 10,287,321, which is a (Continued)

(30) Foreign Application Priority Data

Mar. 17, 2011 (GB) ..................................... 1104514
Feb. 28, 2012 (GB) ..................................... 1203434

(51) Int. Cl.
*C07K 14/005* (2006.01)
*A61K 47/68* (2017.01)
(Continued)

(52) U.S. Cl.
CPC .......... *C07K 14/005* (2013.01); *A61K 38/204* (2013.01); *A61K 38/2013* (2013.01);
(Continued)

(58) Field of Classification Search
CPC .... C07K 14/005; C07K 14/04; C07K 14/045; C07K 14/05; C07K 14/095; C07K 14/11;
(Continued)

(56) References Cited

U.S. PATENT DOCUMENTS 5,585,089 A 12/1996 Queen et al.
5,610,281 A 3/1997 Brenner et al.
(Continued)

FOREIGN PATENT DOCUMENTS

EP 0659438 A1 6/1995
EP 1948802 A1 7/2008
(Continued)

OTHER PUBLICATIONS

Lloyd et al. Protein Engineering, Design & Selection 22:159-168 (Year: 2009).*

(Continued)

*Primary Examiner* — Phuong Huynh
(74) *Attorney, Agent, or Firm* — McNeill Baur PLLC

(57) ABSTRACT

The invention provides an agent for preventing or treating a condition characterised by the presence of unwanted cells, the agent comprising: (i) a targeting moiety that is capable of targeting to the unwanted cells; and (ii) a T cell antigen, wherein the T cell antigen can be released from the targeting moiety by selective cleavage of a cleavage site in the agent in the vicinity of the unwanted cells.

22 Claims, 20 Drawing Sheets

Figure 1:
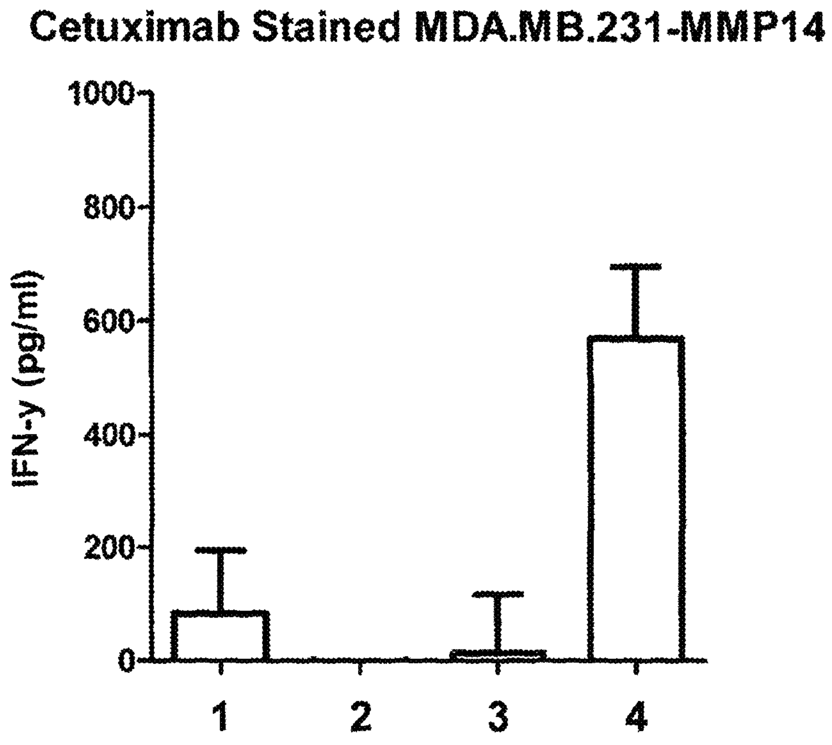

Specification includes a Sequence Listing.

Related U.S. Application Data continuation of application No. 14/660,137, filed on Mar. 17, 2015, now Pat. No. 9,358,282, which is a continuation of application No. 14/005,452, filed as application No. PCT/GB2012/050577 on Mar. 15, 2012, now Pat. No. 9,402,916.

(51) Int. Cl.

| | |
|---|---|
| ***A61K 47/64*** | (2017.01) |
| ***A61K 39/12*** | (2006.01) |
| ***C07K 16/28*** | (2006.01) |
| ***C07K 16/32*** | (2006.01) |
| ***A61K 38/20*** | (2006.01) |
| ***A61K 39/08*** | (2006.01) |
| ***A61K 39/145*** | (2006.01) |
| ***A61K 39/235*** | (2006.01) |
| ***A61K 39/245*** | (2006.01) |
| ***A61K 39/395*** | (2006.01) |
| ***A61K 45/06*** | (2006.01) |
| ***A61K 39/00*** | (2006.01) |
| ***C12N 7/00*** | (2006.01) |
| *C07K 16/30* | (2006.01) |
| *C07K 14/74* | (2006.01) |
| *C07K 14/11* | (2006.01) |
| *C07K 14/045* | (2006.01) |
| *C07K 14/05* | (2006.01) |
| *C07K 14/12* | (2006.01) |
| *C07K 14/04* | (2006.01) |
| *C07K 14/095* | (2006.01) |

(52) U.S. Cl.

CPC .......... *A61K 38/2026* (2013.01); *A61K 39/08* (2013.01); *A61K 39/12* (2013.01); *A61K 39/145* (2013.01); *A61K 39/235* (2013.01); *A61K 39/245* (2013.01); *A61K 39/3955* (2013.01); *A61K 39/39558* (2013.01); *A61K 45/06* (2013.01); *A61K 47/646* (2017.08); *A61K 47/6811* (2017.08); *A61K 47/6855* (2017.08); *A61K 47/6867* (2017.08); *A61K 47/6889* (2017.08); *C07K 16/2863* (2013.01); *C07K 16/2887* (2013.01); *C07K 16/32* (2013.01); *C12N 7/00* (2013.01); *A61K 47/6851* (2017.08); *A61K 47/6853* (2017.08); *A61K 47/6857* (2017.08); *A61K 47/6859* (2017.08); *A61K 47/6861* (2017.08); *A61K 47/6863* (2017.08); *A61K 47/6865* (2017.08); *A61K 47/6869* (2017.08); *A61K 2039/505* (2013.01); *A61K 2039/585* (2013.01); *A61K 2039/6056* (2013.01); *A61K 2039/627* (2013.01); *C07K 14/04* (2013.01); *C07K 14/045* (2013.01); *C07K 14/05* (2013.01); *C07K 14/095* (2013.01); *C07K 14/11* (2013.01); *C07K 14/12* (2013.01); *C07K 14/70539* (2013.01); *C07K 16/2806* (2013.01); *C07K 16/2875* (2013.01); *C07K 16/2878* (2013.01); *C07K 16/30* (2013.01); *C07K 16/3007* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 2317/24* (2013.01); *C07K 2317/622* (2013.01); *C07K 2319/33* (2013.01); *C07K 2319/50* (2013.01); *C12N 2710/16134* (2013.01)

(58) Field of Classification Search

CPC .... C07K 14/12; C07K 16/2863; C07K 16/32; C07K 16/3015; C07K 16/3038; C07K 16/3053; C07K 16/3023; C07K 16/3046; C07K 16/3007; C07K 16/30; C07K 16/2878; C07K 16/2875; C07K 14/70539; C07K 2317/24; C07K 2319/33; C07K 2319/50; C07K 2317/622; A61K 47/6889; A61K 47/646; A61K 47/6811; A61K 47/6853; A61K 47/6855; A61K 47/6857; A61K 47/6859; A61K 47/6851; A61K 47/6865; A61K 47/6869; A61K 47/6863; A61K 47/6861; A61K 39/39558; A61K 39/08; A61K 39/145; A61K 39/235; A61K 39/245; A61K 39/12; A61K 2039/505; A61K 2039/585; A61K 2039/6056; A61K 2039/627; C12N 2710/16134; A61P 3/10; A61P 9/00; A61P 37/08; A61P 37/06; A61P 37/04; A61P 37/00; A61P 35/00; A61P 31/04; A61P 25/28; A61P 25/00; A61P 11/06

See application file for complete search history.

(56) References Cited

U.S. PATENT DOCUMENTS

| | | | |
|---|---|---|---|
| 5,693,762 | A | 12/1997 | Queen et al. |
| 5,698,679 | A | 12/1997 | Nemazee |
| 5,739,116 | A | 4/1998 | Hamann et al. |
| 5,767,285 | A | 6/1998 | Hamann et al. |
| 5,773,001 | A | 6/1998 | Hamann et al. |
| 5,844,093 | A | 12/1998 | Kettleborough et al. |
| 5,877,293 | A | 3/1999 | Adair et al. |
| 6,458,552 | B1 | 10/2002 | Fourie et al. |
| 6,790,939 | B2 | 9/2004 | Reiter et al. |
| 6,969,517 | B2 | 11/2005 | Gillies et al. |
| 7,151,164 | B2 | 12/2006 | Hansen et al. |
| 7,375,186 | B2 | 5/2008 | Borgford |
| 7,378,091 | B2 | 5/2008 | Gudas et al. |
| 7,531,174 | B2 | 5/2009 | Sanicola-Nadel et al. |
| 7,632,499 | B2 | 12/2009 | Davies et al. |
| 7,659,241 | B2 | 2/2010 | Senter et al. |
| 7,790,165 | B2 | 9/2010 | Zhou et al. |
| 7,867,734 | B2 | 1/2011 | Nakano et al. |
| 7,871,613 | B2 | 1/2011 | Kinoshita et al. |
| 7,884,184 | B2 | 2/2011 | De Groot et al. |
| 8,039,597 | B2 | 10/2011 | Raitano et al. |
| 8,309,093 | B2 | 11/2012 | Gudas et al. |
| 8,318,163 | B2 | 11/2012 | Appleton et al. |
| 8,466,264 | B2 | 6/2013 | Appleton et al. |
| 8,877,901 | B2 | 11/2014 | Govindan |
| 8,889,117 | B2 | 11/2014 | Mellman et al. |
| 9,061,073 | B2 | 6/2015 | Fu |
| 9,084,830 | B2 | 7/2015 | Gho et al. |
| 9,138,495 | B2 | 9/2015 | Ballinger et al. |
| 9,149,542 | B2 | 10/2015 | Gho et al. |
| 9,192,677 | B2 | 11/2015 | Teasdale et al. |
| 9,358,282 | B2 | 6/2016 | Cobbold et al. |
| 9,402,916 | B2 | 8/2016 | Cobbold et al. |
| 2004/0001853 | A1 | 1/2004 | George et al. |
| 2004/0086503 | A1 | 5/2004 | Cohen et al. |
| 2004/0214235 | A1 | 10/2004 | Mori et al. |
| 2005/0037001 | A1 | 2/2005 | Germeraad et al. |
| 2005/0054019 | A1 | 3/2005 | Michaud et al. |
| 2006/0045881 | A1 | 3/2006 | Molldrem |
| 2006/0062786 | A1 | 3/2006 | Salcedo et al. |
| 2006/0088522 | A1 | 4/2006 | Boghaert et al. |
| 2007/0031414 | A1 | 2/2007 | Adams |
| 2007/0196376 | A1 | 8/2007 | Raeber et al. |
| 2008/0044419 | A1 | 2/2008 | Yayon |
| 2008/0069816 | A1 | 3/2008 | Yazaki et al. |
| 2008/0138898 | A1 | 6/2008 | Zhou et al. |
| 2008/0286228 | A1 | 11/2008 | Tarantolo et al. |
| 2008/0311134 | A1 | 12/2008 | Junutula et al. |
| 2009/0148436 | A1 | 6/2009 | LaVallie et al. |
| 2009/0175796 | A1 | 7/2009 | Raitano et al. |
| 2009/0175860 | A1 | 7/2009 | Stover et al. |

(56) References Cited

U.S. PATENT DOCUMENTS

2009/0175866 A1 7/2009 Yayon et al.
2009/0181034 A1 7/2009 Gudas et al.
2009/0202546 A1 8/2009 Harris et al.
2009/0214543 A1 8/2009 Zangemeister-Wittke et al.
2010/0008906 A1 1/2010 Glaser et al.
2010/0183618 A1 7/2010 Hasegawa et al.
2010/0233079 A1 9/2010 Jakob et al.
2010/0278838 A1 11/2010 Kinch et al.
2010/0291082 A1 11/2010 Zurawski et al.
2010/0298545 A1 11/2010 Kinch et al.
2010/0330107 A1 12/2010 Gudas et al.
2011/0008840 A1 1/2011 Hoffee et al.
2011/0028696 A1 2/2011 Cardarelli et al.
2011/0144004 A1 6/2011 Borgford
2014/0271618 A1 9/2014 Markel et al.
2015/0098943 A1 4/2015 Cohen et al.
2015/0141625 A1 5/2015 Stoermer et al.
2015/0183881 A1 7/2015 Bedi et al.
2015/0231239 A1* 8/2015 Hung .................... A61K 48/00 514/44 R
2015/0266974 A1 9/2015 Pons et al.
2015/0283260 A1 10/2015 Fu
2015/0297745 A1 10/2015 Cobbold et al.
2015/0307624 A1 10/2015 Bourel et al.
2015/0314014 A1 11/2015 Lauermann
2016/0008480 A1* 1/2016 Lee, II .................. C07K 16/30 424/178.1
2016/0039942 A1 2/2016 Cobbold et al.
2016/0206726 A1 7/2016 Cobbold et al.

FOREIGN PATENT DOCUMENTS

EP 1664270 B1 5/2014
EP 1648513 B1 9/2014
EP 1951313 B1 4/2015
EP 2613810 2/2016
GB 1216649 3/2014
JP 2009529522 A 8/2009
WO 9517212 A 6/1995
WO 1995017212 A1 6/1995
WO 1996034892 A1 11/1996
WO 1997023237 A1 7/1997
WO 1998010651 A1 3/1998
WO 1998018493 A2 5/1998
WO 1998024478 A2 6/1998
WO 1998041641 A1 9/1998
WO 9845331 A2 10/1998
WO 1999002175 A1 1/1999
WO 9945954 9/1999
WO 00006605 2/2000
WO 0012706 3/2000
WO 0244197 6/2002
WO 2003027135 A2 4/2003
WO 2004032962 A1 4/2004
WO 2004069876 A2 8/2004
WO 2003064606 A3 2/2005
WO 2005052004 A2 6/2005
WO 2005061547 A2 7/2005
WO 2005066203 A2 7/2005
WO 2005083431 A2 9/2005
WO 2005087813 A1 9/2005
WO 2007057922 A1 5/2007
WO 2007107764 A1 9/2007
WO 2007136778 A2 11/2007
WO 2007105027 12/2007
WO 2008019366 A2 2/2008
WO 2008052322 A1 5/2008
WO 2008097866 A2 8/2008
WO 2007065027 A3 9/2008
WO 2008143666 A2 11/2008
WO 2008122551 A9 2/2009
WO 2009024771 A2 2/2009
WO 2009025846 A2 2/2009
WO 2009068204 A1 6/2009
WO 2008063113 7/2009
WO 2009032949 A3 12/2009
WO 2010001585 A1 1/2010
WO 2010037837 A2 4/2010
WO 2010111018 A1 9/2010
WO 2010081173 A3 11/2010
WO 2010142990 A1 12/2010
WO 2011056721 A2 5/2011
WO 2011119979 A2 9/2011
WO 2012123755 A1 9/2012
WO 2013082366 A1 6/2013
WO 2013139789 A1 9/2013
WO WO-2016131856 A1 * 8/2016 .............. A61P 31/00

OTHER PUBLICATIONS

Edwards et al., J Mol Biol. 334(1): 103-118 (Year: 2003).*

Shirakawa, H. et al. Glypican-3 is a useful diagnostic marker for a component of hepatocellular carcinoma in human liver cancer Int J Oncol 34:649-656 (2009).

Sienel W et al. Elevated Expression of Carcinoembryonic Antigen-related Cell Adhesion Molecule 1 Promotes Progression of Non-Small Cell Lung Cancer1Clinical Cancer Research 9:2260-2266. (2003).

Silver DA et al. Prostate specific membrane antigen expression in normal and malignant human tissues. Clin Cancer Res 3: 81-85 (1997).

Skubitz KM and Skubitz AP. Interdependency of CEACAM-1,-3,-6, and -8 induced human neutrophil adhesion to endothelial cells. J Transl Med. 6:78 (2008).

Slamon DJ et al. Use of chemotherapy plus a monoclonal antibody against HER2 for metastatic breast cancer that overexpresses HER2. N Engl J Med 344:783-92 (2001).

Small, E.J., et al., "Placebo-Controlled Phase III Trial of Immunologic Therapy with Sipuleucel-T (APC8015) in Patients with Metastatic, Asymptomatic Hormone Refractory Prostate Cancer," Journal of Clinical Oncology 24(19):3089-3094 (2006).

Smith et al. Anti-SLC 44A4 Preclinical evaluation of ASG-5ME, a novel antibody-drug conjugate for pancreatic cancer. AACR 101st Annual Meeting 2010. Poster abstract found. Authors used a mouse monoclonal antibody (M5-121.131) specific for SLC44A4. (abstract).

Smith, D.C., et al., "Exogenous Peptides Delivered by Ricin Require Processing by Signal Peptidase for Transporter Associated with Antigen Processing-Independent MHC Class I restricted Presentation," J. Immunol. 169:99-107 (2002).

Song et al., "Radioimmunotherapy of Solid Tumors: Searching for the Right Target," Curr. Drug Deliv. Jan. 2011;8(1):26-44.

Spizzo G et al. High EpCAM expression is associated with poor prognosis in node-positive breast cancer. Breast Cancer Res Treat 86:207-213 (2004) (abstract).

Spratlin JL et al. Phase I Pharmacologic and Biologic Study of Ramucirumab (IMC-1121B), a Fully Human Immunoglobulin G1 Monoclonal Antibody Targeting the Vascular Endothelial Growth Factor Receptor-2. J Clin Oncol. 28(5):780-787 (2010).

Spratlin JL et al. Ramucirumab (IMC-1121B): A novel attack on angiogenesis. Future Oncol. 6:1085-1094 (2010) (abstract).

Staerz, U., et al., "Hybrid Antibodies Can Target Sites for Attack by T Cells," Nature, vol. 314, pp. 628-631 (Apr. 1985).

Staerz, U.D. and Bevan, M.J., "Hybrid Hybridoma Producing a Bispecific Monoclonal Antibody that can Focus Effector T-Cell Activity," Proc. Natl. Acad. Sci 83: 1453-1457 (1986).

Steffens MG et al. Targeting of renal cell carcinoma with iodine-131-labeled chimeric monoclonal antibody G250. J Clin Oncol 15(4): 1529-1537 (1997) (abstract).

Stein R, et al. Epitope specificity of the anti-(B cell lymphoma) monoclonal antibody, LL2. Cancer Immunol Immunother. 37(5):293-8. Oct. 1993.

Steinhusen U et al. Cleavage and shedding of E-cadherin after induction of apoptosis. J Biol Chem 276(7):4972-80 (2001).

Stirnemann, K., et al., "Sustained Activation and Tumor Targeting of NKT Cells Using a CDIdanti-HER2-scFv Fusion Protein Induce Antitumor Effects in Mice," The Journal of Clinical Investigation 118(3 ):994-1005 (2008).

(56) References Cited

OTHER PUBLICATIONS

Storni et al., "Loading of MHC Class I and II Presentation Pathways by Exogenous Antigens: A Quantitative in Vivo Comparison," J. Immunol 2004; 172:6129-6135.
Subklewe et al., "Dendritic Cells Cross-present Latency Gene Products from Epstein-Barr Virus-transformed B Cells and Expand Tumor-reactive CD8+ Killer T Cells," Brief Definitive Report, J. Exp. Med., Rockefeller University Press, vol. 193, No. 3, Feb. 5, 2001, pp. 405-411.
Sumida T, et al., "Regulatory T cell epitope recognized by T cells from labial salivary glands of patients with Sjögren's syndrome," Arthritis Rheum. Dec. 1997;40(12):2271-3.
Surfus JE et al. Anti-renal-cell carcinoma chimeric antibody G250 facilitates antibody-dependent cellular cytotoxicity with in vitro and in vivo interleukin-2-activated effectors. J Immunother Emphasis Tumor Immunol 19: 184-191 (1996) (abstract).
Sykulev, Y., et al., "Evidence that a Single Peptide-MHC Complex on a Target Cell can Elicit a Cytolytic T Cell Response," Immunity 4:565-571 (1996).
Sylwester, A.W., et al., "Broadly Targeted Human Cytomegalovirus-Specific CD4+ and CD8+ T Cells Dominate the Memory Compartments of Exposed Subjects," The Journal of Experimental Medicine 202(5):673-685 (2005).
Tamiolakis D et al. Distribution of somatostatin in pancreatic ductal adenocarcinoma remodels the normal pattern of the protein during foetal pancreatic development: an immunohistochemical analysis. Clin Exp Med. 5(3):106-11. 2005.
Tandon M et al. Emerging strategies for EphA2 receptor targeting for cancer therapeutics. Expert Opin Ther Targets. 15(1):31-51 (Jan. 2011).
Thie H et al. Rise and Fall of an Anti-MUC1 Specific Antibody. PLoS One. Jan. 14, 2011;6(1):e15921.
Thorsett, E.D., et al., "Dipeptide Mimics. Conformationally Restricted Inhibitors of Angiotensin-Converting Enzyme," Biochemical and Biophysical Research Communications 111(1):166-171(1983).
Tosolini, M., et al., "Clinical Impact of Different Classes of Infiltrating T Cytotoxic and Helper Cells (Thl, Th2, Treg, Thl 7) in Patients with Colorectal Cancer," Cancer Res. 71 (4):1263-1271 (2011).
Trowbridge IS, et al. Biochemical characterization and cellular distribution of a polymorphic, murine cell-surface glycoprotein expressed on lymphoid tissues. Immunogenetics 15(3):299-312. Mar. 1982.
Troyer JK et al. Detection and characterization of the prostate-specific membrane antigen (PSMA) in tissue extracts and body fluids. Int J Cancer 62: 552-558 (1995)(abstract).
Trudel S et al. The inhibitory anti-FGFR3 antibody, PRO-001, is cytotoxic to t(4;14) multiple myeloma cells. Blood 107(10):4039-46 (2006).
Urva SR and JP Balthasar. Target mediated disposition of T84.66, a monoclonal anti-CEA antibody: application in the detection of colorectal cancer xenografts. MAbs 22(1):67-72 (2010).
Veber, D.F ., et al., "Conformationally Restricted Bicyclic Analogs of Somatostatin," Proc. Natl. Acad. Sci. 75(6):2636-2640 (1978).
Vita, R., et al., "The Immune Epitope Database 2.0," Nucleic Acids Research 38:D854-D862 (2010).
Vogel CL et al. Efficacy and safety of trastuzumab as a single agent in first-line treatment of HER2-overexpressing metastatic breast cancer. J Clin Oncol 20:719-26 (2002) (abstract).
Wagner-KR et al. A phase I/II trial of MYO-029 in adult subjects with muscular dystrophy. Ann Neurol 63(5):561-71 (2008) (abstract).
Waldman, T.A., et al., "Immune Receptors: Targets for Therapy of Leukemia/Lymphoma, Autoimmune Diseases and for the Prevention of Allograft Rejection," Annu. Rev. Immunol. 10:675-704 (1992).
Wang, Q.-C., et al., "Induction of Hepatitis C Virus-Specific Cytotoxic T and B Cell Responses by Dendritic Cells Expressing a Modified Antigen Targeting Receptor," World Journal of Gastroenterology 11(4):557-560 (2005).
Wang, Q-C., et al., "Induction of Hepatitis C Virus-Specific Cytotoxic T and B Cell Responses by Dendritic Cells Expressing a Modified Antigen Targeting Receptor," World Journal of Gastroenterology, vol. 11, No. 4, Jan. 28, 2005, pp. 557-560.
Webb S, et al., "Pharma interest surges in antibody drug conjugates," Nat Biotechnol. Apr. 2011;29(4):297-8.
Weiner LM et al. Monoclonal Antibodies for Cancer Immunotherapy. Lancet 373(9668):1033-1040 (2009).
Weiner, Monoclonal Antibodies for Cancer Immunotherapy, Lancet 373(9668):1033-1040 (2009).
Welle S et al. Stimulation of skeletal muscle myofibrillar protein synthesis, p70 S6 kinase phosphorylation, and ribosomal protein S6 phosphorylation by inhibition of myostatin in mature mice. Am J Physiol Endocrinol Metab. 296(3): E567-E572 (2009).
Went P et al. Expression of epithelial cell adhesion molecule (EpCam) in renal epithelial tumors, Am J Surg Pathol 29:83-88 (2005)(abstract).
WHO Drug Information, International Nonproprietary Names for Pharmaceutical Substances (INN) vol. 24, No. 2, 2010 INN_PL103.
Winter, G., et al., "Making Antibodies by Phage Display Technology," Annu. Rev. Immunol. 12:433-455 (1994).
Witte, Monoclonal antibodies targeting the VEGF receptor-2 (Flk1/KDR) as an anti-angiogenic therapeutic strategy, Cancer and Metastasis Reviews 17:155-151 (1998).
Written Opinion of the International Searching Authority for PCT/GB2013/050499 dated Jul. 24, 2013.
Wu et al., Nature Biotechnology 23(9):1137-1146, Sep. 2005.
Hisatsune A et al. Anti-MUC1 antibody inhibits EGF receptor signaling in cancer cells. Biochem Biophys Res Commun 405:377-81 (2011) (abstract).
Hislop, A.D., et al., "Cellular Responses to Viral Infection in Humans: Lessons from Epstein-Barr Virus," Annu. Rev. Immunol. 25:587-617 (2007).
Ho M and Kim H. Glypican-3: a new target for cancer immunotherapy. Eur J Cancer. 47(3):333-8 (Feb. 2011).
Horie R, Watanabe T. CD30: expression and function in health and disease. Semin Immunol. 10(6):457-70. Dec. 1998.
Horoszewicz JS et al. Monoclonal antibodies to a new antigenic marker in epithelial cells and serum of prostatic cancer patients Anticancer Res 7: 927-936 (1987)(abstract).
Howland, S.W., et al., "Inducing Efficient Cross-Priming Using Antigen-Coated Yeast Particles," J. Immunother. 31(7):607-619 (2008).
Hu XF et al. Anti-Cripto Mab inhibit tumour growth and overcome MDR in a human leukaemia MDR cell line by inhibition of Akt and activation of JNK/SAPK and bad death pathways. British Journal of Cancer 96:918-927 (2007).
Huang MF et al. Syndecan-1 and E-cadherin expression in differentiated type of early gastric cancer. World J Gastroenterol 11(19):2975-80 (2005).
Hughes, B., "Antibody-Drug Conjugates for Cancer: Poised to Deliver?," Nature Reviews Drug Discovery 9:665-667 (2010).
Ichikawa K et al. Tumoricidal activity of a novel anti-human DR5 monoclonal antibody without hepatocyte cytotoxicity Nat Med 7:954-960 (2001) (abstract).
Iijima J et al. Cell-cell interaction-dependent regulation of N-acetylglucosaminyltransferase III and the bisected N-glycans in GE11 epithelial cells. Involvement of E-cadherin-mediated cell adhesion. J Biol Chem 281(19):13038-46 (2006).
Inami K et al. Antitumor activity of anti-C-ERC/mesothelin monoclonal antibody in vivo. Cancer Sci. 101(4):969-74 (2010).
International Preliminary Report on Patentability for International Application PCT/GB2012/050577; dated Sep. 17, 2013.
International Preliminary Report on Patentability for PCT/GB2013/050499 dated Sep. 2, 2014.
International Search Report and Written Opinion of the International Searching Authority for International Application No. PCT/GB2012/050577, "Re-Directed Immunotherapy," dated Jun. 29, 2012.
International Search Report for PCT/GB2013/050499 dated Jul. 24, 2013.
International Search Report for PCT/GB2013/052427 dated May 2, 2014.

(56) References Cited

OTHER PUBLICATIONS

Irvine, D.J., et al., "Direct Observation of Ligand Recognition by T Cells," Nature 419:845-849. (2002).
Ishiguro T et al. Anti-glypican 3 antibody as a potential antitumor agent for human liver cancer. Cancer Res. 68(23):9832-8 (2008).
Jaalouk DE et al. The original Pathologische Anatomie Leiden-Endothelium monoclonal antibody recognizes a vascular endothelial growth factor binding site within neuropilin-1. Cancer Res. 67(20):9623-9 (2007).
Japink D et al. CEA in activated macrophages. New diagnostic possibilities for tumor markers in early colorectal cancer. Anticancer Res 29(8):3245-51 (2009).
Jeffrey, S.C., et al., "Dipeptide-Based Highly Potent Doxorubicin Antibody Conjugates," Bioorganic & Medicinal Chemistry Letters 16:358-362 (2006).
Jilaveanu LB, et al. CD70 expression patterns in renal cell carcinoma. Hum Pathol. 43(9):1394-9. Sep. 2012; Epub Mar. 7, 2012.
Jimeno A et al. Epidermal Growth Factor Receptor Dynamics Influences Response to Epidermal Growth Factor Receptor Targeted Agents. Cancer Res (65) (8): 3003-3010 (2005).
Jin H et al. MetMAb, The one-armed 5D5 anti-c-Met antibody, inhibits orthotopic pancreatic tumor growth and improves survival. Cancer Res 68:4360-8 (2008).
Johansson C et al. Novel epitopes on the CA50-carrying antigen: chemical and immunochemical studies. Tumour Biol 12:159-70 (1990) (abstract).
Josson S et al. Tumor-Stromal Interactions Influence Radiation Sensitivity in Epithelial-versus Mesenchymal-Like Prostate Cancer Cells. J Oncol pii: 232831 (2010).
Jubala, CD20 Expression in Normal Canine B Cells and in Canine non-Hodgkin Lymphoma, Vet Pathol 42:468-476 (2005).
Jutila MA, et al. L-selectin serves as an E-selectin ligand on cultured human T lymphoblasts. J Immunol. 169(4): 1768-73. Aug. 15, 2002.
Kakkar T et al. Pharmacokinetics and safety of a fully human hepatocyte growth factor antibody, AMG102, in cynomolgus monkeys. Pharm Res 24:1910 (2007) (abstract).
Kandil D et al. Glypican-3 protein expression in primary and metastatic melanoma: a combined immunohistochemistry and immunocytochemistry study. Cancer. 117(4):271-8 (2009).
Kang et al., Targeted Coating with Antigenic Peptide Renders Tumor Cells Susceptible to CD8+ T Cell-mediated Killing, Molecular Therapy 21(3):542-553 (2013).
Kase S et al. Immunolocalisation of E-cadherin and beta-catenin in human pterygium. Br J Ophthalmol 91(9):1209-12 (2007).
Kawamura, K.S., et al., "In Vivo Generation of Cytotoxic T Cells from Epitopes Displayed on Peptide-Based Delivery Vehicles," Journal of Immunology 168:5709-5715 (2002).
Kirshner J et al. CEACAM1, a cell-cell adhesion molecule, directly associates with annexin II in a three-dimensional model of mammary morphogenesis. Journal of Biological Chemistry 278(50):50338-50345 (2003).
Kischkel F et al. Apo2L/TRAIL-Dependent Recruitment of Endogenous FADD and Caspase-8 to Death Receptors 4 and 5. Immunity vol. 12(6):611-620 (2000).
Klechevsky E, et al. Cross-priming CD8+ T cells by targeting antigens to human dendritic cells through DCIR. Blood. 116(10):1685-97. Sep. 9, 2010; Epub Jun. 7, 2010.
Kohler, et al., "Continuous Cultures of Fused Cells Secreting Antibody of Predefined Specificity," Nature 256:495-497 (1975).
Kolb EA et al. R1507, a fully human monoclonal antibody targeting IGF-1R, is effective alone and in combination with rapamycin in inhibiting growth of osteosarcoma xenografts. Pediatr Blood Cancer. 55(1):67-75. (2010).
Kovtun YV et al. Antibody-drug conjugates designed to eradicate tumors with homogeneous and heterogeneous expression of the target antigen. Cancer Res. 66(6):3214-21 (2006).
Kozak, R.W., et al., "IL-2-PE40 Prevents the Development of Tumors in Mice Injected with IL-2 Receptor Expressing EL4 Transfectant Tumor Cells," Journal of Immunology 145 (8):2766-2771 (1990).
Kreitman RJ, et al. Phase I trial of anti-CD22 recombinant immunotoxin moxetumomab pasudotox (CAT-8015 or HA22) in patients with hairy cell leukemia. J Clin Oncol. 230(15):1822-8. May 20, 2012; Epub Feb. 21, 2012.
Kuenen B et al. A phase I pharmacologic study of necitumumab (IMC-11F8), a fully human IgG1 monoclonal antibody directed against EGFR in patients with advanced solid malignancies. Clin Cancer Res 16(6):1915-1923 (2010).
Kufer, P., et al., "Construction and Biological Activity of a Recombinant Bispecific Single-Chain Antibody Designed for Therapy of Minimal Residual Colorectal Cancer," Cancer Immunology Immunotherapy, vol. 45, pp. 193-197 (1997).
Lagadec P, et al. Involvement of a CD47-dependent pathway in platelet adhesion on inflamed vascular endothelium under flow. Blood. 101(12):4836-43. Jun. 15, 2003; Epub Feb. 27, 2003.
Lamb CA, et al. Invariant chain targets HLA class II molecules to acidic endosomes containing internalized influenza virus. Proc Natl Acad Sci U S A. 88(14):5998-6002. Jul. 15, 1991.
Larche, M. et al. "Functional evidence for a monoclonal antibody that binds to the human IL-4 receptor" Immunology 65: 617-622 (1988).
Lash, A., "Making the Case for Antibody-Drug Conjugates," In Vivo: The Business and Medicine Report:32-38 (2010).
Lazaris AC et al. Immunohistochemical investigation of angiogenic factors in parathyroid proliferative lesions. Eur J Endocrinol. 154(6):827-33 (2006).
Lee J-W et al. EphA2 targeted chemotherapy using an antibody drug conjugate in endometrial carcinoma. Clin Cancer Res. 16(9):2562-70 (2010).
A. Gupta et al., "Identification of critical variants within SLC44A4, an ulcerative colitis susceptibility gene identified in a GWAS in north Indians," Genes and Immunity (2016) 17, 105-109.
Adis R&D Profile: Brentuximab Vedotin, Drugs RD 11(1):85-95 (2011).
Adler et al., Therapeutic Antibodies Against Cancer, Hematol Oncol Clin North Am. 26(3):447-481 (2012).
Akiyama et al., "Characterization of cytomegalovirus pp65-HLA-A24 peptide-specific CTL lines from metastatic melanoma patients", Oncology Reports 22: pp. 185-191 (Mar. 3, 2009).
Al-Ahmadie HA et al. Carbonic anhydrase IX expression in clear cell renal cell carcinoma: an immunohistochemical study comparing 2 antibodies. Am J Surg Pathol 32(3):377-82 (2008) (abstract).
Alderson RF, et al. CAT-8015: a second-generation pseudomonas exotoxin A-based immunotherapy targeting CD22-expressing hematologic malignancies. Clin Cancer Res. 15(3):832-9. Feb. 1, 2009.
Alegretti AP, et al. Expression of CD55 and CD59 on peripheral blood cells from systemic lupus erythematosus (SLE) patients. Cell Immunol. 265(2):127-32. 2010; Epub Aug. 2, 2010.
Alexander, J., et al., "Linear PADRE T Helper Epitope and Carbohydrate B Cell Epitope Conjugates Induce Specific High Titer IgG Antibody Responses," J. Immunol. 164:1625-1633 (2000).
Alisa A, et al. "Human CD4(+) T cells recognize an epitope within alpha-fetoprotein sequence and develop into TGF-beta-producing CD4(+) T cells," J Immunol. Apr. 1, 2008;180(7):5109-17.
Andersen, M. H. et al. "Cytotoxic T Cells" Journal of Investigative Dermatology 126: 32-41 (2006).
Ansuini H et al. Anti-EphA2 Antibodies with Distinct in Vitro Properties Have Equal in Vivo Efficacy in Pancreatic Cancer. J Oncol. 2009:951917 (2009).
Appay V. The physiological role of cytotoxic CD4(+) T-cells: the holy grail? Clin Exp Immunol. 138(1):10-13. 2004.
Arai K, et al., "Preventing effect of anti-ICAM-1 and anti-LFA-1 monoclonal antibodies on murine islet allograft rejection," International Journal of Pancreatology, Aug. 1999, vol. 26, Issue 1, pp. 23-31.
Ariel O, et al. Signal transduction by CD58: the transmembrane isoform transmits signals outside lipid rafts independently of the GPI-anchored isoform. Cell Signal. 21(7):1100-8. Jul. 2009 Epub Mar. 5, 2009.
Arnett et al., "IBC's 21st Annual Antibody Engineering and 8th Annual Antibody Therapeutics International Conferences and 2010 Annual Meeting of the AntibodySociety," mAbs, 3:2, 133-152.

(56) References Cited

OTHER PUBLICATIONS

Arnett SO et al. IBC's 21st Annual Antibody Engineering and 8th Annual Antibody Therapeutics International Conferences and 2010 Annual Meeting of the Antibody Society. Dec. 5-9, 2010, San Diego, CA USA. MAbs. 3(2):133-52. (Epub Mar. 1, 2011). Clinical Trials.gov entry of study NCT01166490. First posted Jul. 21, 2010.
Baeuerle P.A., et al. "BiTE: Teaching antibodies to engage T-cells for cancer therapy." Curr Opin Mol Therapeutics. 11(1):22-30. (Feb. 1, 2009).
Baeuerle, P.A. and Reinhardt, C., "Bispecific T-Cell Engaging Antibodies for Cancer Therapy," Cancer Res. 69( 12):4941-4944 (2009).
Bargou, R., et al., "Tumor Regression in Cancer Patients by Very Low Doses of a T-Cell Engaging Antibody," Science 321:974-977 (2008).
Bast RC et al. A Radioimmunoassay Using a Monoclonal Antibody to Monitor the Course of Epithelial Ovarian Cancer. N Engl J Med 309: 883-887 (1983) (abstract).
Bastholt L et al. Phase I/II clinical and pharmacokinetic study evaluating a fully human monoclonal antibody against EGFr (HuMax-EGFr) in patients with advanced squamous cell carcinoma of the head and neck. Radiother Oncol 85(1):24-28 (2007) (abstract).
Battaglia-A et al. Neuropilin-1 expression identifies a subset of regulatory T cells in human lymph nodes that is modulated by preoperative chemoradiation therapy in cervical cancer Immunology 123(1):129-38 (2008). Epub Nov. 20, 2007.
Becker-Herman S, et al. CD74 is a member of the regulated intramembrane proteolysis-processed protein family. Mol Biol Cell. 16(11):5061-9. Nov. 2005. Epub Aug. 17, 2005.
Bellosillo, B., et al., "Complement-Mediated Cell Death Induced by Rituximab in B-Cell Lymphoproliferative Disorders is Mediated in vitro by a Caspase-Independent Mechanism Involving the Generation of Reactive Oxygen Species," Blood 98(9):2771-2777 (2001).
Bertilaccio, M.T.S., et al., "A Novel Rag2-Gamma2-Xenograft Model of Human CLL," Blood 115(8):1605-1609 (2010).
Bianco C and Salomon DS. Targeting the embryonic gene Cripto-1 in cancer and beyond. Expert Opin Ther Pat. 20(12): 1739-1749 (2010).
Bleumer I et al. A phase II trial of chimeric monoclonal antibody G250 for advanced renal cell carcinoma patients Br J Cancer 90(5):985-990 (2004).
Blumenthal-RD et al. Expression patterns of CEACAM5 and CEACAM6 in primary and metastatic cancers. BMC Cancer 7:2 (2007).
Bogdanovich S et al, Functional improvement of dystrophic muscle by myostatin blockade Nature 420: 418-421 (2002) (abstract).
Bonnet, D. and Dick, J.E., "Human Acute Myeloid Leukemia is Organized as a Hierarchy that Originates from a Primitive Hematopoietic Cell," Nat. Med. 3(7):730-737 (1997).
Borche L, et al. CD43 monoclonal antibodies recognize the large sialoglycoprotein of human leukocytes. Eur J Immunol. 17(10):1523-6. Oct. 1987.
Brodsky FM. A matrix approach to human class II histocompatibility antigens: reactions of four monoclonal antibodies with the products of nine haplotypes. Immunogenetics. 19(3):179-94. 1984.
Bruhl, H., et al., "Depletion of CCR5-Expressing Cells with Bispecific Antibodies and Chemokine Toxins: A New Strategy in the Treatment of Chronic Inflammatory Diseases and HIV," The Journal of Immunology, vol. 166, pp. 2420-2426 (2001).
Bu X et al. Altered expression of MUC2 and MUC5AC in progression of colorectal carcinoma. World J Gastroenterol 16(32): 4089-4094 (2010).
Burgess T et al. Fully human monoclonal antibodies to hepatocyte growth factor with therapeutic potential against hepatocyte growth factor/c-Met-dependent human tumors Cancer Res 66:1721-9 (2006).
Cao B et al. Neutralizing monoclonal antibodies to hepatocyte growth factor/scatter factor (HGF/SF) display antitumor activity in animal models. Proc Natl Acad Sci 98:7443-8 (2001).
Carles-Kinch K et al. Antibody targeting of the EphA2 tyrosine kinase inhibits malignant cell behavior. Cancer Res. 62(10):2840-7 (2002).
Carter P et al. Humanization of an anti-p185HER2 antibody for human cancer therapy. Proc Natl Acad Sci U S A. 89(10):4285-9 1992.
Carter, P.J., "Introduction to Current and Future Protein Therapeutics: A Protein Engineering Perspective," Exp. Cell Res. 317:1261-1269(2011).
Carter, P.J., "Potent Antibody Therapeutics by Design," Nat. Rev. Immunol 6:343-357 (2006).
Chames et al., "Therapeutic Antibodies for the Treatment of Pancreatic Cancer," TheScientificWorldJournal (2010)10:1107-1120.
Chang SS et al. Comparison of anti-prostate-specific membrane antigen antibodies and other immunomarkers in metastatic prostate carcinoma. Urology 57: 1179-1183 (2001)(abstract).
Chang SS. Overview of Prostate-Specific Membrane Antigen. Rev Urol 6(Suppl 10): S13-S18 (2004).
Chauhan SC et al. Aberrant expression of MUC4 in ovarian carcinoma: diagnostic significance alone and in combination with MUC1 and MUC16 (CA125). Mod Pathol 19: 1386-1394 (2006).
Chen F et al., Knockdown of c-FLIPL enhanced AD5-10 anti-death receptor 5 monoclonal antibody-induced apoptosis in human lung cancer cells. Cancer Sci 100 (5): 940-947 (2009).
Chinese Office Action in corresponding CN application No. 201280024084.1, dated Jul. 21, 2015.
Chung WC et al., CREB Mediates Prostaglandin F2α-Induced MUC5AC Overexpression, J Immunol. 182(4):2349-56 (2009).
Cimino A et al. Epithelial cell adhesion molecule (EpCAM) is overexpressed in breast cancer metastases Breast Cancer Res Treat. October 123(3): 701-708 (2010).
Clark, E.A., et al., "Role ofBp35 Cell Surface Polypeptide in Human B-Cell Activation," Proc. Natl. Acad. Sci. 82: 1766-1770 (1985).
Clarke, et al., "Gemtuzumab Ozogamicin: Is There Room for Salvage?" Blood 116(14):2618-2619 (2010).
Oosterwijk E et al. Monoclonal antibody G 250 recognizes a determinant present in renal-cell carcinoma and absent from normal kidney. Int J Cancer 38:489-494 (1986) (abstract).
Osborn L, et al. Amino acid residues required for binding of lymphocyte function-associated antigen 3 (CD58) to its counter-receptor CD2. J Exp Med 181(1):429-34. Jan. 1995.
O'Sullivan MK, et al., "Comparison of two methods of preparing enzyme-antibody conjugates: application of these conjugates for enzyme immunoassay," Anal Biochem. Nov. 15, 1979;100(1):100-8.
O'Sullivan, M.J., et al., "Comparison of Two Methods of Preparing Enzyme-Antibody Conjugates: Application of these Conjugates for Enzyme Immunoassay," Analytical Biochemistry 100: 100-108(1979).
Pan Q et al. Blocking neuropilin-1 function has an additive effect with anti-VEGF to inhibit tumor growth. Cancer Cell. 11(1):53-67 (2007).
Park, B.-W., et al., "Rationally Designed Anti-HER2/neu Peptide Mimetic Disables P185HER2/neu Tyrosine Kinases in vitro and in vivo," Nature Biotechnology 18: 194-198 (2000).
Parsons SA et al. Age-dependent effect of myostatin blockade on disease severity in a murine model of limb-girdle muscular dystrophy. American Journal of Pathology 168(6):1975-1985 (2006).
Pavoni E. et al., Selection, affinity maturation, and characterization of a human scFv antibody against CEA protein, BMC Cancer, Feb. 6:41 (2006).
Pegram MD et al. Phase I dose escalation pharmacokinetic assessment of intravenous humanized anti-MUC1 antibody AS1402 in patients with advanced breast cancer. Breast Cancer Res 11(5): R73 (2009).
Plant, A, et al., "Phospholipid/Alkanethiol Bilayers for Cell-Surface Receptor Studies by Surface Plasmon Resonance," Analytical Biochemistry, vol. 226, pp. 342-348 (1995).
Polski JM and Janney CG. Ber-H2 (CD30) immunohistochemical staining in malignant melanoma. Mod Pathol. 12(9):903-6. Sep. 1999.

(56) References Cited

OTHER PUBLICATIONS

Ponde, D.E., et al., "Development of Anti-EGF Receptor Peptidomimetics (AERP) as Tumor Imaging Agent," Bioorganic & Medicinal Chemistry Letters 21 :2550-2553 (2011 ).

Poon, KA, "Safety Assessment of Antibody Drug Conjugates," Presentation at Northern California Society of Toxicology. May 6, 2010.

Porcelli, S., et al., "Recognition of Cluster of Differentiation 1 Antigens by Human CD4-CD8-Cytolytic T Lymphocytes," Nature 341:447-450 (1989).

Pozner-Moulis S et al. Antibody validation by quantitative analysis of protein expression using expression of Met in breast cancer as a model. Lab Invest 87:251-60 (2007).

Price MR et al. C595—a monoclonal antibody against the protein core of human urinary epithelial mucin commonly expressed in breast carcinoma., Br J Cancer 61: 681-686 (1990).

Pukac, L et al. HGS-ETR1, a Fully Human TRAIL-Receptor 1 Monoclonal Antibody, Induces Cell Death in Multiple Tumour Types in Vitro and in Vivo. Br J Cancer 92.8 (2005): 1430-1441.

Qing, J. et al. Antibody-based targeting of FGFR3 in bladder carcinoma and t(4;14)—positive multiple myeloma in mice. J Clin Invest 119:1216-1229 (2009).

Rader, C., "DARTs Take Aim at BiTEs," Blood 117:4403-4404 (2011).

Rajasagi M. CD44 promotes progenitor homing into the thymus and T cell maturation. J Leukoc Biol. 85(2):251-61. Feb. 2009; Epub Oct. 27, 2008.

Rawlings, N.D., et al., "MEROPS: the Peptidase Database," Nucleic Acids Research 36:D320-D325 (2008).

Reis CA et al. Immunohistochemical study of MUC5AC expression in human gastric carcinomas using a novel monoclonal antibody Int J Cancer 74(1):112-21 (1997).

Response to Office Action from European Patent Office dated Nov. 8, 2013, filed Apr. 14, 2014, for European Patent Application No. 12718715.1 (21 pages).

Rich, D.H., "Inhibitors of cysteine proteases." In Research monographs in cell and tissue physiology vol. 12, Proteinase inhibitors. Barrett AJ, Salvesen G, eds. (Amsterdam: Elsevier.) pp. 153-178 (1986).

Riesterer O et al. Combination of anti-IGF-1R antibody A12 and ionizing radiation in upper respiratory tract cancers. Int J Radiat Oncol Biol Phys. 79(4):1179-87. (2011, Epub Dec. 2, 2010).

Rinderknecht M et al. Phage-Derived Fully Human Monoclonal Antibody Fragments to Human Vascular Endothelial Growth Factor-C Block Its Interaction with VEGF Receptor-2 and 3, PLoS One, Aug. 2010 5(8):1-16.

Romagnoli, P., et al., "Selective Interaction of Ni with an MHC-Bound Peptide," The EMBO Journal 10(6):1303-1306 (1991).

Romero, P., et al., "Photoaffinity Labeling of the T Cell Receptor on Living Cytotoxic T Lymphocytes," The Journal of Immunology 150(9):3825-3831 (1993).

Romond EH et al. Trastuzumab plus adjuvant chemotherapy for operable HER2- positive breast cancer. N Engl J Med 353:1673-84 (2005).

Royer B et al. Population pharmacokinetics of the humanised monoclonal antibody, HuHMFG1 (AS1402), derived from a phase I study on breast cancer. Br J Cancer 102(5):827-32 (2010).

Rump A et al. Binding of ovarian cancer antigen CA125/MUC16 to mesothelin mediates cell adhesion. J Biol Chem 279:9190-9198 (2004).

Saeki N et al., Prostate Stem Cell Antigen: A Jekyll and Hyde Molecule? Clin Cancer Res. 16(14):3533-3538 (2010).

Saffran DC et al. Anti-PSCA mAbs inhibit tumor growth and metastasis formation and prolong the survival of mice bearing human prostate cancer xenogralls. Proc Natl Acad Sci U S A. 98(5):2658-63. (2001).

Sangoi AR et al. Immunohistochemical comparison of MUC1, CA125, and Her2Neu in invasive micropapillary carcinoma of the urinary tract and typical invasive urothelial carcinoma with retraction artifact. Mod Pathol 22:660-667 (2009).

Sathish, Challenges and approaches for the development of safer immunomodulatory biologies, Nature Reviews Drug Discovery 12:306-324 (2013).

Savage, P., et al., "Induction of Viral and Tumour Specific CTL Responses Using Antibody Targeted HLA Class I Peptide Complexes," British Journal of Cancer 86:1336-1342 (2002).

Schaffitzel, C., et al., "Ribosome Display: an in vitro Method for Selection and Evolution of Antibodies from Libraries," Journal of Immunological Methods 231 :119-135 (1999).

Schmiegel, W., et al., "Cytokine-Mediated Enhancement of Epidermal Growth Factor Receptor Expression Provides an Immunological Approach to the Therapy of Pancreatic Cancer," Proc. Natl. Acad. Sci. 94:12622-12626 (1997).

Schoffelen R et al. Pretargeted immuno-positron emission tomography imaging of carcinoembryonic antigen-expressing tumors with a bispecific antibody and a 68Ga- and 18F-labeled hapten peptide in mice with human tumor xenografts. Mol Cancer Ther 9(4):1019-27 (2010).

Schoonooghe S et al. Efficient production of human bivalent and trivalent anti-MUC1 Fab-scFv antibodies in Pichia pastoris. BMC Biotechnol. 9:70 (2009).

Search report from Intellectual Property Office for GB1216649 dated Jan. 17, 2013.

Searle, F., et al., "A Human Choriocarcinoma Xenograft in Nude Mice; a Model for the Study of Antibody Localization," British Journal Cancer 44: 13 7-144 (1981 ).

Seline PC et al. Expression of E and P-cadherin by melanoma cells decreases in progressive melanomas and following ultraviolet radiation. Journal of Investigative Dermatology. 106(6): 1320-1324. (1996).

Senter, P.D., et al., "Anti-Tumor Effects of Antibody-Alkaline Phosphatase Conjugates in Combination with Etoposide Phosphate," Proc Natl Acad. Sci 85:4842-4846 (1988).

Shan L. Magnetic iron microbeads coupled with HEA-125 monoclonal antibody against epithelial cell adhesion molecule, Feb. 24 [Updated Mar. 29, 2011]. In: Molecular Imaging and Contrast Agent Database (MICAD). (2011). Bethesda (MD): National Center for Biotechnology Information (US): 2004-2013. Available from: https://www.ncbi.nlm.nih.gov/books/NBK53693/.

Shen, L., et al., "Important Role of Cathepin S in Generating Peptides for TAP-Independent MHC Class I Crosspresentation in Vivo," Immunity 21:155-165 (2004).

Sherman, D.B. and Spatola, A.F., "Compatibility of Thioamides with Reverse Turn Features: Synthesis and Conformational Analysis of Two Model Cyclic Pseudopeptides Containing Thioamides as Backbone Modifications," J. Am. Chem. Soc. 112:433-441 (1990).

Shibata S et al. A phase I study of a combination of yttrium-90-labeled anti-carcinoembryonic antigen (CEA) antibody and gemcitabine in patients with CEA-producing advanced malignancies. Clin Cancer Res 15(8):2935-41 (2009).

Shimizu M and Imai M. Effect of the antibody immunotherapy by the anti-MUC1 monoclonal antibody to the oral squamous cell carcinoma in vitro. Biol Pharm Bull. 31(12):2288-93 (2008).

Shiomi K et al. Sensitive and specific new enzyme-linked immunosorbent assay for N-ERC/mesothelin increases its potential as a useful serum tumor marker for mesothelioma Clin Cancer Res. 14(5):1431-7 (2008).

Lee SH. Tanibirumab (ttac-0001): A fully human monoclonal antibody targets vascular endothelial growth factor receptor 2 (VEGFR-2) Arch Pharm Res. 34:1223-1226 (2011) (abstract).

Lehmann JC, et al. Overlapping and selective roles of endothelial intercellular adhesion molecule-1 (ICAM-1) and ICAM-2 in lymphocyte trafficking. J Immunol. 171(5):2588-93. Sep. 1, 2003.

Lepin EJ et al. An affinity matured minibody for PET imaging of prostate stem cell antigen (PSCA)—expressing tumors. Eur J Nucl Med Mol Imaging. 37(8):1529-38. (2010).

Lesley J, Trowbridge IS. Genetic characterization of a polymorphic murine cell-surface glycoprotein. Immunogenetics. 15(3):313-20. Mar. 1982.

Leyton JV et al. Engineered humanized diabodies for microPET imaging of prostate stem cell antigen-expressing tumors. Protein Eng Des Sel. 22(3):209-16. (2009).

(56) References Cited

OTHER PUBLICATIONS

Leyton JV et al. Humanized radioiodinated minibody for imaging of prostate stem cell antigen-expressing tumors. Clin Cancer Res. 14(22):7488-96. (2008).
Li S, et al., "Analysis of FOXP3+ regulatory T cells that display apparent viral antigen specificity during chronic hepatitis C virus infection," PLoS Pathog. Dec. 2009;5(12):e1000707. Epub Dec. 24, 2009.
Lim et al., Anti-CD20 monoclonal antibodies: historical and future perspectives, Hematologica 94(1):135-143 (2010).
Litvinov SV et al. Epithelial cell adhesion molecule (EpCAM) modulates cell-cell interactions mediated by classic cadherins. J Cell Biol 139:1337-1348 (1997).
Loffler et al. "A recombinant bispecific single-chain antibody, CD19 x CD3, induces rapid and high lymphoma-directed cytotoxicity by unstimulated T lymphocytes." 95(6):2098-103. (Mar. 15, 2000).
Loisel, S., et al., "Establishment of a Novel Human B-CLL-like Xenograft Model in Nude Mouse," Leukemia Research 29:1347-1352 (2005).
Lopes AD et al. Immunohistochemical and pharmacokinetic characterization of the site-specific immunoconjugateCYT-356 derived from anti-prostate monoclonal antibody 7E11-C5. Cancer Res 50: 6423-6429 (1990).
Lorberboum-Galski, H., et al., "Cytotoxic Activity of an Interleukin 2-Pseudomonas Exotoxin Chimeric Protein Produced in *Escherichia coli*," Proc. Natl. Acad. Sci 85: 1922-1926 (1988).
Lu Y et al. Identification of circulating neuropilin-1 and dose-dependent elevation following anti-neuropilin-1 antibody administration. mAbs 1(4):364-369 (2009).
Luka J et al. Development of a serum biomarker assay that differentiates tumor-associated MUC5AC (NPC-1C Antigen) from normal MUC5AC. J Biomed Biotechnol. 2011:934757. 2011. (Epub Dec. 16, 2010).
Lutterbuese R. et al., "T cell-engaging BiTE antibodies specific for EGFR potently eliminate KRAS- and BRAF-mutated colorectal cancer cell", Proc. Natl. Acad. Sci. 107(28):12605-12610. (Jul. 13, 2010).
Lutterbuese, R., et al., "Potent Control of Tumor Growth by CENCD3-bispecific Single-Chain Antibody Constructs that are not Competitively Inhibited by Soluble CEA," J. Immunother. 32(4):341-352 (2009).
Ma X et al. Flow injection chemiluminescent immunoassay for carcinoembryonic antigen using boronic immunoaffinity column. Sensors 9(12):10389-99 (2009).
Mack, M., et al., "A Small Bispecific Antibody Construct Expressed as a Functional Single-Chain Molecule With High Tumor Cell Cytotoxicity," Proceedings of the National Academy of Sciences, vol. 93, pp. 7021-7025 (Jul. 1995).
Mack, M., et al., "Biologic Properties of a Bispecific Single-Chain Anitbody Directed Against 17-1A (EpCAM) and CD3; Tumor Cell-Dependent T Cell Stimulation and Cytotoxic Activity," The Journal of Immunology, vol. 158, pp. 3965-3971 (1997).
Maddipatla-S et al. Augmented Antitumor Activity against B-Cell Lymphoma by a Combination of Monoclonal Antibodies Targeting TRAIL-R1 and CD20. Clin Cancer Res 13(15):4556-4564 (2007).
Mahato, R., et al., "Prodrugs for Improving Tumor Targetability and Efficiency," Adv. Drug. Deliv. Rev. 63(8):659-670 (2011).
Maiti A et al. TNF-alpha induction of CD44-mediated leukocyte adhesion by sulfation. Science. 282(5390):941-3. Oct. 30, 1998.
Mannello F et al. Increased shedding of soluble fragments of P-cadherin in nipple aspirate fluids from women with breast cancer. Cancer Sci; 99(11):2160-2169 (2008).
Manning EA et al. A vascular endothelial growth factor receptor-2 inhibitor enhances antitumor immunity through an immune-based mechanism. Clin Cancer Res. 13(13):3951-9. (2007).
Martínez-Torrecuadrada J et al. Targeting the extracellular domain of fibroblast growth factor receptor 3 with human single-chain Fv antibodies inhibits bladder carcinoma cell line proliferation. Clin Cancer Res 11(17):6280-90 (2005).
Matsumura, Y. and Maeda, H., "A New Concept for Macromolecular Therapeutics in Cancer Chemotherapy: Mechanism of Tumoritropic Accumulation of Proteins and the Antitumor Agent Smancs," Cancer Res. 46:6387-6392 (1986).
Mayes, S., et al., "New Antibody Drug Treatments for Lymphoma," Expert Opin. Biol. Ther. 11 ( 5):623-640 (2011).
Mazor R, et al. Identification and elimination of an immunodominant T-cell epitope in recombinant immunotoxins based an Pseudomonas exotoxin A. Proc Natl Acad Sci U S A. 109(51):E3597-603 Dec. 18, 2012 Epub Dec. 3, 2012.
Mebratu YA et al. Cigarette smoke suppresses Bik to cause epithelial cell hyperplasia and mucous cell metaplasia. Am J Respir Crit Care Med. 183(11):1531-8 2011. (Epub Feb. 11, 2011).
Melton, R.G., et al., "Covalent Linkage of Carboxypeptidase G2 to Soluble Dextrams-1," Biochemical Pharmacology 36(1):105-112 (1987).
Merritt WM et al. Clinical and biological impact of EphA2 overexpression and angiogenesis in endometrial cancer. Cancer Biol Ther. 10(12):1306-1314 (2010).
Meyer T et al. A Phase I Trial of Radioimmunotherapy with 131I-A5B7 Anti-CEA Antibody in Combination with Combretastatin-A4-Phosphate in Advanced Gastrointestinal Carcinomas. Clin Cancer Res 15(13):4484-4492 (2009).
Meziere, C., et al., "In Vivo T Helper Cell Response to Retro-Inverso Peptidomimetics," J. Immunol. 159:3230-323 7 (1997).
Midorikawa et al. Glypican-3, overexpressed in hepatocellular carcinoma, modulates FGF2 and BMP-7 signaling. Int J Cancer. 103(4):455-65 (2003).
Miyazaki T et al. EphA2 overexpression correlates with poor prognosis in esophageal squamous cell carcinoma. Int J Cancer 103:657-663 (2003).
Molhoj et al. "CD19-/CD3-bispecific antibody of the BiTE class is far superior to tandem diabody with respect to redirected tumor cell lysis", Mol Immunol. 44(8):1935-1943 (Dec. 1, 2006).
Mom CH et al. Mapatumumab, a Fully Human Agonistic Monoclonal Antibody That Targets TRAIL-R1, in Combination with Gemcitabine and Cisplatin: a Phase I Study. Clin Cancer Res 15(17): 5584-5590 (2009).
Moore, P.A., et al., "Application of Dual Affinity Retargeting Molecules to Achieve Optimal Redirected T-Cell Killing of B-Cell Lymphoma," Blood 117(17):4542-4551 (2011).
Mous et al., "Redirection of CMV-specific CTL towards B-CLL via CD20-targeted HLA/CMV complexes," Leukemia 20, pp. 1096-1102 (2006).
Murphy KT et al. Antibody-directed myostatin inhibition improves diaphragm pathology in young but not adult dystrophic mdx mice. Am J Pathol. May 2010; 176(5): 2425-2434 (2010).
Murphy, G., "The ADAMs: Signalling Scissors in the Tumour Microenvironment," Nature Reviews Cancer 8:929-941 (2008).
Non-Final Office Action in corresponding U.S. Appl. No. 14/005,452, dated Jul. 31, 2015.
Non-Final Office Action in corresponding U.S. Appl. No. 14/660,137, dated Oct. 22, 2015.
Notice of Rejection issued in corresponding Japanese Application No. 2013-558513, dated Nov. 8, 2016 (3 pages), and English translation (2 pages).
Oganesyan V et al. Crystallization and preliminary X-ray diffraction analysis of the complex of a human anti-ephrin type-A receptor 2 antibody fragment and its cognate antigen. Acta Crystallogr Sect F Struct Biol Cryst Commun. 66(Pt 6):730-3 (2010).
Ogg, G.S., et al., "Sensitization of Tumour Cells to Lysis by Virus-Specific CTL using Antibody-Targeted MHC Class I/Peptide Complexes," British Journal of Cancer 82( 5): 105 8-1062 (2000).
Olafsen T et al. Characterization of engineered anti-p185HER-2 (scFv-CH3)2 antibody fragments (minibodies) for tumor targeting, Protein Engineering, Design & Selection 17(4):315-323, 2004.
Olafsen-T et al. Targeting, imaging, and therapy using a humanized anti-prostate stem cell antigen (PSCA) antibody. J Immunother. 30(4):396-405 (2007) (abstract).
Onda M, et al. An immunotoxin with greatly reduced immunogenicity by identification and removal of B cell epitopes. Proc Natl Acad Sci U S A. 2105(32):11311-6. Aug. 12, 2008; Epub Aug. 4, 2008.

(56) References Cited

OTHER PUBLICATIONS

Cobleigh MA et al. Multinational study of the efficacy and safety of humanized anti-HER2 monoclonal antibody in women who have HER2-overexpressing metastatic breast cancer that has progressed after chemotherapy for metastatic disease. J Clin Oncol 17:2639-48 (1999) (abstract).
Cochran, Domain-level antibody epitope mapping through yeast surface display of epidermal growth factor receptor fragments, J of Immunological Methods 287:147-158 (2004).
Coffman KT et al. Differential EphA2 Epitope Display on Normal versus Malignant Cells Cancer Res 63:(22) 7907-7912 (2003).
Cretney E et al. TNF-related apoptosis-inducing ligand as a therapeutic agent in autoimmunity and cancer. Immunol Cell Biol 84: 8798 (2006).
De Groot, A.S., et al., "Activation of Natural Regulatory T Cells by IgG Fe-derived Peptide 'Tregitopes'," Blood 112(8):3303-3311 (2008).
Debatin KM et al. Death receptors in chemotherapy and cancer. Oncogene 23:2950-66 (2004).
Deckert M, et al. CD59 molecule: a second ligand for CD2 in T cell adhesion. Eur J Immunol. 22(11):2943-7. Nov. 1992.
Dermer, Another anniversary for the war on cancer, Bio/technology 12:320 (1994).
Donda, A., et al., "In vivo Targeting of an Anti-Tumor Antibody Coupled to Antigenic MHC Class I Complexes Induces Specific Growth Inhibition and Regression of Established Syngeneic Tumor Grafts," Cancer Immunity 3:11 (2003).
Dong H et al. Costimulating aberrant T cell responses by B7-H1 autoantibodies in rheumatoid arthritis. J Clin Invest 111:363-370 (2003).
Duncan RJS et al., "A new reagent which may be used to introduce sulfhydryl groups into proteins, and its use in the preparation of conjugates for immunoassay," Analytical Biochemistry, 132(1):68-73 (Jul. 1, 1983).
Dzionek-A et al., BDCA-2, BDCA-3, and BDCA-4: Three Markers for Distinct Subsets of Dendritic Cells in Human Peripheral Blood. J Immunol 165:6037-6046 (2000).
Eberl, G., et al., "An Anti-CD19 Antibody Coupled to a Tetanus Toxin Peptide Induces Efficient Fas Ligand (FasL)—Mediated Cytotoxicity of a Transformed Human B Cell Line by Specific CD4+ T Cells," Clinical and Experimental Immunology 114:173-178 (1998).
Eder JP et al. Novel Therapeutic Inhibitors of the c-Met Signaling Pathway in Cancer. Clin Cancer Res 15(7):2207-2214 (2009).
Engleman EG, et al. Studies of a human T lymphocyte antigen recognized by a monoclonal antibody. Proc Natl Acad Sci U S A. 78(3):1791-5. Mar. 1981.
Eno-Amooquaye, EA et al. "Altered biodistribution of an antibody-enzyme conjugate modified with polyethylene glycol" Br J Cancer 73:1323-1327 (1996).
Epstein AL, et al. Two new monoclonal antibodies (LN-1, LN-2) reactive in B5 formalin-fixed, paraffin-embedded tissues with follicular center and mantle zone human B lymphocytes and derived tumors. J Immunol. 133(2):1028-1036. Aug. 1984.
Erickson HK et al. Antibody-maytansinoid conjugates are activated in targeted cancer cells by lysosomal degradation and linker-dependent intracellular processing. Cancer Res. 66(8):4426-33 (2006).
European Office Action in corresponding EP Application No. 12718715.1, dated Jul. 23, 2015.
Fan Z et al. Antibody-induced epidermal growth factor receptor dimerization mediates inhibition of autocrine proliferation of A431 squamous carcinoma cells. J Biol Chem 269:27595-602 (1994)(abstract).
Fanelli MA et al. P-cadherin and beta-catenin are useful prognostic markers in breast cancer patients; beta-catenin interacts with heat shock protein Hsp27. Cell Stress and Chaperones 13: 207-220. (2008).
Fattah, O.M., et al., "Peptabody-EGF: A Novel Apoptosis Inducer Targeting ErbB 1 Receptor Overexpressing Cancer Cells," Int. J. Cancer 119:2455-2463 (2006).
Feng Y et al. A novel human monoclonal antibody that binds with high affinity to mesothelin-expressing cells and kills them by antibody-dependent cell-mediated cytotoxicity. Mol Cancer Ther. 8(5):1113-8 (2009).
First Office Action and Search Report from the State Intellectual Property Office of the People's Republic of China for Application No. 201280024084.1, dated Nov. 15, 2014 (18 pages).
Fluhr H, et al. Interferon-gamma and tumor necrosis factor-alpha sensitize primarily resistant human endometrial stromal cells to Fas-mediated apoptosis. J Cell Sci. 120(Pt 23):4126-33. Dec. 1, 2007; Epub Nov. 14, 2007.
Gao J et al. Dual IGF-I/II—neutralizing antibody MEDI-573 potently inhibits IGF signaling and tumor growth. Cancer Res 71:1029-1040 (2011).
Garrett J et al. Antibodies specifically targeting a locally misfolded region of tumor associated EGFR, PNAS 2009, Supplemental Information, 7 pages.
Geretti E and Klagsbrun M. Neuropilins: novel targets for anti-angiogenesis therapies. Cell Adh Migr. 1(2):56-61 (2007).
Germain, C., et al., "MHC Class I-Related Chain A Conjugated to Antitumor Antibodies can Sensitize Tumor Cells to Specific Lysis by Natural Killer Cells," Clin. Cancer Res. 11(20):7516-7522 (2005).
Ghanekar et al., Gamma Interferon Expression in CD8+ T Cells is a Marker for Circulating Cytotoxic T Lymphocytes that Recognize an HLA A2-Restricted Epitope of Human Cytomegalovirus Phosphoprotein pp65, Clin Diagn Lab Immunol 8(3):628-31 (2001).
Ghanekar et al., Gamma Interferon Expression in CD8+ T Cells is a Marker for Circulating Cytotoxic T Lymphocytes that Recognize an HLA A2-Restricted Epitope of Human Cytomegalovirus Phosphoprotein p65, Clin Diagn Lab Immunol 8(3):628-31 (2001).
Giovannoni, L., et al., "Isolation of Anti-angiogenesis Antibodies from a Large Combinatorial Repertoire by Colony Filter Screening," Nucleic Acids Research 29(5):E27 (2001).
Golay, Mechanisms of action of therapeutic monoclonal antibodies: promises and pitfalls of in vitro and in vivo assays, Archives of Biochemistry and Biophysics 526:146-153 (2012).
Gong YP et al. Overexpression of Cripto and its prognostic significance in breast cancer: a study with long-term survival Eur J Surg Oncol 33(4):438-43 (2007) (abstract).
Gonzalez MA et al. An immunohistochemical examination of the expression of E-cadherin, α- and β/γ-catenins, and α2- and β1—integrins in invasive breast cancer. J Pathol 187(5):523-9 (1999).
Grabmaier K et al. Molecular cloning and immunogenicity of renal cell carcinoma-associated antigen G250. Int J Cancer 15;85(6):865-70 (2000).
Grimbert P. Thrombospondin/CD47 interaction: a pathway to generate regulatory T cells from human CD4+ CD25—T cells in response to inflammation. J Immunol. 177(6):3534-41. Sep. 15, 2006.
Gu Z et al. Anti-prostate stem cell antigen monoclonal antibody 1G8 induces cell death in vitro and inhibits tumor growth in vivo via a Fc-independent mechanism. Cancer Res. Oct. 15, 2005;5(20):9495-500. (2005).
Guo-Y et al. A Novel Anti-human DR5 Monoclonal Antibody with Tumoricidal Activity Induces Caspase-dependent and Caspase-independent Cell Death. J Biol Chem 280(51):41940-41952 (2005).
Gura, Systems for identifying new drugs are often faulty, Science 278:1041-1042 (1997).
Hadari Y and J Schlessinger. FGFR3-targeted mAb therapy for bladder cancer and multiple myeloma. J Clin Invest 119(5):1077-9 (2009).
Hassan R and Ho M. Clin Cancer Res. Dec. 15, 2010;16(24):6132-8. Eur J Cancer. 44(1):46-53. (2008).
Hassan R et al. Inhibition of mesothelin-CA-125 interaction in patients with mesothelioma by the anti-mesothelin monoclonal antibody MORAb-009: Implications for cancer therapy. Lung Cancer. 68(3):455-9 (2010).
Hassan R et al. Phase I clinical trial of the chimeric anti-mesothelin monoclonal antibody MORAb-009 in patients with mesothelin-expressing cancers. Clin Cancer Res. 16(24):6132-8 (2010).

(56) References Cited

OTHER PUBLICATIONS

Hassan R et al. Preclinical evaluation of MORAb-009, a chimeric antibody targeting tumor-associated mesothelin, Cancer Immunity 7:20□(2007).
Helft PR et al. A phase I study of cantuzumab mertansine administered as a single intravenous infusion once weekly in patients with advanced solid tumors. Clin Cancer Res. 10(13):4363-8 (2004).
Hellstrom, I., et al., "Monoclonal Mouse Antibodies Raised Against Human Lung Carcinoma," Cancer Research 46:3917-3923 (1986).
Henderikx H et al. Human Single-Chain Fv Antibodies to MUC1 Core Peptide Selected from Phage Display Libraries Recognize Unique Epitopes and Predominantly Bind Adenocarcinoma, Cancer Research 58:4324-4332, Oct. 1998.
Heskamp S et al. ImmunoSPECT and immunoPET of IGF-1R expression with the radiolabeled antibody R1507 in a triple-negative breast cancer model. J Nucl Med. 51(10):1565-72. (2010).
Hirai Y et al. Expression and role of E- and P-cadherin adhesion molecules in embryonic histogenesis. I. Lung epithelial morphogenesis. Development. 105(2):263-70(1989).
Wu Y et al. Mucin glycosylation is altered by pro-inflammatory signaling in pancreatic-cancer cells. J Proteome Res. 8(4): 1876-1886 (2009).
Wu Z et al. Cripto-1 overexpression is involved in the tumorigenesis of nasopharyngeal carcinoma. BMC Cancer 9:315(2009).
Xiao-Feng L et al. HER2-targeting Antibodies Modulate the Cyclin-dependent Kinase Inhibitor p27Kip1 via Multiple Signaling Pathways. Cell Cycle 4:(1) 87-95 (2004).
Xie H et al. Pharmacokinetics and biodistribution of the antitumor immunoconjugate, cantuzumab mertansine (huC242-DM1), and its two components in mice. J Pharmacol Exp Ther. 308(3):1073-82 (2004).
Xing PX et al. Cripto: a novel target for antibody-based cancer immunotherapy. Cancer Research 64:4018-4023 (2004).
Yamauchi N et al. The glypican 3 oncofetal protein is a promising diagnostic marker for hepatocellular carcinoma. Mod Pathol. 18(12):1591-8 (2005).
Yin BW et al. Molecular cloning of the CA125 ovarian cancer antigen: identification as a new mucin, MUC16 J Biol Chem 276:27371-27375 (2001).
Yu Q et al. CEACAM1 (CD66a) promotes human monocyte survival via a phosphatidylinositol 3-kinase- and AKT-dependent pathway. Journal of Biological Chemistry. 281(51):39179-39193 (2006).
Yu, Interaction between Bevacizumab and Murine VEGF-A: A Reassessment, Investigative Ophthalmology & Visual Science 49(2):522 (2008).
Zha J and Lackner MR. Targeting the insulin-like growth factor receptor-1R pathway for cancer therapy. Clin Cancer Res. 16(9):2512-7. (2010).
Zhang-C et al. PF-03732010: A Fully Human Monoclonal Antibody against P-Cadherin with Antitumor and Antimetastatic Activity. Clin Cancer Res (16) (21) 5177-5188 (2010).
Zhou Y et al. Internalizing cancer antibodies from phage libraries selected on tumor cells and yeast displayed tumor antigens. J Mol Biol. 404(1): 88-99 (2010).
Zhou, X., et al.,"The Role of Complement in the Mechanism of Action of Rituximab for B-Cell Lymphoma: Implications for Therapy," The Oncologist 13:954-966 (2008).
Zinkernagel, R. M. et al. "Antigen localisation regulates immune responses in a dose- and time-dependent fashion: a geographical view of immune reactivity" Immunological Reviews 156: 199-209 (1997).
File History of U.S. Appl. No. 14/005,452.
File History of U.S. Appl. No. 14/660,137.
File History of U.S. Appl. No. 14/972,059.
Bocci M et al., "Activin receptor-like kinase 1 is associated with immune cell infiltration and regulates CLEC14A transcription in cancer," Angiogenesis 22(1):117-131 (2019).
Boursalian TE et al., "Targeting CD70 for human therapeutic use," Adv Exp Med Biol. 647:108-19 (2009), Abstract Only.
Chatterjee et al., "The intricate role of CXCR4 in cancer," Adv Cancer Res. 124:31-82 (2014).
Chen et al., "CD2 Is a Novel Immune-Related Prognostic Biomarker of Invasive Breast Carcinoma That Modulates the Tumor Microenvironment," Front Immunol. 12:664845 (2021).
Eskiocak et al., "Differentiated agonistic antibody targeting CD137 eradicates large tumors without hepatotoxicity," JCI Insight 5(5):e133647 (2020).
Flieswasser T et al., "Screening a Broad Range of Solid and Haematological Tumour Types for CD70 Expression Using a Uniform IHC Methodology as Potential Patient Stratification Method," Cancers (Basel) 11(10):1611 (2019).
Glorieux et al., "CD137 expression in cancer cells: regulation and significance," Cancer Commun (Lond) 39:70 (2019).
Han J et al., "MMP11 and CD2 as novel prognostic factors in hormone receptor-negative, HER2-positive breast cancer," Breast Cancer Res Treat. 164(1):41-56 (2017).
Hu-Lowe DD et al., "Targeting activin receptor-like kinase 1 inhibits angiogenesis and tumorigenesis through a mechanism of action complementary to anti-VEGF therapies," Cancer Res. 71(4):1362-73 (2011).
Irenaeus SMM et al., First-in-human study with intratumoral administration of a CD40 agonistic antibody, ADC-1013, in advanced solid malignancies. Int J Cancer. 145(5): 1189-1199 (2019), Abstract Only.
Kim et al., "Prognostic significance of heme oxygenase-1, S100 calcium-binding protein A4, and syndecan-1 expression in primary non-muscle-invasive bladder cancer," Hum Pathol. 45(9):1830-8 (2014), Abstract Only.
Liu CL et al., "Risk of thyroid cancer in patients with thyroiditis: a population-based cohort study," Ann Surg Oncol. 21(3):843-9 (2014), Abstract Only.
Mattie M et al., "The Discovery and Preclinical Development of ASG-5ME, an Antibody-Drug Conjugate Targeting SLC44A4—Positive Epithelial Tumors Including Pancreatic and Prostate Cancer," Mol Cancer Ther. 15(11):2679-2687 (2016), Abstract Only.
O'Connell et al., "CD138 (syndecan-1), a plasma cell marker immunohistochemical profile in hematopoietic and nonhematopoietic neoplasms," Am J Clin Pathol. 121(2):254-63 (2004), Abstract Only.
Richard V et al., "Macrophage migration inhibitory factor involvement in breast cancer (Review)," Int J Oncol. 47(5):1627-33 (2015).
Rüter J et al., "Immune modulation with weekly dosing of an agonist CD40 antibody in a phase I study of patients with advanced solid tumors," Cancer Biol Ther. 10(10):983-93 (2010).
Shah MH et al., "Phase I study of IMGN901, a CD56-targeting antibody-drug conjugate, in patients with CD56-positive solid tumors," Invest New Drugs 34(3):290-9 (2016).
Werner et al., "CXCR4-Directed Imaging in Solid Tumors," Front Oncol. 9:770 (2019).

* cited by examiner

1. Cetuximab alone
2. Cetuximab conjugated with an HLA-mismatched class-I peptide
3. Cetuximab conjugated with NLVPMVATV without the MMP14 cleavage sequence
4. Cetuximab conjugated with NLVPMVATV with the MMP14 cleavage sequence HLA-A*0201-restricted pp65-specific CD8+ T cells

FIGURE 2

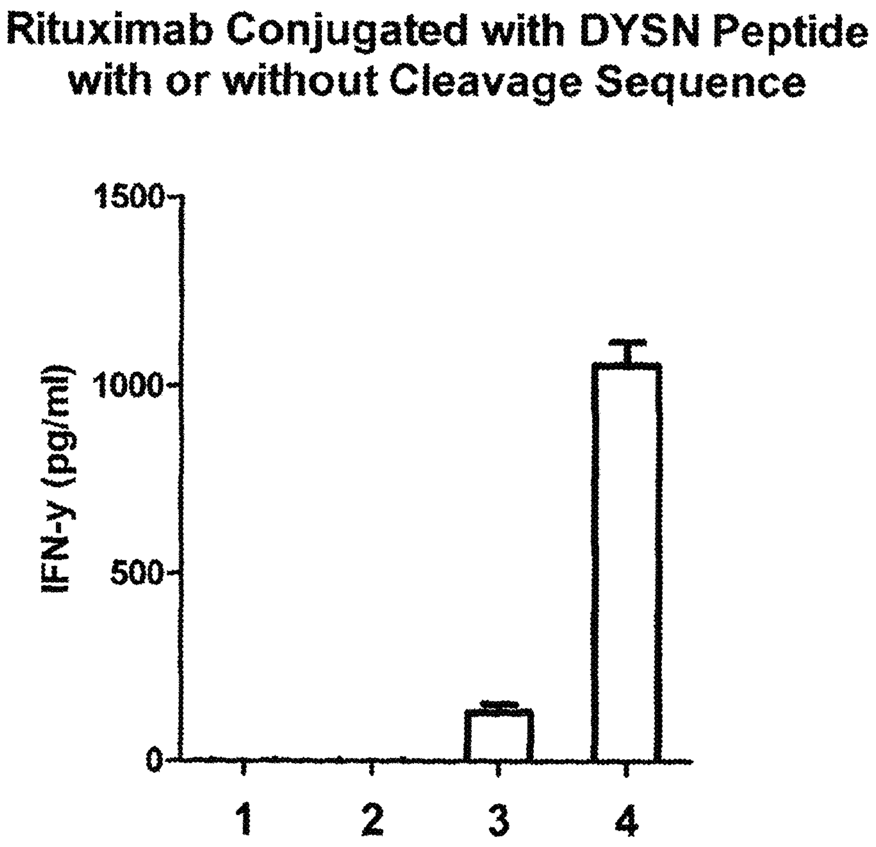

1. Rituximab conjugated with an HLA-mismatched class-I peptide without the protease cleavage sequence
2. Rituximab conjugated with an HLA-mismatched class-I peptide with the protease cleavage sequence
3. Rituximab conjugated with the HLA class-II peptide DYSNTHSTRYV without the protease cleavage sequence
4. Rituximab conjugated with the HLA class-II peptide DYSNTHSTRYV with the protease cleavage sequence HLA-DRβ1*07-restricted glycoprotein B-specific CD4+ T cells

FIGURE 3

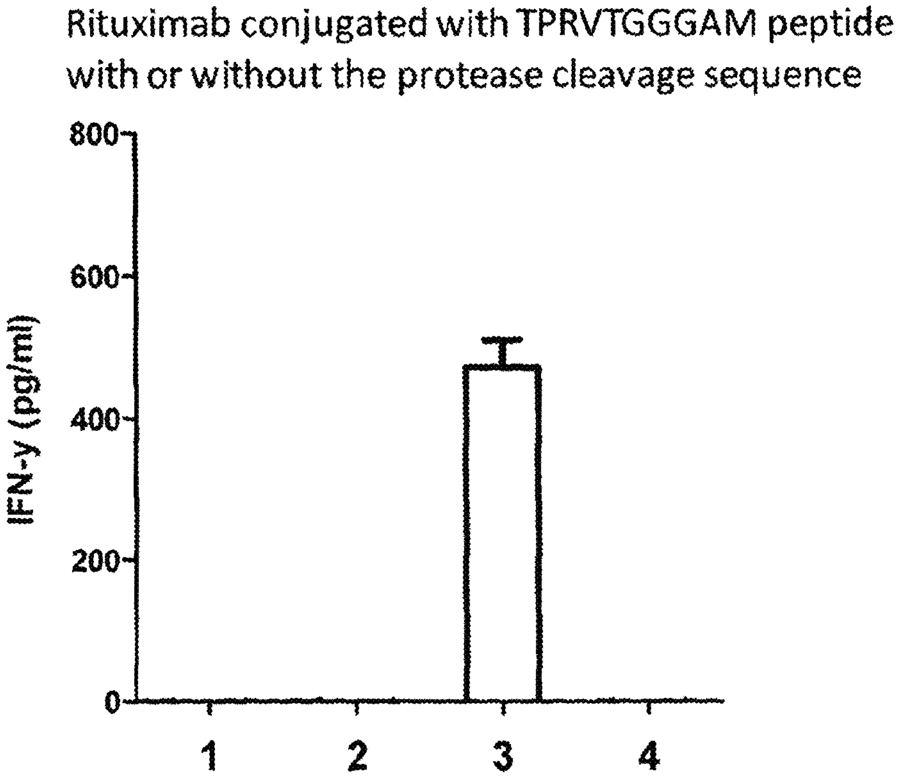

1. Rituximab conjugated with an HLA-mismatched class-I peptide without the protease cleavage sequence
2. Rituximab conjugated with an HLA-mismatched class-I peptide with the protease cleavage sequence
3. Rituximab conjugated with the HLA class-I peptide TPRVTGGGAM with the protease cleavage sequence
4. Rituximab conjugated with the HLA class-I peptide TPRVTGGGAM without the protease cleavage sequence

**HLA-B*0702-restricted pp65-specific CD8+ T cells**

FIGURE 9

A

```
        10         20         30         40         50         60
MESRGRRCPE MISVLGPISG HVLKAVFSRG DTPVLPHETR LLQTGIHVRV SQPSLILVSQ

        70         80         90        100        110        120
YTPDSTPCHR GDNQLQVQHT YFTGSEVENV SVNVHNPTGR SICPSQEPMS IYVYALPLKM

       130        140        150        160        170        180
LNIPSINVHH YPSAAERKHR HLPVADAVIH ASGKQMWQAR LTVSGLAWTR QQNQWKEPDV

       190        200        210        220        230        240
YYTSAFVFPT KDVALRHVVC AHELVCSMEN TRATKMQVIG DQYVKVYLES FCEDVPSGKL

       250        260        270        280        290        300
FMHVTLGSDV EEDLTMTRNP QPFMRPHERN GFTVLCPKNM IIKPGKISHI MLDVAFTSHE

       310        320        330        340        350        360
HFGLLCPKSI PGLSISGNLL MNGQQIFLEV QAIRETVELR QYDPVAALFF FDIDLLLQRG

       370        380        390        400        410        420
PQYSEHPTFT SQYRIQGKLE YRHTWDRHDE GAAQGDDDVW TSGSDSDEEL VTTERKTPRV

       430        440        450        460        470        480
TGGGAMAGAS TSAGRKRKSA SSATACTSGV MTRGRLKAES TVAPEEDTDE DSDNEIHNPA

       490        500        510        520        530        540
VFTWPPWQAG ILARNLVPMV ATVQGQNLKY QEFFWDANDI YRIFAELEGV WQPAAQPKRR

       550        560
RHRQDALPGP CIASTPKKHR G
```

B

(i) RNLVPMVATVTIPVSLRSGGGGSGGGGSC ("RNLV MMP2" - SEQ ID No: 322)
(ii) NLVPMVATVAIPVSLRSGGGGSGGGGSC ("NLV(A) MMP2" - SEQ ID No: 323)
(iii) CSGGGGSGGGGAIPVSLRANLVPMVATV ("NLV MMP2-R" or "NLV MMP2-Reverse" - SEQ ID No: 276)

FIGURE 10
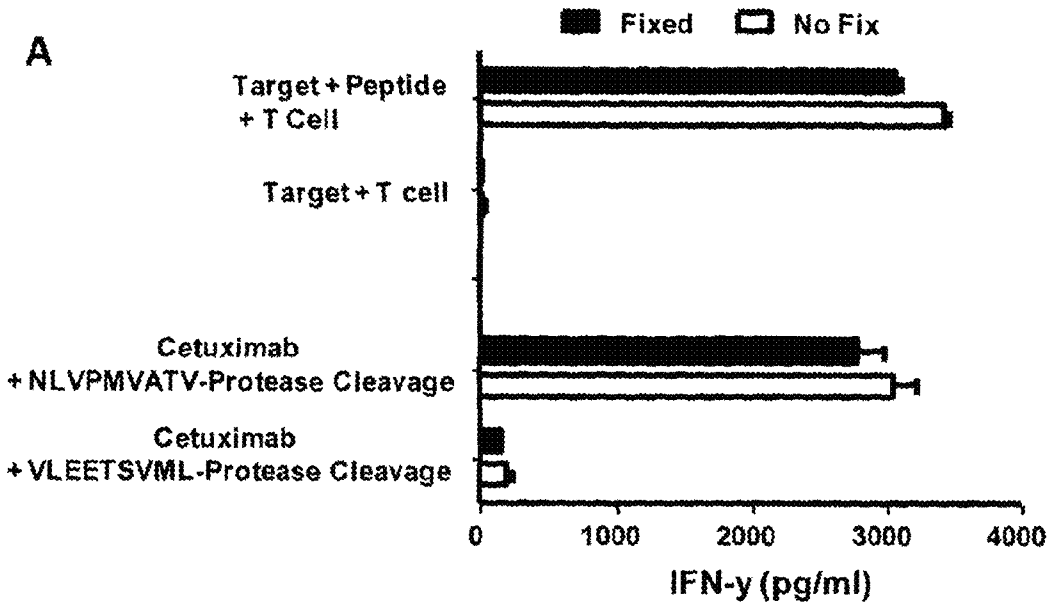
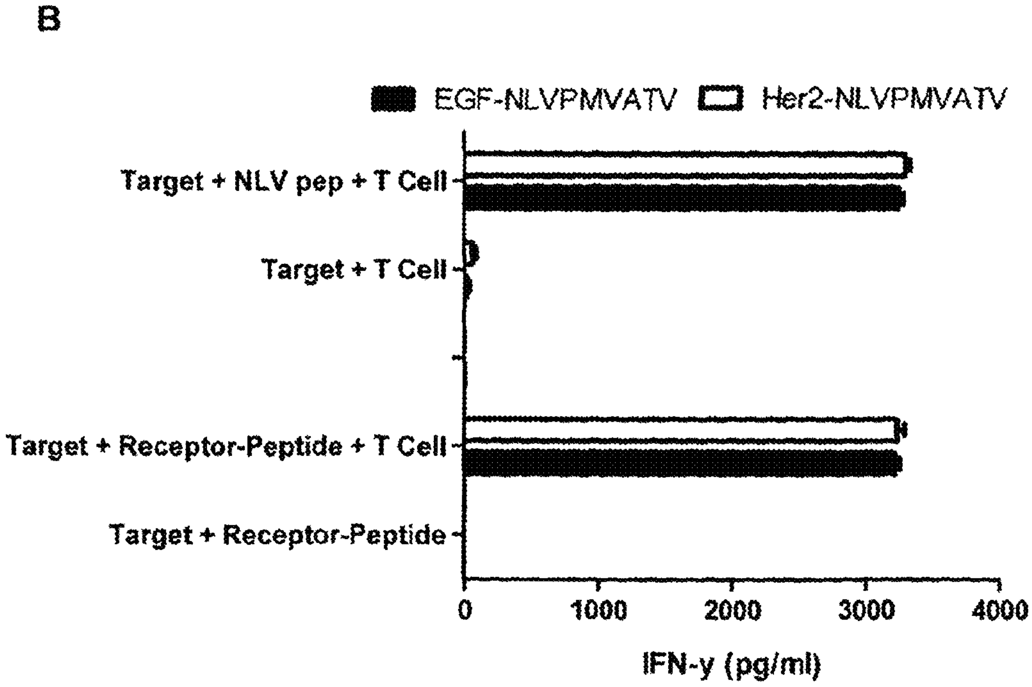

RE-DIRECTED IMMUNOTHERAPY

This application is a continuation of application Ser. No. 14/972,059, filed Dec. 16, 2015, issued as U.S. Pat. No. 10,287,321, which is a continuation of application Ser. No. 14/660,137, filed on Mar. 17, 2015, issued as U.S. Pat. No. 9,358,282, which is a continuation of application Ser. No. 14/005,452, entered the national stage on Sep. 16, 2013, issued as U.S. Pat. No. 9,402,916, which is the US National Stage of International Application No. PCT/GB2012/050577, filed Mar. 15, 2012, which designates the US, published in English, and claims priority under 35 U.S.C. §§ 119 or 365 (c) to GB Application No. 1104514.3, filed Mar. 17, 2011 and GB Application No. 1203434.4, filed Feb. 28, 2012. The entire teachings of the above applications are incorporated herein by reference.

The instant application contains a Sequence Listing submitted via EFS-Web and hereby incorporated by reference in its entirety. Said ASCII copy, created on Oct. 26, 2015, is named 20151026_01131000100US_SeqList.txt, and is 86,211 bytes in size.

The present invention relates to immunotherapeutic agents. In particular, it relates to agents that can be used to prevent or treat a condition characterised by the presence of unwanted cells, such as tumours or other disease causing cells.

Immunotherapeutic strategies for targeting malignant disease are an active area of translational clinical research, and have been for several decades. The current models dictate that cancer represents either a functional or constitutional immunodeficiency which can be treated with immunotherapeutic manipulation of the host. These efforts can be broadly classified into 2 groups. The first serves to augment or support endogenous anti-tumour immunity through measures such as vaccination, cytokine support (IL-2, IFNγ) or reducing immunosuppressant environment (ipilimumab) whilst the second seeks to restore an absolute deficiency with components of a functional immune response (passive immunotherapy with antibodies, TCR transfer, Stem Cell Transplantation and adoptive immunotherapy). These approaches are unified by the argument that a highly effective functional anti-tumour immune response is indeed possible. Although irrefutable evidence exists for an effective anti-tumour immune response in some cases, this central pillar of tumour immunology is overwhelmingly countered by the current clinical reality that despite great efforts, no effective immunotherapeutics are available for the majority of patients with cancer. Almost all cancer vaccination trials have provided negative results, with those providing positive data most frequently demonstrating a small effect. The reality is that therapeutic antibodies, with a few exceptions, offer very modest clinical benefit in the area of oncology.

If a therapeutic strategy could be developed which can efficiently molecularly re-direct an endogenous cytotoxic anti-viral immune response to instead target malignant tissue, this may afford a new powerful and safe approach to treat malignant disease.

The majority of cytotoxic therapeutic antibodies rely on immunological effector mechanisms to deliver their anti-cancer effect such as complement dependent cytotoxicity (CDC) and Antibody Dependent Cellular Cytotoxicity (ADCC). Importantly, all cells (both healthy and malignant) have numerous mechanisms to limit attack by the immune response to avert autoimmunity. This is evident in the context of autoimmune disease where high levels of tissue-reactive antibodies, which although frequently evoke organ inflammation, rarely induce complete organ destruction.

Indeed, autoimmune diseases where complete tissue destruction is observed, such as diabetes mellitus, are known to be dependent on CTL responses rather than antibody-directed mechanisms.

To improve upon the poor efficacy of therapeutic antibodies, immunoconjugates (radionuclides/toxins) and engineered antibodies which better engage with the cytotoxic effector mechanisms (e.g. glycoengineering) have been used. However clinical trials of such agents remain largely disappointing and are plagued by toxicity. One example is antibody-drug conjugates (ADCs) that have been developed to selectively target anti-tumour agents to tumours (see U.S. Pat. Nos. 5,773,001; 5,767,285; 5,739,116; 5,693,762; 5,585,089; US 2006/0088522; US 2011/0008840; U.S. Pat. No. 7,659,241; Hughes (2010) *Nat Drug Discov* 9: 665, Lash (2010); In vivo: *The Business & Medicine Report* 32-38; Mahato et al (2011) *Adv Drug Deliv Rev* 63: 659; Jeffrey et al (2006) *BMCL* 16: 358; *Drugs R D* 11(1): 85-95). ADCs generally comprise a monoclonal antibody against a target present on a tumour cell, a cytotoxic drug, and a linker that attaches the antibody to the drug. However, only a few ADCs are currently in the late stage of clinical development, and of those that are, clinical success has proven elusive.

Thus, there remains a demand for more effective immunotherapeutic agents with greater efficacy and lower toxicity.

The agents of the invention are an example of re-directed immunotherapy. This refers to the concept of re-directing an existing immune response that normally target cells harbouring foreign antigens, to target unwanted cells in conditions such as cancer. The concept requires the presentation of marker antigens on unwanted cells such that they become a target for immune cells.

WO 95/17212 describes conjugates consisting of peptidic T cell antigens and cell binding partners and their use in re-directed immunotherapy. The conjugates comprise a binding partner with selectivity for target cells and a T cell antigen, and are said to induce specific cytotoxicity of T cells in the treatment of cancer, autoimmune diseases, diabetes or allergic diseases. The conjugates are said to be internalised into target cells following binding of the binding partner to surface receptors, and the T cell antigen is processed from the conjugate and expressed on the cell surface in the form of a complex with MHC molecules. Cytotoxicity of T cells for the target cells is thereby induced.

However, which binding partners enable internalisation and hence subsequent presentation of the T cell antigen, and which do not, is difficult to predict from WO 95/17212. Further, the conjugates described in WO 95/17212 do not efficiently target the MHC Class-I antigen processing pathway. An advantage of the MHC Class-I pathway is that, unlike MHC Class-II molecules, MHC Class-I molecules are present on all cell types.

Smith et al (*J Immunol* 169: 99-107, 2002) describe the use of ricin to deliver cytotoxic T cell epitopes into the MHC Class I pathway of tumour cells, such that they are subsequently lysed. However, ricin is highly toxic and since it can bind to most cell types, it is not selective for tumour cells.

The agents of the present invention aim to circumvent all of the above problems whilst improving specificity, and exploit the fact that T cell antigens can be presented without first being internalised into a cell and being engaged in the classical antigen processing pathways. In addition to the classical MHC Class-I processing pathway, which continuously feeds peptides from the intracellular compartment via targeted intracellular proteolysis by the proteosome, peptide transport through the TAP and MHC Class-I peptide loading within the ER, antigens can also be presented without internalisation. This less directed mechanism relies on a short half-life of some MHC Class-I associated peptides due to low affinity of some MHC bound peptides to the MHC molecule. Peptide dissociation provides empty MHC Class-I molecules which are able to bind T cell antigens (e.g. peptides) at the membrane. In the same way, T cell antigens can bind to MHC Class-II molecules and the present invention also circumvents the Class-II antigen processing pathway to directly load antigens at the cell membrane. Further, Group I CD1 molecules (CD1a, CD1b and CD1c) have been shown to present lipids to both cytotoxic alpha beta T cells as well as cytotoxic gamma delta T cells (Porcelli et al (1989) *Nature,* 341, 447-450).

The inventors have found that by introducing a cleavage site in close proximity to the T cell antigen, which cleavage site is selectively cleaved in the vicinity of the unwanted cells, the T cell antigen can be liberated from a targeting moiety in the vicinity of the unwanted cells and can become bound by, for example, empty MHC molecules or Group I CD1 molecules, and elicit a T cell response. In this way, internalisation of the agent into the cell and direction of the antigen into the classical processing pathways is not necessary; the agent can target cells expressing MHC Class-I molecules compared to only MHC Class-II expressing cells as in WO 95/17212; and specificity is increased by virtue of the cleavage site only being cleaved in the vicinity of the unwanted cells. For example, tumour cells secrete proteases that are required by tumours for invasion of local tissues and metastasis, and so by including a tumour-specific protease cleavage site in the agent, the specificity of the agent for the tumour is increased.

It follows that the use of a cleavage site to bypass the requirement for internalisation and classical processing in order for T cell antigens to be efficiently presented to T cells is a key advantage of the invention. The presence of the cleavage site means that all cells become amenable to re-directed immunotherapy, and not just the relatively small population of antigen presenting cells that express MHC Class II molecules. This is especially important for tumours where most tumour cells do not express MHC Class II molecules. The cleavage site also circumvents the challenges involved in ensuring that T cell antigens are not only successfully internalised, but that they correctly enter the appropriate cellular processing pathway to be presented on the cell surface. By by-passing the need for internalisation, the cleavage site further provides the ability to target neighbouring tumour cells and stromal non-malignant tissue such as tumour-fibroblasts of blood vessels. It also circumvents tumour-evasion mechanisms that operate in classical antigen processing. All in all therefore, the cleavage site provides for a simpler and more effective method of re-directing immunotherapy to more cell types.

It is important to note the distinction between the present invention and cross-presentation. In the present invention, the targeting moiety of the agent functions to bring a T cell antigen directly into the vicinity of an unwanted cell. The unwanted cell may then present the T cell antigen, once cleaved from the targeting moiety, on its surface such that the unwanted cell becomes a target for an existing T cell response.

This allows for the redirection of an existing immune response to the unwanted cell directly, and so no co-stimulation by antigen presenting cells (APCs) is necessary. Cross-presentation, on the other hand, refers to the mechanism by which an antigen is transferred to a professional APC which, in turn, presents it on an MHC Class I molecule to a naïve T cell so as to generate a primary cytotoxic T cell response specific for that antigen. The process is important in the activation of naïve T cells which must first recognise class I-associated peptide antigens and also encounter costimulators on APCs, or signals provided by helper T cells. Thus, with cross-presentation, APCs as opposed to unwanted cells are targeted so that APCs may co-stimulate cytotoxic T cells and thereby generate a new immune response.

Improving the efficiency of the cross-presentation of exogenous antigens is a key challenge in the development of vaccines that generate effective cellular immune responses. WO 2008/019366, EP 1 948 802, US 2004/0001853, WO 2005/087813, EP 1 664 270, Kawamura et al (*J Immunol* 168: 5709, 2002), and Howland et al (*J Immunother* 31(7): 607, 2008) describe methods to improve cross-presentation of exogenous antigens by targeting antigens to APCs where they are internalised and presented to naïve T cells. For example, WO 2008/019366 discusses attaching antigens to a particle that can be phagocytosed by APCs such that the antigen can be released in the phagosome of the APC and thereby be cross-presented onto MHC Class I molecules. Similarly, EP 1 948 802 describes attaching an antigen to an antibody Fc fragment so as to promote internalisation of the antigen into the APC. However, none of the above documents mention targeting of antigens to unwanted cells; rather, the antigen is targeted to a specialised subset of APCs which, in turn, activate cytotoxic T cells to kill unwanted cells. Likewise, none of the documents describe the use and redirection of an existing immune response nor do they disclose that the T cell antigen can be presented on the surface of a cell without the need for internalisation.

A first aspect of the invention provides an agent for preventing or treating a condition characterised by the presence of unwanted cells, the agent comprising (i) a targeting moiety that is capable of targeting to the unwanted cells; and (ii) a T cell antigen, wherein the T cell antigen can be released from the targeting moiety by selective cleavage of a cleavage site in the agent in the vicinity of the unwanted cells.

Targeting Moiety

By 'targeting moiety', we include the meaning of any moiety that is capable of targeting to the unwanted cells. Preferably, the targeting moiety is capable of targeting selectively to the unwanted cells. For example, it is preferred if the targeting moiety targets unwanted cells to a greater extent than it does normal cells, and most preferably targets only unwanted cells.

It will be appreciated that binding of the targeting moiety to normal cells may be tolerated if they can be functionally replaced by other therapeutic means or if they are not essential to life. Thus, a targeting moiety that targets to a cancer cell as well as, for example, an endocrine tissue or organ is not precluded. In this case, the targeting moiety acts to redirect an immune response to both unwanted cells and to other cells that can be functionally replaced by therapeutic means. In a life-saving situation for example, the tissue or organ may be sacrificed provided its function was either not essential to life, for instance in the case of the testes, prostate or pancreas, or could be supplied by hormone replacement therapy. Such considerations would apply to the thyroid gland, parathyroids, adrenal cortex and ovaries, for example.

It follows that the targeting moiety may be a moiety that is capable of targeting selectively to unwanted cells as opposed to wanted cells, wherein the unwanted cells may include cells whose presence in a host is undesired and optionally cells whose presence in the host is desired but whose presence can be functionally replaced by therapeutic means.

It is also appreciated that since the cleavage site in the agent confers specificity on where the T cell antigen is released, binding of the targeting moiety to normal cells, in the vicinity of which the cleavage site is not cleaved, may also be tolerated.

Most preferably, however, the targeting moiety targets selectively to unwanted cells as opposed to any other cells.

In one embodiment, the targeting moiety is a specific binding partner of an entity expressed by or associated with the unwanted cell. Typically, the expressed entity is expressed selectively on the unwanted cell. For example, the abundance of the expressed entity is typically 10 or 100 or 500 or 1000 or 5000 or 10000 higher on the unwanted cell than on other cells within the body to be treated. However, as mentioned above, the cleavage site provides additional specificity on where the T cell antigen is released and so the binding partner may bind an entity that is similarly or even underexpressed on unwanted cells relative to other cells within the body.

By "binding partner" we include the meaning of a molecule that binds to an entity expressed by a particular cell. Preferably, the binding partner binds selectively to that entity. For example, it is preferred if the binding partner has a $K_d$ value (dissociation constant) which is at least five or ten times lower (i.e. higher affinity) than for at least one other entity expressed by another cell (e.g. a normal cell type), and preferably more than 100 or 500 times lower. More preferably, the binding partner of that entity has a $K_d$ value more than 1000 or 5000 times lower than for at least one other entity expressed by another cell (e.g. normal cell type). $K_d$ values can be determined readily using methods well known in the art. However, as discussed above, it is appreciated that the binding partner may bind selectively to an entity expressed by an unwanted cell and by a normal cell provided that the normal cell may be functionally replaced or else is not essential to life. For example, in lymphoma, anti-CD20 (which targets all B cells) is very effective and kills all B cells, healthy and malignant. However, this can be tolerated as B cells are not critical for health. Further, in the case of melanoma, lymphoma, prostate cancer, thyroid, testicular or ovarian cancer, targeting healthy counterpart tissue would also be tolerated.

Typically, the binding partner is one that binds to an entity that is present or accessible to the binding partner in significantly greater concentrations in or on unwanted cells than in any normal cells of the host. Thus, the binding partner may bind to a surface molecule or antigen on the unwanted cell that is expressed in considerably higher amounts than on normal cells. Similarly, the binding partner may bind to an entity that has been secreted into the extracellular fluid by the unwanted cells to a greater extent than by normal cells. For example, the binding partner may bind to a tumour associated antigen which is expressed on the cell membrane or which has been secreted into tumour extracellular fluid.

The targeting moiety may be any of a polypeptide, a peptide, a small molecule or a peptidomimetic.

In a preferred embodiment, the targeting moiety is an antibody that binds to an antigen expressed by the unwanted cell. Preferred antibody targets (with examples of unwanted cell types in parentheses) include: Her2/Neu (Epithelial malignancies); CD22 (B cells, autoimmune or malignant); EpCAM (CD326) (Epithelial malignancies); EGFR (epithelial malignancies); PSMA (Prostate Carcinoma); CD30 (B cell malignancies); CD20 (B cells, autoimmune, allergic or malignant); CD33 (Myeloid malignancies); membrane IgE (Allergic B cells); IgE Receptor (CD23) (Mast cells or B cells in allergic disease), CD80 (B cells, autoimmune, allergic or malignant); CD86 (B cells, autoimmune, allergic or malignant); CD2 (T cell or NK cell lymphomas); CA125 (multiple cancers including Ovarian carcinoma); Carbonic Anhydrase IX (multiple cancers including Renal Cell Carcinoma); CD70 (B cells, autoimmune, allergic or malignant); CD74 (B cells, autoimmune, allergic or malignant); CD56 (T cell or NK cell lymphomas); CD40 (B cells, autoimmune, allergic or malignant); CD19 (B cells, autoimmune, allergic or malignant); c-met/HGFR (Gastrointestinal tract and hepatic malignancies; TRAIL-R1 (multiple malignancies including ovarian and colorectal carcinoma); DR5 (multiple malignancies including ovarian and colorectal carcinoma); PD-1 (B cells, autoimmune, allergic or malignant); PDL1 (Multiple malignancies including epithelial adenocarcinoma); IGF-1R (Most malignancies including epithelial adenocarcinoma); VEGF-R2 (The vasculature associated with the majority of malignancies including epithelial adenocarcinomas; Prostate stem cell antigen (PSCA) (Prostate Adenocarcinoma); MUC1 (Epithelial malignancies); CanAg (tumors such as carcinomas of the colon and pancreas); Mesothelin (many tumours including mesothelioma and ovarian and pancreatic adenocarcinoma); P-cadherin (Epithelial malignancies, including breast adenocarcinoma); Myostatin (GDF8) (many tumours including sarcoma and ovarian and pancreatic adenocarcinoma); Cripto (TDGF1) (Epithelial malignancies including colon, breast, lung, ovarian, and pancreatic cancers); ACVRL1/ALK1 (multiple malignancies including leukaemias and lymphomas); MUC5AC (Epithelial malignancies, including breast adenocarcinoma); CEACAM (Epithelial malignancies, including breast adenocarcinoma); CD137 (B cells or T cells, autoimmune, allergic or malignant); CXCR4 (B cells or T cells, autoimmune, allergic or malignant); Neuropilin 1 (Epithelial malignancies, including lung cancer); Glypicans (multiple cancers including liver, brain and breast cancers); HER3/EGFR (Epithelial malignancies); PDGFRa (Epithelial malignancies); EphA2 (multiple cancers including neuroblastoma, melanoma, breast cancer, and small cell lung carcinoma); and CD138 (Myeloma).

Particularly preferred antibodies include an anti-epidermal growth factor receptor antibody such as Cetuximab, an anti-Her2 antibody, an anti-CD20 antibody such as Rituximab, an anti-CD22 antibody such as Inotuzumab, an anti-CD70 antibody, an anti-CD33 antibody such as hp67.6 or Gemtuzumab, an anti-MUC1 antibody such as GP1.4 and SM3, an anti-CD40 antibody, an anti-CD74 antibody, an anti-P-cadherin antibody, an anti-EpCAM antibody, an anti-CD138 antibody, an anti-E-cadherin antibody, an anti-CEA antibody, and an anti-FGFR3 antibody.

Examples of tumour-associated, immune cell-associated and infection reagent-related antigens which may be targeted by the targeting moiety are given in Table 1.

TABLE 1

Cell surface antigens for targeting

| Antigen | Antibody | Existing uses |
|---|---|---|
| a) Tumour Associated Antigens | | |
| Carcino-embryonic Antigen | C46 (Amersham) 85A12 (Unipath) | Imaging and therapy of colon/rectum tumours. |
| Placental Alkaline | H17E2 (ICRF, Travers | Imaging and therapy of |

TABLE 1-continued

| Cell surface antigens for targeting | | |
|---|---|---|
| Antigen | Antibody | Existing uses |
| Phosphatase | & Bodmer) | testicular and ovarian cancers. |
| Pan Carcinoma | NR-LU-10 (NeoRx Corporation) | Imaging and therapy of various carcinomas including small cell lung cancer. |
| Polymorphic Epithelial Mucin (Human milk fat globule) | HMFG1 (Taylor-Papadimitriou, ICRF) | Imaging and therapy of ovarian cancer and pleural effusions. |
| β-human Chorionic Gonadotropin | W14 | Targeting of carboxypeptidase to human xenograft choriocarcinoma in nude mice (Searle et al (1981) *Br. J. Cancer* 44, 137-144). |
| A carbohydrate on Human Carcinomas | L6 (IgG2a)[1] | Targeting of alkaline phosphatase (Senter et al (1988) *PNAS* USA 85, 4842-4846. |
| CD20 Antigen on B Lymphoma (normal and neoplastic) | 1F5 (IgG2a)[2] | Targeting of alkaline phosphatase (Senter et al (1988) *PNAS* USA 85, 4842-4846. |
| b) Immune Cell Antigens | | |
| Pan T Lymphocyte Surface Antigen (CD3) | OKT-3 (Ortho) | As anti-rejection therapy for kidney transplants. |
| B-lymphocyte Surface Antigen (CD22) | RFB4 (Janossy, Royal Free Hospital) | Immunotoxin therapy of B cell lymphoma. |
| Pan T lymphocyte Surface Antigen (CD5) | H65 (Bodmer and Knowles, ICRF; licensed to Xoma Corp., USA) | Immunotoxin treatment of acute graft versus host disease, rheumatoid arthritis. |
| c) Infectious Agent-Related Antigens | | |
| Mumps virus-related | Anti-mumps polyclonal antibody | Antibody conjugated to diphtheria toxin for treatment of mumps. |
| Hepatitis B Surface Antigen | Anti HBs Ag | Immunotoxin against hepatoma. |

[1]Hellström et al (1986) *Cancer Res.* 46, 3917-3923

[2]Clarke et al (1985) *Proc. Natl. Acad. Sci.* USA 82, 1766-1770

Other antigens include alphafoetoprotein, Ca-125 and prostate specific antigen.

Alternatively, the targeting moiety may be any compound or part thereof that specifically binds, in a non-immune sense, to an entity expressed by unwanted cells or otherwise becomes associated with the unwanted cells. Thus, the specific binding partner may be any of a hormone, a growth factor, a cytokine, or a receptor ligand (e.g. agonist or antagonist).

For example, cytokines have previously been used to target toxins to invading bacterial. Using genetic engineering, recombinant proteins have been produced which contain for example IL-2 and a binding domain-deleted *Pseudomonas* exotoxin protein (Lorderboum-Galski et al, 1988 (62)). This immunotoxin was effective in experimental animal models (Kozak et al, 1990 (63)). Fusion proteins have also been produced with IL-4, IL-6, alpha-MSH, EGF and TNF-alpha (reviewed in Waldmann 1992 (35)), all of which are appropriate for use as targeting moieties in the present invention.

Particularly useful targeting moieties include cytokines such as IL-2, EGF, VEGF, Flt3L, HGF, IGF, IL-6, or IL-4. IL-2 and IL-4 can target to adult T cell leukaemia/lymphoma cells which express the high affinity IL-2 receptor whereas normal resting T-cells do not, or to T-cells expressing the IL-4 receptor. It has previously been shown that the monoclonal antibody MR6, which binds to the human IL-4 receptor, can inhibit the IL-4 induced proliferation of cloned helper T cells and the production of IgE by polyclonal B cells (Larche et al, 1988 (36)). Such targeting moieties may be used to eliminate a lymphoid cell subpopulation in autoimmune disease or allergy.

Insulin like growth factors (IGF-1 and IGF-11) are preferentially taken up by malignant cells and so may be used to target tumour cells. Similarly EGF can be used to target malignant cells which upregulate the EGF receptor. Also, tumour associated blood vessels overexpress VEGF receptor and so can be targeted by the family of VEGF growth factors.

Flt3 receptor is overexpressed in leukaemias and may be a therapeutic target for acute and chronic leukaemias and myeloproliferative disorders.

Myeloma cells express IL-6 receptor and also secrete IL-6 which acts in an autocrine fashion to stimulate cell proliferation. Thus IL-6 may be used as a targeting moiety for myeloma.

In another example, the targeting moiety is melanoma stimulating hormone (MSH) which binds to the MSH receptor which is expressed in high numbers in melanoma cells.

It is appreciated that a person skilled in the art can readily select suitable binding partners for any given unwanted cell, for example by identifying surface antigens or molecules specific for that unwanted cell and finding a binding partner for that antigen or molecule. Considerable research has already been carried out on antibodies and fragments thereof to tumour-associated antigens, immune cell antigens and infectious agents, as described above. Thus, conveniently, selecting an appropriate targeting moiety for a given cell type typically involves searching the literature. Alternatively, an unwanted cell is taken from a patient (e.g. by biopsy), and antibodies directed against the cell prepared. Such 'tailor-made' antibodies are already known. It has been demonstrated that antibodies confer binding to tumour cells not only from the patient they have been obtained from but also for a large number of other patients. Thus, a plurality of such antibodies has become commercially available. Other methods of identifying suitable binding partners for a given unwanted cell include genetic approaches (eg microarray), proteomic approaches (eg differential Mass spectrometry), immunological approaches (eg immunising animals with tumour cells and identifying antibody-secreting clones which specifically target malignant cells) and in silico approaches wherein targets are identified using a systems biology approach.

Further selective targets and suitable binding partners are shown in Table 2.

TABLE 2

| Binding partners for tumour-selective targets and tumour-associated antigens | | |
|---|---|---|
| Target | Binding Partner | Disease |
| Truncated EGFR | anti-EGFR mAb | Gliomas |
| Idiotypes | anti-id mAbs | B-cell lymphomas |
| EGFR (c-erbB1) | EGF, TGFα anti-EGFR mAb | Breast cancer |
| c-erbB2 | mAbs | Breast cancer |
| IL-2 receptor | IL-2 anti-Tac mAb | Lymphomas and leukaemias |
| IL-4 receptor | IL-4 | Lymphomas and leukaemias |
| IL-6 receptor | IL-6 | Lymphomas and leukaemias |

TABLE 2-continued

| Binding partners for tumour-selective targets and tumour-associated antigens | | |
|---|---|---|
| Target | Binding Partner | Disease |
| MSH (melanocyte-stimulating hormone) receptor | α-MSH | Melanomas |
| Transferrin receptor (TR) | Transferrin anti-TR mAb | Gliomas |
| gp95/gp97 | mAbs | Melanomas |
| p-glycoprotein cells | mAbs | drug-resistant |
| cluster-1 antigen (N-CAM) | mAbs | Small cell lung carcinomas |
| cluster-w4 | mAbs | Small cell lung carcinomas |
| cluster-5A | mAbs | Small cell lung carcinomas |
| cluster-6 (LeY) | mAbs | Small cell lung carcinomas |
| PLAP (placental alkaline phosphatase) | mAbs | Some seminomas Some ovarian; some non small cell lung cancer |
| CA-125 | mAbs | Lung, ovarian |
| ESA (epithelial specific antigen) | mAbs | carcinoma |
| CD 19, 22, 37 | mAbs | B-cell lymphomas |
| 250 kDa | mAbs | Melanoma |
| proteoglycan p55 | mAbs | Breast cancer |
| TCR-IgH fusion | mAbs | Childhood T-cell leukaemia |
| Blood gp A antigen (in B or O individuals) | mAbs | Gastric and colon tumours |
| Mucin protein core | mAbs | Breast cancer |

Further targets useful in preventing or treating various cancers are provided below.

| Target | Cancer |
|---|---|
| EpCam | Bladder |
| PSMA | Prostate |
| EGFR | Breast |
| | Lung |
| | Glioblastoma |
| | Colon |
| CD20 | Lymphoma |
| CD22 | Lymphoma |
| CD52 | Lymphoma |
| | Leukaemia |

Yet further selective targets useful for preventing or treating various conditions characterised by the presence of unwanted cells are provided below. For all of the examples below, therapeutic antibodies are already available or can be readily prepared by the skilled person.

| Target | Unwanted cell |
|---|---|
| Activin A | Many types of carcinoma, lymphoma, sarcoma and leukaemia |
| activin A, activin B and inhibin B | Many types of carcinoma, lymphoma, sarcoma and leukaemia |
| Adenocarcinoma antigen | Many types of carcinoma, |
| AFP (alpha-fetoprotein) | Many types of carcinoma, |
| amyloid beta (Abeta) | Alzheimer's Disease |
| amyloid beta (Abeta) peptide Aβ40 | Alzheimer's Disease |
| amyloid beta (Abeta) peptide soluble monomer | Alzheimer's Disease |
| amyloid beta (Abeta) peptides Aβ42 and Aβ40 | Alzheimer's Disease |
| ANGPT2 (Ang2, angiopoietin 2) | Multiple carcinomas |
| N-glycolyl GM3 ganglioside (N-glycolylneuraminic acid (NeuGc, NGNA) GM3 gangliosides, NeuGcGM3) Mus musculus IgM-kappa P3 | Brain tumours |
| BSG (basigin, Ok blood group, CD147) | Many types of carcinoma, lymphoma, sarcoma and leukaemia |
| CA 72-4 (tumour associated glycoprotein 72, TAG-72, TAG, HMW mucin-like glycoprotein) | Many types of carcinoma, |
| CA9 (carbonic anhydrase IX, CAIX, MN, G250) | Many types of carcinoma, |
| carcinoma associated antigen CTAA16.88 (complex of cytokeratin polypeptides (35-40 kDa)) | Many types of carcinoma, |
| CCL11 (chemokine (C-C motif) ligand 11, chemokine CC 11, eotaxin1) | Many types of carcinoma and lymphoma/leukaemia |
| CCL2 (chemokine (C-C motif) 2, chemokine CC 2, monocyte chemoattractant protein-1, MCP-1, monocyte chemotactic and activating factor, MCAF, small inducible cytokine A2, SCYA2, HC11) | Many types of carcinoma and lymphoma/leukaemia |
| CCR4 (chemokine (C-C motif) receptor 4, chemokine CC receptor 4, CCR-4, CKR4, k5-5, CD194) | Many types of carcinoma and lymphoma/leukaemia |
| CD14 | Many types of carcinoma and lymphoma/leukaemia |
| CD15 (3-fucosyl-N-acetyl-lactosamine, Lewis x, stage-specific embryonic antigen 1, SSEA-1) | Many types of carcinoma and lymphoma/leukaemia |
| CD19 (B lymphocyte surface antigen B4, Leu-12) | Lymphoma and Acute lymphoblastic leukaemia |
| CD2 (lymphocyte function-antigen 2, LFA-2) | T-cell and NK-cell lymphoma |
| CD200 (OX-2) | T-cell and NK-cell lymphoma |

-continued

| Target | Unwanted cell |
| --- | --- |
| CD22 (sialic acid binding Ig-like lectin 2, SIGLEC2, SIGLEC-2, B-lymphocyte cell adhesion molecule, BL-CAM, Leu-14 | Lymphoma and Acute lymphoblastic leukaemia |
| CD33 (sialic acid binding Ig-like lectin 3, SIGLEC3, SIGLEC-3, gpG7, p67) | Myeloid leukaemia and Stem cells |
| CD38 (ADP-ribosyl cyclase 1, cyclic ADP-ribose hydrolase 1, cADPr hydrolase 1, T10) | Myeloid leukaemia and many types of carcinoma |
| CD40 (tumor necrosis factor receptor superfamily member 5, TNFRSF5, p50) | Lymphoma and many types of carcinoma |
| CD40LG (CD40 ligand, CD40L, tumor necrosis factor ligand superfamily member 5, TNFSF5, tumor necrosis factor related activation protein, TRAP, CD154) | Lymphoma and many types of carcinoma |
| CD44 (homing function and Indian blood group system, chondroitin sulfate proteoglycan 8, CSPG8) | Myeloid leukaemia and many types of carcinoma including cancer stem cells |
| CD5 (T1, LEU-1) | T-cell lymphoma, T-cells and B-cell lymphomas such as chronic lymphocytic leukaemia. |
| CD52 | T-cell lymphoma, T-cells and B-cell lymphomas. Autoimmune induced immune cells may also be targeted. |
| CD6 (Tp120) | T-cell lymphoma, T-cells and B-cell lymphomas such as chronic lymphocytic leukaemia. |
| CD70 (tumor necrosis factor superfamily member 7, TNFSF7, CD27LG, CD27L) | Lymphoma and many types of carcinoma |
| CD74 (major histocompatibility class II invariant chain, MH2) | Lymphoma and many types of carcinoma |
| CD80 (B7-1, CD28LG1) | Lymphoma and many types of carcinoma |
| CD86 (B7-2, CD28LG2) | Lymphoma and many types of carcinoma |
| CEA (anticarcinoembryonic antigen) | Many types of carcinoma, |
| CEACAM3 (carcinoembryonic antigen-related cell adhesion molecule 3, CGM1, CD66d) | Many types of carcinoma, |
| CEACAM5 (carcinoembryonic antigen-related cell adhesion molecule 5, CEA, CD66e) | Many types of carcinoma, |
| CEACAM8 (carcinoembryonic antigen-related cell adhesion molecule 8, NCA-95, nonspecific cross-reacting antigen 95 kDa, granulocyte cell antigen, CGM6, CD66b) | Many types of carcinoma, |
| ClfA (Clumping factor A) | Many types of carcinoma, |
| complement C3b, C4b | Many types of unwanted cells. |
| CSF2 (colony stimulating factor 2 (granulocyte-macrophage), granulocyte-macrophage colony stimulating factor, GM-CSF) | Myeloid diseases |
| CSF2RA (colony-stimulating factor 2(granulocyte-macrophage) receptor alpha subunit, GM-CSF-R-alpha, CD116) | Myeloid diseases |
| CSPG4 (chondroitin sulfate proteoglycan 4, high molecular weight-melanoma-associated antigen, HMW-MAA) | Many types of carcinoma, lymphoma, sarcoma and leukaemia |
| CTLA4 (cytotoxic T lymphocyte-associated antigen 4, CD152) | Regulatory T-cells and unwanted immune cells. |
| ED-B (fibronectin extra domain B) | Many types of carcinoma, |
| EGFR (epidermal growth factor receptor, receptor tyrosine-protein kinase erbB-1, ERBB1, HER1, HER-1, ERBB) | Many types of carcinoma, lymphoma, sarcoma and leukaemia |
| EPCAM (epithelial cell adhesion molecule, tumor-associated calcium signal transducer 1, TACSTD1, gastrointestinal tumor-associated protein 2, GA733-2, epithelial glycoprotein 2, EGP-2, epithelial cell adhesion molecule, Ep-CAM, KSA, KS1/4 antigen, M4S, tumor antigen 17-1A, EpCAM, CD326) | Many types of carcinoma, lymphoma, sarcoma and leukaemia |
| ERBB2 (epidermal growth factor receptor 2, receptor tyrosine-protein kinase erbB-2, EGFR2, HER2, HER-2, p185c-erbB2, NEU, CD340 | Many types of carcinoma, lymphoma, sarcoma and leukaemia |
| ERBB3 (receptor tyrosine-protein kinase erbB-3, HER3) | Many types of carcinoma, lymphoma, sarcoma and leukaemia |
| FAP (fibroblast activation protein, alpha) | Many types of carcinoma, lymphoma, sarcoma and leukaemia. |
| FCER2 (immunoglobulin E Fc receptor low affinity II, Fc epsilon RII, CD23) | Many types of carcinoma, lymphoma, sarcoma and leukaemia in B-cells. |
| FCGR1 (immunoglobulin G Fc receptor high affinity I, Fc gamma RI, CD64, encoded by human FCGR1A, FCGR1B, FCGR1C) | Many types of carcinoma, lymphoma, sarcoma and leukaemia. |
| fibrin II beta chain (NH2 terminus) | Many types of carcinoma, lymphoma, sarcoma and leukaemia. |

-continued

| Target | Unwanted cell |
|---|---|
| FLT1 (fms-related tyrosine kinase 1, vascular endothelial growth factor receptor 1, VEGFR-1, VEGFR, FLT, FRT, vascular permeability factor receptor) | Many types of carcinoma, sarcoma, lymphoma, sarcoma and leukaemia. In particular tumour blood vessels. |
| FOLH1 (folate hydrolase, prostate specific membrane antigen, PSMA) | Many types of carcinoma, lymphoma, sarcoma and leukaemia in particular prostate carcinoma and unwanted prostate tissue. |
| FOLR1 (folate receptor 1, folate receptor FR alpha, FR-alpha, adult folate-binding protein, FBP, ovarian tumor-associated antigen MOv18) | Many types of carcinoma, lymphoma, sarcoma and leukaemia |
| GD2 ganglioside | Brain tumours and unwanted neuronal tissue. |
| GD3 ganglioside | Brain tumours and unwanted neuronal tissue. |
| GLP1R (glucagon-like peptide 1 receptor) | Many types of carcinoma, lymphoma, sarcoma and leukaemia |
| GPNMB (glycoprotein transmembrane NMB, hematopoeitic growth factor inducible neurokinin-1 type, HGFIN) | Many types of carcinoma, lymphoma, sarcoma and leukaemia |
| hapten NP-cap (4-hydroxy-3-nitrophenacetyl caproic acid) | Many types of carcinoma, lymphoma, sarcoma and leukaemia |
| HAVCR1 (hepatitis A virus cellular receptor 1, T-cell immunoglobulin and mucin domain-containing protein 1, TIM1, KIM-1) | Hepatitis A infected cells. |
| HBV (hepatitis B virus) | HBV infected cells |
| HCMV (human cytomegalovirus) gB glycoprotein | CMV infected cells. |
| HCV (hepatitis C virus) | HCV infected cells |
| heat shock protein 90 homolog | Many types of carcinoma, lymphoma, sarcoma and leukaemia |
| HGF (hepatocyte growth factor, scatter factor, SF, hepatopoeitin A) | Hepatoma and hepatocellular carcinoma. Also unwanted hepatic tissue. |
| HIV-1 (human immunodeficiency virus) | HIV infected cells |
| HLA-DR10 (DRB1*1001) | Autologous or Allogeneic MHC Class-II expressing cells including tumour cells |
| HLA-DRB (HLA-DR beta) | Autologous or Allogeneic MHC Class-II expressing cells including tumour cells |
| HSV (herpes simplex virus) | HSV infected cells |
| ICAM1 (intercellular adhesion molecule 1, ICAM-1, CD54) | Many types of carcinoma, lymphoma, sarcoma and leukaemia |
| ICAM3 (intercellular adhesion molecule 3, ICAM-3, CD50) | Many types of carcinoma, lymphoma, sarcoma and leukaemia |
| Membrane Immunoglobulin IgE | IgE secreting B-cells and Plasma cells (cuasing allergic disease). |
| IgE Fc | IgE secreting B-cells and Plasma cells (cuasing allergic disease). |
| IGF1R (insulin-like growth factor 1 receptor, IGF1-R, IGF-1R, CD221) | Most types of carcinoma, lymphoma, sarcoma and leukaemia |
| IGHE connecting region (CO) M1 prime (in alternatively spliced heavy chain of membrane IgE on B cells | IgE secreting cells such as B-cells and plasma cells. Particularly unwanted in allergic disease. |
| IL2RA (interleukin-2 receptor, alpha subunit, IL-2RA, TAC, CD25) | B-cells and T-cells in either malignant or autoimmune disease. |
| IL2RB (interleukin-2 receptor beta subunit, IL-2RB, p70, CD122) | B-cells and T-cells in either malignant or autoimmune disease. |
| IL5RA (interleukin 5 receptor alpha subunit, CD125) | B-cells and T-cells in either malignant or autoimmune disease. |
| IL6R (interleukin 6 receptor, IL-6R, CD126) | B-cells and T-cells in either malignant or autoimmune disease. |
| ITGA2 {integrin alpha 2, GPIa, subunit of the alpha2beta1 integrin (VLA-2, collagen receptor), CD49b) | Many types of carcinoma, lymphoma, leukaemias. |
| ITGA2B_ITGB3 (integrin alpha2b_beta3, integrin $\alpha$IIb$\beta$3, GPIIbIIIa, fibrinogen receptor, CD41_CD61) | Many types of carcinoma, lymphoma, leukaemias. |
| ITGA4 (integrin alpha 4 subunit, CD49d) | Many types of carcinoma, lymphoma, leukaemias. |
| ITGA4_ITGB7 (integrin alpha4_beta7, integrin $\alpha4\beta7$, lymphocyte Peyer's patch adhesion molecule 1, LPAM-1) | Many types of carcinoma, lymphoma, leukaemias. |
| ITGA5 (integrin alpha 5 subunit, CD49e) | Many types of carcinoma, lymphoma, leukaemias. |
| ITGAE_ITGB7 (integrin alphaE_beta7, integrin $\alpha$E$\beta$7, human mucosal lymphocyte antigen 1, HML-1) | Many types of carcinoma, lymphoma, leukaemias. |
| ITGAL (integrin alpha L subunit, lymphocyte function associated antigen 1, CD11a) | Many types of carcinoma, lymphoma, leukaemias. |

-continued

| Target | Unwanted cell |
|---|---|
| ITGAV_ITGB3 (integrin alphaV_beta3, integrin aVβ3, CD51_GPIIIa, vitronectin receptor, VNR, CD51_CD61 | Many types of carcinoma, lymphoma, leukaemias. |
| ITGB1 (integrin beta1 subunit, GPIIa, CD29) | Many types of carcinoma, lymphoma, leukaemias. |
| ITGB2 (integrin beta2 subunit, LFA-1, MAC-1, CD18) | Many types of carcinoma, lymphoma, leukaemias. |
| KDR (kinase insert domain receptor, vascular endothelial growth factor receptor 2, VEGFR2, VEGF-R2, FLK1, CD309) | Many types of carcinoma, lymphoma, leukaemias. |
| LTA (lymphotoxin alpha, TNF superfamily member 1, TNFSF1, LT) | Many types of carcinoma, lymphoma, leukaemias. |
| LTB (lymphotoxin beta, TNF superfamily member 3, TNFSF3, p33) | Many types of carcinoma, lymphoma, leukaemias. |
| MET (met proto-oncogene, hepatocyte growth factor HGF receptor, HGFR, scatter factor SF receptor, HGF/SF receptor, tyrosine protein kinase c-met, papillary renal cell carcinoma 2, RCCP2) | Many types of carcinoma, lymphoma, leukaemias. |
| MS4A1 (membrane-spanning 4-domains subfamily A member 1, CD20) | Many types of carcinoma, lymphoma, leukaemias. |
| MSLN (mesothelin, pre-pro-megakaryocyte-potentiating factor, megakaryocyte potentiating factor, MPF, CAK1) | Many types of carcinoma, lymphoma, leukaemias. |
| MST1R (macrophage stimulating 1 receptor, macrophage stimulating protein receptor, MSP receptor, c-met-related tyrosine kinase, protein-tyrosine kinase 8, PTK8, RON, p185-Ron, CD136) | Many types of carcinoma, lymphoma, leukaemias. |
| MSTN (myostatin, growth differentiation factor 8, GDF8) | Many types of carcinoma, lymphoma, leukaemias. |
| MUC1 (mucin 1, polymorphic epithelial mucin, PEM, episialin, CD227) | Many types of carcinoma, lymphoma, leukaemias. |
| MUC1 sialylated carbohydrate, tumour-associated (CA242, cancer antigen 242) | Many types of carcinoma, lymphoma, leukaemias. |
| MUC16 (mucin 16, MUC-16, cancer antigen 125, CA125) | Many types of carcinoma, lymphoma, leukaemias. |
| MUC5AC (mucin 5AC, mucin 5 subtypes A and C tracheobronchial/gastric) | Many types of carcinoma, lymphoma, leukaemias. |
| N-glycolyl GM3 ganglioside (N-glycolylneuraminic acid (NeuGc, NGNA) GM3 ganglioside, NeuGcGM3) | Brain tumours and unwanted neural tissue. |
| NCA-90 (nonspecific cross-reacting antigens 90 kDa glycoproteins, granulocyte cell antigen) | Many types of carcinoma, lymphoma, sarcoma and leukaemia |
| NCAM1 (neural cell adhesion molecule 1, NCAM-1, NCAM, CD56) | Brain tumours and unwanted neural tissue also many types of carcinoma and lymphoma. |
| Nectin-4 | Many types of carcinoma, lymphoma, sarcoma and leukaemia |
| NGF (nerve growth factor, nerve growth factor beta polypeptide, NGFB, beta-NGF) | Many types of carcinoma, lymphoma, sarcoma and leukaemia |
| NIP-cap (3-iodo-4-hydroxy-5-nitrophenyl-acetyl caproic acid) | Many types of carcinoma, lymphoma, sarcoma and leukaemia |
| NRP1 (neuropilin 1, NRP, vascular endothelial cell growth factor 165 receptor, VEGF165 receptor, VEGF165R, CD304) | Many types of carcinoma, lymphoma, sarcoma and leukaemia |
| PDGFRA (platelet-derived growth factor receptor alpha subunit, PDGFR2, CD140a) | Many types of carcinoma, lymphoma, sarcoma and leukaemia |
| phosphatidylserine | Many types of carcinoma, lymphoma, sarcoma and leukaemia particularly apoptotic cells. |
| PSCA (prostate stem cell antigen) | Many types of carcinoma and leukaemia. |
| RSV (human respiratory syncytial virus, glycoprotein F) | RSV infected cells |
| RTN4 (reticulon 4, neurite outgrowth inhibitor, NOGO) | Many types of carcinoma, lymphoma, sarcoma and leukaemia |
| SDC1 (syndecan-1, CD138) | Unwanted plasma cells found in plasma cell dyscrasias, particularly Myeloma, Amyloidosis and MGUS. |
| SELE (E-selectin, CD62E) | Many types of carcinoma and lymphoma. |
| SELL (L-selectin, CD62) | Many types of carcinoma and lymphoma. |
| SELP (P-selectin, CD62) | Many types of carcinoma and lymphoma. |
| SFRP1 (selected frizzled-related protein 1, fusion regulatory protein 1, FRP-1) | Many types of carcinoma and lymphoma. |
| SLAMF7 (SLAM family member 7, CD2 subset 1, CS1, CD2-like receptor-activating cytotoxic cells, CRACC, 19A24, CD319) | Many types of unwanted cells including tumour cells and those involved in autoimmune disease. |

-continued

| Target | Unwanted cell |
|---|---|
| SLC3A2 (solute carrier family 3 (activators of dibasic and neutral amino acid transport) member 2, 4F2 antigen heavy chain, 4F2HC, CD98 heavy chain, CD98hc, CD98) | Many types of unwanted cells including tumour cells and those involved in inflammatory disease. |
| SOST (sclerostin) | Bone disease including oesteosarcoma and osteoporosis. |
| *Staphylococcus* epidermidis lipoteichoic acid | *Staphylococcus* infected tissue. |
| T cell receptor (TR) TR alpha_beta | T-cell lymphoma or autoimmune-causing T-cells. |
| TGFB1 (transforming growth factor beta1, TGF beta) | Many types of unwanted cells including tumour cells and those involved in fibrotic disease. |
| TGFB2 (transforming growth factor beta 2) | Many types of unwanted cells including tumour cells and those involved in fibrotic disease. |
| TNF (tumor necrosis factor (TNF) superfamily member 2, TNFSF2, TNF-alpha, TNFA) | Many types of unwanted cells including tumour cells and those involved in inflammatory disease. |
| TNFRSF10A (tumor necrosis factor receptor (TNFR) superfamily member 10A, death receptor 4, DR4, TNF-related apoptosis-inducing ligand receptor 1, TRAILR1, TRAIL-R1, TR-1, CD261) | Many types of unwanted cells including tumour cells and those involved in inflammatory disease. |
| TNFRSF10B (tumor necrosis factor receptor (TNFR) superfamily member 10B, death receptor 5, DR5, TNF-related apoptosis-inducing ligand receptor 2, TRAILR2, TRAIL-R2, TR-2, CD262) | Many types of unwanted cells including tumour cells and those involved in inflammatory disease. |
| TNFRSF12A (tumor necrosis factor receptor (TNFR) superfamily member 12A, fibroblast growth factor (FGF)-inducible 14 kDa protein, Fn14, TNF-like weak inducer of apoptosis (Tweak) receptor, Tweak receptor, TweakR, CD266 | Many types of unwanted cells including tumour cells and those involved in inflammatory disease. |
| TNFRSF8 (tumor necrosis factor receptor (TNFR) superfamily member 8, CD30) | Many types of unwanted cells including tumour cells (in particular lymphoma) and those involved in inflammatory disease. |
| TNFRSF9 (tumor necrosis factor receptor (TNFR) superfamily member 9, 4-1BB, T cell antigen ILA, CD137 | Many types of unwanted cells including tumour cells and those involved in inflammatory and autoimmune disease. |
| TNFSF11 (tumor necrosis factor (TNF) superfamily member 11, osteoclast differentiation factor, ODF, OPGL, RANKL, TRANCE, CD254) | Many types of unwanted cells including tumour cells and those involved in inflammatory and autoimmune disease. |
| TNFSF13 (tumor necrosis factor (TNF) superfamily member 13, a proliferation-including ligand, APRIL, CD256 | Many types of unwanted cells including tumour cells and those involved in inflammatory and autoimmune disease. |
| TNFSF13B (tumor necrosis factor (TNF) superfamily member 13B, B cell activating factor, BAFF, TALL1, BLyS, B lymphocyte activator, CD257) | Many types of unwanted cells including tumour cells and those involved in inflammatory and autoimmune disease. |
| TNFSF14 (tumor necrosis factor (TNF) superfamily member 14, LIGHT, HVEM-L, CD258) | Many types of unwanted cells including tumour cells and those involved in inflammatory and autoimmune disease. |
| TNFSF4 (tumor necrosis factor (TNF) superfamily member 4, OX40 ligand, OX-40L, TAX transcriptionally-activated glycoprotein 1, TXGP1, gp34, CD252) | Many types of unwanted cells including tumour cells and those involved in inflammatory and autoimmune disease. |
| TPBG (trophoblast glycoprotein, 5T4) | Multiple carcinomas. |
| TYRP1 (tyrosinase-related protein 1, 5,6-dihydroxyindole-2-carboxylic acid oxidase, DHICA oxidase, TRP1, melanoma antigen gp75) | Multiple carcinomas. |
| VAP-1 (vascular adhesion protein) | Multiple carcinomas and hepatomas. |
| VEGFA (vascular endothelial growth factor A, VEGF-A, VEGF) | Multiple carcinomas and hepatomas. |
| VIM (vimentin) | Multiple carcinomas and hepatomas. |

As used herein, the term “antibody” includes but is not limited to polyclonal, monoclonal, chimeric, single chain, Fab fragments, fragments produced by a Fab expression library and bispecific antibodies. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. A targeting moiety comprising only part of an antibody may be advantageous by virtue of optimising the rate of clearance from the blood and may be less likely to undergo non-specific binding due to the Fc part. Also included are domain antibodies (dAbs), diabodies, camelid antibodies and engineered camelid antibodies. Furthermore, for administration to humans, the antibodies and fragments thereof may be humanised antibodies, which are now well known in the art (Janeway et al (2001) *Immunobiology,* 5th ed., Garland Publishing); An et al (2009) *Therapeutic Monoclonal Antibodies*: From Bench to Clinic, ISBN: 978-0-470-11791-0).

Also included are asymmetric IgG-like antibodies (eg triomab/quadroma, Trion Pharma/Fresenius Biotech; knobs-into-holes, Genentech; Cross MAbs, Roche; electrostatically matched antibodies, AMGEN; LUZ-Y, Genentech; strand exchange engineered domain (SEED) body, EMD Serono; biolonic, Merus; and Fab-exchanged antibodies, Genmab), symmetric IgG-like antibodies (eg dual targeting (DT)-Ig, GSK/Domantis; two-in-one antibody, Genentech; cross-linked MAbs, karmanos cancer center; $mAb^2$, F-star; and Coy X-body, Coy X/Pfizer), IgG fusions (eg dual variable domain (DVD)-Ig, Abbott; IgG-like bispecific antibodies, Eli Lilly; Ts2Ab, Medimmune/AZ; BsAb, ZymoGenetics; HERCULES, Biogen Idec; TvAb, Roche) Fc fusions (eg ScFv/Fc fusions, Academic Institution; SCORPION, Emergent BioSolutions/Trubion, ZymoGenetics/BMS; dual affinity retargeting technology (Fc-DART), MacroGenics; dual $(ScFv)_2$-Fab, National Research Center for Antibody Medicine) Fab fusions (eg $F(ab)_2$, Medarex/AMGEN; dual-action or Bis-Fab, Genentech; Dock-and-Lock (DNL), ImmunoMedics; bivalent bispecific, Biotechnol; and Fab-Fv, UCB-Celltech), ScFv- and diabody-based antibodies (eg bispecific T cell engagers (BiTEs), Micromet; tandem diabodies (Tandab), Affimed; DARTs, MacroGenics; Single-chain diabody, Academic; TCR-like antibodies, AIT, Receptor Logics; human serum albumin ScFv fusion, Merrimack; and COMBODIES, Epigen Biotech), IgG/non-IgG fusions (eg immunocytokins, EMDSerono, Philogen, ImmunGene, ImmunoMedics; superantigen fusion protein, Active Biotech; and immune mobilising mTCR Against Cancer, ImmTAC) and oligoclonal antibodies (eg Symphogen and Merus).

The antibody may possess any of the antibody-like scaffolds described by Carter (2006) "Potent antibody therapeutics by design", *Nat Rev Immunol.* 6(5): 343-57, and Carter (2011) "Introduction to current and future protein therapeutics: a protein engineering perspective", *Exp Cell Res.* 317(9): 1261-9. incorporated herein by reference, together with the specificity determining regions described herein. Thus, the term "antibody" also includes affibodies and non-immunoglobulin based frameworks. Examples include adnectins, anticalins, affilins, trans-bodies, darpins, trimerX, microproteins, fynomers, avimers, centgrins and kalbitor (ecallantide).

The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli* or yeast, thus allowing convenient production in the laboratory and economical production on a commercial scale.

The antibody may be of any of the IgG, IgE, IgA, IgM and IgD classes and may be derived from any species. If the antibody is an IgG, it may be any of IgG1, IgG2, IgG3 or IgG4. It is preferred, however, that when the agent is for administration to a particular host, that the antibody, or at least the constant regions thereof, are derived from that host. For example, when the agent is to be administered to a human, the antibody is preferably a human antibody or a humanized antibody, and so on.

Suitable antibodies that bind to particular antigens expressed by unwanted cells can be made by the skilled person using technology long-established in the art. Methods of preparation of monoclonal antibodies and antibody fragments are well known in the art and include hybridoma technology (Kohler & Milstein (1975) "Continuous cultures of fused cells secreting antibody of predefined specificity. *Nature* 256: 495-497); antibody phage display (Winter et al (1994) "Making antibodies by phage display technology." *Annu. Rev. Immunol.* 12: 433-455); ribosome display (Schaffitzel et al (1999) "Ribosome display: an in vitro method for selection and evolution of antibodies from libraries." *J. Immunol. Methods* 231: 119-135); and iterative colony filter screening (Giovannoni et al (2001) "Isolation of anti-angiogenesis antibodies from a large combinatorial repertoire by colony filter screening." *Nucleic Acids Res.* 29: E27). Further, antibodies and antibody fragments suitable for use in the present invention are described, for example, in the following publications: "*Monoclonal Hybridoma Antibodies: Techniques and Application*", Hurrell (CRC Press, 1982); "*Monoclonal Antibodies: A Manual of Techniques*", H. Zola, CRC Press, 1987, ISBN: 0-84936-476-0; "Antibodies: A Laboratory Manual" 1st Edition, Harlow & Lane, Eds, Cold Spring Harbor Laboratory Press, New York, 1988. ISBN 0-87969-314-2; "*Using Antibodies: A Laboratory Manual*" 2nd Edition, Harlow & Lane, Eds, Cold Spring Harbor Laboratory Press, New York, 1999. ISBN 0-87969-543-9; and "*Handbook of Therapeutic Antibodies*" Stefan Dübel, Ed., 1st Edition,—Wiley-VCH, Weinheim, 2007. ISBN: 3-527-31453-9.

As an alternative to the targeting moiety being a specific binding partner, the targeting moiety may be a non-specific molecule that is capable, following administration to a subject, of accumulating in the vicinity of the unwanted cells. For example, it is known that macromolecules accumulate non-specifically in tumours. Macromolecules known to accumulate in tumours non-specifically include albumin, immunoglobulins, transferrin, liposomes, nanoparticles (eg colloidal nanoparticles) and biodegradable polymers including dextrans, polyethylene glycol, polylysine and hydroxypropylmethylacrylamide. Macromolecules accumulate in human xenografted tumours in nude mice up to about 2.0% of administered dose per gram of tumour. Macromolecules such as polyethylene glycol and dextrans have been found to modify the clearance rate of substances to which they are attached and modify their concentration in tumours (Melton et al, 1987; Eno-Ammoquaye et al, 1996). In exceptional tumours, a non-specific macromolecule may accumulate in greater concentration than an antibody directed at the secreted antigen (Searle et al, 1981).

The discovery that such macromolecules accumulate in tumours has been called the Enhanced Permeability and Retention (EPR) effect, and has been attributed to the leakiness of tumour capillaries and deficient lymphatic drainage (Matsumura & Macda, 1986).

Thus, when the unwanted cells are tumour cells, the targeting moiety may be any of these macromolecules which accumulate in tumours. Preferably, the macromolecule used in the invention is hydrophilic and is characterised by being soluble in body fluids and in conventional fluids for parenteral administration. Suitably, the macromolecule is biodegradable so that systemic accumulation during repeated administration is avoided. Clearly, however, it must not be degraded so fast as to fail to accumulate at the site of the unwanted cells (e.g. tumour). Preferably, the molecular weight and size of the agent comprising such a macromolecule targeting moiety exceeds that of the renal threshold for urinary excretion (MW 60 000), as this helps the blood concentration to be sufficient to provide an effective blood: tumour concentration gradient. A molecular weight of up to at least 800 000 is generally suitable, for example up to 160

000. The macromolecule is preferably one which is not readily captured by the reticuloendothelial system. The molecular weights given exclude any water of hydration.

Macromolecules that are available as sub-units and are not biodegradable may be linked by biodegradable linking units so that the non-biodegradable components are filtered through the kidneys and excreted in the urine.

Alternatively, it is preferred if the polymer used to make the macromolecule is not biodegradable such that the molecular weight of any non-biodegradable portion of the conjugate should be less than the renal threshold (circa 70000) so that after degradation of the biodegradable portion the residual non-biodegradeable portion is excreted through the kidneys.

Conveniently, the macromolecule may be any of a dextran; a polyamino acid; a nanoparticle (eg colloidal nanoparticle), or a non-tumour-specific protein such as an immunoglobulin, an albumin or a transferrin. Suitably, it may be a copolymer of styrene and maleic anhydride, or may be polyaspartic acid, poly-L-lysine, polyethyleneimine or polyethylene glycol.

It is appreciated that such macromolecules are used in melanocyte-directed enzyme prodrug therapy (MDEPT), as described in WO 1998/024478.

Unwanted Cell

The unwanted cell may be any cell whose presence in a host is undesired. Thus, the cell may be a tumour cell (benign or malignant), a cell from a tumour microenvironment such as tumour fibroblasts or tumour blood vessels, a virally infected cell, a cell introduced as part of gene therapy, or a normal cell which one wishes to destroy for a particular reason. For instance, it may be desirable to eliminate a subpopulation of immune cells such as T lymphocytes in autoimmune disease or such as B lymphocytes in allergic disease.

By a 'condition characterised by the presence of unwanted cells' we include any biological or medical condition or disorder in which at least part of the pathology is mediated by the presence of unwanted cells. The condition may be caused by the presence of the unwanted cells or else the presence of the unwanted cells may be an effect of the condition. Examples of particular conditions include tumours (benign or malignant), autoimmune conditions, cardiovascular diseases, degenerative diseases, diabetes, allergic disease (eg asthma), neurodegenerative diseases such as Alzheimer's, transplantation patients and infectious diseases. It will be appreciated that the agent also has utility in regenerative medicine (eg laboratory grown organs or tissues). It is particularly preferred if the condition is a tumour (eg a malignant disease) and the unwanted cells are tumour cells or tumour associated tissue.

For autoimmune disease, the unwanted cells may represent cells of the adaptive or innate immune response, preferably T cells, but more preferably B cells. For cardiovascular disease, the unwanted cells may represent cells within atheromatous lesions such as macrophages. For degenerative diseases, the unwanted cells may represent cells which induce the neurodegenerative changes, for instance in Alzheimer's disease they may be microglia or astrocytes. For other degenerative diseases any cell which facilitates the process of degeneration or apoptosis may be considered a target. For processes such as aging where unwanted tissue builds up, for example in benign prostatic hyperplasis, non-malignant prostatic tissue would be a preferred target. For allergic disease, cells which participate in the allergic reaction such as tissue mast cells may be considered an ideal target, but also IgE secreting cells such as plasma cells or B cells. In transplantation, alloreactive lymphocytes would represent a preferred target cell. In the context of infectious disease, any cell harbouring a virus, bacteria or fungal pathogen may be considered a preferred target cell for example an HIV infected cell.

In an embodiment the unwanted cell is not an antigen presenting cell such as a professional antigen presenting cell with cross-presentation capability.

T Cell Antigen

By a 'T cell antigen' we include the meaning of any antigen which can be presented to a T cell so as to elicit a T cell response. For example, the T cell antigen may be presented to a T cell by an MHC molecule or by a Group I CD1 molecule. Once the antigen is presented on the surface of the cell, the cell is recognised as foreign and becomes the target of T cells, some of which have the natural function of eliminating foreign cells either infected by foreign organisms such as viruses, fungi, bacteria, mycobacteria or protozoa, or which have become cancerous (eg malignant). Thus, it will be appreciated that the T cell antigen may be one that is capable of being presented by a molecule on an unwanted cell. It is possible, however, that the T cell antigen may be presented on a cell other than an unwanted cell but still in the vicinity of an unwanted cell, and by virtue of subsequent T cell activation, an unwanted cell is killed, for example by local production of cytokines by activated T cells. Such indirect killing may be desirable, for example to target tumour blood vessels and/or stromal cells which support tumour growth.

It will be appreciated that the T cell antigen is one that can elicit an existing T cell response in the subject to which the agent of the invention is administered. Typically, the T cell antigen is not one which generates a new primary T cell response for that antigen via cross-presentation in APCs. To put it another way, the T cell antigen is one to which a number of T cells in the subject are already sensitised to. Determining whether a subject's cells are sensitised to a given antigen can be done by contacting isolated peripheral mononuclear blood cells from the subject with the antigen and using standard assays for cell proliferation, as described further below and in the Examples.

In an embodiment, the agent of the invention is not one which generates a new T cell response specific for the T cell antigen contained in it. Accordingly, the invention includes an agent for preventing or treating a condition characterised by the presence of unwanted cells, the agent comprising (i) a targeting moiety that is capable of targeting to the unwanted cells; and (ii) a T cell antigen, wherein the T cell antigen can be released from the targeting moiety by selective cleavage of a cleavage site in the agent in the vicinity of the unwanted cells, and wherein the T cell antigen is capable of eliciting an existing T cell response in a subject.

By 'T cell', we include all types of T cell including CD4+, CD8+, γδ T cells, and NK-T cells. Preferably, the T cell is a cytotoxic T cell such that a cytotoxic T cell response is elicited.

As is known in the art, the mechanism of antigen presentation will depend upon the type of T cell. Generally, CD4+ T cells recognise peptide antigens bound to MHC Class II molecules, CD8+ T cells recognise peptide antigens bound to MHC Class I molecules, γδ T cells recognise small phosphorylated molecules, alkyl amines or lipids bound to group I CD1 molecules, and NK-T cells recognise lipid antigens bound to group I CD1 molecules. It is understood that any presentation route may be used provided that the antigen elicits a T cell response. Thus, the T cell antigen may be one that is capable of binding to an MHC Class I or MHC Class II molecule, or one that is capable of binding to a group I CD1 molecule.

Preferably, the T cell antigen is an immunodominant antigen (eg an antigen that elicits an existing immunodominant response). By 'Immunodominant' we include the meaning that the antigen elicits a T cell response with high magnitude, sensitivity, tissue homing characteristics and efficiency in killing antigen bearing cells. Generally, an immunodominant response comprises more than 0.1% of a subject's $CD8^+$ or $CD4^+$ T cells. Determining the extent of a T cell response for a given antigen can be done for example by contacting isolated peripheral mononuclear blood cells from the subject with the antigen and using standard assays for cell proliferation known in the art. Suitable assays for determining the extent of an immune response include ELISpot, intracellular cytokine staining, HLA-peptide tetramer staining, proliferation assay, activation assays (eg CD69), CD107 mobilisation assays or metabolic assays (eg MTT).

Examples of suitable T cell antigens include any of a peptide, a polypeptide, a phosphopeptide or a lipid such as a phospholipid or a sphingolipid, and further examples of each of these are provided below.

When the T cell antigen is a peptide or polypeptide, typically it is one that is capable of being recognised by a T cell receptor when bound to an MHC molecule. The T cell antigen may be an MHC Class I restricted antigen that binds only to MHC Class I molecules, or it may be an MHC Class II restricted antigen that binds only to MHC Class II molecules. It is appreciated that the antigen may bind only to particular variant MHC Class I and/or MHC Class II molecules (e.g. natural variants found in particular subjects), or that the antigen may be capable of binding to any MHC Class I and/or MHC Class II molecule (i.e. the antigen is promiscuous).

In one embodiment, the T cell antigen is capable of binding to a MHC Class I molecule such as any of HLA-A, HLA-B and HLA-C. Since MHC Class I molecules are expressed on all cell types, this allows to agent of the invention to redirect an immune response to any unwanted cell. Most preferably, the peptide is capable of binding to HLA types A1, A2.1, A3.2, A11, A24, B7, B8, B35, B44, Cw1, Cw2, Cw3, Cw4 and Cw6 or mixtures thereof, which are believed to cover more than 90% of the Caucasian and Asian populations.

In another embodiment, the T cell antigen is capable of binding to a MHC Class II molecule such as any of HLA-DP, HLA-DQ or HLA-DR. Common MHC Class II types include DR1, DR3, DR4, DR7, DR52, DQ1, DQ2, DQ4, DQ8 and DP1. MHC Class II molecules are expressed on immune cells including antigen presenting cells such as dendritic cells, B cells and macrophages. Thus, when the T cell antigen is MHC Class II restricted, the agent of the invention may be used to treat conditions such as lymphomas or autoimmune diseases.

An example of a promiscuous peptide that may be used is the PADRE MHC Class-II epitope defined in Alexander et al (2000) The Journal of Immunology 164: 1625-1633; aKXVAAWTLKAAaZC (a=d-Alanine, X=L-cyclohexylalanine, Z=aminocaproic acid)) (SEQ ID No: 1). Since this epitope is artificial, it would first need to be introduced to the patient in a vaccine to generate an immune response prior to administering the agent of the invention. Another promiscuous peptide that may be used is the tetanus fragment C peptide.

Conveniently, the T cell antigen is an immunogenic peptide that is recognised by an MHC molecule. Such peptides usually have a length of 9 to 22 amino acids (for recognition in the MHC Class II complex) or of 8 to 13 amino acids (for recognition in the MHC Class I complex). Preferably, the peptide is an immunodominant peptide.

Examples of immunodominant peptides include viral derived peptides that elicit endogenous anti-viral responses. Thus, the peptide may be derived from an endogenous virus such as Varicella-Zoster virus, Herpes simplex virus, cytomegalovirus, Epstein Barr virus, or influenza. Particularly preferred examples include peptides derived from human cytomegalovirus (CMV or Human herpesvirus 5/HHV5) or Epstein-Barr Virus (EBV or HHV4); herpesviruses such as HHV1, HHV2 and HHV3; influenza virus A; influenza virus B; rhinovirus; adenovirus; and Hepadnaviridae.

For human cytomegalovirus (HHV5) the immunodominant antigens are well characterised (see Sylwester A W et al J Exp Med. 2005 Sep. 5; 202(5):673-85, incorporated herein by reference), and any such antigen described in Sylwester et al may be used in the present invention. In particular, Sylester et al synthesised consecutive 15mer peptides, overlapping by 10 amino acids, for 213 predicted human CMV proteins. This generated 13,687 peptides that were arranged in ORF or sub-ORF specific mixes. Peptides derived from ORFs UL55 (gB), UL 83 (pp65), UL 86, UL 99 (pp28), UL 122 (IE2), UL 36, UL 48, UL32 (pp150), UL 113, IRS-1, UL 123 (IE1), UL25, UL 141, UL 52 and UL 82 (pp71) were found to elicit the most CD 4+ T cell responses, and so it is particularly preferred if the peptide is derived from one of these ORFs. Alternatively, peptides derived from ORFs UL48, UL83 (pp66), UL 123 (IE1), UL 123 (IE2), US 32, UL 28, US 29, US3, UL 32 (pp150), UL 55 (gB), UL 94, UL 69, UL 105, UL 82 (pp71) and UL 99 (pp28) were found to elicit the most CD 8+ T cell responses, and so it is particularly preferred if the peptide is derived from one of these ORFs.

Particular cytomegalovirus T cell antigens are listed below.

CD8+ T cell epitopes for cytomegalovirus antigens such as IE1 include YILEETSVM (SEQ ID No: 2), YVLEETSVM (SEQ ID No: 3), VLEETSVML (SEQ ID No: 4), VLAELVKQI (SEQ ID No: 5), ATTFLQTMLR (SEQ ID No: 6), EVISVMKRR (SEQ ID No: 7), CRVLCCYVL (SEQ ID No: 8), ELRRKMMYM (SEQ ID No: 9), ELKRKMIYM (SEQ ID No: 10), QIKVRVDMV (SEQ ID No: 11), CVETMCNEY (SEQ ID No: 12), RRKMMYMCY (SEQ ID No: 13), KRKMIYMCY (SEQ ID No: 14), RRIEEICMK (SEQ ID No: 15), DELRRKMMY (SEQ ID No: 16), KEVNSQLSL (SEQ ID No: 17), EEAIVAYTL (SEQ ID No: 18) and FPKTTNGCSQA (SEQ ID No: 19); for pp65 they include YSEHPTFTSQY (SEQ ID No: 20), NLVPMVATV (SEQ ID No: 21), MLNIPSINV (SEQ ID No: 22), RIFAELEGV (SEQ ID No: 23), QYDVPAALF (SEQ ID No: 24), FTSQYRIQGKL (SEQ ID No: 25), VYALPLKML (SEQ ID No: 26), QYVKVYLESF (SEQ ID No: 27), FVFPTKDVALR (SEQ ID No: 28), YTPDSTPCHR (SEQ ID No: 29), DTPVLPHETR (SEQ ID No: 30), TPRVTGGGAM (SEQ ID No: 31), RPHERNGFTVL (SEQ ID No: 32), IPSINVHHY (SEQ ID No: 33), FPTKDVAL (SEQ ID No: 34), CPSQEPMSIYVY (SEQ ID No: 35), QPSLILVSQY (SEQ ID No: 36), SEHPTFTSQY (SEQ ID No: 37), EFFDANDIY (SEQ ID No: 38); for pp150 they include TTVYPPSSTAK (SEQ ID No: 39), QTVTSTPVQGR (SEQ ID No: 40), NVRRSWEEL (SEQ ID No: 41), KARDHLAVL (SEQ ID No: 42); for gB they include RIWCLVVCV (SEQ ID No: 43); and for pp50 they include VTEHDTLLY (SEQ ID No: 44), RGDPFDKNY (SEQ ID No: 45), TVRSHCVSK (SEQ ID No: 46).

CD4+ T cell epitopes for cytomegalovirus antigens such as pp65 include PQYSEHPTFTSQYRIQ (SEQ ID No: 47), FTSQYRIQGKLEYRHT (SEQ ID No: 48), LLQTGIHVRVSQPSL (SEQ ID No: 49), NPQPFMRPHERNGFT (SEQ ID No: 50), EPDVYYTSAFVFPTK (SEQ ID No: 51), IIKPGKISHIMLDVA (SEQ ID No: 52), AGILARNLVPMVATV (SEQ ID No: 53), KYQEFFWDANDIYRI (SEQ ID No: 54); for gB they include DYSNTHSTRYV (SEQ ID No: 55), CMLTITTARSKYPYH (SEQ ID No: 56), and VFETSGGLVVFWQGI (SEQ ID No: 57); for IE1 they include VRVDMVRHRIKEHMLKKYTQ (SEQ ID No: 58) and NYIVPEDKREMWMACIKELH (SEQ ID No: 59); and for gH they include HELLVLVKKAQL (SEQ ID No: 60).

For Epstein Barr Virus (EBV or HHV4), immunodominant proteins are also well characterised and are provided in Hislop A D et al Annu Rev Immunol. 2007; 25:587-617 (incorporated herein by reference). A list of T cell epitopes, adapted from Hislop et al is provided below.

TABLE 3

CD8+ and CD4+ T cell epitopes identified in EBV lytic and latent cycle proteins (adapted from Hislop et al)

CD8+ T cell epitopes

| EBV Antigen | Epitope coordinates | Epitope sequence | SEQ ID No | HLA restriction |
|---|---|---|---|---|
| Latent cycle proteins | | | | |
| EBNA1 | 72-80 | RPQKRPSCI | 61 | B7 |
| | 407-415 | HPVGEADYF | 62 | B53 |
| | 407-417 | HPVGEADYFEY | 63 | B35.01 |
| | 528-536 | IPQCRLTPL | 64 | B7 |
| | 574-582 | VLKDAIKDL | 65 | A2.03 |
| EBNA2 | 14-23 | YHLIVDTDSL | 66 | B38 |
| | 42-51 | DTPLIPLTIF | 67 | A2/B51 |
| | 234-242 | RPTELQPTP | 68 | B55 |
| EBNA3A | 158-166 | QAKWRLQTL | 69 | B8 |
| | 176-184 | AYSSWMYSY | 70 | A30.02 |
| | 246-253 | RYSIFFDY | 71 | A24 |
| | 325-333 | FLRGRAYGL | 72 | B8 |
| | 378-387 | KRPPIFIRRL | 73 | B27 |
| | 379-387 | RPPIFIRRL | 74 | B7 |
| | 406-414 | LEKARGSTY | 75 | B62 |
| | 450-458 | HLAAQGMAY | 76 | |
| | 458-466 | YPLHEQHGM | 77 | B35.01 |
| | 491-499 | VFSDGRVAC | 78 | A29 |
| | 502-510 | VPAPAGPIV | 79 | B7 |
| | 596-604 | SVRDRLARL | 80 | A2 |
| | 603-611 | RLRAEAQVK | 81 | A3 |
| | 617-625 | VQPPQLTLQV | 82 | B46 |
| EBNA3B | 149-157 | HRCQAIRKK | 83 | B27.05 |
| | 217-225 | TYSAGIVQI | 84 | A24.02 |
| | 244-254 | RRARSLSAERY | 85 | B27.02 |
| | 279-287 | VSFIEFVGW | 86 | B58 |
| | 399-408 | AVFDRKSDAK | 87 | A11 |
| | 416-424 | IVTDFSVIK | 88 | A11 |
| | 488-496 | AVLLHEESM | 89 | B35.01 |
| | 657-666 | VEITPYKPTW | 90 | B44 |
| EBNA3C | 163-171 | EGGVGWRHW | 91 | B44.03 |
| | 213-222 | QNGALAINTF | 92 | B62 |
| | 249-258 | LRGKWQRRYR | 93 | B27.05 |
| | 258-266 | RRIYDLIEL | 94 | B27.02/.04/.05 |
| | 271-278 | HHIWQNLL | 95 | B39 |
| | 281-290 | EENLLDFVRF | 96 | B44.02 |
| | 284-293 | LLDFVRFMGV | 97 | A2.01 |
| | 285-293 | LDFVRFMGV | 98 | B37 |
| | 335-343 | KEHVIQNAF | 99 | B44.02 |
| | 343-351 | FRKAQIQGL | 100 | B27.05 |
| | 881-889 | QPRAPIRPI | 101 | B7 |
| EBNA-LP | 284-292 | SLREWLLRI | 102 | A2 |
| LMP1 | 38-46 | FWLYIVMSD | 103 | |
| | 72-82 | FRRDLLCPLGA | 104 | B40 |
| | 125-133 | YLLEMLWRL | 105 | A2 |
| | 159-167 | YLQQNWWTL | 106 | A2 |
| | 166-174 | TLLVDLLWL | 107 | A2 |
| | 375-386 | DPHGPVQLSYYD | 108 | B51.1 |

TABLE 3-continued

CD8+ and CD4+ T cell epitopes identified in EBV lytic and latent cycle proteins (adapted from Hislop et al)

| | | | | |
|---|---|---|---|---|
| LMP2 | 1-9 | MGSLEMVPM | 109 | B35.01 |
| | 61-75 | EDPYWGNGDRHSDYQ | 110 | |
| | 121-134 | NPVCLPVIVAPYLF | 111 | |
| | 125-133 | LPVIVAPYL | 112 | B53 |
| | 131-139 | PYLFWLAAI | 113 | A23 |
| | 141-154 | ASCFTASVSTVVTA | 114 | |
| | 144-152 | FTASVSTVV | 115 | A68 |
| | 200-208 | IEDPPFNSL | 116 | B40.01 |
| | 236-244 | RRRWRRLTV | 117 | B27.04 |
| | 237-245 | RRWRRLTVC | 118 | B14.02 |
| | 240-250 | RRLTVCGGIMF | 119 | B27 |
| | 243-251 | TVCGGIMFL | 120 | A1 |
| | 249-262 | MFLACVLVLIVDAV | 121 | |
| | 257-265 | LIVDAVLQL | 122 | A2 |
| | 293-301 | GLGTLGAAI | 123 | A2 |
| | 329-337 | LLWTLVVLL | 124 | A2.01 |
| | 340-350 | SSCSSCPLSKI | 125 | A11 |
| | 349-358 | ILLARLFLY | 126 | A29 |
| | 356-364 | FLYALALLL | 127 | A2 |
| | 419-427 | TYGPVFMCL | 128 | A24 |
| | 426-434 | CLGGLLTMV | 129 | A2.01 |
| | 442-451 | VMSNTLLSAW | 130 | A25 |
| | 453-461 | LTAGFLIFL | 131 | A2.06 |
| | 447-455 | LLSAWILTA | 132 | A2 |
| Lytic Cycle Proteins | | | | |
| BRLF1 | 25-39 | LVSDYCNVLNKEFT | 133 | B18 |
| | 25-33 | LVSDYCNVL | 134 | A2.05 |
| | 28-37 | DYCNVLNKEF | 135 | A24 |
| | 91-99 | AENAGNDAC | 136 | B45 |
| | 101-115 | IACPIVMRYYVLDHLI | 137 | A24/C2 |
| | 109-117 | YVLDHLIVV | 138 | A2.01 |
| | 121-135 | FFIQAPSNRVMIPAT | 139 | |
| | 134-142 | ATIGTAMYK | 140 | A11 |
| | 145-159 | KHSRVRAYTYSKVLG | 141 | A3 |
| | 225-239 | RALIKTLPRASYSSH | 142 | A2 |
| | 393-407 | ERPIFPHPSKPTFLP | 143 | Cw4 |
| | 529-543 | QKEEAAICGQMDLS | 144 | B61 |
| | 441-455 | EVCQPKRIRPFHPPG | 145 | |
| BZLF1 | 52-64 | LPEPLPQGQLTAY | 146 | B35.08 |
| | 54-63 | EPLPQGQLTAY | 147 | B35.01 |
| | 81-89 | APENAYQAY | 148 | B35.01 |
| | 101-115 | LQHYREVAA | 149 | C8 |
| | 172-183 | DSELEIKRYKNR | 150 | B18 |
| | 186-201 | RKCCRAKFKQLLQHYR | 151 | C6 |
| | 190-197 | RAKFKQLL | 152 | B8 |
| | 209-217 | SENDRLRLL | 153 | B60 |
| BMLF1 | 265-273 | KDTWLDARM | 154 | |
| | 280-288 | GLCTLVAML | 155 | A2.01 |
| | 397-405 | DEVEFLGHY | 156 | B18 |
| | 435-444 | SRLVRAILSP | 157 | B14 |
| BMRF1 | 20-28 | CYDHAQTHL | 158 | A2 |
| | 86-100 | FRNLAYGRTCVLGKE | 159 | C3/C10 |
| | 116-128 | RPQGGSRPEFVKL | 160 | B7 |
| | 208-216 | TLDYKPLSV | 161 | A2.01 |
| | 268-276 | YRSGIIAVV | 162 | C6 |
| | 268-276 | YRSGIIAVV | 162 | B39 |
| | 286-295 | LPLDLSVILF | 163 | B53 |
| BARF0 | | LLWAARPRL | 164 | A2 |
| BCRF1 | 3-11 | RRLVVTLQC | 165 | B27 |
| BALF2 | 418-426 | ARYAYYLQF | 166 | B27 |
| BILF2 | 240-248 | RRRKGWIPL | 167 | B27 |
| BLLF1 (gp350) | | VLQWASLAV | 168 | A2 |

TABLE 3-continued

CD8+ and CD4+ T cell epitopes identified in EBV lytic and latent cycle proteins (adapted from Hislop et al)

| | | | | |
|---|---|---|---|---|
| BALF4 | 276-284 | FLDKGTYTL | 169 | A2 |
| (gp110) | | ILIYNGWYA | 170 | A2 |
| | | VPGSETMCY | 171 | B35 |
| | | APGWLIWTY | 172 | B35 |
| BXLF2 | | TLFIGSHVV | 173 | A2.01 |
| (gp85) | | SLVIVTTFV | 174 | A2.01 |
| | | LMIIPLINV | 175 | A2.01 |

CD4+ T cell epitopes

| EBV Antigen | Epitope coordinates | Epitope sequence | (SEQ ID No) | HLA restriction |
|---|---|---|---|---|
| | | Latent cycle proteins | | |
| EBNA1 | 71-85 | RRPQKRPSCIGCKGT | (176) | |
| | 403-417 | RPFFHPVGEADYFEY | (177) | |
| | 429-448 | VPPGAIEQGPADDPGEGPST | (178) | |
| | 434-458 | IEQGPTDDPGEGPSTGPRGQ GDGGR | (179) | |
| | 455-469 | DGGRRKKGGWFGRHR | (180) | |
| | 474-493 | SNPKFENIAEGLRVLLARSH | (181) | |
| | 475-489 | NPKFENIAEGLRALL | (182) | |
| | 479-498 | ENIAEGLRVLLARSHVERTT | (183) | DQ7 |
| | 481-500 | IAEGLRALLARSHVERTTDE | (184) | DQ2/3 |
| | 485-499 | LRALLARSHVERTTD | (185) | |
| | 499-523 | EEGNWVAGVFVYGGSKTSLY NLRRG | (186) | |
| | 509-528 | VYGGSKTSLYNLRRGTALAI | (187) | DR11 |
| | 515-528 | TSLYNLRRGTALAI | (188) | DR1 |
| | 518-530 | YNLRRGTALAIPQ | (189) | DP3 |
| | 519-533 | NLRRGRTALAIPQCRL | (190) | |
| | 519-543 | EEGNWVAGVFVYGGSKTSLYN LRRG | (186) | |
| | 527-541 | AIPQCRLTPLSRLPF | (191) | DR13 |
| | 529-543 | PQCRLTPLSRLPFGM | (192) | DR14 |
| | 544-563 | APGPGPQPLRESIVCYFM (S43) | (193) | |
| | 549-568 | PQPGPLRESIVCYFMVFLQT (S44) | (194) | |
| | 551-570 | PGPLRESIVCYFMVFLQTHI | (195) | DR1 |
| | 554-573 | LRESIVCYFMVFLQTHIFAE | (196) | |
| | 554-578 | LRESIVCYFMVFLQTHI-FAEVLKDA | (197) | |
| | 561-573 | YFMVFLQTHIFAE | (198) | DR11, 12, 13 |
| | 563-577 | MVFLQTHIFAEVLKD | (199) | DR15 |
| | 564-583 | VFLQTHIFAEVLKDAIKDL | (200) | DP5 |
| | 574-593 | VLKDAIKDLVMTKPAPTCNI | (201) | |
| | 589-613 | PTCNIKVTVCSFDDGVDLPPW FPPM | (202) | |
| | 594-613 | RVTVCSFDDGVDLPPWFPPM | (203) | |
| | 607-619 | PPWFPPMVEGAAA | (204) | DQ2 |
| EBNA2 | 11-30 | GQTYHLIVDTLALHGGQTYH | (205) | DR4 |
| | 46-65 | IPLTIFVGENTGVPPPLPPP | (206) | |
| | 131-150 | MRMLWMANYIVRQSRGDRGL | (207) | |
| | 206-225 | LPPATLVPPRPTRPTTLPP | (208) | |
| | 276-295 | PRSTVFYNIPPMPLPPSQL | (209) | DR7, 52a, 52b, 52c |
| | 280-290 | TVFYNIPPMPL | (210) | DQ2/DQ7 |
| | 301-320 | PAQPPPGVINDQQLHHLPSG | (211) | DR17 |
| EBNA3A | 364-383 | EDLPCIVSRGGPKVKRPPIF | (212) | DR15 |
| | 780-799 | GPWVPEQWMFQGAPPSQGTP | (213) | DR1 |
| | 649-668 | QVADVVRAPGVPAMQPQYF | (214) | |
| EBNA3B | | | | |
| EBNA3C | 66-80 | NRGWMQRIRRRRRR | (215) | |
| | 100-119 | PHDITYPYTARNIRDAACRAV | (216) | DR16 |
| | 141-155 | ILCFVMAARQRLQDI | (217) | DR13 |
| | 386-400 | SDDELPYIDPNMEPV | (218) | DQ5 |
| | 401-415 | QQRPVMFVSRVPAKK | (219) | |
| | 546-560 | QKRAAPPTVSPSDTG | (220) | |
| | 586-600 | PPAAGPPAAGPRILA | (221) | |

TABLE 3-continued

| CD8+ and CD4+ T cell epitopes identified in EBV lytic and latent cycle proteins (adapted from Hislop et al) | | | | |
|---|---|---|---|---|
| | 626-640 | PPVVRMFMRERQLPQ | (222) | |
| | 649-660 | PQCFWEMRAGREITQ | (223) | |
| | 741-760 | PAPQAPYQGYQEPPAPQAPY | (224) | DR1/DR4 |
| | 916-930 | PSMPFASDYSQGAFT | (225) | |
| | 961-986 | AQEILSDNSEISVFPK | (226) | |
| LMP1 | 11-30 | GPPRPPLGPPLSSSIGLALL | (227) | DR7 & DR9 |
| | 130-144 | LWRLGATIWQLLAFF | (228) | |
| | 181-206 | LIWMYYHGPRHTDEHHHDDS | (229) | DR16 |
| | 206-225 | QATDDSSHESDSNSNEGRHH | (230) | DQ2 |
| | 211-236 | SSHESDSNSNEGRHHLLVSG | (231) | DQB1*0601 |
| | 212-226 | SGHESDSNSNEGRHHH | (232) | |
| | 340-354 | TDGGGGHSHDSGHGG | (233) | |
| LMP2 | 73-87 | DYQPLGTQDQSLYLG | (234) | DR4 or DR16 |
| | 149-163 | STVVTATGLALSLLL | (235) | |
| | 169-182 | SSYAAAQRKLLTPV | (236) | |
| | 189-208 | VTFFAICLTWRIEDPPFNSI | (237) | DRB1*0901 |
| | 194-213 | ICLTWRIEDPPFNSILFALL | (238) | DRB1*1001 |
| | 224-243 | VLVMLVLLILAYRRRWRRLT | (239) | |
| | 385-398 | STEFIPNLFCMLLL | (240) | |
| | 419-438 | TYGPVFMSLGGLLTMVAGAV | (241) | DQB1*0601 |
| Lytic Cycle Proteins | | | | |
| BHRF1 | 171-189 | AGLTLSLLVICSYLFISRG | (242) | DR2 |
| | 122-133 | PYYVVDLSVRGM | (243) | DR4 |
| | 45-57 | TVVLRYHVLLEEI | (244) | DR4 |
| BZLF1 | 174-188 | ELEIKRYKNRVASRK | (245) | DR13 |
| | 207-221 | KSSENDRLRLLLKQM | (246) | DQB1*0402 |
| BLLF1 (gp350) | 61-81 | LDLFGQLTPHTKAVYQPRGA | (247) | DRw15 |
| | 65-79 | FGQLTPHTKAVYQPR | (248) | DRB1*1301 |
| | 130-144 | VYFQDVFGTMWCHHA | (249) | DQB1*0402 |
| | 163-183 | DNCNSTNITAVVRAQGLDVTL | (250) | DRw11 |
| BALF4 | 482-496 | AWCLEQKRQNMVLRE | (251) | DPB1*1301 |
| (gp110) | 575-589 | DNEIFLTKKMTEVCQ | (252) | DRB1*0801 |

Further examples of immunodominant peptides include HLA-A*0201-restricted epitopes (HCMV pp65 495-504—NLVPMVATV (SEQ ID No: 21), HCMV IE1 VLEETSVML (SEQ ID No: 4), EBV LMP-2 356-364 FLYALALLL (SEQ ID No: 127), EBV BMLF-1 259-267 GLCTLVAML (SEQ ID No: 155)); HLA-A*0101-restricted epitopes (HCMV pp50 245-253—VTEHDTLLY (SEQ ID No: 44); HCMV pp65 363-373—YSEHPTFTSQY) (SEQ ID No: 20); HLA-A*0301-restricted epitopes (HCMV pp50—TVRSHCVSK (SEQ ID No: 46); HLA-B*0702-restricted epitopes (HCMV pp65 417-426 TPRVTGGGAM (SEQ ID No: 31), pp65 265-275 RPHERNGFTVL (SEQ ID No: 32)); and HLA-B*0801-restricted epitopes (HCMV IE1 88-96—ELKRKMMYM (SEQ ID No: 253), IE1 88-96 QIKVRVDMV (SEQ ID No: 11), EBV BZLF-1 190-197 RAKFKQLL (SEQ ID No: 152), any of which may be used in the context of the invention.

It is appreciated that the T cell antigen (e.g. peptide) may be one derived from a live vaccine such as Measles, Mumps, Rubella (MMR) or HHV3; or one derived from intracellular bacteria such as mycobacteria, particularly those evoked through immunization with BCG. Such peptides are well known in the art. Similarly, the T cell antigen (e.g. peptide) may be derived from the tetanus toxoid such as P2, P4 or P30. Thus, it will be understood that the T cell antigen (e.g. peptide) may be one that elicits an existing immune response in a subject that has been generated by prior vaccination against an infectious agent. It follows that in order to increase the number of T cells sensitised to a T cell antigen, it may be desirable to vaccinate or boost a subject with a vaccine that comprises the T cell antigen. For example, the subject may be vaccinated with a tetanus toxin, before being administered the agent of the invention comprising the relevant T cell antigen.

It will be appreciated that because many people are vaccinated in childhood with these vaccines, they are likely to contain T cells which are sensitized to these T cell antigens. Thus, in one embodiment the T cell antigen is one which is found in a childhood vaccine.

Although not preferred, the T cell antigen (eg peptide) may also be one that elicits an existing immune response in a subject that has been generated by exposing that subject's T cells to the antigen in vitro.

Peptides can be produced by well known chemical procedures, such as solution or solid-phase synthesis, or semi-synthesis in solution beginning with protein fragments coupled through conventional solution methods as is known in the art. Alternatively, the peptide can be synthesised by established methods including recombinant methods.

Although it is preferred that the T cell antigen is a polypeptide or peptide, it is known that other antigens are also capable of eliciting immune responses and so have utility in the present invention. For example, γδ T cells do not recognise MHC-associated peptide antigens and are not MHC restricted. Some γδ T cell clones recognise small phosphorylated molecules, pyrophosphorylated compounds (eg HMBPP (E-4-hydroxy-3-methyl-but-2-enyl-pyrophosphate) and IPP (isopentenyl pyrophosphate)), alkyl amines or lipids (e.g. phosphorylated lipids) that may be presented by 'non-classical' class I MHC-like molecules called CD1 molecules. Similarly, NK-T cells (e.g. Vα24Vβ11 cells) recognise lipids (e.g. ceramides such as α-gal-ceramide) bound to CD1 molecules. Thus, the T cell antigen may be any of these molecules that are known to elicit a T cell response.

When the agent is for treating autoimmune or allergic diseases, it will be appreciated that the T cell antigen may be an autoantigen or allergen respectively. In this way the immune response that is contributing to the disorder is redirected to unwanted cells so as to combat the disorder.

It is appreciated that the T cell antigen may be chemically modified provided that it is still capable of eliciting a T cell response. Such chemical modification may include, for instance, the addition of a metal such as nickel, since it has been shown that in certain allergic patients there are T cells which recognise a peptide with a bound nickel atom (Romagnoli et al 1991, EMBO J 10: 1303-1306). The T cell antigen can also be modified by an organic molecule which enhances the immunogenicity (Romero et al 1993, J Immunol 150: 3825-3831). Other modifications include phosphorylation, acetylation, alkylation, acylation, citrulination, nitration, sulphation and hydroxylation, forming salts with acids or bases, forming an ester or amide of a terminal carboxyl group, and attaching amino acid protecting groups such as N-t-butoxycarbonal.

When the T cell antigen is a peptide, it is appreciated that it may comprise naturally occurring amino acids encoded by DNA, and/or one or more non-natural amino acids, including amino acids in the "D" isomeric form, provided that it is recognised by the corresponding T cell. Thus, the peptide may be a peptide 'mimetic' ie peptidomimetic which mimics the structural features of any of the peptides mentioned above. For example, the T cell antigen may be a retro-inverso peptide.

Similarly, the T cell antigen, when a peptide, may be a mimotope, ie a peptide composed of natural or non-natural amino acids that mimics the structure of the natural epitope. Mimotopes often stimulate T cells more potently.

Preferably, the T cell antigens are substantially non-toxic in the absence of T lymphocytes. By 'substantially non-toxic' we mean that the antigens have considerably lower or preferably no detectable toxicity, compared to toxins such as *Pseudomonas* exotoxin.

The skilled person will be able to identify further T cell antigens that may be used in the invention using the database available at www.immuneepitope.org (Vita R, Zarebski L, Greenbaum J A, Emami H, Hoof I, Salimi N, Damle R, Sette A, Peters B. The immune epitope database 2.0. *Nucleic Acids Res.* 2010 January; 38 (Database issue):D854-62. Epub 2009 Nov. 11).

Selective Cleavage

By "released from the targeting moiety by selective cleavage of a cleavage site in the agent in the vicinity of the unwanted cells" we include the meaning that the T cell antigen is released from the targeting moiety by means of a cleavage site between the T cell antigen and targeting moiety being cleaved selectively in the vicinity of the unwanted cells.

By "cleavage site that is cleavable selectively in the vicinity of the unwanted cells" we include the meaning of a site that can only be cleaved by a molecule which resides selectively in the vicinity of the unwanted cells, so as to release the T cell antigen from the targeting moiety. Preferably, the molecule that cleaves the cleavage site resides in the vicinity of the unwanted cells at a concentration at least five times or ten times higher than the concentration of the molecule outside the vicinity of the unwanted cells, and more preferably at a concentration at least 100 or 500 or 1000 times higher. Most preferably, the molecule that cleaves the cleavage site is found only in the vicinity of the unwanted cells. For example, when the unwanted cells are particular tumour cells (e.g. breast tumour cells), the cleavage site may be one that is cleaved by a molecule which resides selectively in the particular tumour (e.g. breast tumour) but which molecule does not reside outside the vicinity of the particular tumour (e.g. breast tumour).

By 'in the vicinity of cells', we include the meaning of either at or near to the surface of the cells, or both, or in the environment that immediately surrounds the cells e.g. blood, lymph, and other body fluids. In a particularly preferred embodiment, the cleavage site is selectively cleaved outside of the unwanted cell, at or near its surface, so that the T cell antigen can be presented by the unwanted cell to T cells without needing to be internalised.

The cleavage site is selectively cleaved in the vicinity of the unwanted cells so that the T cell antigen is preferentially presented by unwanted cells rather than by wanted cells. Thus, it is preferred that the cleavage site is one that is selectively cleaved such that the T cell antigen is released in the vicinity of (e.g. at or near to the cell surface) the unwanted cells at least five times or ten times more than the extent to which it is released in the vicinity of wanted cells, and more preferably at least 100 or 500 or 1000 times more. Most preferably, the T cell antigen is not released in the vicinity of wanted cells, and therefore not presented by wanted cells.

For a given unwanted cell, the skilled person will be able to identify an appropriate cleavage site that is selectively cleavable in the vicinity of the unwanted cell, using established methods in the art. For example, which proteases cleave which peptides can be assessed by consulting peptide libraries and studying an MS analysis of the fragmentation profile following cleavage. Also, published literature of protease cleavage motifs and peptide cleavage data can be searched as described further below. Gene expression and proteomic data may also be analysed to identify which proteases are expressed by particular unwanted cells.

By virtue of the cleavage site being selectively cleavable in the vicinity of the unwanted cells, the T cell antigen is selectively released in the vicinity of the unwanted cells. The inventors believe that this allows the unwanted cells to present the T cell antigen to T cells, thereby redirecting an existing immune response to the unwanted cells.

In a preferred embodiment, the cleavage site is one that is cleaved in the vicinity of the unwanted cells and outside the unwanted cells, for example at the cell surface. In this way, the T cell antigen can be released in the vicinity of the external surface of the cell and presented to a T cell directly, without the need to be internalised and engage the appropriate processing pathways. Accordingly, the invention includes an agent for preventing or treating a condition characterised by the presence of unwanted cells, the agent comprising (i) a targeting moiety that is capable of targeting to the unwanted cells; and (ii) a T cell antigen, wherein the T cell antigen can be released from the targeting moiety by selective cleavage of a cleavage site in the agent in the vicinity of and outside of the unwanted cells. Preferably, the T cell antigen is one which does not generate a new primary T cell response for that antigen, but rather elicits an existing T cell response in a subject.

The inventors also believe, however, that the T cell antigen may be released inside the cell, without the need to undergo classical antigen processing, and still be presented to a T cell. Thus, it will be understood that the cleavage site need not be cleaved at the surface of the cell but may be cleaved within the cell, for example via a receptor cycling pathway or in near-membrane compartments such as vesicles (e.g. pinocytic vesicles).

The cleavage site may be one that is cleavable by an enzyme such as any of a protease, a nuclease, a lipase, a lyase, a phosphatase or a carbohydrase, which may or may not be membrane bound.

Generally, the cleavage site is a protease cleavage site. Thus, when the unwanted cells are tumour cells, the cleavage site may be cleavable selectively by proteases that reside in the vicinity of the tumour cells. In other words, the protease cleavage site may be one that is cleavable by a tumour associated protease. It is well known that during tumour development, tumours aberrantly express proteases which allow them to invade local tissues and eventually metastasise.

The protease may include any of a cysteine protease (including the Cathepsin family B, L, S etc), an aspartyl protease (including Cathepsin D and E) and a serine protease (including Cathepsin A and G, Thrombin, Plasmin, Urokinase, Tissue Plasminogen Activator). The protease may be a metalloproteinase (MMP1-28) including both membrane bound (MMP14-17 and MMP24-25) and secreted forms (MMP1-13 and MMP18-23 and MMP26-28). The protease may belong to the A Disintegrin and Metalloproteinase (ADAM) and A Disintegrin, or Metalloproteinase with Thrombospondin Motifs (ADAMTS) families of proteases. Other examples include CD10 (CALLA) and prostate specific antigen (PSA). It is appreciated that the proteases may or may not be membrane bound.

Protease cleavage sites are well known in the scientific literature, and linker sequences comprising such cleavage sites can be readily constructed using established genetic engineering techniques, or by synthetic synthesis techniques known in the art.

The protease cleavage site may be one that is cleavable by any of the proteases listed in Table 4 below, which indicates the expression of selected proteases in various tumour types. Candidate substrates for the proteases are provided. Thus, in order to treat a particular tumour type, the skilled person will typically select a protease cleavage site that is selectively cleaved by a protease known to be highly expressed in that tumour type, as seen from the table. For example, to treat breast cancer, it is preferred to use a protease cleavage site cleavable by any of uPA, tPA, matriptase, matriptase 2, Cathepsin K, Cathepsin O, MMP1, MMP2, MMP3, MMP11, MMP12, MMP17, ADAM9, ADAM12, ADAM15, ADAM17, ADAM28 or ADAMTS15, and so on.

Similarly, Table 5 lists tumour sites in which ADAM protease overexpression has been reported, and so in an embodiment, the cleavage site is selectively cleavable by one of the ADAM proteases listed in Table 5. Accordingly, the agent may be used to prevent or treat the corresponding tumour type.

The cleavage site may be selectively cleavable by any of the following human proteases (MEROPS peptidase database number provided in parentheses; Rawlings N.D., Morton F. R., Kok, C. Y., Kong, J. & Barrett A. J. (2008) MEROPS: the peptidase database. *Nucleic Acids Res.* 36 Database issue, D320-325): pepsin A (MER000885), gastricsin (MER000894), memapsin-2 (MER005870), renin (MER000917), cathepsin D (MER000911), cathepsin E (MER000944), memapsin-1 (MER005534), napsin A (MER004981), Mername-AA034 peptidase (MER014038), pepsin A4 (MER037290), pepsin A5 (*Homo sapiens*) (MER037291), hCG1733572 (*Homo sapiens*)-type putative peptidase (MER107386), napsin B pseudogene (MER004982), CYMP g.p. (*Homo sapiens*) (MER002929), subfamily A1A unassigned peptidases (MER181559), mouse mammary tumor virus retropepsin (MER048030), rabbit endogenous retrovirus endopeptidase (MER043650), S71-related human endogenous retropepsin (MER001812), RTVL-H-type putative peptidase (MER047117), RTVL-H-type putative peptidase (MER047133), RTVL-H-type putative peptidase (MER047160), RTVL-H-type putative peptidase (MER047206), RTVL-H-type putative peptidase (MER047253), RTVL-H-type putative peptidase (MER047260), RTVL-H-type putative peptidase (MER047291), RTVL-H-type putative peptidase (MER047418), RTVL-H-type putative peptidase (MER047440), RTVL-H-type putative peptidase (MER047479), RTVL-H-type putative peptidase (MER047559), RTVL-H-type putative peptidase (MER047583), RTVL-H-type putative peptidase (MER015446), human endogenous retrovirus retropepsin homologue 1 (MER015479), human endogenous retrovirus retropepsin homologue 2 (MER015481), endogenous retrovirus retropepsin pseudogene 1 (*Homo sapiens* chromosome 14) (MER029977), endogenous retrovirus retropepsin pseudogene 2 (*Homo sapiens* chromosome 8) (MER029665), endogenous retrovirus retropepsin pseudogene 3 (*Homo sapiens* chromosome 17) (MER002660), endogenous retrovirus retropepsin pseudogene 3 (*Homo sapiens* chromosome 17) (MER030286), endogenous retrovirus retropepsin pseudogene 3 (*Homo sapiens* chromosome 17) (MER047144), endogenous retrovirus retropepsin pseudogene 5 (*Homo sapiens* chromosome 12) (MER029664), endogenous retrovirus retropepsin pseudogene 6 (*Homo sapiens* chromosome 7) (MER002094), endogenous retrovirus retropepsin pseudogene 7 (*Homo sapiens* chromosome 6) (MER029776), endogenous retrovirus retropepsin pseudogene 8 (*Homo sapiens* chromosome Y) (MER030291), endogenous retrovirus retropepsin pseudogene 9 (*Homo sapiens* chromosome 19) (MER029680), endogenous retrovirus retropepsin pseudogene 10 (*Homo sapiens* chromosome 12) (MER002848), endogenous retrovirus retropepsin pseudogene 11 (*Homo sapiens* chromosome 17) (MER004378), endogenous retrovirus retropepsin pseudogene 12 (*Homo sapiens* chromosome 11) (MER003344), endogenous retrovirus retropepsin pseudogene 13 (*Homo sapiens* chromosome 2 and similar) (MER029779), endogenous retrovirus retropepsin pseudogene 14 (*Homo sapiens* chromosome 2) (MER029778), endogenous retrovirus retropepsin pseudogene 15 (*Homo sapiens* chromosome 4) (MER047158), endogenous retrovirus retropepsin pseudogene 15 (*Homo sapiens* chromosome 4) (MER047332), endogenous retrovirus retropepsin pseudogene 15 (*Homo sapiens* chromosome 4) (MER003182), endogenous retrovirus retropepsin pseudogene 16 (MER047165), endogenous retrovirus retropepsin pseudogene 16 (MER047178), endogenous retrovirus retropepsin pseudogene 16 (MER047200), endogenous retrovirus retropepsin pseudogene 16 (MER047315), endogenous retrovirus retropepsin pseudogene 16 (MER047405), endogenous retrovirus retropepsin pseudogene 16 (MER030292), endogenous retrovirus retropepsin pseudogene 17 (*Homo sapiens* chromosome 8) (MER005305), endogenous retrovirus retropepsin pseudogene 18 (*Homo sapiens* chromosome 4) (MER030288), endogenous retrovirus retropepsin pseudogene 19 (*Homo sapiens* chromosome 16) (MER001740), endogenous retrovirus retropepsin pseudogene 21 (*Homo sapiens*) (MER047222), endogenous retrovirus retropepsin pseudogene 21 (*Homo sapiens*) (MER047454), endogenous retrovirus retropepsin pseudogene 21 (*Homo sapiens*) (MER047477), endogenous retrovirus retropepsin pseudogene 21 (*Homo sapiens*) (MER004403), endogenous retrovirus retropepsin pseudogene 22 (*Homo sapiens* chromosome X) (MER030287), subfamily A2A non-peptidase homologues (MER047046), subfamily A2A non-peptidase homologues (MER047052), subfamily A2A non-peptidase homologues (MER047076), subfamily A2A non-peptidase homologues (MER047080), subfamily A2A non-peptidase homologues (MER047088), subfamily A2A non-peptidase homologues (MER047089), subfamily A2A non-peptidase homologues (MER047091), subfamily A2A non-peptidase homologues (MER047092), subfamily A2A non-peptidase homologues (MER047093), subfamily A2A non-peptidase homologues (MER047094), subfamily A2A non-peptidase homologues (MER047097), subfamily A2A non-peptidase homologues (MER047099), subfamily A2A non-peptidase homologues (MER047101), subfamily A2A non-peptidase homologues (MER047102), subfamily A2A non-peptidase homologues (MER047107), subfamily A2A non-peptidase homologues (MER047108), subfamily A2A non-peptidase homologues (MER047109), subfamily A2A non-peptidase homologues (MER047110), subfamily A2A non-peptidase homologues (MER047111), subfamily A2A non-peptidase homologues (MER047114), subfamily A2A non-peptidase homologues (MER047118), subfamily A2A non-peptidase homologues (MER047121), subfamily A2A non-peptidase homologues (MER047122), subfamily A2A non-peptidase homologues (MER047126), subfamily A2A non-peptidase homologues (MER047129), subfamily A2A non-peptidase homologues (MER047130), subfamily A2A non-peptidase homologues (MER047134), subfamily A2A non-peptidase homologues (MER047135), subfamily A2A non-peptidase homologues (MER047137), subfamily A2A non-peptidase homologues (MER047140), subfamily A2A non-peptidase homologues (MER047141), subfamily A2A non-peptidase homologues (MER047142), subfamily A2A non-peptidase homologues (MER047148), subfamily A2A non-peptidase homologues (MER047149), subfamily A2A non-peptidase homologues (MER047151), subfamily A2A non-peptidase homologues (MER047154), subfamily A2A non-peptidase homologues (MER047155), subfamily A2A non-peptidase homologues (MER047156), subfamily A2A non-peptidase homologues (MER047157), subfamily A2A non-peptidase homologues (MER047159), subfamily A2A non-peptidase homologues (MER047161), subfamily A2A non-peptidase homologues (MER047163), subfamily A2A non-peptidase homologues (MER047166), subfamily A2A non-peptidase homologues (MER047171), subfamily A2A non-peptidase homologues (MER047173), subfamily A2A non-peptidase homologues (MER047174), subfamily A2A non-peptidase homologues (MER047179), subfamily A2A non-peptidase homologues (MER047183), subfamily A2A non-peptidase homologues (MER047186), subfamily A2A non-peptidase homologues (MER047190), subfamily A2A non-peptidase homologues (MER047191), subfamily A2A non-peptidase homologues (MER047196), subfamily A2A non-peptidase homologues (MER047198), subfamily A2A non-peptidase homologues (MER047199), subfamily A2A non-peptidase homologues (MER047201), subfamily A2A non-peptidase homologues (MER047202), subfamily A2A non-peptidase homologues (MER047203), subfamily A2A non-peptidase homologues (MER047204), subfamily A2A non-peptidase homologues (MER047205), subfamily A2A non-peptidase homologues (MER047207), subfamily A2A non-peptidase homologues (MER047208), subfamily A2A non-peptidase homologues (MER047210), subfamily A2A non-peptidase homologues (MER047211), subfamily A2A non-peptidase homologues (MER047212), subfamily A2A non-peptidase homologues (MER047213), subfamily A2A non-peptidase homologues (MER047215), subfamily A2A non-peptidase homologues (MER047216), subfamily A2A non-peptidase homologues (MER047218), subfamily A2A non-peptidase homologues (MER047219), subfamily A2A non-peptidase homologues (MER047221), subfamily A2A non-peptidase homologues (MER047224), subfamily A2A non-peptidase homologues (MER047225), subfamily A2A non-peptidase homologues (MER047226), subfamily A2A non-peptidase homologues (MER047227), subfamily A2A non-peptidase homologues (MER047230), subfamily A2A non-peptidase homologues (MER047232), subfamily A2A non-peptidase homologues (MER047233), subfamily A2A non-peptidase homologues (MER047234), subfamily A2A non-peptidase homologues (MER047236), subfamily A2A non-peptidase homologues (MER047238), subfamily A2A non-peptidase homologues (MER047239), subfamily A2A non-peptidase homologues (MER047240), subfamily A2A non-peptidase homologues (MER047242), subfamily A2A non-peptidase homologues (MER047243), subfamily A2A non-peptidase homologues (MER047249), subfamily A2A non-peptidase homologues (MER047251), subfamily A2A non-peptidase homologues (MER047252), subfamily A2A non-peptidase homologues (MER047254), subfamily A2A non-peptidase homologues (MER047255), subfamily A2A non-peptidase homologues (MER047263), subfamily A2A non-peptidase homologues (MER047265), subfamily A2A non-peptidase homologues (MER047266), subfamily A2A non-peptidase homologues (MER047267), subfamily A2A non-peptidase homologues (MER047268), subfamily A2A non-peptidase homologues (MER047269), subfamily A2A non-peptidase homologues (MER047272), subfamily A2A non-peptidase homologues (MER047273), subfamily A2A non-peptidase homologues (MER047274), subfamily A2A non-peptidase homologues (MER047275), subfamily A2A non-peptidase homologues (MER047276), subfamily A2A non-peptidase homologues (MER047279), subfamily A2A non-peptidase homologues (MER047280), subfamily A2A non-peptidase homologues (MER047281), subfamily A2A non-peptidase homologues (MER047282), subfamily A2A non-peptidase homologues (MER047284), subfamily A2A non-peptidase homologues (MER047285), subfamily A2A non-peptidase homologues (MER047289), subfamily A2A non-peptidase homologues (MER047290), subfamily A2A non-peptidase homologues (MER047294), subfamily A2A non-peptidase homologues (MER047295), subfamily A2A non-peptidase homologues (MER047298), subfamily A2A non-peptidase homologues (MER047300), subfamily A2A non-peptidase homologues (MER047302), subfamily A2A non-peptidase homologues (MER047304), subfamily A2A non-peptidase homologues (MER047305), subfamily A2A non-peptidase homologues (MER047306), subfamily A2A non-peptidase homologues (MER047307), subfamily A2A non-peptidase homologues (MER047310), subfamily A2A non-peptidase homologues (MER047311), subfamily A2A non-peptidase homologues (MER047314), subfamily A2A non-peptidase homologues (MER047318), subfamily A2A non-peptidase homologues (MER047320), subfamily A2A non-peptidase homologues (MER047321), subfamily A2A non-peptidase homologues (MER047322), subfamily A2A non-peptidase homologues (MER047326), subfamily A2A non-peptidase homologues (MER047327), subfamily A2A non-peptidase homologues (MER047330), subfamily A2A non-peptidase homologues (MER047333), subfamily A2A non-peptidase homologues (MER047362), subfamily A2A non-peptidase homologues (MER047366), subfamily A2A non-peptidase homologues (MER047369), subfamily A2A non-peptidase homologues (MER047370), subfamily A2A non-peptidase homologues (MER047371), subfamily A2A non-peptidase homologues (MER047375), subfamily A2A non-peptidase homologues (MER047376), subfamily A2A non-peptidase homologues (MER047381), subfamily A2A non-peptidase homologues (MER047383), subfamily A2A non-peptidase homologues (MER047384), subfamily A2A non-peptidase homologues (MER047385), subfamily A2A non-peptidase homologues (MER047388), subfamily A2A non-peptidase homologues (MER047389), subfamily A2A non-peptidase homologues (MER047391), subfamily A2A non-peptidase homologues (MER047394), subfamily A2A non-peptidase homologues (MER047396), subfamily A2A non-peptidase homologues (MER047400), subfamily A2A non-peptidase homologues (MER047401), subfamily A2A non-peptidase homologues (MER047403), subfamily A2A non-peptidase homologues (MER047406), subfamily A2A non-peptidase homologues (MER047407), subfamily A2A non-peptidase homologues (MER047410), subfamily A2A non-peptidase homologues (MER047411), subfamily A2A non-peptidase homologues (MER047413), subfamily A2A non-peptidase homologues (MER047414), subfamily A2A non-peptidase homologues (MER047416), subfamily A2A non-peptidase homologues (MER047417), subfamily A2A non-peptidase homologues (MER047420), subfamily A2A non-peptidase homologues (MER047423), subfamily A2A non-peptidase homologues (MER047424), subfamily A2A non-peptidase homologues (MER047428), subfamily A2A non-peptidase homologues (MER047429), subfamily A2A non-peptidase homologues (MER047431), subfamily A2A non-peptidase homologues (MER047434), subfamily A2A non-peptidase homologues (MER047439), subfamily A2A non-peptidase homologues (MER047442), subfamily A2A non-peptidase homologues (MER047445), subfamily A2A non-peptidase homologues (MER047449), subfamily A2A non-peptidase homologues (MER047450), subfamily A2A non-peptidase homologues (MER047452), subfamily A2A non-peptidase homologues (MER047455), subfamily A2A non-peptidase homologues (MER047457), subfamily A2A non-peptidase homologues (MER047458), subfamily A2A non-peptidase homologues (MER047459), subfamily A2A non-peptidase homologues (MER047463), subfamily A2A non-peptidase homologues (MER047468), subfamily A2A non-peptidase homologues (MER047469), subfamily A2A non-peptidase homologues (MER047470), subfamily A2A non-peptidase homologues (MER047476), subfamily A2A non-peptidase homologues (MER047478), subfamily A2A non-peptidase homologues (MER047483), subfamily A2A non-peptidase homologues (MER047488), subfamily A2A non-peptidase homologues (MER047489), subfamily A2A non-peptidase homologues (MER047490), subfamily A2A non-peptidase homologues (MER047493), subfamily A2A non-peptidase homologues (MER047494), subfamily A2A non-peptidase homologues (MER047495), subfamily A2A non-peptidase homologues (MER047496), subfamily A2A non-peptidase homologues (MER047497), subfamily A2A non-peptidase homologues (MER047499), subfamily A2A non-peptidase homologues (MER047502), subfamily A2A non-peptidase homologues (MER047504), subfamily A2A non-peptidase homologues (MER047511), subfamily A2A non-peptidase homologues (MER047513), subfamily A2A non-peptidase homologues (MER047514), subfamily A2A non-peptidase homologues (MER047515), subfamily A2A non-peptidase homologues (MER047516), subfamily A2A non-peptidase homologues (MER047520), subfamily A2A non-peptidase homologues (MER047533), subfamily A2A non-peptidase homologues (MER047537), subfamily A2A non-peptidase homologues (MER047569), subfamily A2A non-peptidase homologues (MER047570), subfamily A2A non-peptidase homologues (MER047584), subfamily A2A non-peptidase homologues (MER047603), subfamily A2A non-peptidase homologues (MER047604), subfamily A2A non-peptidase homologues (MER047606), subfamily A2A non-peptidase homologues (MER047609), subfamily A2A non-peptidase homologues (MER047616), subfamily A2A non-peptidase homologues (MER047619), subfamily A2A non-peptidase homologues (MER047648), subfamily A2A non-peptidase homologues (MER047649), subfamily A2A non-peptidase homologues (MER047662), subfamily A2A non-peptidase homologues (MER048004), subfamily A2A non-peptidase homologues (MER048018), subfamily A2A non-peptidase homologues (MER048019), subfamily A2A non-peptidase homologues (MER048023), subfamily A2A non-peptidase homologues (MER048037), subfamily A2A unassigned peptidases (MER047164), subfamily A2A unassigned peptidases (MER047231), subfamily A2A unassigned peptidases (MER047386), skin aspartic protease (MER057097), presenilin 1 (MER005221), presenilin 2 (MER005223), impas 1 peptidase (MER019701), impas 1 peptidase (MER184722), impas 4 peptidase (MER019715), impas 2 peptidase (MER019708), impas 5 peptidase (MER019712), impas 3 peptidase (MER019711), possible family A22 pseudogene (*Homo sapiens* chromosome 18) (MER029974), possible family A22 pseudogene (*Homo sapiens* chromosome 11) (MER023159), cathepsin V (MER004437), cathepsin X (MER004508), cathepsin F (MER004980), cathepsin L (MER000622), cathepsin S (MER000633), cathepsin 0 (MER001690), cathepsin K (MER000644), cathepsin W (MER003756), cathepsin H (MER000629), cathepsin B (MER000686), dipeptidyl-peptidase I (MER001937), bleomycin hydrolase (animal) (MER002481), tubulointerstitial nephritis antigen (MER016137), tubulointerstitial nephritis antigen-related protein (MER021799), cathepsin L-like pseudogene 1 (*Homo sapiens*) (MER002789), cathepsin B-like pseudogene (chromosome 4, *Homo sapiens*) (MER029469), cathepsin B-like pseudogene (chromosome 1, *Homo sapiens*) (MER029457), CTSLL2 g.p. (*Homo sapiens*) (MER005210), CTSLL3 g.p. (*Homo sapiens*) (MER005209), calpain-1 (MER000770), calpain-2 (MER000964), calpain-3 (MER001446), calpain-9 (MER004042), calpain-8 (MER021474), calpain-15 (MER004745), calpain-5 (MER002939), calpain-11 (MER005844), calpain-12 (MER029889), calpain-10 (MER013510), calpain-13 (MER020139), calpain-14 (MER029744), Mername-AA253 peptidase (MER005537), calpamodulin (MER000718), hypothetical protein 940251 (MER003201), ubiquitinyl hydrolase-L1 (MER000832), ubiquitinyl hydrolase-L3 (MER000836), ubiquitinyl hydrolase-BAP1 (MER003989), ubiquitinyl hydrolase-UCH37 (MER005539), ubiquitin-specific peptidase 5 (MER002066), ubiquitin-specific peptidase 6 (MER000863), ubiquitin-specific peptidase 4 (MER001795), ubiquitin-specific peptidase 8 (MER001884), ubiquitin-specific peptidase 13 (MER002627), ubiquitin-specific peptidase 2 (MER004834), ubiquitin-specific peptidase 11 (MER002693), ubiquitin-specific peptidase 14

(MER002667), ubiquitin-specific peptidase 7 (MER002896), ubiquitin-specific peptidase 9X (MER005877), ubiquitin-specific peptidase 10 (MER004439), ubiquitin-specific peptidase 1 (MER004978), ubiquitin-specific peptidase 12 (MER005454), ubiquitin-specific peptidase 16 (MER005493), ubiquitin-specific peptidase 15 (MER005427), ubiquitin-specific peptidase 17 (MER002900), ubiquitin-specific peptidase 19 (MER005428), ubiquitin-specific peptidase 20 (MER005494), ubiquitin-specific peptidase 3 (MER005513), ubiquitin-specific peptidase 9Y (MER004314), ubiquitin-specific peptidase 18 (MER005641), ubiquitin-specific peptidase 21 (MER006258), ubiquitin-specific peptidase 22 (MER012130), ubiquitin-specific peptidase 33 (MER014335), ubiquitin-specific peptidase 29 (MER012093), ubiquitin-specific peptidase 25 (MER011115), ubiquitin-specific peptidase 36 (MER014033), ubiquitin-specific peptidase 32 (MER014290), ubiquitin-specific peptidase 26 (*Homo sapiens*-type) (MER014292), ubiquitin-specific peptidase 24 (MER005706), ubiquitin-specific peptidase 42 (MER011852), ubiquitin-specific peptidase 46 (MER014629), ubiquitin-specific peptidase 37 (MER014633), ubiquitin-specific peptidase 28 (MER014634), ubiquitin-specific peptidase 47 (MER014636), ubiquitin-specific peptidase 38 (MER014637), ubiquitin-specific peptidase 44 (MER014638), ubiquitin-specific peptidase 50 (MER030315), ubiquitin-specific peptidase 35 (MER014646), ubiquitin-specific peptidase 30 (MER014649), Mername-AA091 peptidase (MER014743), ubiquitin-specific peptidase 45 (MER030314), ubiquitin-specific peptidase 51 (MER014769), ubiquitin-specific peptidase 34 (MER014780), ubiquitin-specific peptidase 48 (MER064620), ubiquitin-specific peptidase 40 (MER015483), ubiquitin-specific peptidase 41 (MER045268), ubiquitin-specific peptidase 31 (MER015493), Mername-AA129 peptidase (MER016485), ubiquitin-specific peptidase 49 (MER016486), Mername-AA187 peptidase (MER052579), USP17-like peptidase (MER030192), ubiquitin-specific peptidase 54 (MER028714), ubiquitin-specific peptidase 53 (MER027329), ubiquitin-specific endopeptidase 39 [misleading] (MER064621), Mername-AA090 non-peptidase homologue (MER014739), ubiquitin-specific peptidase 43 [misleading] (MER030140), ubiquitin-specific peptidase 52 [misleading] (MER030317), NEK2 pseudogene (MER014736), C19 pseudogene (*Homo sapiens: chromosome* 5) (MER029972), Mername-AA088 peptidase (MER014750), autophagin-2 (MER013564), autophagin-1 (MER013561), autophagin-3 (MER014316), autophagin-4 (MER064622), Cezanne deubiquitinylating peptidase (MER029042), Cezanne-2 peptidase (MER029044), tumor necrosis factor alpha-induced protein 3 (MER029050), trabid peptidase (MER029052), VCIP135 deubiquitinating peptidase (MER152304), otubain-1 (MER029056), otubain-2 (MER029061), CylD protein (MER030104), UfSP1 peptidase (MER042724), UfSP2 peptidase (MER060306), DUBA deubiquitinylating enzyme (MER086098), KIAA0459 (*Homo sapiens*)-like protein (MER122467), Otud1 protein (MER125457), glycosyltransferase 28 domain containing 1, isoform CRA_c (*Homo sapiens*)-like (MER123606), hin1L g.p. (*Homo sapiens*) (MER139816), ataxin-3 (MER099998), ATXN3L putative peptidase (MER115261), Josephin domain containing 1 (*Homo sapiens*) (MER125334), Josephin domain containing 2 (*Homo sapiens*) (MER124068), YOD1 peptidase (MER116559), legumain (plant alpha form) (MER044591), legumain (MER001800), glycosylphosphatidylinositol:protein transamidase (MER002479), legumain pseudogene (*Homo sapiens*) (MER029741), family C13 unassigned peptidases (MER175813), caspase-1 (MER000850), caspase-3 (MER000853), caspase-7 (MER002705), caspase-6 (MER002708), caspase-2 (MER001644), caspase-4 (MER001938), caspase-5 (MER002240), caspase-8 (MER002849), caspase-9 (MER002707), caspase-10 (MER002579), caspase-14 (MER012083), paracaspase (MER019325), Mername-AA143 peptidase (MER021304), Mername-AA186 peptidase (MER020516), putative caspase (*Homo sapiens*) (MER021463), FLIP protein (MER003026), Mername-AA142 protein (MER021316), caspase-12 pseudogene (*Homo sapiens*) (MER019698), Mername-AA093 caspase pseudogene (MER014766), subfamily C14A non-peptidase homologues (MER185329), subfamily C14A non-peptidase homologues (MER179956), separase (*Homo sapiens*-type) (MER011775), separase-like pseudogene (MER014797), SENP1 peptidase (MER011012), SENP3 peptidase (MER011019), SENP6 peptidase (MER011109), SENP2 peptidase (MER012183), SENP5 peptidase (MER014032), SENP7 peptidase (MER014095), SENP8 peptidase (MER016161), SENP4 peptidase (MER005557), pyroglutamyl-peptidase I (chordate) (MER011032), Mername-AA073 peptidase (MER029978), Sonic hedgehog protein (MER002539), Indian hedgehog protein (MER002538), Desert hedgehog protein (MER012170), dipeptidyl-peptidase III (MER004252), Mername-AA164 protein (MER020410), LOC138971 g.p. (*Homo sapiens*) (MER020074), Atp23 peptidase (MER060642), prenyl peptidase 1 (MER004246), aminopeptidase N (MER000997), aminopeptidase A (MER001012), leukotriene A4 hydrolase (MER001013), pyroglutamyl-peptidase II (MER012221), cytosol alanyl aminopeptidase (MER002746), cystinyl aminopeptidase (MER002060), aminopeptidase B (MER001494), aminopeptidase PILS (MER005331), arginyl aminopeptidase-like 1 (MER012271), leukocyte-derived arginine aminopeptidase (MER002968), aminopeptidase Q (MER052595), aminopeptidase 0 (MER019730), Tata binding protein associated factor (MER026493), angiotensin-converting enzyme peptidase unit 1 (MER004967), angiotensin-converting enzyme peptidase unit 2 (MER001019), angiotensin-converting enzyme-2 (MER011061), Mername-AA153 protein (MER020514), thimet oligopeptidase (MER001737), neurolysin (MER010991), mitochondrial intermediate peptidase (MER003665), Mername-AA154 protein (MER021317), leishmanolysin-2 (MER014492), leishmanolysin-3 (MER180031), matrix metallopeptidase-1 (MER001063), matrix metallopeptidase-8 (MER001084), matrix metallopeptidase-2 (MER001080), matrix metallopeptidase-9 (MER001085), matrix metallopeptidase-3 (MER001068), matrix metallopeptidase-10 (*Homo sapiens*-type) (MER001072), matrix metallopeptidase-11 (MER001075), matrix metallopeptidase-7 (MER001092), matrix metallopeptidase-12 (MER001089), matrix metallopeptidase-13 (MER001411), membrane-type matrix metallopeptidase-1 (MER001077), membrane-type matrix metallopeptidase-2 (MER002383), membrane-type matrix metallopeptidase-3 (MER002384), membrane-type matrix metallopeptidase-4 (MER002595), matrix metallopeptidase-20 (MER003021), matrix metallopeptidase-19 (MER002076), matrix metallopeptidase-23B (MER004766), membrane-type matrix metallopeptidase-5

(MER005638), membrane-type matrix metallopeptidase-6 (MER012071), matrix metallopeptidase-21 (MER006101), matrix metallopeptidase-22 (MER014098), matrix metallopeptidase-26 (MER012072), matrix metallopeptidase-28 (MER013587), matrix metallopeptidase-23A (MER037217), macrophage elastase homologue (chromosome 8, *Homo sapiens*) (MER030035), Mername-AA156 protein (MER021309), matrix metallopeptidase-like 1 (MER045280), subfamily M10A non-peptidase homologues (MER175912), subfamily M10A non-peptidase homologues (MER187997), subfamily M10A non-peptidase homologues (MER187998), subfamily M10A non-peptidase homologues (MER180000), meprin alpha subunit (MER001111), meprin beta subunit (MER005213), procollagen C-peptidase (MER001113), mammalian tolloid-like 1 protein (MER005124), mammalian-type tolloid-like 2 protein (MER005866), ADAMTS9 peptidase (MER012092), ADAMTS14 peptidase (MER016700), ADAMTS15 peptidase (MER017029), ADAMTS16 peptidase (MER015689), ADAMTS17 peptidase (MER016302), ADAMTS18 peptidase (MER016090), ADAMTS19 peptidase (MER015663), ADAM8 peptidase (MER003902), ADAM9 peptidase (MER001140), ADAM10 peptidase (MER002382), ADAM12 peptidase (MER005107), ADAM19 peptidase (MER012241), ADAM15 peptidase (MER002386), ADAM17 peptidase (MER003094), ADAM20 peptidase (MER004725), ADAMDEC1 peptidase (MER000743), ADAMTS3 peptidase (MER005100), ADAMTS4 peptidase (MER005101), ADAMTS1 peptidase (MER005546), ADAM28 peptidase (*Homo sapiens*-type) (MER005495), ADAMTS5 peptidase (MER005548), ADAMTS8 peptidase (MER005545), ADAMTS6 peptidase (MER005893), ADAMTS7 peptidase (MER005894), ADAM30 peptidase (MER006268), ADAM21 peptidase (*Homo sapiens*-type) (MER004726), ADAMTS10 peptidase (MER014331), ADAMTS12 peptidase (MER014337), ADAMTS13 peptidase (MER015450), ADAM33 peptidase (MER015143), ovastacin (MER029996), ADAMTS20 peptidase (*Homo sapiens*-type) (MER026906), procollagen I N-peptidase (MER004985), ADAM2 protein (MER003090), ADAM6 protein (MER047044), ADAM7 protein (MER005109), ADAM18 protein (MER012230), ADAM32 protein (MER026938), non-peptidase homologue (*Homo sapiens* chromosome 4) (MER029973), family M12 non-peptidase homologue (*Homo sapiens* chromosome 16) (MER047654), family M12 non-peptidase homologue (*Homo sapiens* chromosome 15) (MER047250), ADAM3B protein (*Homo sapiens*-type) (MER005199), ADAM11 protein (MER001146), ADAM22 protein (MER005102), ADAM23 protein (MER005103), ADAM29 protein (MER006267), protein similar to ADAM21 peptidase preproprotein (*Homo sapiens*) (MER026944), Mername-AA225 peptidase homologue (*Homo sapiens*) (MER047474), putative ADAM pseudogene (chromosome 4, *Homo sapiens*) (MER029975), ADAM3A g.p. (*Homo sapiens*) (MER005200), ADAM1 g.p. (*Homo sapiens*) (MER003912), subfamily M12B non-peptidase homologues (MER188210), subfamily M12B non-peptidase homologues (MER188211), subfamily M12B non-peptidase homologues (MER188212), subfamily M12B non-peptidase homologues (MER188220), neprilysin (MER001050), endothelin-converting enzyme 1 (MER001057), endothelin-converting enzyme 2 (MER004776), DINE peptidase (MER005197), neprilysin-2 (MER013406), Kell blood-group protein (MER001054), PHEX peptidase (MER002062), i-AAA peptidase (MER001246), i-AAA peptidase (MER005755), paraplegin (MER004454), Afg3-like protein 2 (MER005496), Afg3-like protein 1A (MER014306), pappalysin-1 (MER002217), pappalysin-2 (MER014521), farnesylated-protein converting enzyme 1 (MER002646), metalloprotease-related protein-1 (MER030873), aminopeptidase AMZ2 (MER011907), aminopeptidase AMZ1 (MER058242), carboxypeptidase A1 (MER001190), carboxypeptidase A2 (MER001608), carboxypeptidase B (MER001194), carboxypeptidase N (MER001198), carboxypeptidase E (MER001199), carboxypeptidase M (MER001205), carboxypeptidase U (MER001193), carboxypeptidase A3 (MER001187), metallocarboxypeptidase D peptidase unit 1 (MER003781), metallocarboxypeptidase Z (MER003428), metallocarboxypeptidase D peptidase unit 2 (MER004963), carboxypeptidase A4 (MER013421), carboxypeptidase A6 (MER013456), carboxypeptidase A5 (MER017121), metallocarboxypeptidase 0 (MER016044), cytosolic carboxypeptidase-like protein 5 (MER033174), cytosolic carboxypeptidase 3 (MER033176), cytosolic carboxypeptidase 6 (MER033178), cytosolic carboxypeptidase 1 (MER033179), cytosolic carboxypeptidase 2 (MER037713), metallocarboxypeptidase D non-peptidase unit (MER004964), adipocyte-enhancer binding protein 1 (MER003889), carboxypeptidase-like protein X1 (MER013404), carboxypeptidase-like protein X2 (MER078764), cytosolic carboxypeptidase (MER026952), family M14 non-peptidase homologues (MER199530), insulysin (MER001214), mitochondrial processing peptidase beta-subunit (MER004497), nardilysin (MER003883), eupitrilysin (MER004877), mitochondrial processing peptidase non-peptidase alpha subunit (MER001413), ubiquinol-cytochrome c reductase core protein I (MER003543), ubiquinol-cytochrome c reductase core protein II (MER003544), ubiquinol-cytochrome c reductase core protein domain 2 (MER043998), insulysin unit 2 (MER046821), nardilysin unit 2 (MER046874), insulysin unit 3 (MER078753), mitochondrial processing peptidase subunit alpha unit 2 (MER124489), nardilysin unit 3 (MER142856), LOC133083 g.p. (*Homo sapiens*) (MER021876), subfamily M16B non-peptidase homologues (MER188757), leucyl aminopeptidase (animal) (MER003100), Mername-AA040 peptidase (MER003919), leucyl aminopeptidase-1 (*Caenorhabditis*-type) (MER013416), methionyl aminopeptidase 1 (MER001342), methionyl aminopeptidase 2 (MER001728), aminopeptidase P2 (MER004498), Xaa-Pro dipeptidase (eukaryote) (MER001248), aminopeptidase P1 (MER004321), mitochondrial intermediate cleaving peptidase 55 kDa (MER013463), mitochondrial methionyl aminopeptidase (MER014055), Mername-AA020 peptidase homologue (MER010972), proliferation-association protein 1 (MER005497), chromatin-specific transcription elongation factor 140 kDa subunit (MER026495), proliferation-associated protein 1-like (*Homo sapiens* chromosome X) (MER029983), Mername-AA226 peptidase homologue (*Homo sapiens*) (MER056262), Mername-AA227 peptidase homologue (*Homo sapiens*) (MER047299), subfamily M24A non-peptidase homologues (MER179893), aspartyl aminopeptidase (MER003373), Gly-Xaa carboxypeptidase (MER033182), carnosine dipeptidase II (MER014551), carnosine dipeptidase I (MER015142), Mername-AA161 protein (MER021873), aminoacylase (MER001271), glutamate carboxypeptidase II (MER002104), NAALADASE L peptidase (MER005239), glutamate carboxypeptidase III (MER005238), plasma glutamate carboxypeptidase (MER005244), Mername-AA103 peptidase (MER015091), Fxna peptidase (MER029965), transferrin receptor protein (MER002105), transferrin receptor 2 protein (MER005152), glutaminyl cyclise (MER015095), glutamate carboxypeptidase II (*Homo sapiens*)-type non-peptidase homologue (MER026971), nicalin (MER044627), membrane dipeptidase (MER001260), membrane-bound dipeptidase-2 (MER013499), membrane-bound dipeptidase-3 (MER013496), dihydro-orotase (MER005767), dihydropyrimidinase (MER033266), dihydropyrimidinase related protein-1 (MER030143), dihydropyrimidinase related protein-(MER030155), dihydropyrimidinase related protein-3 (MER030151), dihydropyrimidinase related protein-4 (MER030149), dihydropyrimidinase related protein-5 (MER030136), hypothetical protein like 5730457F11RIK (MER033184), 1300019j08rik protein (MER033186)), guanine aminohydrolase (MER037714), Kae1 putative peptidase (MER001577), OSGEPL1-like protein (MER013498), S2P peptidase (MER004458), subfamily M23B non-peptidase homologues (MER199845), subfamily M23B non-peptidase homologues (MER199846), subfamily M23B non-peptidase homologues (MER199847), subfamily M23B non-peptidase homologues (MER137320), subfamily M23B non-peptidase homologues (MER201557), subfamily M23B non-peptidase homologues (MER199417), subfamily M23B non-peptidase homologues (MER199418), subfamily M23B non-peptidase homologues (MER199419), subfamily M23B non-peptidase homologues (MER199420), subfamily M23B non-peptidase homologues (MER175932), subfamily M23B non-peptidase homologues (MER199665), Poh1 peptidase (MER020382), Jab1/MPN domain metalloenzyme (MER022057), Mername-AA165 peptidase (MER021865), Brcc36 isopeptidase (MER021890), histone H2A deubiquitinase MYSM1 (MER021887), AMSH deubiquitinating peptidase (MER030146), putative peptidase (*Homo sapiens* chromosome 2) (MER029970), Mername-AA168 protein (MER021886), COP9 signalosome subunit 6 (MER030137), 26S proteasome non-ATPase regulatory subunit 7 (MER030134), eukaryotic translation initiation factor 3 subunit 5 (MER030133), IFP38 peptidase homologue (MER030132), subfamily M67A non-peptidase homologues (MER191181), subfamily M67A unassigned peptidases (MER191144), granzyme B (*Homo sapiens*-type) (MER000168), testisin (MER005212), tryptase beta (MER000136), kallikrein-related peptidase 5 (MER005544), corin (MER005881), kallikrein-related peptidase 12 (MER006038), DESC1 peptidase (MER006298), tryptase gamma 1 (MER011036), kallikrein-related peptidase 14 (MER011038), hyaluronan-binding peptidase (MER003612), transmembrane peptidase, serine 4 (MER011104), intestinal serine peptidase (rodent) (MER016130), adrenal secretory serine peptidase (MER003734), tryptase delta 1 (*Homo sapiens*) (MER005948), matriptase-3 (MER029902), marapsin (MER006119), tryptase-6 (MER006118), ovochymase-1 domain 1 (MER099182), transmembrane peptidase, serine 3 (MER005926), kallikrein-related peptidase 15 (MER000064), Mername-AA031 peptidase (MER014054), TMPRSS13 peptidase (MER014226), Mername-AA038 peptidase (MER062848), Mername-AA204 peptidase (MER029980), cationic trypsin (*Homo sapiens*-type) (MER000020), elastase-2 (MER000118), mannan-binding lectin-associated serine peptidase-3 (MER031968), cathepsin G (MER000082), myeloblastin (MER000170), granzyme A (MER001379), granzyme M (MER001541), chymase (*Homo sapiens*-type) (MER000123), tryptase alpha (MER000135), granzyme K (MER001936), granzyme H (MER000166), chymotrypsin B (MER000001), elastase-1 (MER003733), pancreatic endopeptidase E (MER000149), pancreatic elastase II (MER000146), enteropeptidase (MER002068), chymotrypsin C (MER000761), prostasin (MER002460), kallikrein 1 (MER000093), kallikrein-related peptidase 2 (MER000094), kallikrein-related peptidase 3 (MER000115), mesotrypsin (MER000022), complement component C1r-like peptidase (MER016352), complement factor D (MER000130), complement component activated C1r (MER000238), complement component activated C1s (MER000239), complement component C2a (MER000231), complement factor B (MER000229), mannan-binding lectin-associated serine peptidase 1 (MER000244), complement factor I (MER000228), pancreatic endopeptidase E form B (MER000150), pancreatic elastase IIB (MER000147), coagulation factor XIIa (MER000187), plasma kallikrein (MER000203) coagulation factor Xia (MER000210), coagulation factor IXa (MER000216), coagulation factor Vila (MER000215), coagulation factor Xa (MER000212), thrombin (MER000188), protein C (activated) (MER000222), acrosin (MER000078), hepsin (MER000156), hepatocyte growth factor activator (MER000186), mannan-binding lectin-associated serine peptidase 2 (MER002758), u-plasminogen activator (MER000195), t-plasminogen activator (MER000192), plasmin (MER000175), kallikrein-related peptidase 6 (MER002580), neurotrypsin (MER004171), kallikrein-related peptidase 8 (MER005400), kallikrein-related peptidase 10 (MER003645), epitheliasin (MER003736), kallikrein-related peptidase 4 (MER005266), prosemin (MER004214), chymopasin (MER001503), kallikrein-related peptidase 11 (MER004861), kallikrein-related peptidase 11 (MER216142), trypsin-2 type A (MER000021), HtrA1 peptidase (*Homo sapiens*-type) (MER002577), HtrA2 peptidase (MER208413), HtrA2 peptidase (MER004093), HtrA3 peptidase (MER014795), HtrA4 peptidase (MER016351), Tysndl peptidase (MER050461), TMPRSS12 peptidase (MER017085), HAT-like putative peptidase 2 (MER021884), trypsin C (MER021898), kallikrein-related peptidase 7 (MER002001), matriptase (MER003735), kallikrein-related peptidase 13 (MER005269), kallikrein-related peptidase 9 (MER005270), matriptase-2 (MER005278), umbelical vein peptidase (MER005421), LCLP peptidase (MER001900), spinesin (MER014385), marapsin-2 (MER021929), complement factor D-like putative peptidase (MER056164), ovochymase-2 (MER022410), HAT-like 4 peptidase (MER044589), ovochymase 1 domain 1 (MER022412), epidermis-specific SP-like putative peptidase (MER029900), testis serine peptidase 5 (MER029901), Mername-AA258 peptidase (MER000285), polyserase-IA unit 1 (MER030879), polyserase-IA unit 2 (MER030880), testis serine peptidase 2 (human-type) (MER033187), hypothetical acrosin-like peptidase (*Homo sapiens*) (MER033253), HAT-like 5 peptidase (MER028215), polyserase-3 unit 1 (MER061763), polyserase-3 unit 2 (MER061748), peptidase similar to tryptophan/serine protease (MER056263), polyserase-2 unit 1 (MER061777), Mername-AA123 peptidase (MER021930), HAT-like 2 peptidase (MER099184), hCG2041452-like protein (MER099172), hCG22067 (*Homo sapiens*) (MER099169), brain-rescue-factor-1 (*Homo sapiens*) (MER098873), hCG2041108 (*Homo sapiens*) (MER099173), polyserase-2 unit 2 (MER061760), polyserase-2 unit 3 (MER065694), Mername-AA201 (peptidase homologue) MER099175, secreted trypsin-like serine peptidase homologue (MER030000), polyserase-1A unit 3 (MER029880), azurocidin (MER000119), haptoglobin-1 (MER000233), haptoglobin-related protein (MER000235), macrophage-stimulating protein (MER001546), hepatocyte growth factor (MER000185), protein Z (MER000227), TESP1 protein (MER047214), LOC136242 protein (MER016132), plasma kallikrein-like protein 4 (MER016346), PRSS35 protein (MER016350), DKFZp586H2123-like protein (MER066474), apolipoprotein (MER000183), psi-KLK1 pseudogene (*Homo sapiens*) (MER033287), tryptase pseudogene I (MER015077), tryptase pseudogene II (MER015078), tryptase pseudogene III (MER015079), subfamily S1A unassigned peptidases (MER216982), subfamily S1A unassigned peptidases (MER216148), amidophosphoribosyltransferase precursor (MER003314), glutamine-fructose-6-phosphate transaminase 1 (MER003322), glutamine:fructose-6-phosphate amidotransferase (MER012158), Mername-AA144 protein (MER021319), asparagine synthetase (MER033254), family C44 non-peptidase homologues (MER159286), family C44 unassigned peptidases (MER185625) family C44 unassigned peptidases (MER185626), secernin 1 (MER045376), secernin 2 (MER064573), secernin 3 (MER064582), acid ceramidase precursor (MER100794), N-acylethanolamine acid amidase precursor (MER141667), proteasome catalytic subunit 1 (MER000556), proteasome catalytic subunit 2 (MER002625), proteasome catalytic subunit 3 (MER002149), proteasome catalytic subunit 1i (MER000552), proteasome catalytic subunit 2i (MER001515), proteasome catalytic subunit 3i (MER000555), proteasome catalytic subunit 5t (MER026203), protein serine kinase c17 (MER026497), proteasome subunit alpha 6 (MER000557), proteasome subunit alpha 2 (MER000550), proteasome subunit alpha 4 (MER000554), proteasome subunit alpha 7 (MER033250), proteasome subunit alpha 5 (MER000558), proteasome subunit alpha 1 (MER000549), proteasome subunit alpha 3 (MER000553), proteasome subunit XAPC7 (MER004372), proteasome subunit beta 3 (MER001710), proteasome subunit beta 2 (MER002676), proteasome subunit beta 1 (MER000551), proteasome subunit beta 4 (MER001711), Mername-AA230 peptidase homologue (*Homo sapiens*) (MER047329), Mername-AA231 pseudogene (*Homo sapiens*) (MER047172), Mername-AA232 pseudogene (*Homo sapiens*) (MER047316), glycosylasparaginase precursor (MER003299), isoaspartyl dipeptidase (threonine type) (MER031622), taspase-1 (MER016969), gamma-glutamyltransferase 5 (mammalian-type) (MER001977), gamma-glutamyltransferase 1 (mammalian-type) (MER001629), gamma-glutamyltransferase 2 (*Homo sapiens*) (MER001976), gamma-glutamyltransferase-like protein 4 (MER002721), gamma-glutamyltransferase-like protein 3 (MER016970), similar to gamma-glutamyltransferase 1 precursor (*Homo sapiens*) (MER026204), similar to gamma-glutamyltransferase 1 precursor (*Homo sapiens*) (MER026205), Mername-AA211 putative peptidase (MER026207), gamma-glutamyltransferase 6 (MER159283), gamma-glutamyl transpeptidase homologue (chromosome 2, *Homo sapiens*) (MER037241), polycystin-1 (MER126824), KIAA1879 protein (MER159329), polycystic kidney disease 1-like 3 (MER172554), gamma-glutamyl hydrolase (MER002963), guanine 5"-monophosphate synthetase (MER043387), carbamoyl-phosphate synthase (*Homo sapiens*-type) (MER078640), dihydro-orotase (N-terminal unit) (*Homo sapiens*-type) (MER060647), DJ-1 putative peptidase (MER003390), Mername-AA100 putative peptidase (MER014802), Mername-AA101 non-peptidase homologue (MER014803), KIAA0361 protein (*Homo sapiens*-type) (MER042827), FLJ34283 protein (*Homo sapiens*) (MER044553), non-peptidase homologue chromosome 21 open reading frame 33 (*Homo sapiens*) (MER160094), family C56 non-peptidase homologues (MER177016), family C56 non-peptidase homologues (MER176613), family C56 non-peptidase homologues (MER176918), EGF-like module containing mucin-like hormone receptor-like 2 (MER037230), CD97 antigen (human type) (MER037286), EGF-like module containing mucin-like hormone receptor-like 3 (MER037288), EGF-like module containing mucin-like hormone receptor-like 1 (MER037278), EGF-like module containing mucin-like hormone receptor-like 4 (MER037294), cadherin EGF LAG seven-pass G-type receptor 2 precursor (*Homo sapiens*) (MER045397), Gpr64 (*Mus musculus*)-type protein (MER123205), GPR56 (*Homo sapiens*)-type protein (MER122057), latrophilin 2 (MER122199), latrophilin-1 (MER126380), latrophilin 3 (MER124612), protocadherin Flamingo 2 (MER124239), ETL protein (MER126267), G protein-coupled receptor 112 (MER126114), seven transmembrane helix receptor (MER125448), Gpr114 protein (MER159320), GPR126 vascular inducible G protein-coupled receptor (MER140015), GPR125 (*Homo sapiens*)-type protein (MER159279), GPR116 (*Homo sapiens*)-type G-protein coupled receptor (MER159280), GPR128 (*Homo sapiens*)-type G-protein coupled receptor (MER162015), GPR133 (*Homo sapiens*)-type protein (MER159334), GPR110 G-protein coupled receptor (MER159277), GPR97 protein (MER159322), KPG_006 protein (MER161773), KPG_008 protein (MER161835), KPG_009 protein (MER159335), unassigned homologue (MER166269), GPR113 protein (MER159352), brain-specific angiogenesis inhibitor 2 (MER159746), PIDD auto-processing protein unit 1 (MER020001), PIDD auto-processing protein unit 2 (MER063690), MUC1 self-cleaving mucin (MER074260), dystroglycan (MER054741), proprotein convertase 9 (MER022416), site-1 peptidase (MER001948), furin (MER000375), proprotein convertase 1 (MER000376), proprotein convertase 2 (MER000377), proprotein convertase 4 (MER028255), PACE4 proprotein convertase (MER000383), proprotein convertase 5 (MER002578), proprotein convertase 7 (MER002984), tripeptidyl-peptidase II (MER000355), subfamily S8A non-peptidase homologues (MER201339), subfamily S8A non-peptidase homologues (MER191613), subfamily S8A unassigned peptidases (MER191611), subfamily S8A unassigned peptidases (MER191612), subfamily S8A unassigned peptidases (MER191614), tripeptidyl-peptidase I (MER003575), prolyl oligopeptidase (MER000393), dipeptidyl-peptidase IV (eukaryote) (MER000401), acylaminoacyl-peptidase (MER000408), fibroblast activation protein alpha subunit (MER000399), PREPL A protein (MER004227), dipeptidyl-peptidase 8 (MER013484), dipeptidyl-peptidase 9 (MER004923), FLJ1 putative peptidase (MER017240), Mername-AA194 putative peptidase (MER017353), Mername-AA195 putative peptidase (MER017367), Mername-AA196 putative peptidase (MER017368), Mername-AA197 putative peptidase (MER017371), C14orf29 protein (MER033244), hypothetical protein (MER033245), hypothetical esterase/lipase/thioesterase (MER047309), protein bat5 (MER037840), hypothetical protein flj40219 (MER033212), hypothetical protein 937464 (MER033240), hypothetical protein flj33678 (MER033241), dipeptidylpeptidase homologue DPP6 (MER000403), dipeptidylpeptidase homologue DPP10 (MER005988), protein similar to *Mus musculus* chromosome 20 open reading frame 135 (MER037845), kynurenine formamidase (MER046020), thyroglobulin precursor (MER011604), acetylcholinesterase (MER033188), cholinesterase (MER033198), carboxylesterase D1 (MER033213), liver carboxylesterase (MER033220), carboxylesterase 3 (MER033224), carboxylesterase 2 (MER033226), bile salt-dependent lipase (MER033227), carboxylesterase-related protein (MER033231), neuroligin 3 (MER033232), neuroligin 4, X-linked (MER033235), neuroligin 4, Y-linked (MER033236), esterase D (MER043126), arylacetamide deacetylase (MER033237), KIAA1363-like protein (MER033242), hormone-sensitive lipase (MER033274), neuroligin 1 (MER033280), neuroligin 2 (MER033283), family S9 non-peptidase homologues (MER212939), family S9 non-peptidase homologues (MER211490), subfamily S9C unassigned peptidases (MER192341), family S9 unassigned peptidases (MER209181), family S9 unassigned peptidases (MER200434), family S9 unassigned peptidases (MER209507), family S9 unassigned peptidases (MER209142), serine carboxypeptidase A (MER000430), vitellogenic carboxypeptidase-like protein (MER005492), RISC peptidase (MER010960), family S15 unassigned peptidases (MER199442), family S15 unassigned peptidases (MER200437), family S15 unassigned peptidases (MER212825), lysosomal Pro-Xaa carboxypeptidase (MER000446), dipeptidyl-peptidase II (MER004952), thymus-specific serine peptidase (MER005538), epoxide hydrolase-like putative peptidase (MER031614), Loc328574-like protein (MER033246), abhydrolase domain-containing protein 4 (MER031616), epoxide hydrolase (MER000432), mesoderm specific transcript protein (MER199890), mesoderm specific transcript protein (MER017123), cytosolic epoxide hydrolase (MER029997), cytosolic epoxide hydrolase (MER213866), similar to hypothetical protein F1122408 (MER031608), CGI-58 putative peptidase (MER030163), Williams-Beuren syndrome critical region protein 21 epoxide hydrolase (MER031610), epoxide hydrolase (MER031612), hypothetical protein 922408 (epoxide hydrolase) (MER031617), monoglyceride lipase (MER033247), hypothetical protein (MER033249), valacyclovir hydrolase (MER033259), Ccg1-interacting factor b (MER210738), glycosylasparaginase precursor (MER003299), isoaspartyl dipeptidase (threonine type) (MER031622), taspase-1 (MER016969), gamma-glutamyltransferase 5 (mammalian-type) (MER001977), gamma-glutamyltransferase 1 (mammalian-type) (MER001629), gamma-glutamyltransferase 2 (*Homo sapiens*) (MER001976), gamma-glutamyltransferase-like protein 4 (MER002721), gamma-glutamyltransferase-like protein 3 (MER016970), similar to gamma-glutamyltransferase 1 precursor (*Homo sapiens*) (MER026204), similar to gamma-glutamyltransferase 1 precursor (*Homo sapiens*) (MER026205). Mername-AA211 putative peptidase (MER026207), gamma-glutamyltransferase 6 (MER159283), gamma-glutamyl transpeptidase homologue (chromosome 2, *Homo sapiens*) (MER037241), polycystin-1 (MER126824), KIAA1879 protein (MER159329), polycystic kidney disease 1-like 3 (MER172554), gamma-glutamyl hydrolase (MER002963), guanine 5"-monophosphate synthetase (MER043387), carbamoyl-phosphate synthase (*Homo sapiens*-type) (MER078640), dihydro-orotase (N-terminal unit) (*Homo sapiens*-type) (MER060647). DJ-1 putative peptidase (MER003390). Mername-AA100 putative peptidase (MER014802). Mername-AA101 non-peptidase homologue (MER014803). KIAA0361 protein (*Homo sapiens*-type) (MER042827). F1134283 protein (*Homo sapiens*) (MER044553), non-peptidase homologue chromosome 21 open reading frame 33 (*Homo sapiens*) (MER160094), family C56 non-peptidase homologues (MER177016), family C56 non-peptidase homologues (MER176613), family C56 non-peptidase homologues (MER176918). EGF-like module containing mucin-like hormone receptor-like 2 (MER037230). CD97 antigen (human type) (MER037286). EGF-like module containing mucin-like hormone receptor-like 3 (MER037288). EGF-like module containing mucin-like hormone receptor-like 1 (MER037278). EGF-like module containing mucin-like hormone receptor-like 4 (MER037294), cadherin EGF LAG seven-pass G-type receptor 2 precursor (*Homo sapiens*) (MER045397), Gpr64 (*Mus musculus*)-type protein (MER123205). GPR56 (*Homo sapiens*)-type protein (MER122057), latrophilin 2 (MER122199), latrophilin-1 (MER126380), latrophilin 3 (MER124612), protocadherin Flamingo 2 (MER124239). ETL protein (MER126267). G protein-coupled receptor 112 (MER126114), seven transmembrane helix receptor (MER125448). Gpr114 protein (MER159320). GPR126 vascular inducible G protein-coupled receptor (MER140015). GPR125 (*Homo sapiens*)-type protein (MER159279). GPR116 (*Homo sapiens*)-type G-protein coupled receptor (MER159280). GPR128 (*Homo sapiens*)-type G-protein coupled receptor (MER162015). GPR133 (*Homo sapiens*)-type protein (MER159334) GPR110 G-protein coupled receptor (MER159277), GPR97 protein (MER159322), KPG_006 protein (MER161773) KPG_008 protein (MER161835), KPG_009 protein (MER159335), unassigned homologue (MER166269), GPR113 protein (MER159352), brain-specific angiogenesis inhibitor 2 (MER159746), PIDD auto-processing protein unit 1 (MER020001), PIDD auto-processing protein unit 2 (MER063690), MUC1 self-cleaving mucin (MER074260), dystroglycan (MER054741), proprotein convertase 9 (MER022416), site-1 peptidase (MER001948), furin (MER000375), proprotein convertase 1 (MER000376), proprotein convertase 2 (MER000377), proprotein convertase 4 (MER028255), PACE4 proprotein convertase (MER000383), proprotein convertase 5 (MER002578), proprotein convertase 7 (MER002984), tripeptidyl-peptidase II (MER000355), subfamily S8A non-peptidase homologues (MER201339), subfamily S8A non-peptidase homologues (MER191613), subfamily S8A unassigned peptidases (MER191611), subfamily S8A unassigned peptidases (MER191612), subfamily S8A unassigned peptidases (MER191614), tripeptidyl-peptidase I (MER003575), prolyl oligopeptidase (MER000393), dipeptidyl-peptidase IV (eukaryote) (MER000401), acylaminoacyl-peptidase (MER000408), fibroblast activation protein alpha subunit (MER000399), PREPL A protein (MER004227), dipeptidyl-peptidase 8 (MER013484), dipeptidyl-peptidase 9 (MER004923), FLJ1 putative peptidase (MER017240), Mername-AA194 putative peptidase (MER017353), Mername-AA195 putative peptidase (MER017367), Mername-AA196 putative peptidase (MER017368), Mername-AA197 putative peptidase (MER017371), C14orf29 protein (MER033244), hypothetical protein (MER033245), hypothetical esterase/lipase/thioesterase (MER047309), protein bat5 (MER037840), hypothetical protein flj40219 (MER033212), hypothetical protein flj37464 (MER033240), hypothetical protein flj33678 (MER033241), dipeptidylpeptidase homologue DPP6 (MER000403), dipeptidylpeptidase homologue DPP10 (MER005988), protein similar to *Mus musculus* chromosome 20 open reading frame 135 (MER037845), kynurenine formamidase (MER046020), thyroglobulin precursor (MER011604), acetylcholinesterase (MER033188), cholinesterase (MER033198), carboxylesterase D1 (MER033213), liver carboxylesterase (MER033220), carboxylesterase 3 (MER033224), carboxylesterase 2 (MER033226), bile salt-dependent lipase (MER033227), carboxylesterase-related protein (MER033231), neuroligin 3 (MER033232), neuroligin 4, X-linked (MER033235), neuroligin 4, Y-linked (MER033236), esterase D (MER043126), arylacetamide deacetylase (MER033237), KIAA1363-like protein (MER033242), hormone-sensitive lipase (MER033274), neuroligin 1 (MER033280), neuroligin 2 (MER033283), family S9 non-peptidase homologues (MER212939), family S9 non-peptidase homologues (MER211490), subfamily S9C unassigned peptidases (MER192341), family S9 unassigned peptidases (MER209181), family S9 unassigned peptidases (MER200434), family S9 unassigned peptidases (MER209507), family S9 unassigned peptidases (MER209142), serine carboxypeptidase A (MER000430), vitellogenic carboxypeptidase-like protein (MER005492), RISC peptidase (MER010960), family S15 unassigned peptidases (MER199442), family S15 unassigned peptidases (MER200437), family S15 unassigned peptidases (MER212825), lysosomal Pro-Xaa carboxypeptidase (MER000446), dipeptidyl-peptidase II (MER004952), thymus-specific serine peptidase (MER005538), epoxide hydrolase-like putative peptidase (MER031614), Loc328574-like protein (MER033246), abhydrolase domain-containing protein 4 (MER031616), epoxide hydrolase (MER000432), mesoderm specific transcript protein (MER199890), mesoderm specific transcript protein (MER017123), cytosolic epoxide hydrolase (MER029997), cytosolic epoxide hydrolase (MER213866), similar to hypothetical protein FLJ22408 (MER031608), CGI-58 putative peptidase (MER030163), Williams-Beuren syndrome critical region protein 21 epoxide hydrolase (MER031610), epoxide hydrolase (MER031612), hypothetical protein flj22408 (epoxide hydrolase) (MER031617), monoglyceride lipase (MER033247), hypothetical protein (MER033249), valacyclovir hydrolase (MER033259), Ccg1-interacting factor b (MER210738).

It will be appreciated that for a given unwanted cell type, the skilled person can readily determine an appropriate protease cleavage site to use, for example by consulting scientific literature to determine which proteases are overexpressed by that cell type. Oncomine (www.oncomine.org) is an online cancer gene expression database, and so when the agent of the invention is for treating cancer, the skilled person may search the Oncomine database to identify a particular protease cleavage site that will be appropriate for treating a given cancer type. Alternative databases include European Bioinformatic Institute (//www.ebi.ac.uk) in particular (www.ebi.ac.uk/gxa). Protease databases include PMAP (www.proteolysis.org), ExPASy Peptide Cutter (ca.expasy.org/tools/peptide cutter) and PMAP.Cut DB (cutdb.burnham.org).

It is noted that it may be desirable to screen a library of peptides incorporating multiple potential cleavage sites and evaluating the optimal cleavage site for a given unwanted cell (eg tumour). Such peptides may be useful as linkers to join the T cell antigen to the targeting moiety as discussed below.

TABLE 4

Matrix showing preferred protease cleavage sites for treating particular tumours

| Protease | | Substrate | Breast | Ovarian | Endometrial | Cervical | Bladder | Renal | Melanoma | Lung-NSLC |
|---|---|---|---|---|---|---|---|---|---|---|
| Serine | | | | | | | | | | |
| urokinase-type plasminogen activator | uPA | CPGR-VVGG (SEQ ID No: 254) | ● | ● | ● | ● | ● | | ● | ● |
| | tPA | CPGR-VVGG (SEQ ID No: 254) | ● | | | | | | | |
| | Cathepsin A | | | | | | | | ● | |
| | Cathepsin G | | | | | | | | | |
| | Plasmin | GGR-X (SEQ ID No: 256) | | | | | | | | |
| | C1s | YLGR-SYKV (SEQ ID No: 257) or MQLGR-X (SEQ ID No: 258) | | | | | | | | |
| | MASP2 | SLGR-KIQI (SEQ ID No: 259) | | | | | | | | |
| | Thrombin | LVPRGS (SEQ ID No: 260) | | | | | | | | |
| | Trypsin | XXXR-X (SEQ ID No: 261) | | | | | | | | |
| | Chymotrypsin | | | | | | | | | |
| | Elastase 1 | | | | | | | | | |
| Leucocyte/Neut Elastase | Elastase 2 | AAPV-X (SEQ ID No: 262) | | | | | | | | |
| Leucocyte/Neut Elastase | Elastase 2 | AAPV-X (SEQ ID No: 262) | | | | | | | | |
| MT-SP1/ST14 | Matriptase | KQLR-VVNG (SEQ ID No: 263) or KQSR-KFVP (SEQ ID No: 264) | ● | ● | | | | | | |
| MT-SP2 | Matriptase2 | | ● | | | | | | | |
| TMPRSS1 | Hepsin | | | ● | | | | ● | | |
| | TMPRSS2 | GGR-X (SEQ ID No: 256) | | | | | | | | |
| | TMPRSS3 | | | | | | | | | |
| | TMPRSS4 | | | | | | | | | |
| PSA | Prostate Specific Antigen | SSKYQ (SEQ ID No: 265) or HSSKLQL (SEQ ID No: 266) | | | | | | | | |

TABLE 4-continued

| Matrix showing preferred protease cleavage sites for treating particular tumours | | | | | | | | | | |
|---|---|---|---|---|---|---|---|---|---|---|
| Leucocyte/Neut Elastase | Elastase 2 | AAPV-X (SEQ ID No: 262) | | | | | | | | |
| MT-SP1/ST14 | Matriptase | KQLR-VVNG (SEQ ID No: 263) | ● | ● | | | | | | |
| MT-SP2 | Matriptase2 | | ● | | | | | | | |
| TMPRSS1 | Hepsin | | | ● | | | | ● | | |
| | TMPRSS2 | GGR-X (SEQ ID No: 256) | | | | | | | | |
| | TMPRSS3 | | | | | | | | | |
| | TMPRSS4 | | | | | | | | | |
| PSA | Prostate Specific Antigen | SSKYQ (SEQ ID No: 265) or HSSKLQL (SEQ ID No: 266) | | | | | | | | |
| Cysteine | | | | | | | | | | |
| | Cathepsin B | GGGG-F (SEQ ID No: 267) | | ● | | | | | | ● |
| | Cathepsin L | | | | | | | | | |
| | Cathepsin F | | | | | | | | | |
| | Cathepsin H | | | | | | | | | |
| | Cathepsin K | | ● | | | | | | ● | |
| | Cathepsin L1 | | | | | | | | | |
| | Cathepsin L2 | | | | | | | | | |
| | Cathepsin O | | ● | | | | | | | |
| | Cathepsin W | | | | | | | | | |
| | Cathepsin S | | | | | | | | | |
| | Cathepsin Z (or X) | | | | | | | | | |
| Aspartic | | | | | | | | | | |
| | Cathepsin D | | | | | | | | ● | |
| | Cathepsin E | | | | | | | | | |
| Metallo | | | | | | | | | | |
| Collagenase 1 | MMP1 | PLG-LLG (SEQ ID No: 268) | ● | | | | | | | ● |
| Gelatinase A | MMP2 | PQG-IAGQ (SEQ ID No: 269) or PVGLIG (SEQ ID No: 270) | ● | ● | | ● | ● | | | |
| Stromelysin | MMP3 | | ● | | | | | | | |
| | MMP4 | | | | | | | | | |
| | MMP5 | | | | | | | | | |
| | MMP6 | | | | | | | | | |
| Matrilysin | MMP7 | | | | | | | | | |
| Collagenase 2 | MMP8 | | | | | | | | | |
| Gelatinase B | MMP9 | PQG-IAGQ (SEQ ID No: 269) or PRA-LY (SEQ ID No: 271) | | | | | ● | | ● | |
| | MMP10 | | | | | | | | | |
| | MMP11 | | ● | | | | | | | |
| | MMP12 | | ● | | | | | | | |
| | MMP13 | | | | | | | | | |
| | MMP14 | PRH-LR (SEQ ID No: 272) | | ● | | ● | ● | | | ● |
| | MMP15 | | ● | | | | | | | ● |
| | MMP16 | | | | | | | | | |
| | MMP17 | | ● | | | | | | | |
| | MMP18 | | | | | | | | | |
| | MMP19 | | | | | | | | | |
| | MMP20 | | | | | | | | | |
| | MMP21 | | | | | | | | | |
| | MMP23A | | | | | | | | | |
| | MMP23B | | | | | | | | | |
| | MMP24 | | | | | | | | | |
| | MMP25 | | | | | | | | | |
| | MMP26 | | | | ● | | | | | |
| | MMP27 | | | | | | | | | |
| | MMP28 | | | | | | | | | |
| | ADAM2 | | | | | | | | | |
| | ADAM7 | | | | | | | | | |
| | ADAM8 | | | ● | | | | ● | | ● |
| | ADAM9 | | | | | | | | | ● |
| | ADAM10 | | | ● | ● | | | | | |
| Metallo | | | | | | | | | | |
| | ADAM11 | | | | | | | | | |
| | ADAM12 | | ● | | | | ● | | | |
| | ADAM15 | | ● | | | | | | | ● |

TABLE 4-continued

Matrix showing preferred protease cleavage sites for treating particular tumours

| | | | | | |
|---|---|---|---|---|---|
| | ADAM17 | ● | ● | ● | ● |
| | ADAM18/27 | | | | |
| | ADAM19 | | | ● | |
| | ADAM20 | | | | |
| | ADAM21/31 | | | | |
| | ADAM22 | | | | |
| | ADAM23 | | | | |
| | ADAM28 | ● | | ● | |
| | ADAM29 | | | | |
| | ADAM30 | | | | |
| | ADAM33 | | | | |
| | ADAMTS1 | | | | |
| | ADAMTS2 | | | | |
| | ADAMTS3 | | | | |
| | ADAMTS4 | | | | |
| | ADAMTS5/11 | | | | |
| | ADAMTS6 | | | | |
| | ADAMTS7 | | | | |
| | ADAMTS8 | | | | |
| | ADAMTS9 | | | | |
| | ADAMTS10 | | | | |
| | ADAMTS12 | | | | |
| | ADAMTS13 | | | | |
| | ADAMTS14 | | | | |
| | ADAMTS15 | ● | | | |
| | ADAMTS16 | | | | |
| | ADAMTS17 | | | | |
| | ADAMTS18 | | | | |
| | ADAMTS19 | | | | |
| | ADAMTS20 | | | | |

| Protease | | Lung-SLC | Prostate | Testicular | Thyroid | Brain | Oesophageal | Gastric | Pancreatic | Colorectal | Liver | Leukaemia |
|---|---|---|---|---|---|---|---|---|---|---|---|---|
| Serine | | | | | | | | | | | | |
| urokinase-type plasminogen activator | uPA | | ● | | | | ● | ● | ● | ● | | |
| | tPA | | | | | | | | | | | |
| | Cathepsin A | | | | | | | | | | | |
| | Cathepsin G | | | | | | | | | | | |
| | Plasmin | | | | | | | | | | | |
| | C1s | | | | | | | | | | | |
| | MASP2 | | | | | | | | | | | |
| | Thrombin | | | | | | | | | | | |
| | Trypsin | | | | | | | | | | | |
| | Chymotrypsin | | | | | | | | | | | |
| | Elastase 1 | | | | | | | | | | | |
| Leucocyte/Neut Elastase | Elastase 2 | | | | | | | | | | | |
| Leucocyte/Neut Elastase | Elastase 2 | | | | | | | | | | | |
| MT-SP1/ST14 | Matriptase | | ● | | | | | | | ● | | |
| MT-SP2 | Matriptase2 | | | | | | | | | | | |
| TMPRSS1 | Hepsin | | ● | | | | | | | | | |
| | TMPRSS2 | | ● | | | | | | | | | |
| | TMPRSS3 | | | | | | | | | | | |
| | TMPRSS4 | | | | | | | ● | ● | ● | | |
| PSA | Prostate Specific Antigen | | ● | | | | | | | | | |
| Leucocyte/Neut Elastase | Elastase 2 | | | | | | | | | | | |
| MT-SP1/ST14 | Matriptase | | ● | | | | | | | ● | | |
| MT-SP2 | Matriptase2 | | | | | | | | | | | |
| TMPRSS1 | Hepsin | | ● | | | | | | | | | |
| | TMPRSS2 | | ● | | | | | | | | | |
| | TMPRSS3 | | | | | | | | | | | |
| | TMPRSS4 | | | | | | | ● | ● | ● | | |
| PSA | Prostate Specific Antigen | | ● | | | | | | | | | |
| Cysteine | | | | | | | | | | | | |
| | Cathepsin B | ● | | | | ● | | | | | | |
| | Cathepsin L | | | | | | | | | | | |
| | Cathepsin F | | | | | | | | | | | |
| | Cathepsin H | | ● | | | | | | | | | |

TABLE 4-continued

Matrix showing preferred protease cleavage sites for treating particular tumours

| | | | | | | | | | | | |
|---|---|---|---|---|---|---|---|---|---|---|---|
| | Cathepsin K | | ● | | | | | | | | |
| | Cathepsin L1 | | | | | | | | | | |
| | Cathepsin L2 | | | | | | | | | | |
| | Cathepsin O | | | | | | | | | | |
| | Cathepsin W | | | | | | | | | | |
| | Cathepsin S | | | | ● | | | | | | |
| | Cathepsin Z (or X) | | | | | | | | | | |
| Aspartic | | | | | | | | | | | |
| | Cathepsin D | | | ● | ● | | | | | ● | |
| | Cathepsin E | | | | | | | | | | |
| Metallo | | | | | | | | | | | |
| Collagenase 1 | MMP1 | ● | ● | | | ● | ● | ● | ● | | |
| Gelatinase A | MMP2 | | ● | | | | ● | | | | ● |
| Stromelysin | MMP3 | | | | | | | | | | |
| | MMP4 | | | | | | | | | | |
| | MMP5 | | | | | | | | | | |
| | MMP6 | | | | | | | | | | |
| Matrilysin | MMP7 | | | | | | ● | | ● | | ● |
| Collagenase 2 | MMP8 | | | | | | | | | | |
| Gelatinase B | MMP9 | | ● | | | | | | | | |
| | MMP10 | | | | | | | | | | |
| | MMP11 | | | | | | | | | | |
| | MMP12 | | | | | | | | | | |
| | MMP13 | | | | | | | | | | |
| | MMP14 | ● | ● | ● | ● | | ● | ● | ● | ● | |
| | MMP15 | | ● | | | | | | | | |
| | MMP16 | | | | | | | | | | |
| | MMP17 | | | | | | | | | | |
| | MMP18 | | | | | | | | | | |
| | MMP19 | | | | | | | | | | |
| | MMP20 | | | | | | | | | | |
| | MMP21 | | | | | | | | | | |
| | MMP23A | | | | | | | | | | |
| | MMP23B | | | | | | | | ● | | |
| | MMP24 | | | | ● | | | | | | |
| | MMP25 | | | | | | | | | | |
| | MMP26 | | ● | | | | | | | | |
| | MMP27 | | | | | | | | | | |
| | MMP28 | | | | | | ● | ● | ● | | |
| | | | ● | | | | | | | | |
| | ADAM2 | | | | | | | | | | |
| | ADAM7 | | | | | | | | | | |
| | ADAM8 | ● | | | ● | | | ● | | | |
| | ADAM9 | ● | ● | | | | ● | ● | | ● | |
| | ADAM10 | | ● | | | ● | | | ● | | ● |
| Metallo | | | | | | | | | | | |
| | ADAM11 | | | | | | | | | | |
| | ADAM12 | | | | ● | | ● | | ● | ● | |
| | ADAM15 | ● | ● | | | | ● | | | | |
| | ADAM17 | ● | ● | | | | ● | ● | ● | ● | |
| | ADAM18/27 | | | | | | | | | | |
| | ADAM19 | | | | ● | | | | | | |
| | ADAM20 | | | | | | | | | | |
| | ADAM21/31 | | | | | | | | | | |
| | ADAM22 | | | | | | | | | | |
| | ADAM23 | | | | | | | | | | |
| | ADAM28 | | | | | | | | | | |
| | ADAM29 | | | | | | | | | | |
| | ADAM30 | | | | | | | | | | |
| | ADAM33 | | | | | | | | | | |
| | ADAMTS1 | | | | | | | | | | |
| | ADAMTS2 | | | | | | | | | | |
| | ADAMTS3 | | | | | | | | | | |
| | ADAMTS4 | | | | | | | | | | |
| | ADAMTS5/11 | | | | | | | | | | |
| | ADAMTS6 | | | | | | | | | | |
| | ADAMTS7 | | | | | | | | | | |
| | ADAMTS8 | | | | | | | | ● | | |
| | ADAMTS9 | | | | | | | | | | |
| | ADAMTS10 | | | | | | | | | | |
| | ADAMTS12 | | | | | | | | | | |
| | ADAMTS13 | | | | | | | | | | |
| | ADAMTS14 | | | | | | | | | | |
| | ADAMTS15 | | | | | | | | | | |
| | ADAMTS16 | | | | | | | | | | |
| | ADAMTS17 | | | | | | | | | | |

TABLE 4-continued

Matrix showing preferred protease cleavage sites for treating particular tumours

| |
|---|
| ADAMTS18 |
| ADAMTS19 |
| ADAMTS20 |

| Protease | | Myeloma | NHL | Hodgkin's | AML | ALL | CLL | Model Cell line |
|---|---|---|---|---|---|---|---|---|
| Serine | | | | | | | | |
| urokinase-type plasminogen activator | uPA | ● | ● | ● | ● | ● | ● | |
| | tPA | | | | | | | |
| | Cathepsin A | | | | | | | |
| | Cathepsin G | | | | | | | |
| | Plasmin | | | | | | | |
| | C1s | | | | | | | |
| | MASP2 | | | | | | | |
| | Thrombin | | | | | | | |
| | Trypsin | | | | | | | |
| | Chymotrypsin | | | | | | | |
| | Elastase 1 | | | | | | | |
| Leucocyte/Neut Elastase | Elastase 2 | | | | | | | |
| Leucocyte/Neut Elastase | Elastase 2 | | | | | | | |
| MT-SP1/ST14 | Matriptase | | | | | | | |
| MT-SP2 | Matriptase2 | | | | | | | |
| TMPRSS1 | Hepsin | | | | | | | |
| | TMPRSS2 | | | | | | | |
| | TMPRSS3 | | | | | | | |
| | TMPRSS4 | | | | | | | |
| PSA | Prostate Specific Antigen | | | | | | | |
| Leucocyte/Neut Elastase | Elastase 2 | | | | | | | |
| MT-SP1/ST14 | Matriptase | | | | | | | |
| MT-SP2 | Matriptase2 | | | | | | | |
| TMPRSS1 | Hepsin | | | | | | | |
| | TMPRSS2 | | | | | | | |
| | TMPRSS3 | | | | | | | |
| | TMPRSS4 | | | | | | | |
| PSA | Prostate Specific Antigen | | | | | | | |
| Cysteine | | | | | | | | |
| | Cathepsin B | | | | | | | |
| | Cathepsin L | | | | | | | |
| | Cathepsin F | | | | | | | |
| | Cathepsin H | | | | | | | |
| | Cathepsin K | | | | | | | |
| | Cathepsin L1 | | | | | | | |
| | Cathepsin L2 | | | | | | | |
| | Cathepsin O | | | | | | | |
| | Cathepsin W | | | | | | | |
| | Cathepsin S | | | | | | | |
| | Cathepsin Z (or X) | | | | | | | |
| Aspartic | | | | | | | | |
| | Cathepsin D | | | | | | | |
| | Cathepsin E | | | | | | | |
| Metallo | | | | | | | | |
| Collagenase 1 | MMP1 | ● | | | | | | PMA Activated U937 and MCF7 cells, MDA-MB231 |
| Gelatinase A | MMP2 | | | | ● | ● | | Colo205, HT29 |
| Stromelysin | MMP3 | | | | | | | |
| | MMP4 | | | | | | | |
| | MMP5 | | | | | | | |
| | MMP6 | | | | | | | |

TABLE 4-continued

Matrix showing preferred protease cleavage sites for treating particular tumours

| | | | | |
|---|---|---|---|---|
| Matrilysin | MMP7 | | | |
| Collagenase 2 | MMP8 | | | |
| Gelatinase B | MMP9 | ● | | MCF7, PC3 |
| | MMP10 | | | |
| | MMP11 | | | |
| | MMP12 | | | |
| | MMP13 | | | |
| | MMP14 | | | |
| | MMP15 | | | |
| | MMP16 | | | |
| | MMP17 | | | |
| | MMP18 | | | |
| | MMP19 | | THP-1, HL-60 | |
| | MMP20 | | | |
| | MMP21 | | | |
| | MMP23A | | | |
| | MMP23B | | | |
| | MMP24 | | | |
| | MMP25 | | | |
| | MMP26 | | | |
| | MMP27 | | | |
| | MMP28 | | | |
| | ADAM2 | | | |
| | ADAM7 | | | |
| | ADAM8 | | | |
| | ADAM9 | | | |
| | ADAM10 | | | |
| Metallo | | | | |
| | ADAM11 | | | |
| | ADAM12 | | | |
| | ADAM15 | | | |
| | ADAM17 | | | LNCaP, MDA-MB231, MCF7 express ADAM17. Colo205 express barely any |
| | ADAM18/27 | | | |
| | ADAM19 | | | |
| | ADAM20 | | | |
| | ADAM21/31 | | | |
| | ADAM22 | | | |
| | ADAM23 | | | |
| | ADAM28 | | | |
| | ADAM29 | | | |
| | ADAM30 | | | |
| | ADAM33 | | | |
| | ADAMTS1 | | | |
| | ADAMTS2 | | | |
| | ADAMTS3 | | | |
| | ADAMTS4 | | | |
| | ADAMTS5/11 | | | |
| | ADAMTS6 | | | |
| | ADAMTS7 | | | |
| | ADAMTS8 | | | |
| | ADAMTS9 | | | |
| | ADAMTS10 | | | |
| | ADAMTS12 | | | |
| | ADAMTS13 | | | |
| | ADAMTS14 | | | |
| | ADAMTS15 | | | |
| | ADAMTS16 | | | |
| | ADAMTS17 | | | |
| | ADAMTS18 | | | |
| | ADAMTS19 | | | |
| | ADAMTS20 | | | |

TABLE 5

| Tumour sites in which ADAM overexpression has been reported | |
|---|---|
| Protein | Tumour expression |
| ADAM8 | Brain, kidney, lung, pancreas |
| ADAM9 | Breast, gastric, liver, lung, pancreas, prostate |
| ADAM10 | Colon, gastric, leukaemia, prostate, uterus, ovary |
| ADAM12 | Bladder, brain, breast, colon, gastric, liver |
| ADAM15 | Breast, gastric, lung, prostate |
| ADAM17 | Brain, breast, colon, gastric, kidney, liver, lung, ovary, pancreas, prostate |
| ADAM19 | Brain, kidney |
| ADAM28 | Breast, kidney, lung |

A number of the proteolytic ADAMs (a disintegrin and metalloproteinase) have been detected in cancers and mRNA or protein levels have been found to be upregulated relative to normal tissue (adapted from Nature Reviews Cancer 8, 932-941 (December 2008)|doi: 10.1038/nrc2459).

In one embodiment, the protease may be an esterase.

Other cleavage sites include linkages which are labile under certain conditions in the vicinity of unwanted cells (eg tumour microenvironment). For example, the cleavage site may comprise disulphide bonds, which can be reduced in the hypoxic tumour microenvironment, or may comprise pH sensitive moieties that break in acidic conditions. It will be understood, however, that the cleavage site must be selectively cleavable in the vicinity of the unwanted cells and so such linkages must be more labile and preferably only labile in the vicinity of unwanted cells compared to in the vicinity of wanted cells.

Alternatively, the cleavage site may comprise nucleic acid (eg DNA or RNA) that is selectively cleavable in the vicinity of unwanted cells (eg by nucleases). Other cleavage sites include phosphate, lipid or disulphide containing moieties that may be cleavable by appropriate enzymes.

Synthesis of Agent of Invention

Conveniently, the T cell antigen is joined to the targeting moiety by a linker. By 'linker' we include the meaning of a chemical moiety that attaches the targeting moiety to the T cell antigen, and which comprises a cleavage site that is cleavable selectively in the vicinity of the unwanted cells as described herein.

It is appreciated that the T cell antigen may either be bound covalently or non-covalently to the targeting moiety.

Preferably, the T cell antigen is covalently attached to the targeting moiety.

In one embodiment, the T cell antigen and targeting moiety are covalently attached by a linker.

Thus, the T cell antigen (e.g. peptide) and targeting moiety may be conveniently linked by any of the conventional ways of cross-linking molecules, such as those generally described in O'Sullivan et al *Anal. Biochem.* (1979) 100, 100-108, and as described in Example 2. For example, one of the T cell antigen (e.g. peptide) or targeting moiety may be enriched with thiol groups and the other reacted with a bifunctional agent capable of reacting with those thiol groups, for example the N-hydroxysuccinimide ester of iodoacetic acid (NHIA) or N-succinimidyl-3-(2-pyridyldithio)propionate (SPDP), a heterobifunctional cross-linking agent which incorporates a disulphide bridge between the conjugated species. Amide and thioether bonds, for example achieved with m-maleimidobenzoyl-N-hydroxysuccinimide ester, are generally more stable in vivo than disulphide bonds.

It is known that bis-maleimide reagents allow the attachment of a thiol group (e.g. thiol group of a cysteine residue of an antibody) to another thiol-containing moiety (e.g. thiol group of a T cell antigen or a linker intermediate), in a sequential or concurrent fashion. Other functional groups besides maleimide, which are reactive with a thiol group include iodoacetamide, bromoacetamide, vinyl pyridine, disulfide, pyridyl disulfide, isocyanate, and isothiocyanate.

Further useful cross-linking agents include S-acetylthioglycolic acid N-hydroxysuccinimide ester (SATA) which is a thiolating reagent for primary amines which allows deprotection of the sulphydryl group under mild conditions (Julian et al (1983) *Anal. Biochem.* 132, 68), dimethylsuberimidate dihydrochloride and N,N'-o-phenylenedimaleimide.

Particularly preferred crosslinking agents include sulfosuccinimidyl 4-[N-maleimidomethyl]cyclohexane-1-carboxylate (Sulfo-SMCC), sulfosuccinimidyl 6-(3'-[2-pyridyldithio]-propionamido) hexanoate (Sulfo-LC-SPDP) and N-[ß-Maleimidopropionic acid] hydrazide, trifluoroacetic acid salt (BMPH).

It will be understood that a large number of homobifunctional and heterobifunctional crosslinking chemistries would be appropriate to join the targeting moiety to the T cell antigen, and any such chemistry may be used. For example, Click Chemistry using Staudinger Ligation Chemistry (phosphine-azido chemistry) may be used.

It is appreciated that the T cell antigen and targeting moiety do not need to be cross-linked directly to each other, but may be attached via one or more spacer moieties. For example, the T cell antigen may be crosslinked to a chemical moiety which in turn is crosslinked to the targeting moiety. In one embodiment, such a spacer moiety may comprise a cleavage site that is cleavable selectively in the vicinity of the unwanted cells, as discussed below. It will be appreciated that the spacer moiety may serve to prevent steric hindrance and facilitate protease cleavage.

Tables 6 and 7 provide examples of suitable T cell antigen peptides and how they may be incorporated into the agent of the invention. For example, the T cell antigen peptide may be joined to a protease cleavage site via a first spacer moiety, and the protease cleavage site in turn joined to a linker moiety via a second spacer moiety. The linker may be used to attach the final peptide to the targeting moiety. Tables 6 and 7 also list the proteases that cleave the corresponding protease cleavage sites.

Further examples of peptides containing a T cell antigen and protease cleavage site, that may be incorporated into the agent of the invention (e.g. by attachment to an appropriate targeting moiety such as an antibody) are listed in the table below.

| Peptide sequence | Epitope | Protease that sequence is cleavable by |
|---|---|---|
| KTPRVTGGGAMAIPVSLRSGGGGSGGGGSC (SEQ ID No: 273) | TPRVTGGGAM (SEQ ID No: 31) | MMP2 |
| DDYSNTHSTRYVTIPVSLRSGGGGSGGGGSC (SEQ ID No: 274) | DYSNTHSTRYV (SEQ ID No: 55) | MMP2 |
| RNLVPMVATVQIPVSLRSGGGGSGGGGSC (SEQ ID No: 275) | NLVPMVATV (SEQ ID No: 21) | MMP2 |
| CSGGGGSGGGGAIPVSLRANLVPMVATV (SEQ ID No: 276) | NLVPMVATV (SEQ ID No: 21) | MMP2 |
| YVLEETSVMLIPVSLRSGGGGSGGGGSC (SEQ ID No: 277) | YVLEETSVM (SEQ ID No: 3) | MMP2 |
| NLVPMVATVQGALALALALC (SEQ ID No: 278) | NLVPMVATV (SEQ ID No: 21) | CD10 |
| NLVPMVATVQGPLGALALALALALALALALALALALC (SEQ ID No: 279) | NLVPMVATV (SEQ ID No: 21) | CD10 |
| NLVPMVATVLPRSAKELRC (SEQ ID No: 280) | NLVPMVATV (SEQ ID No: 21) | MT1-MMP |

In a particularly preferred embodiment when the T cell antigen is a peptide, the T cell antigen peptide is attached to the targeting moiety, either directly or indirectly through a spacer moiety, at its N-terminus. This is illustrated in FIG. 9B, which lists three peptides that comprise a T cell epitope and a protease cleavage site. Peptides (i) and (ii) have the T cell epitope at the N-terminus so that the epitope is attached to the targeting moiety via a spacer moiety (comprising a protease cleavage site and a cysteine coupling residue) joined to the C-terminus of the epitope. In contrast, peptide (iii) comprises the same T cell epitope but the epitope is attached to the targeting moiety via a spacer moiety (comprising a protease cleavage site and a cysteine coupling reside) joined to the N-terminus of the epitope. In peptides (i) and (ii), the N-terminus of the T-cell epitope is further away from the targeting moiety (configuration: N terminus-(T cell epitope)-C-terminus—Targeting moiety), whereas in peptide (iii), the C-terminus of the T-cell epitope is further away from the targeting moiety (configuration: C-terminus-(T cell epitope)-N-terminus—Targeting moiety). In other words, the configuration of peptide (iii) is the reverse of that of peptides (i) and (ii). Although both configurations may be used in the context of the invention, the configuration of peptide (iii) is preferred. Table 7 provides examples of a suitable T cell antigen and how it may be incorporated into the agent of the invention such that the T cell antigen would be attached to the targeting moiety, either directly or indirectly through a spacer moiety at its N-terminus.

In view of the above, it is appreciated that the invention provides an agent for preventing or treating a condition characterised by the presence of unwanted cells, the agent comprising (i) a targeting moiety that is capable of targeting to the unwanted cells; (ii) a T cell antigen; and (iii) a cleavable site between the targeting moiety and T cell antigen, wherein the cleavable site can be selectively cleaved in the vicinity of the unwanted cells.

In a specific embodiment where the T cell antigen and targeting moiety are covalently attached and where both the antigen and targeting moiety are peptides or polypeptides, it is appreciated that the two components may be part of a fusion polypeptide that may be encoded by a nucleic acid molecule. The invention includes such a nucleic acid molecule and host cells containing them. For example, an antibody targeting moiety may be genetically engineered to contain the T cell antigen using genetic engineering techniques well established in the art. Thus, it will be appreciated that the T cell antigen may be embedded within the polypeptide sequence of the targeting moiety, provided that it can be released so as to be capable of being presented on an unwanted cell to elicit a T cell response. For example, the T cell antigen may reside within the polypeptide of the targeting moiety and be flanked by two cleavage sites which each may be selectively cleaved in the vicinity of the unwanted cell. Alternatively, the T cell antigen may reside at one terminus of the targeting moiety and be released by virtue of one cleavage site being cleaved. Suitably, the T cell antigen and the targeting moiety are joined so that both portions retain their respective activities such that the agent may be targeted to an unwanted cell and the T cell antigen may be presented by the unwanted cell so as to elicit an immune response. The T cell antigen and targeting moiety portions are typically joined by a linker peptide which comprises a cleavage site that is cleavable selectively in the vicinity of the unwanted cells as described below. Suitable linker peptides are those that typically adopt a random coil conformation, for example the polypeptide may contain alanine or proline or a mixture of alanine plus proline residues. Preferably, the linker contains between 2 and 100 amino acid residues, more preferably between 2 and 50 and still more preferably between 4 and 20. A particular example of having both the targeting moiety and T cell antigen as part of the same polypeptide is illustrated in FIG. 7, wherein an ScFv antibody-like fragment, a protease cleavage site and a T-cell epitope are encoded as a single polypeptide chain. It will be appreciated that such polypeptides are within the scope of the invention including the polypeptide of the specific example given in FIG. 7D.

Polynucleotides which encode suitable targeting moieties are known in the art or can be readily designed from known sequences such as from sequences of proteins known to interact with surface markers expressed on unwanted cells or contained in nucleotide sequence databases such as the GenBank, EMBL and dbEST databases.

Polynucleotides which encode suitable T cell antigens are known in the art or can readily be designed from known sequences and made.

Polynucleotides which encode suitable linker peptides can readily be designed from linker peptide sequences and made.

Thus, polynucleotides which encode the agents used in the invention can readily be constructed using well known genetic engineering techniques.

TABLE 6

Examples of peptide T cell antigens, spacers and linkers. By 'final peptide' we mean the peptide that is attached to the targeting moiety, for example by crosslinkind via a cysteine thiol group

| Epitope | Spacer 1 | Cleavage | Spacer2 | Linker | Final Peptide | Protease |
|---|---|---|---|---|---|---|
| NLVPMVATV (SEQ ID No: 21) | Q | KWNKVVALSR (SEQ ID No: 281) | ASALASAL (SEQ ID No: 282) | C | NLVPMVATVQKWNKWALSRASALASALC (SEQ ID No: 283) | |
| NLVPMVATV (SEQ ID No: 21) | Q | HSSKLQL (SEQ ID No: 266) | GGGSGGGGS (SEQ ID No: 284) | C | NLVPMVATVQHSSKLQLGGGSGGGGSC (SEQ ID No: 285) | PSA |
| NLVPMVATV (SEQ ID No: 21) | Q | GGGGF (SEQ ID No: 267) | GGGGFGGGGF (SEQ ID No: 286) | C | NLVPMVATVQGGGGFGGGGFGGGGFC (SEQ ID No: 287) | Cathepsin B |
| NLVPMVATV (SEQ ID No: 21) | Q | KQSRKFVP (SEQ ID No: 264) | GGGSGGGGS (SEQ ID No: 284) | C | NLVPMVATVQKQSRKFVPGGGSGGGGSC (SEQ ID No: 288) | Matriptase |
| NLVPMVATV (SEQ ID No: 21) | Q | CPGRVVGG (SEQ ID No: 254) | GGGSGGGGS (SEQ ID No: 284) | C | NLVPMVATVQCPGRVVGGGGGSGGGGSC (SEQ ID No: 289) | UPa |
| NLVPMVATV (SEQ ID No: 21) | Q | YLGRSYKV (SEQ ID No: 257) | GGGSGGGGS (SEQ ID No: 284) | C | NLVPMVATVQYLGRSYKVGGGSGGGGSC (SEQ ID No: 290) | C1s |
| NLVPMVATV (SEQ ID No: 21) | Q | GPQGIASQ (SEQ ID No: 291) | GGGSGGGGS (SEQ ID No: 284) | C | NLVPMVATVQGPQGIASQGGGSGGGGSC (SEQ ID No: 292) | MMP2/MMP9 |
| NLVPMVATV (SEQ ID No: 21) | Q | PQG-IAGQ (SEQ ID No: 269) | GGGSGGGGS (SEQ ID No: 284) | C | NLVPMVATVQPQG-IAGQGGGSGGGGSC (SEQ ID No: 293) | MMP2/MMP9 |
| NLVPMVATV (SEQ ID No: 21) | Q | VLKVLKVLK (SEQ ID No: 294) | GGGSGGGGS (SEQ ID No: 284) | C | NLVPMVATVQVLKVLKVLKGGGSGGGGSC (SEQ ID No: 295) | |

TABLE 7

Examples of peptide T cell antigens, spacers and linkers. By 'final peptide' we mean the peptide that is attached to the targeting moiety, for example by crosslinkind via a cysteine thiol group

| Linker | Spacer 1 | Cleavage | Spacer 2 | Epitope | Final Peptide | Protease |
|---|---|---|---|---|---|---|
| C | SGGGGSGGGG (SEQ ID No: 296) | CPGRVVGG (SEQ ID No: 254) | A | NLVPMVATV (SEQ ID No: 21) | CSGGGGSGGGGCPGRVVGGANLVPMVATV (SEQ ID No: 297) | uPa/tPA |
| C | SGGGGSGGGG (SEQ ID No: 296) | GGR | A | NLVPMVATV (SEQ ID No: 21) | CSGGGGSGGGGGGRANLVPMVATV (SEQ ID No: 298) | Plasmin/ TMPRSS2 |
| C | SGGGGSGGGG (SEQ ID No: 296) | YLGRSYKV (SEQ ID No: 257) | A | NLVPMVATV (SEQ ID No: 21) | CSGGGGSGGGGYLGRSYKVANLVPMVATV (SEQ ID No: 299) | C1s |

TABLE 7-continued

Examples of peptide T cell antigens, spacers and linkers. By 'final peptide' we mean the peptide that is attached to the targeting moiety, for example by crosslinkind via a cysteine thiol group

| Linker | Spacer 1 | Cleavage | Spacer 2 | Epitope | Final Peptide | Protease |
|---|---|---|---|---|---|---|
| C | SGGGGSGGGG (SEQ ID No: 296) | SLGRKIQI (SEQ ID No: 259) | A | NLVPMVATV (SEQ ID No: 21) | CSGGGGSGGGGSLGRKIQIANLVPMVATV (SEQ ID No: 300) | MASP2 |
| C | SGGGGSGGGG (SEQ ID No: 296) | LVPRGS (SEQ ID No: 260) | A | NLVPMVATV (SEQ ID No: 21) | CSGGGGSGGGGLVPRGSANLVPMVATV (SEQ ID No: 301) | Thrombin |
| C | SGGGGSG (SEQ ID No: 302) | GGGR (SEQ ID No: 303) | A | NLVPMVATV (SEQ ID No: 21) | CSGGGGSGGGGRANLVPMVATV (SEQ ID No: 304) | Trypsin |
| C | SGGGGSGGGG (SEQ ID No: 296) | AAPV (SEQ ID No: 262) | A | NLVPMVATV (SEQ ID No: 21) | CSGGGGSGGGGAAPVANLVPMVATV (SEQ ID No: 305) | Elastase 2 |
| C | SGGGGSGGGG (SEQ ID No: 296) | KQLRVVNG (SEQ ID No: 263) | A | NLVPMVATV (SEQ ID No: 21) | CSGGGGSGGGGKQLRVVNGANLVPMVATV (SEQ ID No: 306) | MT-SP1/ST14 |
| C | SGGGGSGGGG (SEQ ID No: 296) | SSKYQ (SEQ ID No: 265) | A | NLVPMVATV (SEQ ID No: 21) | CSGGGGSGGGGSSKYQANLVPMVATV (SEQ ID No: 307) | PSA |
| C | SGGGGSGGGG (SEQ ID No: 296) | GGGGF (SEQ ID No: 267) | A | NLVPMVATV (SEQ ID No: 21) | CSGGGGSGGGGGGGGFANLVPMVATV (SEQ ID No: 308) | Cathepsin B |

The nucleic acid is then expressed in a suitable host to produce an agent of the invention. Thus, the nucleic acid encoding the agent of the invention may be used in accordance with known techniques, appropriately modified in view of the teachings contained herein, to construct an expression vector, which is then used to transform an appropriate host cell for the expression and production of the agent of the invention of the invention.

It is appreciated that the nucleic acid encoding the agent of the invention may be joined to a wide variety of other nucleic acid sequences for introduction into an appropriate host. The companion nucleic acid will depend upon the nature of the host, the manner of the introduction of the nucleic acid into the host, and whether episomal maintenance or integration is desired, as is well known in the art.

In an alternative embodiment, the T cell antigen and targeting moiety are non-covalently attached. For non-covalent bindings, immunological bindings or such binding as via biotin/avidin or streptavidin, respectively, are preferred. For example, the targeting moiety may be a bispecific antibody, one specificity of which is directed to an entity expressed by the unwanted cell and one specificity of which is directed to the T cell antigen or part thereof. Also, it is possible to couple the T cell antigen to another substance against which, in turn, the specificity of the bispecific antibody will be directed to. For instance, the T cell antigen may contain further peptidic sequences which are recognised by the bispecific antibody. Another possibility involves coupling the targeting moiety, for example to streptavidin whilst the T cell antigen is coupled to biotin, and vice versa. Other means by which non-covalent interactions can be formed include leucine zipper sequences or affinity bonds. In any event, between the T cell antigen and targeting moiety there must be a cleavage site that is cleavable selectively in the vicinity of the unwanted cells, such that the T cell antigen can be released from the targeting moiety.

Amino acid residues described herein are generally in the natural "L" isomeric form. However, residues in the "D" isomeric form can be substituted for L-amino acid residues in certain situations, provided that the agent of the invention still retains its function, namely to prevent or treat a condition characterised by the presence of unwanted cells. The definition also includes, unless otherwise specifically indicated, chemically-modified amino acids, including amino acid analogues (such as penicillamine, 3-mercapto-D-valine), naturally-occurring non-proteogenic amino acids (such as norleucine), beta-amino acids, azapeptides, N-methylated amino acids and chemically-synthesised compounds that have properties known in the art to be characteristic of an amino acid. The term "proteogenic" indicates that the amino acid can be incorporated into a protein in a cell through well-known metabolic pathways. The definition also includes amino acids in which the functional side group has been chemically derivatised. Such derivatised molecules include, for example, those molecules in which free amino groups have been derivatised to form amine hydrochlorides, p-toluene sulfonyl groups, carbobenzoxy groups, t-butyloxycarbonyl groups, chloroacetyl groups or formyl groups. Free carboxyl groups may be derivatised to form salts, methyl and ethyl esters or other types of esters or hydrazides. Free hydroxyl groups may be derivatised to form O-acyl or O-alkyl derivatives. Also included as derivatives are those peptide portions that contain one or more naturally occurring amino acid derivatives of the twenty standard amino acids.

Accordingly, it is appreciated that the peptide portions of the agent of the invention can be peptide "mimetics", i.e. peptidomimetics which mimic the structural features of peptides comprising or consisting of the amino acid sequence as described herein. Peptidomimetics can be even more advantageous in therapeutic use, in the resistance to degradation, in permeability or in possible oral administration.

A primary goal in the design of peptide mimetics has been to reduce the susceptibility of mimetics to cleavage and inactivation by peptidases. In one approach, such as disclosed by Sherman et al (1990), one or more amide bonds have been replaced in an essentially isosteric manner by a variety of chemical functional groups. This stepwise approach has met with some success in that active analogues have been obtained. In some instances, these analogues have been shown to possess longer biological half-lives than their naturally-occurring counterparts. In another approach, a variety of uncoded or modified amino acids such as D-amino acids and N-methyl amino acids have been used to modify mammalian peptides. Alternatively, a presumed bioactive conformation has been stabilised by a covalent modification, such as cyclization or by incorporation of γ-lactam or other types of bridges (Veber et al, 1978) and Thorsett et al, 1983). Another approach, disclosed by Rich (1986) has been to design peptide mimics through the application of the transition state analogue concept in enzyme inhibitor design. For example, it is known that the secondary alcohol of statine mimics the tetrahedral transition state of the sessile amide bond of the pepsin substrate. Other approaches include the use of azapeptides and beta-amino acids.

Also included in the definition of 'peptidomimetics', are retro-inverso peptides. By retro-inverso peptides (also known as all-D-retro or retro-enantio peptides) we include the meaning of a peptide in which all of the L-amino acids are replaced with D-amino acids and the peptide bonds are reversed. Thus, the peptides are composed of D-amino acids assembled in the reverse order from that of the parent L-sequence. Retro-inverso peptides can be synthesised by methods known in the art, for example such as those described in Meziere et al (1997) *J. Immunol.* 159 3230-3237. This approach involves making pseudopeptides containing changes involving the backbone, and not the orientation of side chains which remain very similar to the parent peptide. Retro-inverse peptides are much more resistant to proteolysis.

Therefore, it will be appreciated that when any of the targeting moiety, T cell antigen, cleavage site, spacer moieties and targeting moiety as described herein are peptides or polypeptides, any one or more of those peptides or polypeptides may be substituted for a corresponding peptidomimetic that retains the respective activity of the parent peptide or polypeptide. This may help to confer protease resistance on the agent of the invention and thereby improve its stability. Thus, for example, when a T cell antigen is attached to a targeting moiety via one or more peptide spacer moieties, it may be desirable for one or more of those spacer moieties to be peptidomimetics, e.g. wherein one or more of the naturally occurring amino acids of the spacer moieties are replaced or modified, for example, to improve stability.

Another approach to increase stability of peptide portions of the agent of the invention is to have stabilising groups at one or both termini. Typical stabilising groups include amido, acetyl, benzyl, phenyl, tosyl, alkoxycarbonyl, alkyl carbonyl, benzyloxycarbonyl and the like end group modifications. Additional modifications include using a "D" amino acid in place of a "L" amino acid at the termini, and amide rather than amino or carboxy termini or acetyl rather than amino termini, to inhibit exopeptidase activity. Thus, it is appreciated that whenever the agent of the invention has an exposed peptide terminus, that terminus may have a capping moiety, preferably a moiety that is less than 200 Da in molecular weight. Further capping moieties include a naftyl group or a polyethylene glycol group. It is appreciated that retro-inverso peptides are already relatively stable and so may not require additional capping moieties.

Preferably, the agent of the invention has a half-life in plasma of at least 24 hours at 37° C.

It may be desirable to modify the agent of the invention so that it can be more easily detected, for example by biotinylating it or by incorporating any detectable label known in the art such as radiolabels, fluorescent labels or enzymatic labels.

A particular preferred embodiment of the invention provides an agent for preventing or treating cancer, the agent comprising:

i) a targeting moiety that is capable of targeting to the cancer; and ii) an immunogenic T cell peptide, wherein the T cell peptide can be released from the targeting moiety by selective cleavage in the vicinity of the cancer.

The cancer may be any cancer such as breast cancer, ovarian cancer, endometrial cancer, cervical cancer, bladder cancer, renal cancer, melanoma, lung cancer, prostate cancer, testicular cancer, thyroid cancer, brain cancer, oesophageal cancer, gastric cancer, pancreatic cancer, colorectal cancer, liver cancer, leukaemia, myeloma, non-Hodgkin's lymphoma, Hodgkin's lymphoma, acute myeloid leukaemia, acute lymphoblastic leukaemia, chronic lymphoblastic leukaemia, lymphoproliferative disorder, myelodysplastic disorder, myeloproliferative disease and premalignant disease.

As described above, the inventors have shown that agents of the invention may be used to redirect existing immune responses to kill particular unwanted cells in a specific manner. Since any unwanted cell may be targeted in this way, the agents of the invention offer significant therapeutic potential.

Accordingly, a second aspect of the invention provides a method of preventing or treating a condition characterised by the presence of unwanted cells, the method comprising administering an agent according to the first aspect of the invention to a subject.

Thus, the method may involve identifying a subject who has a condition or who is at risk of developing a condition characterised by unwanted cells (eg cancer), administering the agent according to the first aspect of the invention to the subject, and monitoring the levels of the unwanted cells in the subject either by conducting tests to determine the number of unwanted cells or by monitoring the clinical symptoms of the subject. Depending on the results of the monitoring step, it may be necessary to administer more of the agent.

Similarly, the invention includes an agent according to the first aspect of the invention for use in preventing or treating a condition characterised by the presence of unwanted cells.

The invention also includes the use of an agent according to the first aspect of the invention in the manufacture of a medicament for preventing or treating a condition characterised by the presence of unwanted cells.

Preferences for the condition and unwanted cells, are as described above with respect to the first aspect of the invention. Preferably, the unwanted cells are tumour cells and the condition is a tumour.

By preventing or treating a condition we include the meaning of reducing or alleviating symptoms in a patient (i.e. palliative use), preventing symptoms from worsening or progressing, treating the disorder (e.g. by inhibition or elimination of the causative agent), or prevention of the condition or disorder in a subject who is free therefrom.

It will be appreciated that the agents of the invention lend themselves to personalised medicine in the clinic whereby the most appropriate agent to be administered to the patient is determined, and either selected or prepared in the clinic. For example, before the step of administering the agent to the subject, any one of the following may be determined: (i) the MHC alleles of the subject, (ii) the cytotoxic T cell response of the subject to a T cell antigen and (iii) the expression profile of the unwanted cell with regards to a molecule which may be the target of the targeting moiety and/or an enzyme which is able to cleave the cleavage site in the agent of the invention. The MHC alleles of a subject can be assessed by serological assays at the antigen level or by using DNA assays at the genetic level. Determining whether a given antigen stimulates a specific cytotoxic T cell response in a subject can be done by contacting isolated peripheral mononuclear blood cells from the subject with the antigen and using standard assays for cell proliferation. Assessing the expression profile of the unwanted cell may be carried out on a biopsy sample using routine assays for measuring nucleic acid (e.g. DNA or RNA transcripts) or protein levels. For example, transcriptomic or proteomic techniques may be used. In this way, it will be possible to identify tailored targeting moieties that bind specifically to, for example, surface markers expressed by the unwanted cell. It may also be possible to identify appropriate protease cleavage sites that may be selectively cleaved in the vicinity of the unwanted cells.

Thus the method of the second aspect of the invention may include the steps of (i) identifying a subject who has a condition, or who is at risk of developing a condition characterised by the presence of unwanted cells (eg cancer), (ii) taking a sample from the subject, (iii) analysing the sample to identify the optimum targeting moiety, T cell antigen and/or cleavage site for preventing or treating the condition in that subject, (iii) preparing the agent of the invention, (iv) administering the agent to the subject, and (v) monitoring the levels of unwanted cells in the subject either by conducting tests to determine the number of unwanted cells or by monitoring the clinical symptoms of the subject.

It is appreciated that an apparatus may be used to select and optionally prepare the most appropriate agent to be used for a particular patient. For example, the apparatus may perform an automated analysis of one or more samples from the subject, and based on this analysis select and optionally prepare a tailor-made agent for that subject. Thus the apparatus may perform serological assays on the sample to determine a subject's MHC alleles and based on this test various peptides for their efficiency in eliciting cytotoxic T cell response, so as to identify the best T cell antigen for use in that patient. Similarly, the apparatus may carry out an expression profile of unwanted cells from the subject (eg from a biopsy sample) so as to determine a suitable targeting moiety that will bind to the unwanted cell and/or determine a suitable cleavage site that will be selectively cleaved in the vicinity of the unwanted cell.

By performing any one or more of these steps in the clinic an agent tailored for a particular subject can be prepared. For example, the agent can contain a T cell antigen that is known to bind to patient's MHC molecules and elicit a strong T cell response, a targeting moiety that is known to bind selectively to surface markers expressed by the unwanted cell, and a protease cleavage site that allows the release of the T cell antigen in the vicinity of the unwanted cells.

In one embodiment, the subject is administered a further therapeutic agent in addition to the agent according to the first aspect of the invention. For example, when administering the agent to prevent or treat a particular condition, a further therapeutic agent known to be useful for combating that condition may be administered. As an example, when the agent is for treating cancer, a further anti-cancer agent (eg anti-neoplastic chemotherapy) may be administered to the subject alongside the agent of the invention. Similarly, the further therapeutic agent may be one that is known to have therapeutic application in allergic disease, inflammatory disease, regenerative medicine and neuroregenerative disease.

It is appreciated that the further therapeutic agent may be administered at the same time as the agent of the invention (i.e. simultaneous administration optionally in a co-formulation) or at a different time to the agent of the invention (i.e. sequential administration).

The further therapeutic agent may be any one or more of a vaccine; an immuno stimulatory drug; an anti-cancer agent; an agent inhibiting an antibody response against the agent of the invention; and/or a protease inhibitor.

For example, in order to boost the effector immune response against the particular T cell antigen used, it may be desirable to vaccinate the subject with the T cell antigen; and/or administer immunostimulating agents such as IL-2, IL-7, IFNα, GM-CSF, metformin, lenalidomide; and/or administer anti-immunoregulatory agents such as Ipilimumab; all of which may be considered as further therapeutic agents.

It is also appreciated that if the subject is one to whom is administered immunosuppressive agents, that these immunosuppressive agents are withdrawn from the subject (e.g. by suspending treatment) when or before being administered the agent of the invention.

Similarly, it may be desirable to employ methods aimed at circumventing any immunogenicity issues relating to the agent of the invention whereby an adverse antibody response is elicited in vivo. For example, the subject may also be administered one or more agents that are known to inhibit the activity of B cells, such as any of Rituximab, cyclophosphamide, Syk inhibitors, an anti-BAFF antibody (eg Belimumab), an anti-CD22 antibody, an anti-CD20 antibody and an anti-CD19 antibody, all of which may be considered as further therapeutic agents. In this case, it is particularly preferred if the inhibitor of B cells is administered to the subject prior to the agent of the invention, eg as a pre-treatment to ablate B cells.

In another embodiment, it may be appropriate to administer a particular protease inhibitor so as to improve the target selectivity of the agent of the invention. For example, if a targeting moiety is known to bind cells in both the heart and breast tissue, but only those in the breast are to be targeted, it may be desirable to administer an agent that selectively inhibits the protease responsible for releasing the T cell antigen, in the heart but not the breast. In other words, an agent is administered to inhibit a protease that is capable of releasing the T cell antigen but which protease resides in the vicinity (eg at or near the surface of) of wanted cells but not in the vicinity (eg at or near the surface of) of unwanted cells. This is particularly useful in the event that a protease cleavage site of the agent of the invention is cleavable by multiple proteases, some of which reside in the vicinity of unwanted cells and some of which reside in the vicinity of wanted cells. In this case, targeting specificity may be improved by administering a protease inhibitor that inhibits a protease that resides in the vicinity of wanted cells but nevertheless is capable of cleaving the cleavage site and therefore releasing the T cell antigen from the agent of the invention. The effect of administering the inhibitor would be to ensure that the T cell antigen is preferentially released in the vicinity of the unwanted cells. For instance, if a subject with cancer also has active rheumatoid arthritis where MMP2 and other proteases are active, and the one or more cleavage sites in the agent of the invention are cleavable by multiple proteases including MMP2, it may be beneficial to inhibit MMP2 to prevent cleavage of the agent at the arthritic joint but retain cleavage at the cancer site by another protease.

The invention thus includes a composition comprising (i) an agent according to the first aspect of the invention and (ii) a further therapeutic agent, for use in preventing or treating a condition characterised by the presence of unwanted cells. Given that the agent of the invention and the further therapeutic agent may be administered simultaneously or sequentially, it will be appreciated that the invention includes an agent according to the first aspect of the invention for use in preventing or treating a condition characterised by the presence of unwanted cells in a subject who is administered a further therapeutic agent. It also follows that the invention includes a therapeutic agent for use in preventing or treating a condition characterised by the presence of unwanted cells in a subject who is administered an agent according to the first aspect of the invention.

Similarly, the invention includes a use of a composition comprising (i) an agent according to the first aspect of the invention and (ii) a further therapeutic agent, in the manufacture of a medicament for preventing or treating a condition characterised by the presence of unwanted cells. Again, given that the agent of the invention and the further therapeutic agent may be administered simultaneously or sequentially, it will be appreciated that the invention includes the use of a composition comprising an agent according to the first aspect of the invention in the manufacture of a medicament for preventing or treating a condition characterised by the presence of unwanted cells in a subject who is administered a further therapeutic agent. It also follows that the invention includes the use of a therapeutic agent in the manufacture of a medicament for preventing or treating a condition characterised by the presence of unwanted cells in a subject who is administered an agent according to the first aspect of the invention.

The invention also provides a composition comprising (i) an agent according to the first aspect of the invention and (ii) a further therapeutic agent suitable for preventing or treating the same condition characterised by the presence of unwanted cells. It is appreciated that the therapeutic agent mentioned in the immediately preceding two paragraphs may be agents suitable for treating the same condition characterised by the presence of unwanted cells, as treatable by the agents of the invention.

A third aspect of the invention provides an agent according to the first aspect of the invention for use in medicine.

A fourth aspect of the invention a pharmaceutical composition comprising an agent according to the first aspect of the invention, and a pharmaceutically acceptable carrier, diluent or excipient.

Whilst it is possible for the agent of the invention to be administered alone, it is preferable to present it as a pharmaceutical formulation, together with one or more acceptable carriers. The carrier(s) must be "acceptable" in the sense of being compatible with the therapeutic agent and not deleterious to the recipients thereof. Typically, the carriers will be water or saline which will be sterile and pyrogen free.

Where appropriate, the formulations may conveniently be presented in unit dosage form and may be prepared by any of the methods well known in the art of pharmacy. Such methods include the step of bringing into association the active ingredient (agent for treating or preventing a condition characterised by unwanted cells) with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The agent of the invention can be administered in the form of a suppository or pessary, or they may be applied topically in the form of a lotion, solution, cream, ointment or dusting powder. The agent may also be transdermally administered, for example, by the use of a skin patch.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The amount of the agent which is administered to the individual is an amount effective to combat the particular individual's condition. The amount may be determined by the physician.

Preferably, in the context of any aspect of the invention described herein, the subject to be treated is a human. Alternatively, the subject may be an animal, for example a domesticated animal (for example a dog or cat), laboratory animal (for example laboratory rodent, for example mouse, rat or rabbit) or an animal important in agriculture (i.e. livestock), for example horses, cattle, sheep or goats.

The invention provides a kit of parts for preventing or treating a condition characterised by the presence of unwanted cells, the kit comprising: (i) a targeting moiety that is capable of targeting to the unwanted cells and which is attached to a first binding partner, and (ii) a T cell antigen that is attached to a second binding partner which is capable of binding to the first binding partner, wherein the T cell antigen can be released from the second binding partner by selective cleavage of a cleavage site between the second binding partner and T cell antigen in the vicinity of the unwanted cells.

Preferences for the condition, unwanted cells, targeting moiety and T cell antigen are as defined above. It is particularly preferred if the kit of parts is for preventing or treating cancer.

By the first and second binding partners, we include the meaning of any two moieties which bind to each other selectively. Most preferably, the first and second binding partners only bind to each other and not to any other moieties. Non-covalent binding such as between biotin/avidin or streptavidin, or immunological bindings are preferred. Thus, the first binding partner may be biotin and the second binding partner may be avidin, and vice versa. Alternatively, the first binding partner may be an antigen and the second binding partner may be an antibody specific for that antigen, and vice versa. However, any pair of first and second binding partners that selectively bind to each other may be used, and suitable pairs will be known to the skilled person.

It will be appreciated that the kit allows one to first administer the targeting moiety to the subject, and establish the correct localisation of the targeting moiety in the subject (for example by the targeting moiety being detectably labelled (eg radiolabelled)) before administering the T cell antigen. The T cell antigen is then targeted to the unwanted cells by virtue of the second binding partner binding to the first binding partner. Once in the vicinity of the unwanted cells, the T cell antigen will be released from the second binding partner by selective cleavage of a cleavage site between the second binding partner and T cell antigen, allowing it to be presented on the surface of the unwanted cells so as to re-direct an existing immune response to the unwanted cells.

Accordingly, the invention further provides a method of preventing or treating a condition characterised by the presence of unwanted cells, the method comprising administering (i) a targeting moiety that is capable of targeting to the unwanted cells and which is attached to a first binding partner, and (ii) a T cell antigen that is attached to a second binding partner which is capable of binding to the first binding partner, wherein the T cell antigen can be released from the second binding partner by selective cleavage of a cleavage site between the second binding partner and T cell antigen in the vicinity of the unwanted cells, to the subject. Preferably, the targeting moiety is administered before the T cell antigen, for example to allow to correct localisation of the targeting moiety at the unwanted cells to be established. However, the targeting moiety may be administered at the same time as the T cell antigen.

Similarly, the invention provides a targeting moiety that is capable of targeting to unwanted cells and which is attached to a first binding partner, and a T cell antigen that is attached to a second binding partner which is capable of binding to the first binding partner, wherein the T cell antigen can be released from the second binding partner by selective cleavage of a cleavage site between the second binding partner and T cell antigen in the vicinity of the unwanted cells, for use in preventing or treating a condition characterised by unwanted cells in a subject. Preferably, the targeting moiety is administered before the T cell antigen, for example to allow to correct localisation of the targeting moiety at the unwanted cells to be established. However, the targeting moiety may be administered at the same time as the T cell antigen. It is appreciated that the targeting moiety and T cell antigen may be attached to each other by binding of the first and second binding partners.

A further kit of parts provided by the invention comprises (i) a targeting moiety that is capable of targeting to unwanted cells, (ii) a T cell antigen, and (iii) one or more means or reagents to assess one or more of a subject's (a) MHC alleles, (b) cytotoxic T cell response to a T cell antigen and (c) expression profile of an unwanted cell in the subject.

Preferences for the targeting moiety and T cell antigen include those as described herein. It will be appreciated that this kit of parts may be useful in tailoring a particular agent as defined in the first aspect of the invention for a given patient. Suitable means or reagents that can be used to assess a subject's (a) MHC alleles, (b) cytotoxic T cell response to a T cell antigen and (c) expression profile of an unwanted cell in the subject, are well known and widely available in the art. In one embodiment, the kit of parts comprises the agent of the first aspect of the invention and the kit may be used to determine whether that agent is suitable for a particular patient.

The invention also provides a molecule comprising (i) a T cell antigen and (ii) a cleavage site; wherein the cleavage site contains a linking moiety to allow the molecule to be attached to a targeting moiety which targeting moiety is capable of targeting to unwanted cells, and wherein the cleavage site can be selectively cleaved in the vicinity of the unwanted cells.

It is appreciated that the molecule may represent the part of the agent of the first aspect of the invention, without the targeting moiety. Thus, preferences for the T cell antigen, the cleavage site, how the cleavage site is attached to the targeting moiety (e.g. via a linker moiety comprising a thiol group such a cysteine residue), the targeting moiety and unwanted cells include all of those defined above with respect to the first aspect of the invention.

In a particular embodiment, the molecule comprises those final peptides listed in Table 6 above, wherein the 'epitope' listed in Table 6 corresponds to the T cell antigen of the molecule, and wherein the 'cleavage sequence' listed in Table 6 corresponds to the cleavage site. Thus, the molecule may comprise or consist of any of the peptides:

(SEQ ID No: 283)
NLVPMVATVQKWNKWALSRASALASALC, (SEQ ID No: 285)
NLVPMVATVQHSSKLQLGGGSGGGGSC, (SEQ ID No: 287)
NLVPMVATVQGGGGFGGGGFGGGGFC, (SEQ ID No: 288)
NLVPMVATVQKQSRKFVPGGGSGGGGSC, (SEQ ID No: 289)
NLVPMVATVQCPGRVVGGGGGSGGGGSC, (SEQ ID No: 290)
NLVPMVATVQYLGRSYKVGGGSGGGGSC, (SEQ ID No: 292)
NLVPMVATVQGPQGIASQGGGSGGGGSC, (SEQ ID No: 293)
NLVPMVATVQPQG-
IAGQGGGSGGGGSC,
and (SEQ ID No: 295)
NLVPMVATVQVLKVLKVLKGGGSGGGGSC.

In a particular embodiment, the molecule comprises those final peptides listed in Table 7 above, wherein the 'epitope' listed in Table 7 corresponds to the T cell antigen of the molecule, and wherein the 'cleavage site' listed in Table 7 corresponds to the cleavage site. Thus, the molecule may comprise or consist of any of the peptides:

(SEQ ID No: 297)
CSGGGGSGGGGCPGRVVGGANLVPMVATV, (SEQ ID No: 298)
CSGGGGSGGGGGGRANLVPMVATV, (SEQ ID No: 299)
CSGGGGSGGGGYLGRSYKVANLVPMVATV, (SEQ ID No: 300)
CSGGGGSGGGGSLGRKIQIANLVPMVATV, (SEQ ID No: 301)
CSGGGGSGGGGLVPRGSANLVPMVATV, (SEQ ID No: 304)
CSGGGGSGGGGRANLVPMVATV, (SEQ ID No: 305)
CSGGGGSGGGGAAPVANLVPMVATV, (SEQ ID No: 306)
CSGGGGSGGGGKQLRVVNGANLVPMVATV, (SEQ ID No: 307)
CSGGGGSGGGGSSKYQANLVPMVATV,
and (SEQ ID No: 308)
CSGGGGSGGGGGGGGFANLVPMVATV.

In another embodiment, the molecule comprises or consists of any of the following peptides:

(SEQ ID No: 273)
KTPRVTGGGAMAIPVSLRSGGGGSGGGGSC, (SEQ ID No: 274)
DDYSNTHSTRYVTIPVSLRSGGGGSGGGGSC,

-continued (SEQ ID No: 275)
RNLVPMVATVQIPVSLRSGGGGSGGGGSC, (SEQ ID No: 277)
YVLEETSVMLIPVSLRSGGGGSGGGGSC, (SEQ ID No: 278)
NLVPMVATVQGALALALALC, (SEQ ID No: 279)
NLVPMVATVQGPLGALALALALALALALALALALC,
or (SEQ ID No: 280)
NLVPMVATVLPRSAKELRC.

In an embodiment, the targeting moiety described herein is Cetuximab, the T cell antigen comprises NLVPMVATV (SEQ ID No: 21) and the cleavage site comprises a MMP14 cleavage sequence.

In an embodiment, the targeting moiety described herein is Rituximab, the T cell antigen comprises DYSNTHSTRYV (SEQ ID No: 55) and the cleavage site comprises a MMP2 cleavage sequence.

In an embodiment, the targeting moiety described herein is Rituximab, the T cell antigen is TPRVTGGGAM (SEQ ID No: 31) and the cleavage site comprises a MMP2 cleavage sequence.

In an embodiment, the targeting moiety described herein is hP67.6 (Gemtuzumab parent antibody), the T cell antigen is TPRVTGGGAM (SEQ ID No: 31) and the cleavage site comprises a MMP2 cleavage sequence.

In an embodiment, the targeting moiety described herein is Cetuximab, the T cell antigen comprises NLVPMVATV (SEQ ID No: 21) and the cleavage site comprises any of the following cleavage sequences: a uPa/tPa cleavage sequence (CPGR-VVGG) (SEQ ID No: 254), a Plasmin/TMPRSS2 cleavage sequence (GGR-X) (SEQ ID No: 256), a C1s cleavage (YLGR-SYKV) (SEQ ID No: 257), a MASP2 cleavage sequence (SLGR-KIQI) (SEQ ID No: 259), a thrombin cleavage sequence (LVPRGS) (SEQ ID No: 260), a trypsin cleavage sequence (XXXR-X) (SEQ ID No: 261), an elastase 2 cleavage sequence (AAPV-X) (SEQ ID No: 262), a MT-SP1/ST14 cleavage sequence (KQLR-VVNG) (SEQ ID No: 263), a PSA cleavage sequence (SSKYQ) (SEQ ID No: 265), or a Cathepsin B cleavage sequence (GGGG-F) (SEQ ID No: 267).

The invention will be described in further detail with the aid of the following Figures and Examples.

FIG. 1: MDA.MB.231 cells transduced with MMP14 stained with Cetuximab conjugated to NLVPMVATV (SEQ ID No: 21) containing MMP14 cleavage sequence (NLVPMVATVLPRSAKELRC (SEQ ID No: 280) linked to Cetuximab using Sulpho-SMCC).

FIG. 2: B-LCL cells stained with Rituximab conjugated to the HLA class-II peptide DYSNTHSTRYV (SEQ ID No: 55) containing a protease cleavage sequence (DDYSNTHSTRYVTIPVSLRSGGGGSGGGGSC) (SEQ ID No: 274).

FIG. 3: B-LCL cells stained with Rituximab conjugated to the HLA class-I peptide TPRVTGGGAM (SEQ ID No: 31) containing a protease cleavage sequence (KTPRVTGGGA-MAIPVSLRSGGGGSGGGGSC) (SEQ ID No: 273) linked to Rituximab using Sulpho-SMCC.

Figure 4A:
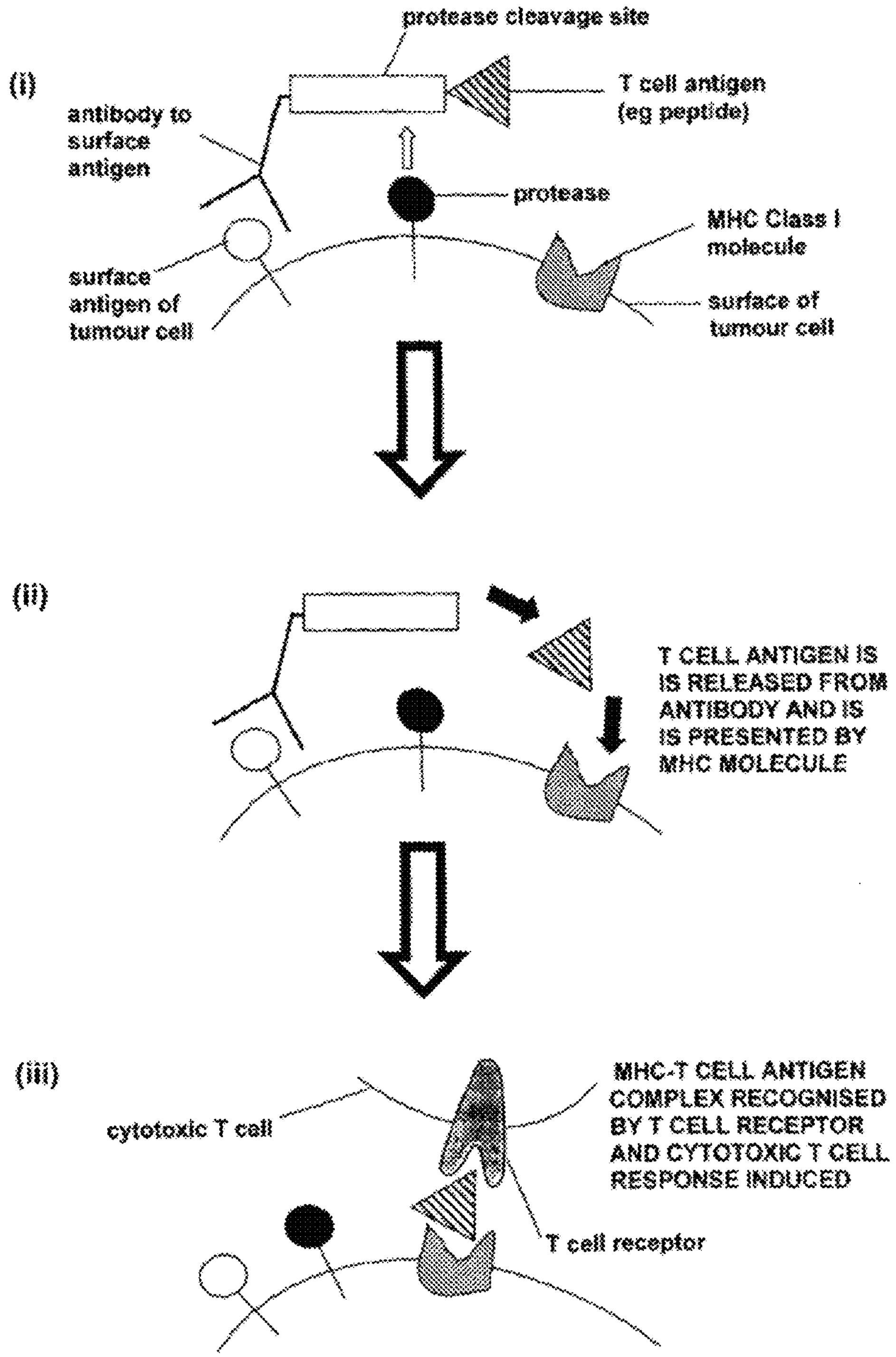
Figure 4B:
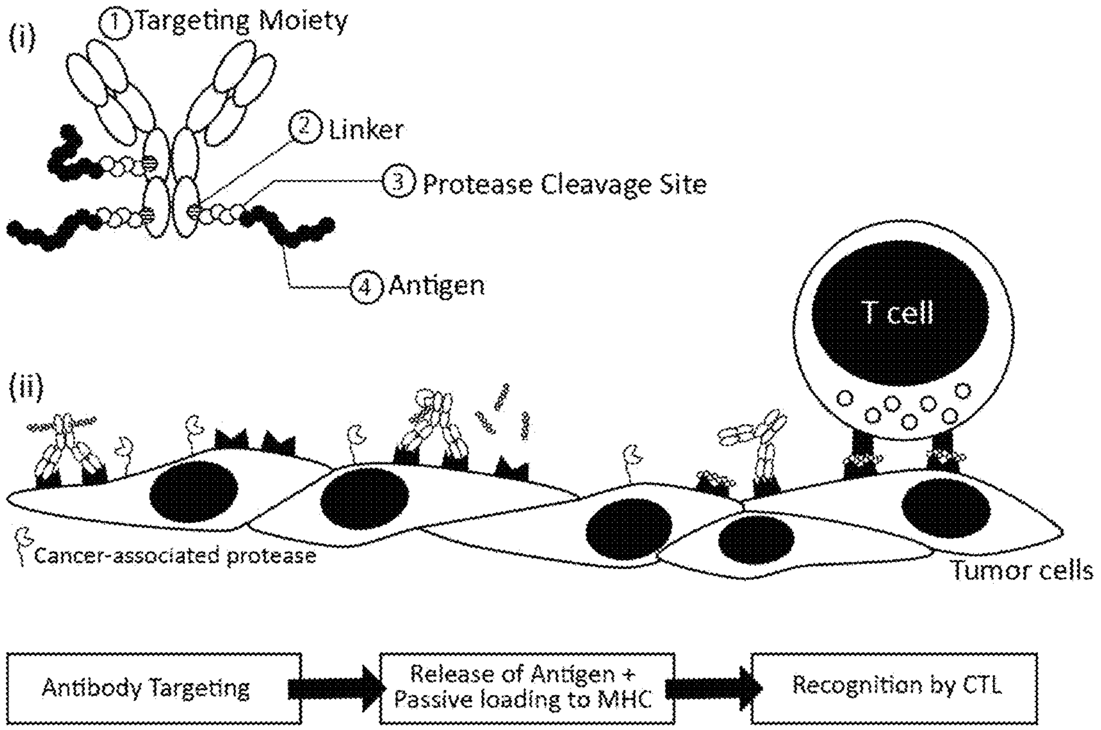

FIGS. 4A-4B: (A) Schematic diagram of an exemplary embodiment of the invention. (B) Schematic showing design and mechanism of viral peptide delivery. (i) Preferred targeting molecule consisting of a monoclonal antibody able to target a tumour cell, covalently linked to a synthetic peptide containing a protease recognition domain and a T cell peptide antigen. (ii) The peptide-conjugate is delivered to the target cell via a specific antibody and the peptide is cleaved in the proximity of the tumour cell. The released smaller viral peptide is passively binds to empty to empty MHC class I or II molecules on the cell surface. The MHC-peptide complexes are then recognised and by specific circulating T-cells mediating tumour cell-lysis.

FIGS. 5A-5C: In vitro activity of redirected virus-specific T cells. (A) Recognition of a lymphoblastoid lymphoma cell lines by $CD8^+$ cytomegalovirus-specific cytotoxic T lymphocytes through conjugation of the cognate antigen TPRVTGGGAM (SEQ ID No: 31) peptide to Rituximab (anti-CD20). Recognition is only present if the peptide is flanked by the MMP2 cleavage motif. Controls are tumour cells alone, CTLs alone and tumour cells pulsed with free TPR peptide (KTPRVTGGGA-MAIPVSLRSGGGGSGGGGSC) (SEQ ID No: 273) linked to Rituximab using Sulpho-SMCC. (B) Redirection of $CD4^+$ cytomegalovirus-specific T cells specific for $HLA-DR7^+$ restricted epitope DYSNTHSTRYV (SEQ ID No: 55) (DYSN). Lymphoblastoid cell lines were incubated with Rituximab crosslinked with the DYSN peptide without a cleavage site (IPDDYSNTHSTRYVC) (SEQ ID No: 309), "DYSN-Protease Cleavage Site" which contains a protease cleavage site (DDYSNTHSTRYV-TIPVSLRSGGGGSGGGGSC) (SEQ ID No: 274) or a control peptide and washed. Tumour cells were then incubated overnight with DYSN-specific $CD4^+$ T cells and T cell recognition determined using IFNγ release by ELISA. The inclusion of a protease cleavage site adjacent to the DYSN peptide dramatically increases recognition of the tumour cells by $CD4^+$ T cells. (C) Application toward breast carcinoma cell line MDA-MB231 using cytomegalovirus-specific $CD8^+$ CTL specific for cytomegalovirus pp65 (NLVPMVATV) (SEQ ID No: 21) epitope. Conjugation of the peptide combined with a MMP14 cleavage site mediates killing of the cells (NLVPMVATVLPRSAKELRC; SEQ ID No: 280) linked to Cetuximab using Sulpho-SMCC. Further data not shown indicates that a peptide conjugate lacking the MMP14 cleavage site shows killing comparable to Cetuximab alone.

Figure 6A:
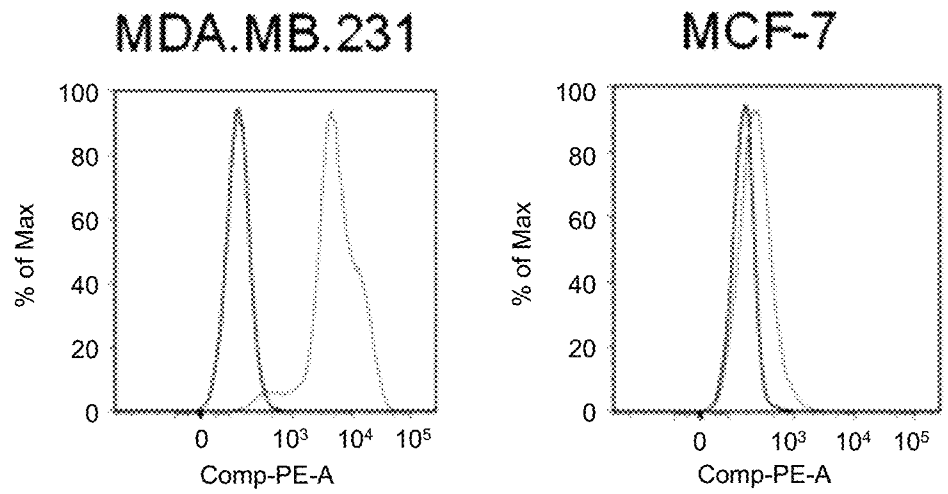
Figure 6B:
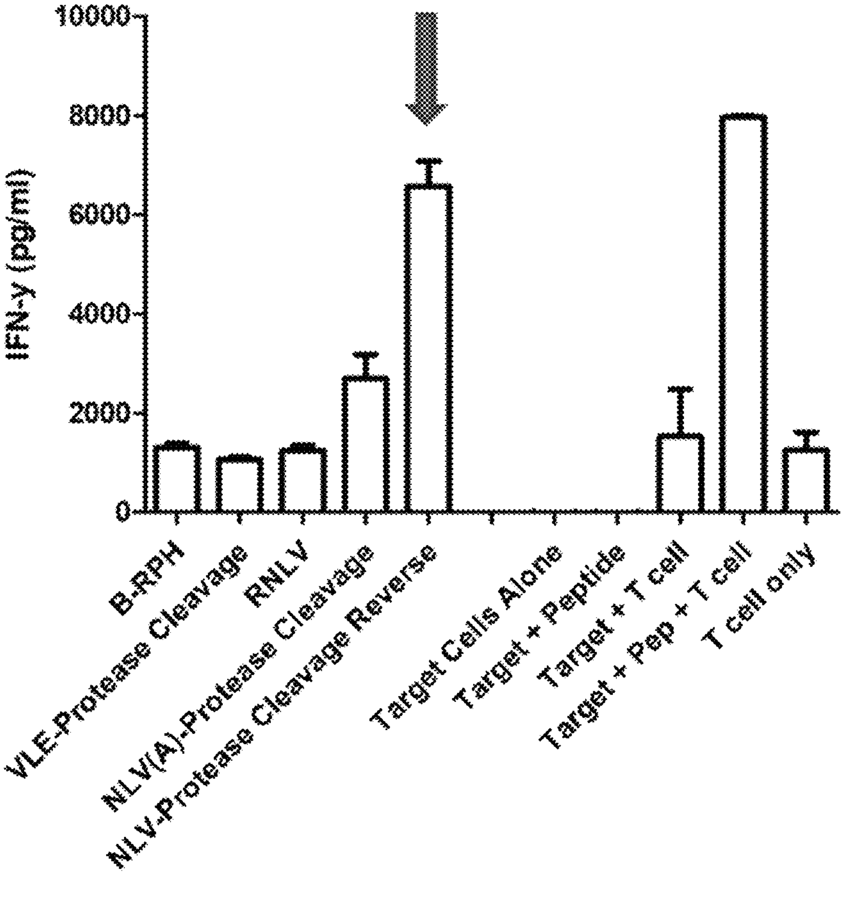
Figure 6C:
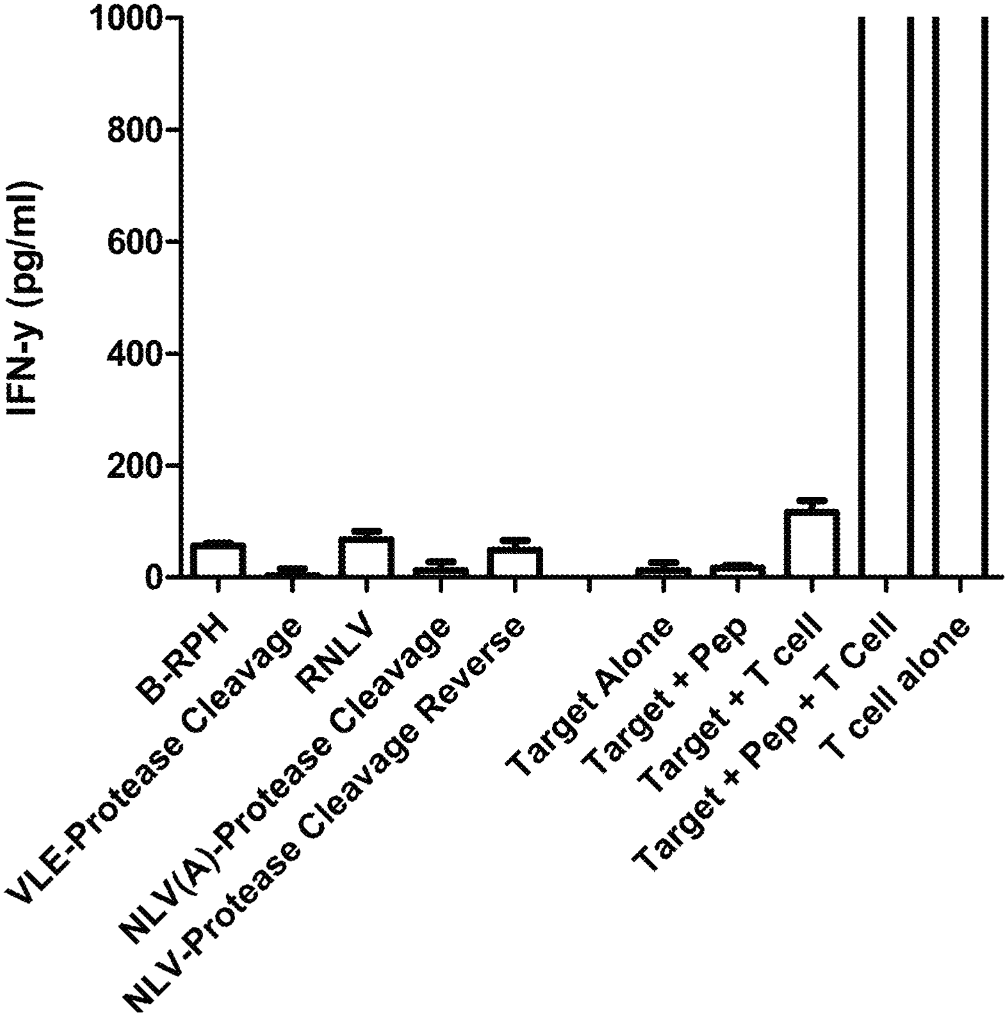

FIGS. 6A-6C: In vitro and in vivo targeting of tumour cell lines using APEC approach. (A) EGFR expression on two breast carcinoma cell lines MCF7 and MB-MDA231. (B) Successful targeting of EGFR+ cell line MDA-MB231 using NLVPMVATV (SEQ ID No: 21) peptide containing a protease cleavage site (CSGGGGSGGGGAIPVSLRANLVPM-VATV; SEQ ID No: 276) conjugated to Cetuximab. Arrow denotes efficient recognition by T cells of APEC treated cells. (C) MCF-7 which does not express EGFR is not targeted by Cetuximab immunoconjugate. In both (B) and (C), the B-RPH is a HLA-mismatched peptide deigned to not be recognised by the T cells and the VLE-protease cleavage peptide is an HLA-matched peptide. This peptide is designed to be a control for the protease cleavage sequence to ensure that the T cells do not recognise a portion of the protease cleavage sequence. As the response to the VLE-protease cleavage peptide is negligible, the response seen with the NLV-protease cleavage peptide is borne against the NLVPMVATV (SEQ ID No: 21) sequence and not the protease cleavage sequence.

Figure 7A:
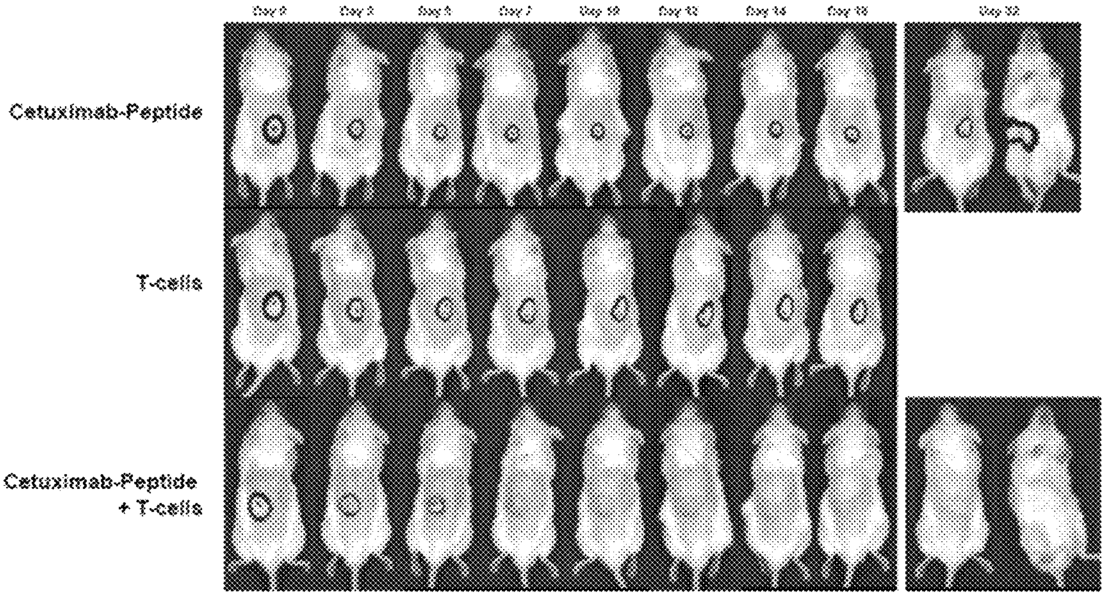
Figure 7B:
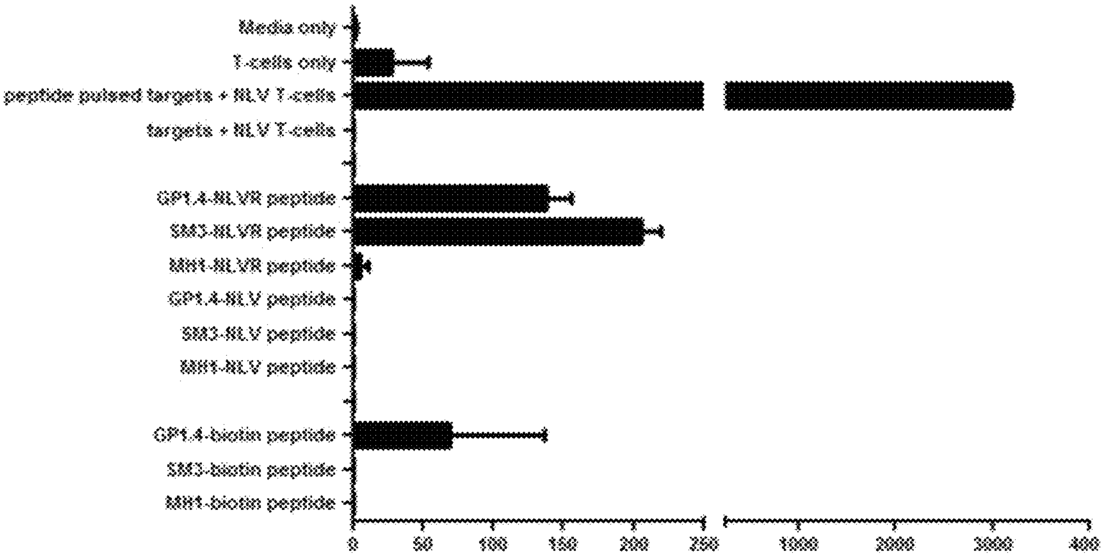

FIGS. 7A-7D: In vivo targeting of tumour cell lines using APEC approach. (A) in vivo xenograft data demonstrating that the human MDA-MB-231 breast cancer cell line can be eradicated by CMV-specific T cells when Cetuximab-peptide conjugates are given via intraperitoneal injection. Cetuximab-peptide complexes alone are unable to control the tumour growth (upper), whilst neither are CMV-specific T-cells (middle). However the combination of both cause eradication of this aggressive breast cancer tumour in vivo. (B) Successful targeting of colorectal cell line Colo205 using anti-Muc1 antibodies linked with CMV-specific T cell epitope and protease cleavage site. GP1.4 and SM3 are well-characterised anti-MUC1 specific antibodies. (C) This anti-Muc1 antibody-peptide conjugate also very efficiently targets pancreatic carcinoma cell line Panc1. MH1, SM3 and GP1.4 are all well-characterised MUC1-specific monoclonal antibodies. MH1 is specific for the cytoplasmic tail of MUC1 and therefore does not bind to intact tumour cells, whereas, SM3 and GP1.4 bind to the extracellular portion of MUC1 glycoprotein. For FIG. 7A, the peptide used is the NLV peptide using the reverse sequence (CSGGGGSGGG-GAIPVSLRANLVPMVATV) (SEQ ID No: 276). In FIGS. 7B and C, the peptides are as follows NLVR (CSGGGGSGGGGAIPVSLRANLVPMVATV) (SEQ ID No: 276) containing the protease cleavage site, RNLV (RNLVPMVATVQIPVSLRSGGGGSGGGGSC) (SEQ ID No: 275) containing the same protease cleavage site as NLV-R and differing from NLV-R in the orientation of the viral epitope and the biotin peptide (Biotin-PFMR-PHERNGFTVLC: SEQ ID No: 320) which does not contain the protease cleavage sequence and is used as a control peptide. (D) Single chain fragment V (scFv) protein construct encoding for the same peptide sequence as used in (A) but contained within the scFv single polypeptide chain demonstrates activity against MDA-MB-231 cell line in vitro. The protease recognition site within the ScFv construct is IPVSLRS (SEQ ID No: 310).

Figure 8:
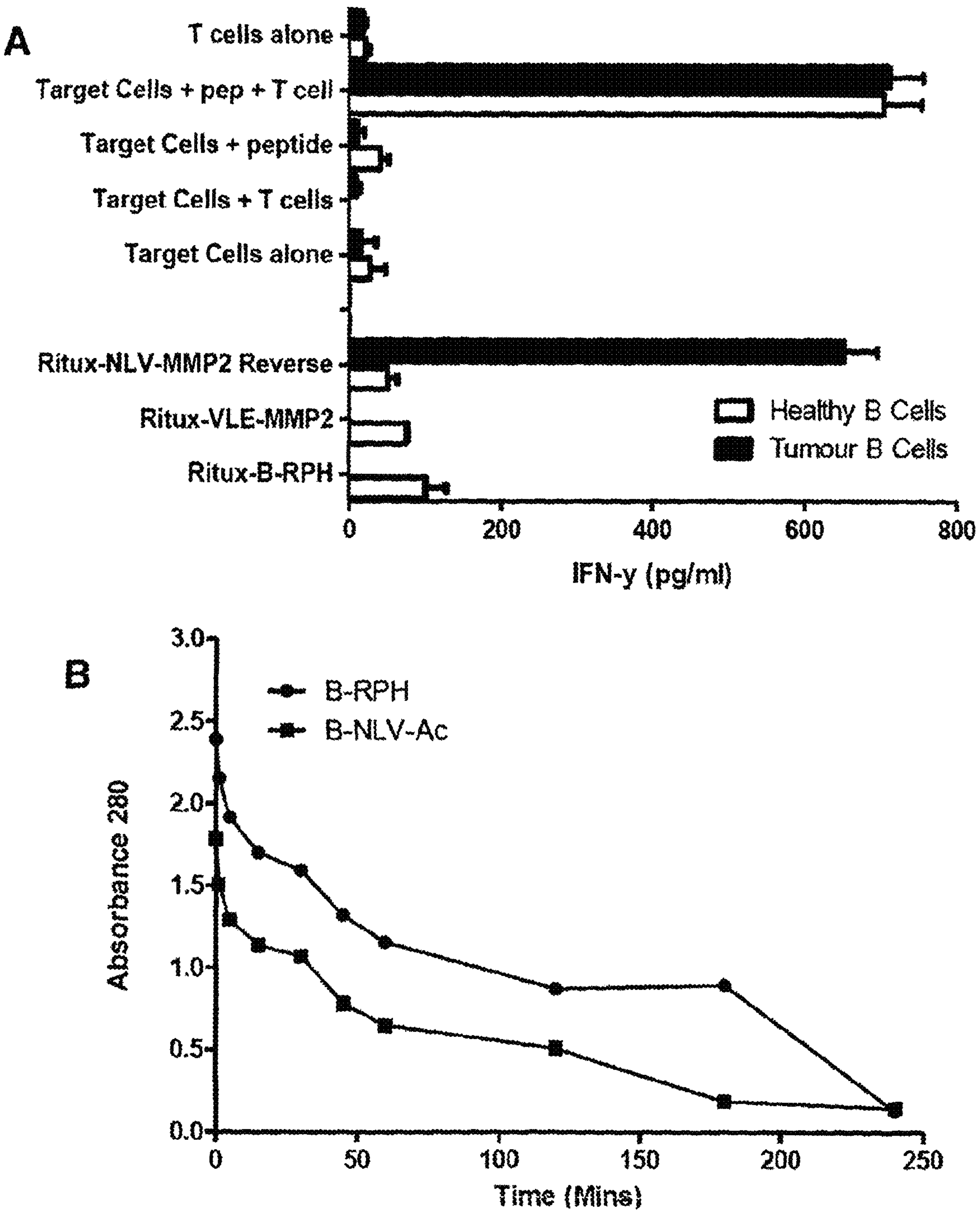

FIGS. 8A-8B: Plasma stability of the antibody-peptide conjugate and specific targeting of tumour B cells. (A) Recognition of a lymphoblastoid cell line or healthy B cells by CD8+ cytomegalovirus specific cytotoxic T cells after labelling cells with Rituximab conjugated with MHC class I peptides derived from cytomegalovirus. There is no recognition of healthy B cells whereas there is recognition of target cells only in the presence of the viral peptide the T cells are specific for. This data demonstrates the specificity of the APEC for malignant cells compared with healthy tissue. (B) The antibody peptide-epitope conjugate (APEC) was incubated at 37° C. in human plasma and assayed by ELISA to determine stability of the peptide conjugation. The half-life of the APEC is ~50 minutes and is not altered by the addition of an acetyl group at the C terminus of the peptide. In FIG. 8, the peptide sequences used were NLV-Protease Cleavage-Reverse (CSGGGGSGGGGAIPVSLRANLVPM-VATV) (SEQ ID No: 276) containing the protease cleavage site IPVSLRS (SEQ ID No: 310), VLE-Protease Cleavage (YVLEETSVMLIPVSLRSGGGGSGGGGSC) (SEQ ID No: 277) containing the protease cleavage site IPVSLRS (SEQ ID No: 310) and Biotin-RPH (Biotin-PFMR-PHERNGFTVLC: SEQ ID No: 320) used as a control peptide without the protease cleavage sequence.

FIGS. 9A-9B: (A) Amino acid sequence of cytomegalovirus pp 65 protein (SEQ ID No: 318); (B) Amino acid sequence of some peptide constructs referenced in the Examples. Key: bold and underlined=T-cell epitope; boxed=flexible linker; italics=protease recognition site; boxed and bold=epitope extension reside as per parent pp 65; double underlined=coupling residue bearing a sulfhydryl.

FIGS. 10A-10B: (A) The dependency of external proteolytic activity: target cells are lightly fixed in paraformaldehyde or not and then incubated with either peptide (NLVPMVATV) (SEQ ID No: 21) or Cetuximab conjugated with either an irrelevant peptide (VLE) or cognate peptide (NLVPMVATV: SEQ ID No: 21-protease cleavage site) and incubated with NLVPMVATV (SEQ ID No: 21)—specific T-cells. Data demonstrate that fixed cells are able to process antibody-peptide conjugates and thus internalisation is not necessary for processing. (B) Data demonstrating that receptor peptide agonists (NLVPMVATVAIPVSLRSAAAF-CDGFYACYMDV (SEQ ID No: 311)=Her2/neu agonist peptide [FCDGFYACYMDV] (SEQ ID No: 312) with NLVPMVATV (SEQ ID No: 21) and protease cleavage site AIPVSLR (SEQ ID No: 313); NLVPMVATVAIPVSLR-SAAAYCRDYDYDGRYFDCY (SEQ ID No: 314)=EGFR agonist peptide (YCRDYDYDGRYFDCY) (SEQ ID No: 319) with the viral peptide NLVPMVATV (SEQ ID No: 21) and protease cleavage site AIPVSLR (SEQ ID No: 313)) can be used to re-direct T-cells against EGFR+ tumour cells) (Ponde et al, *Bioorg Med Chem Lett* 21(8): 2550-3).

Figure 11:
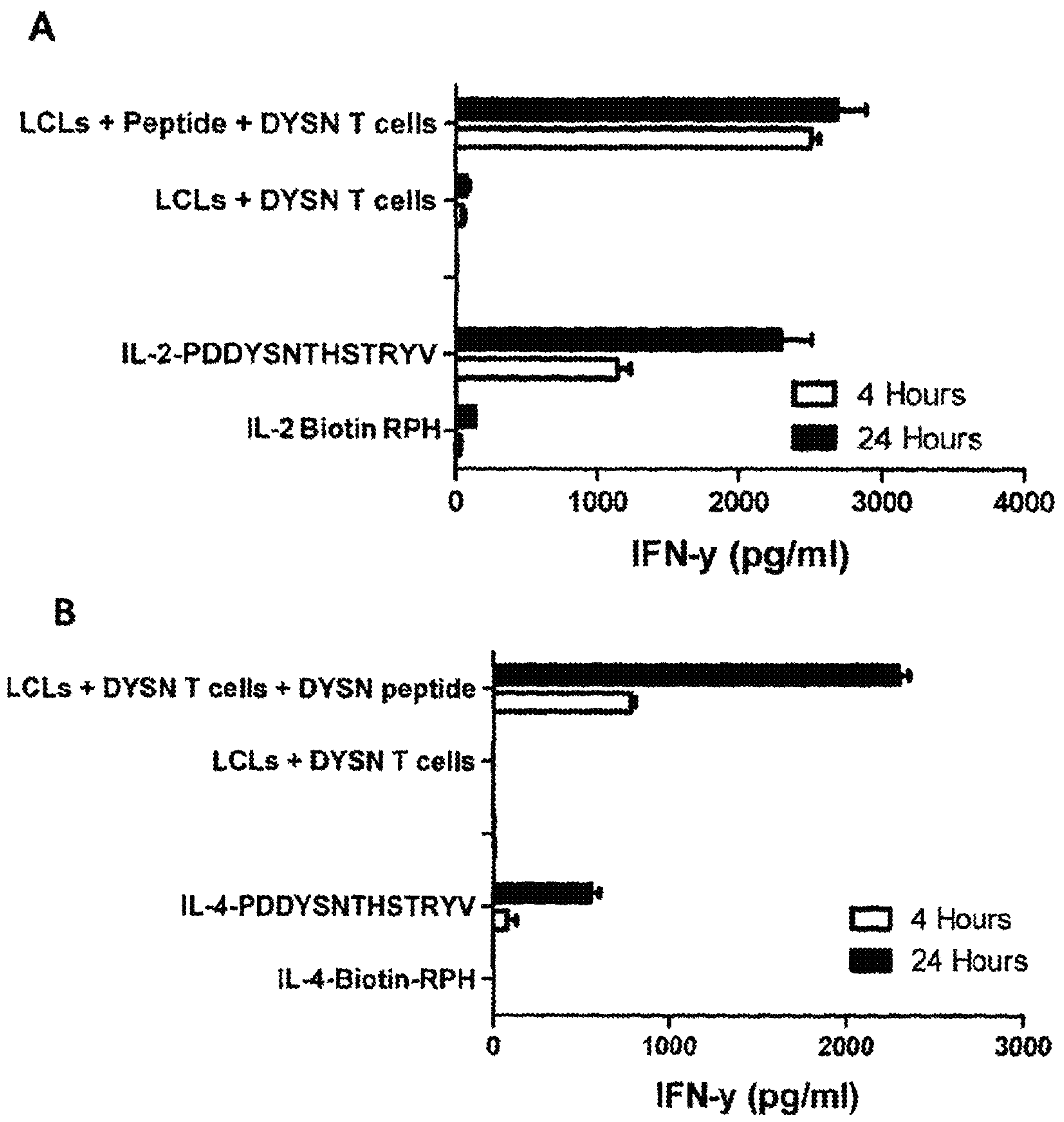

FIGS. 11A-11B: (A) Demonstration that cytokines can be used as targeting moiety with IL-2 (A) and IL-4 (B) being conjugated with HLA-class II peptide (DR7-restricted) PDDYSNTHSTRYVC (SEQ ID No: 309) and using the Biotin-RPH (Biotin-PFMRPHERNGFTVLC; SEQ ID No: 320) as a control peptide. After labelling target cells with cytokine-peptide complex, and culturing with DYSN-specific CD4 T cells for either 4 or 24 hours, there is a strong T cell response towards target cells labelled with the DR7-restricted peptide (PDDYSN) and no response when using the control peptide (Biotin-RPH) after 4 and 24 hours (A) and 24 hours (B).

Figure 12:
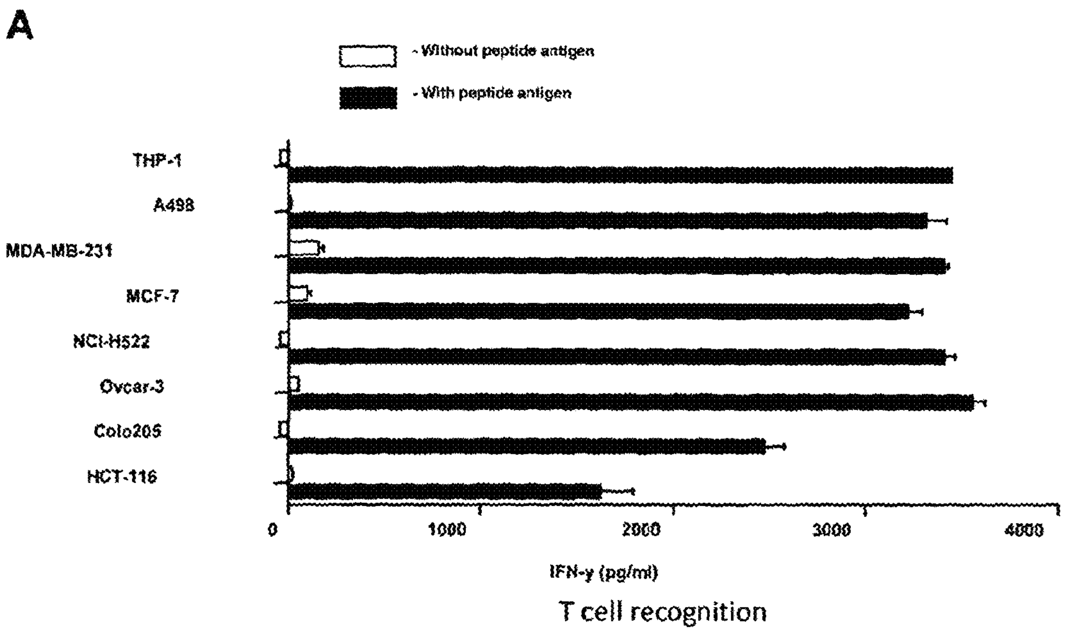
Figure 13A:
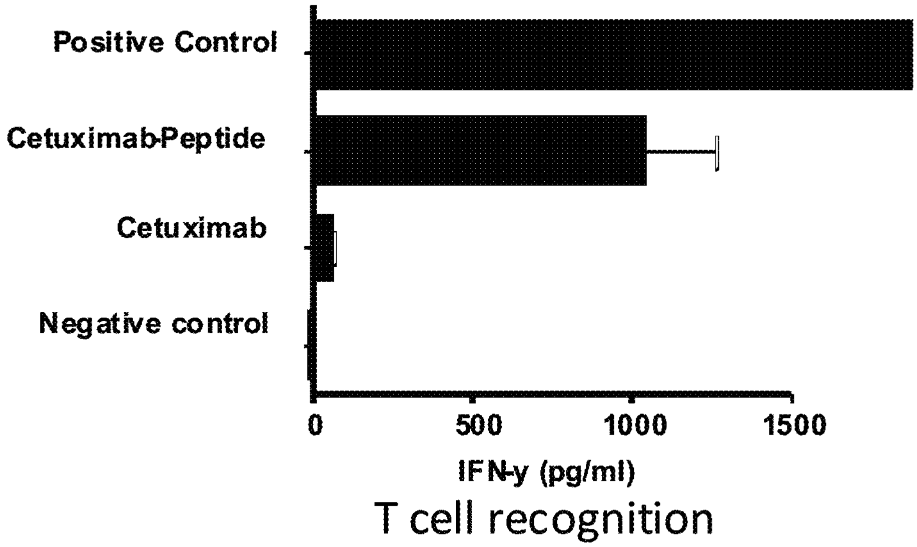
Figure 13B:
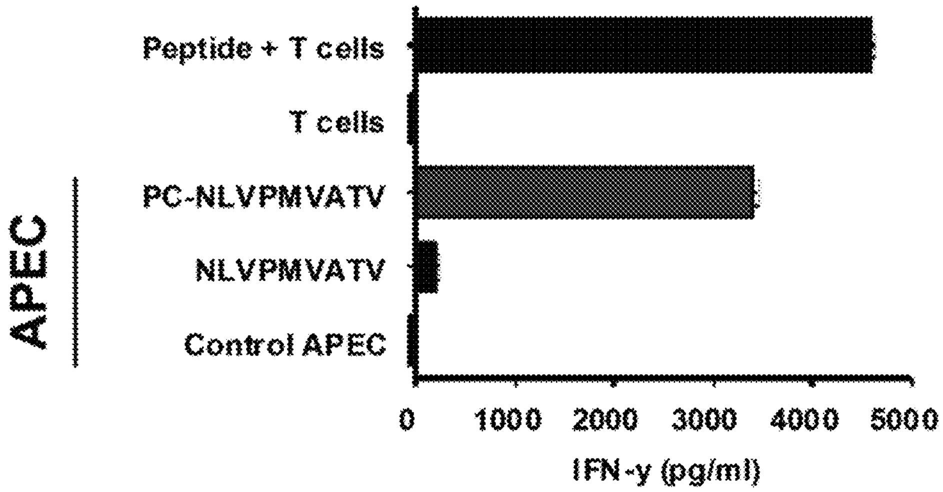
Figure 13C:
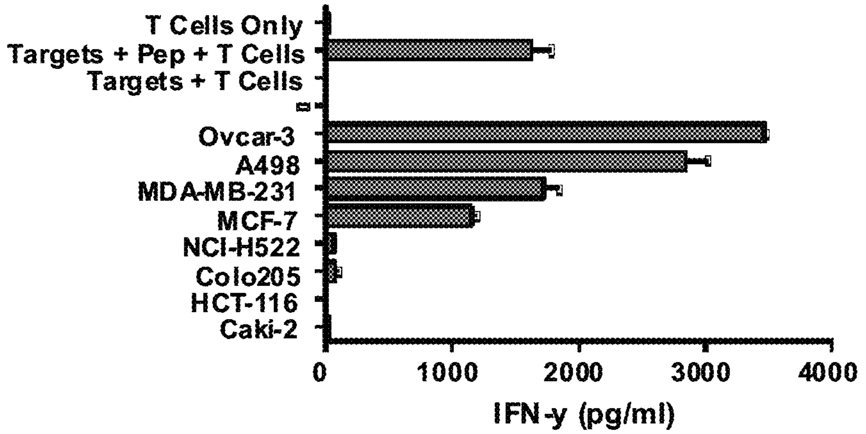
Figure 13D:
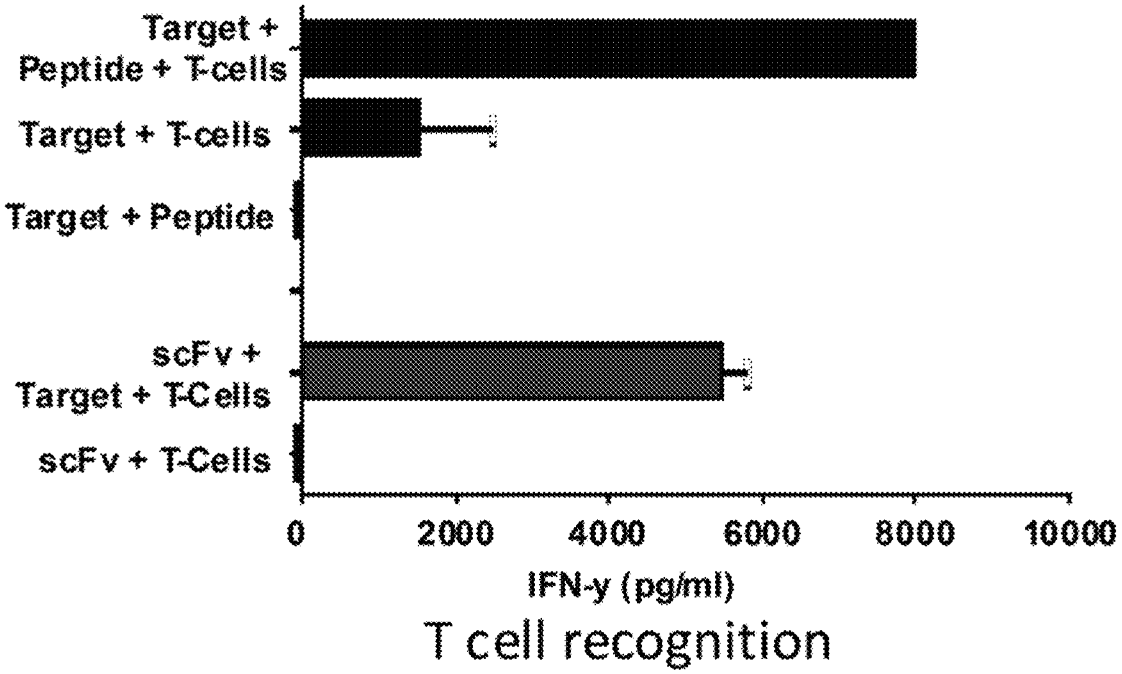
Figure 13E:
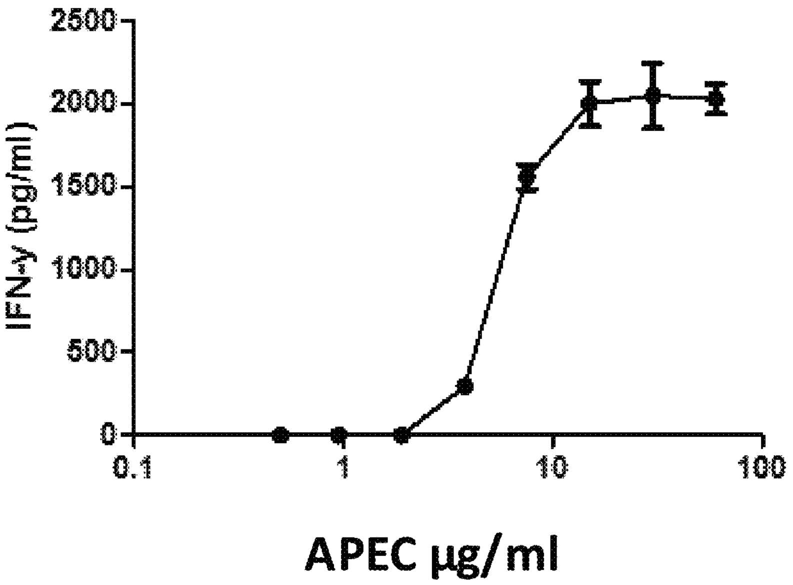
Figure 14A:
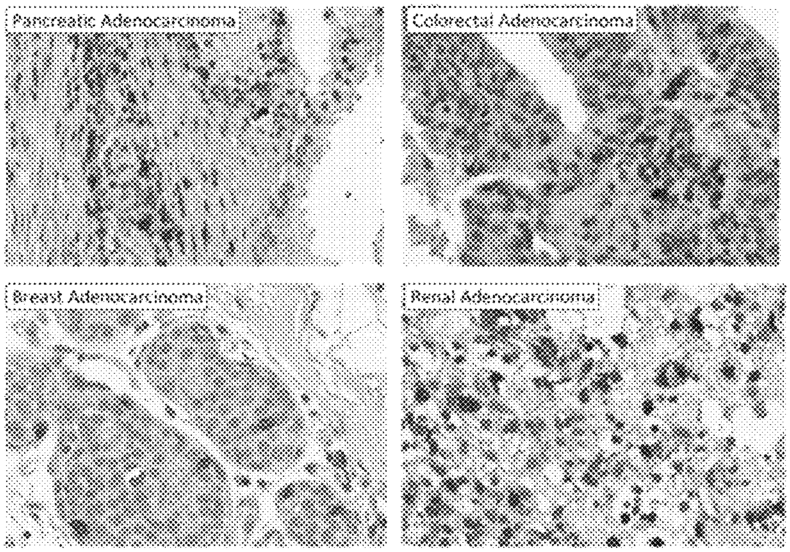
Figure 14B:
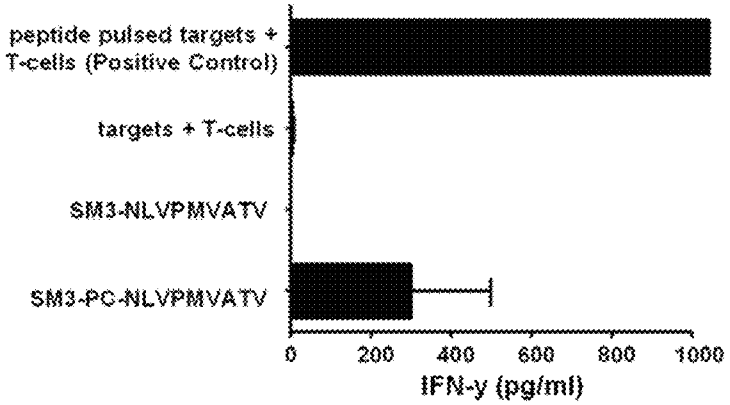
Figure 14C:
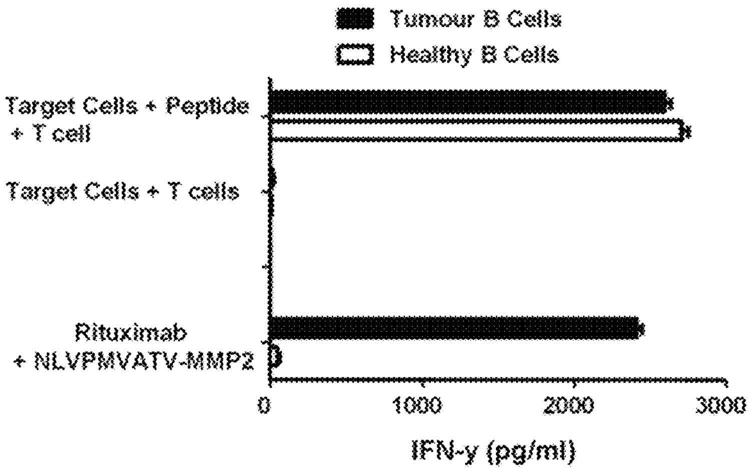
Figure 14D:
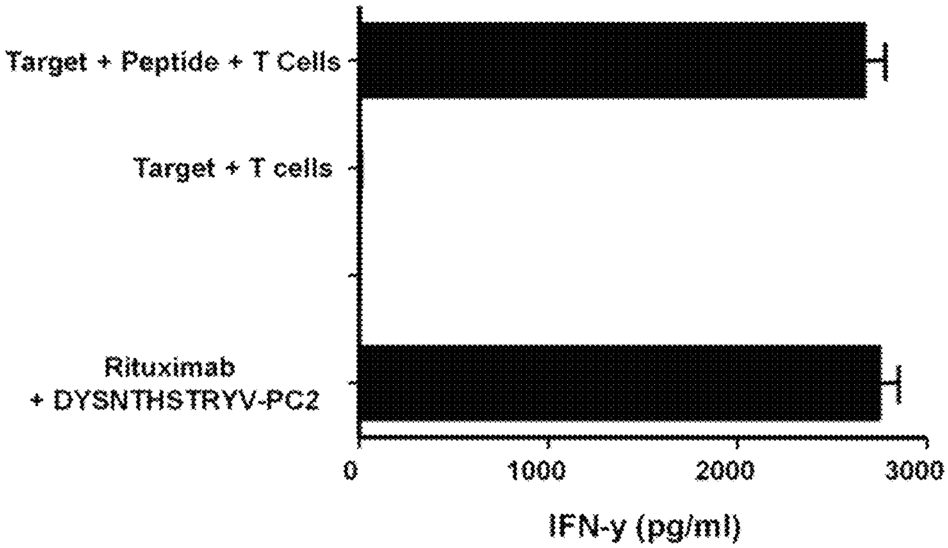
Figure 14E:
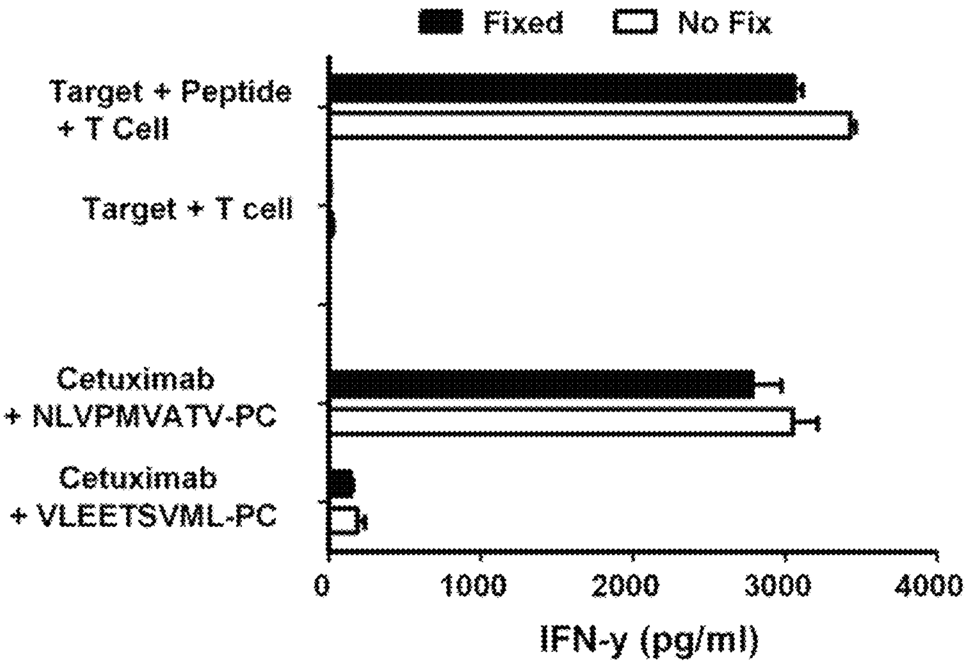
Figure 14F:
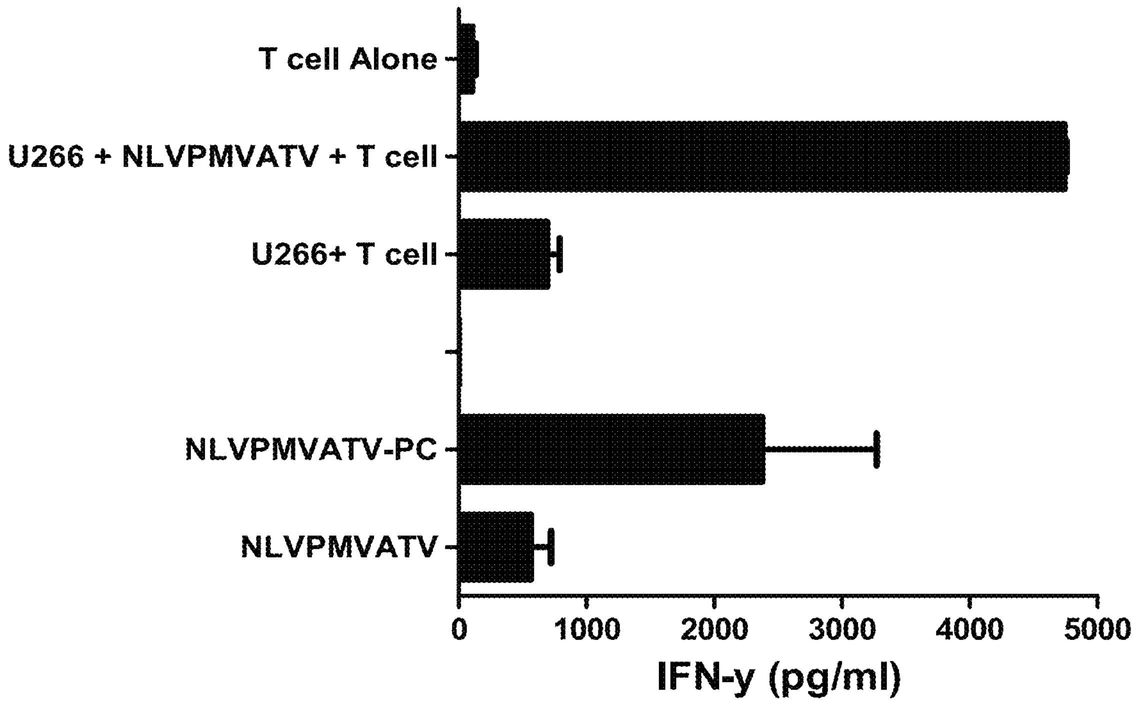

FIG. 12: T cell recognition by range of tumour cell lines. Eight HLA-A*0201 NCI-60 cell lines are all recognised by HLA-A*0201-restricted CMV-specific T-cells when pulsed with cognate antigen.

FIGS. 13A-13E: in vitro targeting of human carcinoma cell lines using antibody-peptide-epitope conjugate (APEC) approach. (A) Early data showing that Cetuximab-peptide conjugates could be used to target carcinoma cell lines. Positive control is cognate viral peptide pulsed tumours—as in FIG. 12. (B) The introduction of a protease cleavage site in the peptide is critical for effective targeting of tumour cells. Peptides not bearing a cleavage sequence (PC) are not cleaved and therefore not recognised by T-cells. (C) Using Cetuximab-MMP2-NLVPMVATV (SEQ ID No: 21) APEC we can successfully target 4 out of 7 HLA-A*0201 NCI-60 cell lines. NCI-H522 and Colo205 are also weakly recognised, whereas HCT-116 is not recognised. Caki-2 is not HLA-A*0201 and serves only as a control. (D) We have produced scFv protein based upon Cetuximab sequence and N-terminally linked MMP2-NLVPMVATV (SEQ ID No: 21). This agent is also able to target MDA-MB-231 tumour cells in vitro (shown in red). (E) Assessment of in vitro potency of Cetuximab APEC. These experiments suggest an EC50 of between 2-5 ug/ml (13-30 nM). In FIG. 13, when the peptide epitope is NLVPMVATV (SEQ ID No: 21), the peptides used were CSGGGGSGGGGAIPVSLRANLVPM-VATV (SEQ ID No: 276) ('NLVPMVATV-PC') that contains the protease cleavage sequence AIPVSLR (SEQ ID No: 313), and CSGGGGSGGGGANLVPMVATV (SEQ ID No: 315) ('NLVPMVATV) that does not contain a protease cleavage site.

FIGS. 14A-14F: (A) Immunohistochemistry of 4 human adenocarcinomas showing CD8+ T cells by immunohistochemistry reveal abundant CD8+ T-cell infiltrate in human carcinomas. (B) Using Anti-Muc1(SM3)-(Protease Cleavage)-NLVPMVATV (SEQ ID No: 21) APEC we can successfully target the pancreatic carcinoma cell line Panc-1. (C) Using Rituximab-Protease Cleavage)-NLVPMVATV (SEQ ID No: 21) APEC we can differentially target a model tumour B cell line (LCLs) (black bars) and avoid targeting healthy B cells (white bars). (D) Using Rituximab-PC-DYSNTHSTRYV (SEQ ID No: 55) APEC we can successfully target a model tumour B cell line (LCLs) using HLA Class-II derived peptides eliciting a CD4+ T cell response. (E) Using Cetuximab-MMP2-NLVPMVATV (SEQ ID No: 21) APEC we can successfully target cells previously fixed (black bars) at a similar level to that seen in unfixed cells (white bars). (F) Using anti-CD138 antibody to target the myeloma cell line U266. PC=Protease Cleavage. 'U266+NLVPMVATV (SEQ ID No: 21)+T cell' corresponds to the native 9 amino acid peptide alone as a free peptide epitope (i.e. no linker etc), and serves as a positive control as it is essentially the maximum possible response. In FIG. 14, when the peptide epitope is NLVPMVATV (SEQ ID No: 21), the peptides used were CSGGGGSGGGGAIPVSL-RANLVPMVATV (SEQ ID No: 276) ('NLVPMVATV-PC') that contains the protease cleavage sequence AIPVSLR (SEQ ID No: 313), and CSGGGGSGGGGANLVPMVATV (SEQ ID No: 315) ('NLVPMVATV) that does not contain a protease cleavage site.

EXAMPLE 1: STIMULATION OF T CELLS BY CETUXIMAB—NLVPMVATV (SEQ ID NO: 21) CONJUGATE

Summary

We contacted breast cancer cells with an agent comprising Cetuximab conjugated to a HLA-B7 peptide with and without a cleavage site. Subsequent exposure to T cells resulted in the generation of a T cell response when the breast cancer cells were contacted with the agent that contained the cleavage site.

Results

MDA.MB.231 cells, often used as a model for breast cancer, were transduced with the MMP14 gene to ensure expression of the MMP14 protein within the cell. After staining the target cells ($1\times10^5$) with Cetuximab either unconjugated (1) or conjugated to RPHERNGFTVL (SEQ ID No: 32), a HLA-B7 peptide (2), NLVPMVATV (SEQ ID No: 21) without the MMP14 cleavage sequence (3) or NLVPMVATV (SEQ ID No: 21) including the cleavage sequence (4), stained cells were incubated overnight. The following day, the cells were washed and NLV-specific T cells were added to the culture ($1\times10^4$) and incubated overnight. Supernatant was harvested and an ELISA used to determine the presence of IFN-γ in each culture, n=3. The results are shown in FIG. 1.

There was very little IFN-γ release from T cells cultured together with cells stained using Cetuximab alone and cetuximab conjugated with the mismatched HLA-peptide. T cells cultured with cells stained using cetuximab conjugated with the correct peptide but lacking the MMP14 cleavage site also produced very little IFN-γ whereas T cells cultured with the cells stained using cetuximab conjugated with the correct peptide containing the MMP14 cleavage site produced a large amount of IFN-γ.

EXAMPLE 2: STIMULATION OF $CD4^+$ T CELLS BY RITUXIMAB—DYSNTHSTRYV (SEQ ID NO: 55) CONJUGATE

Summary

We contacted B-lymphoblastoid cells (B-LCL) with an agent comprising Rituximab conjugated to a cytomegalovirus HLA Class-II restricted peptide DYSNTHSTRYV (SEQ ID No: 55) with and without a cleavage site. Subsequent exposure to $CD4^+$ T cells resulted in the generation of a T cell response when the B-LCL cells were contacted with the agent that contained the cleavage site.

Results

After staining the B-LCL cells with Rituximab conjugated to an irrelevant mismatched peptide RPHERNGFTVL (SEQ ID No: 32), a HLA-B7 peptide, not containing the protease cleavage sequence (1), an irrelevant, mismatched HLA class-I peptide VLEEETSVML (SEQ ID No: 316), an HLAA-A2 peptide, with the protease cleavage sequence (2), the relevant peptide DYSNTHSTRYV (SEQ ID No: 55) without the protease cleavage sequence (3), or the relevant peptide DYSNTHSTRYV (SEQ ID No: 55) including the protease cleavage sequence (4), stained cells were incubated overnight. The following day, the cells were washed and DYSN-specific $CD4^+$ T cells were added to the culture and incubated overnight. Supernatant was harvested to determine the presence of IFN-γ in each culture, n=3. There was very little IFN-γ release from $CD4^+$ T cells cultured together with cells stained using Rituximab conjugated with the mismatched HLA-peptide without the protease cleavage site. $CD4^+$ T cells cultured with cells stained using Rituximab conjugated with the correct peptide but lacking the protease cleavage site also produced very little IFN-γ whereas T cells cultured with the cells stained using Rituximab conjugated with the correct peptide containing the protease cleavage site produced a large amount of IFN-γ. However, when T cells were cultured with Rituximab conjugated with the HLA-mismatched peptide containing the protease cleavage site, there was no IFN-γ produced. The results are shown in FIG. 2.

A similar example showing stimulation of $CD4^+$ T cells by Rituximab-TPRVTGGGAM conjugate is shown in FIG. 3.

EXAMPLE 3: STANDARD OPERATING PROCEDURE FOR CHEMICAL CONJUGATION OF CYSTEINYLATED PEPTIDE TO ANTIBODY

1. Cysteinylated peptides dissolved in DMSO to final concentration of 5 mg/ml.
2. Weigh 1 mg Sulfosuccinimidyl 4-[N-maleimidomethyl] cyclohexane-1-carboxylate (Sulfo-SMCC) and dissolve in 500 μl phosphate buffered saline (PBS).
   a. Other heterobifuctional cross-linkers could be used in place of Sulfo-SMCC e.g. Sulfosuccinimidyl 6-(3'-[2-pyridyldithio]-propionamido) hexanoate (Sulfo-LC-SPDP) and N-[ß-Maleimidopropionic acid] hydrazide, trifluoroacetic acid salt (BMPH) amongst others.
3. Add 20 μl antibody (1 mg/ml, 20 μg antibody) to dissolved Sulfo-SMCC and incubate at room temperature for 1 hour.
4. Wash a Protein G column (GE Healthcare) by firstly spinning the column at 13,000 rpm for 30 seconds to remove the ethanol (storage buffer).
5. Add 500 μl PBS and mix protein G beads well before spinning at 13,000 rpm for 30 seconds. Remove eluate and repeat a further two times.
6. Add antibody-SMCC to protein G column, mix well and incubate for 5 minutes. Centrifuge at 13,000 rpm for 30 seconds and remove eluate.
7. Wash antibody by adding 500 μl PBS and mixing the beads well before spinning at 13,000 rpm for 30 seconds and removing eluate. Repeat this step a further two times.
8. To elute the bound antibody, add 125 μl 0.1M acetic acid to the beads and incubate for 2 minutes at room temperature. Place column in a 1.5 ml eppendorf and spin at 13,000 rpm for 30 seconds and collect eluate.
9. Repeat step 8.
10. Add 250 μl 0.2M $Na_2HCO_3$ and allow to stand at room temperature for 5 minutes.
11. Add 2 μl peptide, previously dissolved in DMSO, to the SMCC-activated antibody and incubate at room temperature for 2 hours.
12. Repeat steps 4 to 10 to remove excess unbound peptide from the antibody.
13. After adding 250 μl 0.2M $Na_2HCO_3$, add a further 500 μl PBS before storage. Antibody can now be used to stain cells.
14. Store antibody at 4° C.

EXAMPLE 4: TREATMENT OF BREAST CANCER

An agent comprising Cetuximab that is attached to a peptide T cell antigen such as NLVPMVATV (SEQ ID No: 21), derived from a cytomegalovirus, via a linker comprising a PRSA-KELR (SEQ ID No: 321) protease cleavage site (cleavable by Matrix metalloproteinase 14 (MMP14)) is prepared. The agent is formulated with a pharmaceutically acceptable excipient and administered to patient with an epithelial malignancy such as breast cancer. The agent, Cetuximab, is targeted to breast cancer cells and upon binding comes into contact with MMP14. The cleavage of the protease cleavage site releases the T cell antigen, NLVPMVATV (SEQ ID No: 21), which subsequently binds to the HLA-A*0201 molecules on the surface of the breast cancer cell. The breast cancer cells expressing the T cell antigen is targeted by the host immune system for cytolysis by the effector CD8 T cells.

EXAMPLE 5: TREATMENT OF B-CELL LYMPHOMA (EG CHRONIC LYMPHOCYTIC LEUKAEMIA)

An agent comprising Rituximab that is attached to a HLA class-II peptide T cell antigen such as DYSNTHSTRYV (SEQ ID No: 55), derived from a cytomegalovirus, via a linker comprising a TIPV-SLRS (SEQ ID No: 317) protease cleavage site (cleavable by Matrix metalloproteinase 2 (MMP2)) is prepared. The agent is formulated with a pharmaceutically acceptable excipient and administered to patient with B cell lymphoma (eg chronic lymphocytic leukaemia). The agent, Rituximab, is targeted to B cells and upon binding comes into contact with a protease. The subsequent cleavage of the protease cleavage site releases the T cell antigen, DYSNTHSTRYV (SEQ ID No: 55), which subsequently binds to the HLA-DR*0107 molecules on the surface of the B cell. The B cells expressing the T cell antigen would then be targeted by the host immune system for cytolysis by the effector CD4 T cells.

EXAMPLE 6: TREATMENT OF BOWEL CANCER

An agent comprising Cetuximab that is attached to a peptide T cell antigen derived from a cytomegalovirus via a linker comprising a CPGR-VVGG (SEQ ID No: 254) protease cleavage site (cleavable by uPA) is prepared. The agent is formulated with a pharmaceutically acceptable excipient and administered to a bowel cancer patient.

EXAMPLE 7: TREATMENT OF B CELL LYMPHOMA (EG CHRONIC LYMPHOCYTIC LEUKAEMIA (CLL))

An agent comprising Rituximab that is attached to a peptide T cell antigen derived from a cytomegalovirus via a linker comprising a PQG-IAGQ (SEQ ID No: 269) protease cleavage site (cleavable by MMP2) is prepared. The agent is formulated with a pharmaceutically acceptable excipient and administered to a B cell lymphoma (eg CLL) cancer patient.

EXAMPLE 8: STIMULATION OF T CELLS BY RITUXIMAB—TPRVTGGGAM (SEQ ID NO: 31) CONJUGATE

Summary

We contacted B-lymphoblastoid cells (B-LCL) with an agent comprising Rituximab conjugated to a cytomegalovirus peptide TPRVTGGGAM (SEQ ID No: 31) with and without a cleavage site. Subsequent exposure to T cells resulted in the generation of a T cell response when the B-LCL cells were contacted with the agent that contained the cleavage site.

Results

After staining the cells with Rituximab conjugated to RPHERNGFTVL (SEQ ID No: 32), a HLA-B7 peptide (1), an irrelevant, mis-matched HLA class-I peptide, VLEEETSVML (SEQ ID No: 316), (a HLA-A2 peptide) containing the protease cleavage sequence (2), the relevant peptide TPRVTGGGAM (SEQ ID No: 31) with the protease cleavage sequence (3) or the relevant peptide TPRVTGGGAM (SEQ ID No: 31) without the cleavage sequence (4), stained cells were incubated overnight at 37° C. The following day, the cells were washed and TPR-specific T cells were added to the culture and incubated overnight. Supernatant was harvested to determine the presence of IFN-γ in each culture, n=3. The results are shown in FIG. 3.

There was very little IFN-γ release from T cells cultured together with cells stained using Rituximab conjugated with the mismatched HLA-peptide with or without the protease cleavage site (1 & 2). T cells cultured with cells stained using Rituximab conjugated with the correct peptide but lacking the protease cleavage site also produced very little IFN-γ (4) whereas T cells cultured with the cells stained using Rituximab conjugated with the correct peptide containing the protease cleavage site (3) produced a large amount of IFN-γ.

EXAMPLE 9: TREATMENT OF B CELL LYMPHOMA (EG CHRONIC LYMPHOCYTIC LEUKAEMIA)

An agent comprising Rituximab that is attached to a HLA class-I peptide T cell antigen such as TPRVTGGGAM (SEQ ID No: 31), derived from a cytomegalovirus, via a linker comprising a TIPV-SLRS (SEQ ID No: 317) protease cleavage site (cleavable by Matrix metalloproteinase 2 (MMP2)) is prepared. The agent is formulated with a pharmaceutically acceptable excipient and administered to patients with B cell lymphoma (eg chronic lymphocytic leukaemia). The agent, Rituximab, is targeted to B cells and upon binding comes into contact with a protease. The cleavage of the protease cleavage site releases the T cell antigen, TPRVTGGGAM (SEQ ID No: 31), which subsequently binds to the HLA-B*0702 molecules on the surface of the B cell. The B cells expressing the T cell antigen would then be targeted by the host immune system for cytolysis by the effector CD8 T cells.

EXAMPLE 10: TUMOR TARGETING BY RE-DIRECTING ANTI-VIRAL IMMUNE RESPONSES IN VITRO AND IN VIVO

Summary

We have shown that antibodies can be engineered to deliver and release viral peptides at the tumor site by exploiting a tumor-associated proteolytic environment thus allowing resident anti-viral T cells to specifically kill tumor cells. We screened 15 HLA-A2$^+$ tumor cell lines (THP-1 (acute monocytic leukemia cell line); A498 (renal cell carcinoma); MDA-MB-231 and MCF-7 (breast cell adenocarcinomas); NCI-H522 (non-small cell lung carcinoma); Ovcar-3 (ovarian adenocarcinoma); Colo205 and HCT-116 (colorectal carcinoma)) and showed that 100% are recognized and killed by human anti-viral T cells when pulsed with cognate viral peptides (FIG. 12). Furthermore we used both molecular and cellular approaches to demonstrate that immunodominant anti-viral CD8+ T cells are present in a variety of human tumors providing a rationale for such an approach.

Results

Figure 5:
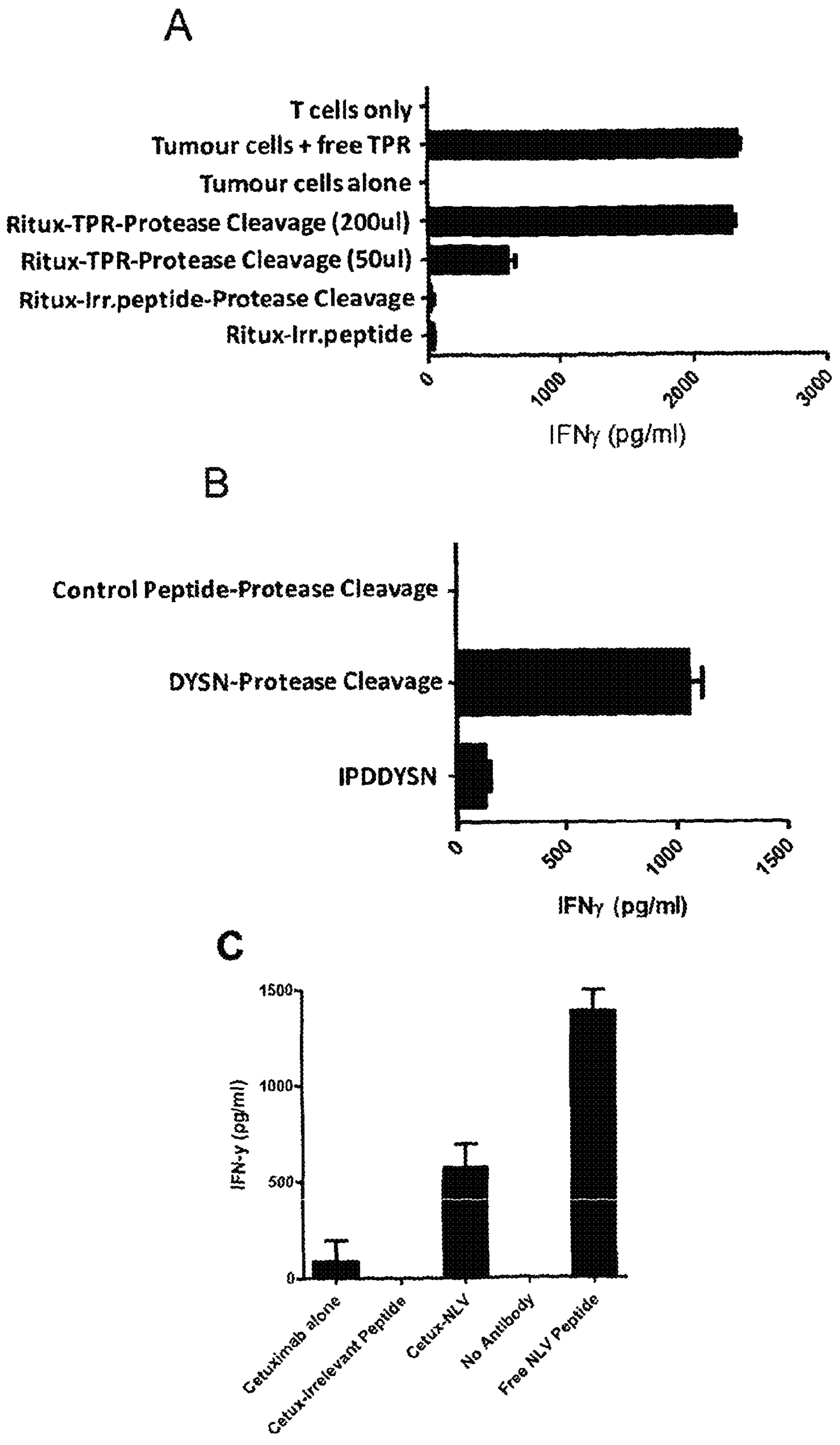

Antibody-peptide epitope conjugates (APEC) were generated, through covalently linking T cell epitope peptides with clinically available antibodies Cetuximab and Rituximab. Neither APEC in solution nor plate-bound were able to activate cognate T cells. Healthy CD20+ B cells bound Ritixumab-APEC (RPEC) but were unable to activate T cells in vitro. However, CD20+ lymphoma cell lines were able to be efficiently targeted by T cells when bound by RPEC in vitro through proteolytic release of bound peptide demonstrating differential tumor targeting (FIG. 5).

Figure 7C:
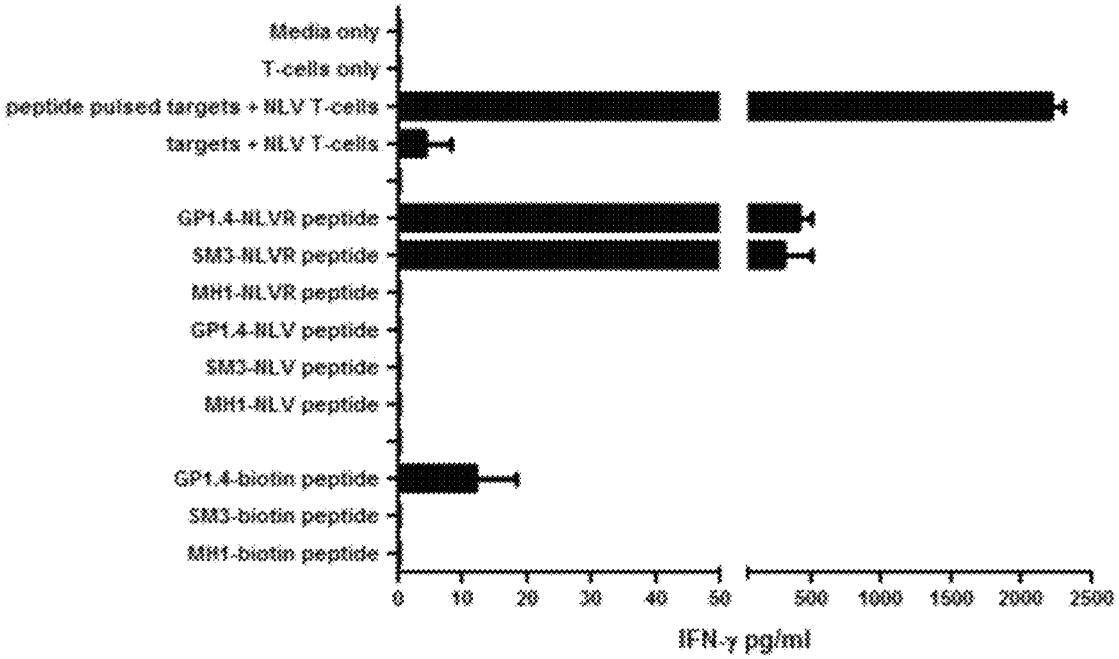

Using breast cancer as a solid tumor model, EGF receptor was targeted on the malignant cell line MDA-MB-231 using Cetuximab-APEC (OPEC). Results demonstrate T cell recognition when target cells were bound by OPEC (p<0.01) (FIG. 6). FIGS. 7B and 7C also demonstrate successful targeting of colorectal adenocarcinoma cell lines and pancreatic carcinoma cell lines using an anti-Muc1 antibody peptide conjugate.

In vivo data using a xenograft mouse model demonstrate significant efficacy in mice treated with the OPEC and T cells compared with mice treated with either T cells alone or with OPEC alone (see FIG. 7A). Because the conjugates are given by intraperitoneal injection and the tumour is given subcutaneously, these data also demonstrate plasma stability in vivo.

Figure 7D:
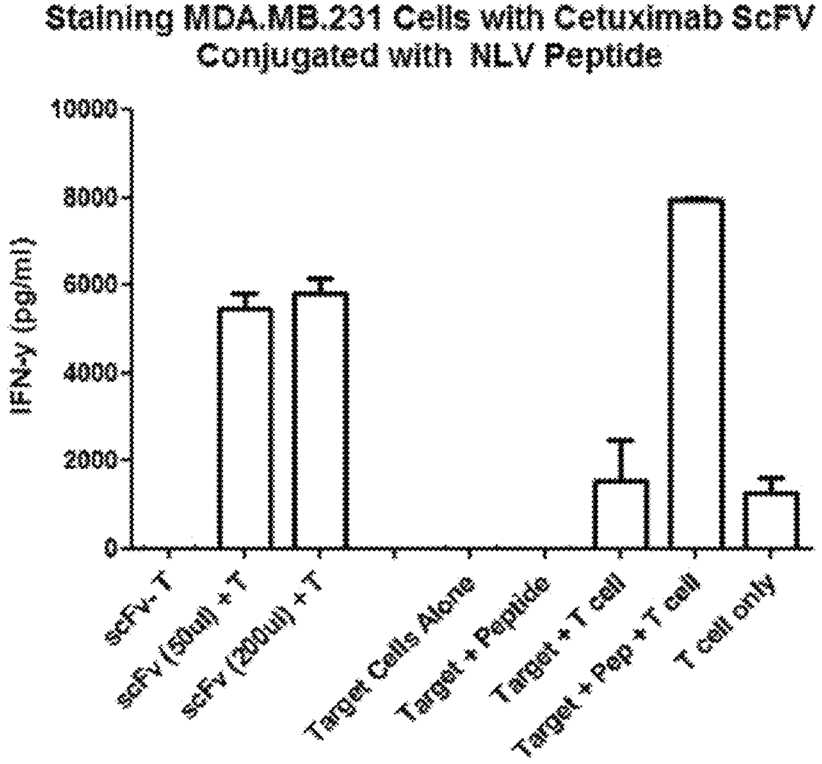

FIG. 7D demonstrates successful targeting of T cells using a protein that contains a viral peptide sequence as part of its polypeptide chain. A single chain fragment V (scFv) antibody-like construct was prepared, encoding a protease recognition domain and T cell epitope, and shown to efficiently target MDA-MB-231 cells in vitro.

FIG. 8A shows that the conjugates according to the invention may be used to selectively target cancer cells. Following labelling of lymphoblastoid cells or healthy B cells with Rituximab conjugated with viral peptide, there is no recognition of healthy B cells whereas there is recognition of lymphoblastoid cells only in the presence of the viral peptide that the T cells are specific for.

FIG. 8B demonstrates plasma and serum stability of conjugates according to the invention.

FIG. 10A demonstrates the mechanism of action of the Cetuximab-peptide complex occurring at the cell surface and not by way of internalisation of the whole complex. By chemical fixation of target cells, internalisation of the complex is inhibited and a positive IFN-γ response using fixed cells would demonstrate external processing of the APEC. The results show that target cells chemically fixed demonstrate a similar ability to induce IFN-γ production by T cells when they are incubated with Cetuximab-NLVPMVATV-Protease Cleavage as that seen when target cells have not been chemically fixed. Similarly, chemically fixed target cells cannot induce an IFN-γ response when labelled with an irrelevant APEC (Cetuximab-VLEETSVML-Protease Cleavage) similar to that seen in untreated target cells.

FIG. 10B demonstrates the ability to use a peptide as a targeting moiety in place of an antibody. Peptides which directly bind to either EGF receptor or Her2/neu receptor were synthesised containing a protease cleavage sequence and the viral epitope named receptor peptides (EGF-NLVPMVATV (NLVPMVATVAIPVSLR-SAAAYCRDYDYDGRYFDCY) (SEQ ID No: 314) Ponde et al (2011) *Bioorg Med Chem Lett,* 21 or Her2-NLVPM-VATV (NLVPMVATVAIPVSLRSAAAFCDGFYA-CYMDV) (SEQ ID No: 311) Park et al (2000) *Nat Biotech* 18). Target cells labelled with either peptide were able to induce an IFN-γ response from viral-specific CD8+ T cells similar to that seen when target cells were pulsed with exogenous viral peptide. When either receptor peptide is removed, the target cells were not recognised by the T cells.

FIG. 13 shows that antibody peptide epitope complexes (APEC) formed of anti-EGFR Cetuximab and peptides were able to re-target antigen specific T cells to target these malignant cell lines, but only when the peptide contained a protease cleavage site.

FIG. 14 shows that antigen specific T cells are at the tumour site and that other antibodies may be used in the approach (eg anti-MUC1 antibody SM3). The figure also demonstrates selective targeting of malignant cells compared to healthy cells. For example, the anti-CD20 Rituximab APEC efficiently targets malignant lymphoma cells in vitro but spares healthy B cells derived from peripheral blood (FIG. 14C). The figure also shows the applicability toward MHC Class-II restricted peptides using CD4+ cytotoxic T cells (FIG. 14D), and that the APEC approach does not require the antigen processing capacity of target cells (FIG. 14E) suggesting that peptide cleavage is occurring at the cell membrane.

Discussion

Targeting tumors in this way bypasses the requirement of an intact antigen processing system in the tumor cell. We believe that the processing of the protease cleavage site and subsequent loading of peptide onto MHC class I/II molecules occurs extracellularly, without the requirement of classical antigen processing components.

Furthermore, the results demonstrate that conjugating peptides to different antibodies allows targeting of many different malignancies including breast cancer, multiple myeloma, acute myeloid leukemia and pancreatic cancer. Therefore, the immunotherapeutic potential of this mechanism is far-reaching.

Xenograft Studies

Xenograft models use NOG mice (NOD Rag2$^{-/-}$γc$^{-/-}$) (M. Ito et al., *Blood* 100, 3175 (2002)). Tumour cell lines are grown using standard laboratory tissue culture techniques and injected subcutaneously in Matrigel and left to engraft for ~7 days. Human CD4+ and CD8+ T cells are cultured using standard techniques and cultured from healthy laboratory donors. $10^6$ T cells are infused into each study mouse intraperitoneally. Antibody or APEC is injected into the intraperitoneal cavity. Mice are injected with 120 mg/kg luciferin weekly and growth and metastatic dissemination of the cells monitored using IVIS Spectrum (Caliper Lifesciences). Quantitation of outgrowth kinetics is determined and metastasis quantified by measuring luminescent signal from each organ at the experimental endpoint.

REFERENCES

Bargou, R., Leo, E., Zugmaier, G., Klinger, M., Goebeler, M., Knop, S., Noppeney, R., Viardot, A., Hess, G., Schuler, M., Einsele, H., Brandl, C., Wolf, A., Kirchinger, P., Klappers, P., Schmidt, M., Riethmuller, G., Reinhardt, C., Baeuerle, P.A., & Kufer, P. (2008) Tumor regression in cancer patients by very low doses of a T cell-engaging antibody. *Science* 321, 974-977.

Bargou R, Leo E, Zugmaier G, et al (2008) *Science* 321 (5891), 974-977.

Bellosillo, B., Villamor, N., Lopez-Guillermo, A., Marce, S., Esteve, J., Campo, E., Colomer, D., & Montserrat, E. (2001) Complement-mediated cell death induced by rituximab in B-celllymphoproliferative disorders is mediated in vitro by a caspase-independent mechanism involving the generation of reactive oxygen species. *Blood* 98, 2771-2777.

Baeuerle P A, Reinhardt C. (2009) *Cancer Res* 69(12), 4941-4944.

Bertilaccio, M. T., Scielzo, C., Simonetti, G., Ponzoni, M., Apollonio, B., Fazi, C., Scarfo, L., Rocchi, M., Muzio, M., Caligaris-Cappio, F., & Ghia, P. (2010) A novel Rag2−/−gammac−/−-xenograft model of human CLL. *Blood* 115, 1605-1609.

Bonnet, D. & Dick, J. E. (1997) Human acute myeloid leukemia is organized as a hierarchy that originates from a primitive hematopoietic cell. *Nat.Med.* 3, 730-737.

Clarke, W. T. & Marks, P. W. (2010) Gemtuzumab ozogamicin: is there room for salvage? *Blood* 116, 2618-2619.

Irvine, D. J., Purbhoo, M. A., Krogsgaard, M., & Davis, M. M. (2002) Direct observation of ligand recognition by T cells. *Nature* 419, 845-849.

Loisel, S., Ster, K. L., Quintin-Roue, I., Pers, J. O., Bordron, A., Youinou, P., & Berthou, C. (2005) Establishment of a novel human B-CLL-like xenograft model in nude mouse. *Leuk. Res.* 29, 1347-1352.

Lutterbuese, R., Raum, T., Kischel, R., Lutterbuese, P., Schlereth, B., Schaller, E., Mangold, S., Rau, D., Meier, P., Kiener, P.A., Mulgrew, K., Oberst, M. D., Hammond, S. A., Baeuerle, P. A., & Kufer, P. (2009) Potent control of tumor growth by CEA/CD3-bispecific single-chain antibody constructs that are not competitively inhibited by soluble CEA. *J. Immunother.* 32, 341-352.

Mayes, S., Brown, N., & Illidge, T. M. (2011) New antibody drug treatments for lymphoma. *Expert. Opin. Biol. Ther.*

Moore P A, Zhang W, Rainey G J, et al (2011) *Blood* 28; 117(17), 4542-51.

Schmiegel, W., Schmielau, J., Henne-Bruns, D., Juhl, H., Roeder, C., Buggisch, P., Onur, A., Kremer, B., Kalthoff, H., & Jensen, E. V. (1997) Cytokine-mediated enhancement of epidermal growth factor receptor expression provides an immunological approach to the therapy of pancreatic cancer. *Proc. Natl. Acad. Sci* USA, 94, 12622-12626.

Park B W, Zhang H T, Wu C, Berezov A, Zhang X, Dua R, Wang Q, Kao G, O'Rourke D M, Greene M I, Murali R. (2000). Rationally designed anti-HER2/neu peptide mimetic disables P185HER2/neu tyrosine kinases in vitro and in vivo. *Nature Biotechnology,* 18 (2), 194-8

Ponde D E, Su Z, Berezov A, Zhang H, Alavi A, Greene M I, Murali R. (2011) Development of anti-EGF receptor peptidomimetics (AERP) as tumor imaging agent. *Bioorganic and Medicinal Chemical Letters,* 21 (8), 2550-3.

Small E J, Schellhammer P F, Higano C S, et al (2006) *J Clin Oncol* 24(19), 3089-3094.

Staerz U D Bevan M J. (1986) *Proc Natl Acad Sci USA* 83(5), 1453-1457.

Sykulev, Y., Joo, M., Vturina, I., Tsomides, T. J., & Eisen, H. N. (1996) Evidence that a single peptide-MHC complex on a target cell can elicit a cytolytic T cell response. *Immunity.,* 4, 565-571.

Tosolini, M., Kirilovsky, A., Mlecnik, B., Fredriksen, T., Mauger, S., Bindea, G., Berger, A., Bruneval, P., Fridman, W. H., Pages, F., & Galon, J. (2011) Clinical impact of different classes of infiltrating T cytotoxic and helper cells (Thl, th2, treg, th17) in patients with colorectal cancer. *Cancer Res.,* 71, 1263-1271.

Zhou, X., Hu, W., & Qin, X. (2008) The role of complement in the mechanism of action of rituximab for B-cell lymphoma: implications for therapy. *Oncologist.,* 13, 954-966.

The invention claimed is:

1. An agent for retargeting T cells to solid tumor cells, the agent comprising:

(i) a targeting moiety that is capable of targeting to the solid tumor cells, wherein the targeting moiety is an antibody or antigen binding fragment thereof that binds a solid tumor antigen; and (ii) more than one viral T cell epitope that each elicit an existing immune response in the subject and that each bind to a HLA molecule on the surface of the cancer cell of the human subject and has a HLA matched to the subject, (iii) more than one peptide linker each comprising a peptide cleavage site cleavable by a tumor associated protease and wherein each linker can be selectively cleaved by a tumor associated protease to release each T cell epitope in the vicinity of, and outside of, the solid tumor cells, wherein each peptide linker is separately attached to the targeting moiety, wherein each linker attaches a single T cell epitope to the targeting moiety, and wherein the solid tumor is not a lymphoma.

2. The agent according to claim 1, wherein at least some of the peptide cleavage sites are the same.

3. The agent according to claim 1, wherein at least some of the peptide cleavage sites are not the same.

4. The agent according to claim 1, wherein the tumor associated protease is Cathepsin B, Cathepsin L, Cathepsin S, Cathepsin D, Cathepsin E, Cathepsin A, Cathepsin G, Thrombin, Plasmin, Urokinase, Tissue Plasminogen Activator, Metalloproteinase 1 (MMP1), MMP2, MMP3, MMP4, MMP7, MMP8, MMP9, MMP10, MMP11, MMP12, MMP13, MMP14, MMP15, MMP16, MMP17, MMP20, MMP21, MMP23, MMP24, MMP25, MMP26, MMP28, ADAM, ADAMTS, CD10 (CALLA), or prostate specific antigen.

5. The agent according to claim 1, wherein the more than one T cell epitopes are the same.

6. The agent according to claim 1, wherein the more than one T cell epitopes are not the same.

7. The agent according to claim 1, wherein one or more T cell epitope is from any of Varicella Zoster virus, Herpes simplex virus, cytomegalovirus, Epstein Barr virus, adenovirus, rhinovirus, or influenza virus.

8. The agent according to claim 1, wherein one or more T cell epitope is an MHC Class I restricted antigen, an MHC Class II restricted antigen, or an antigen that is capable of binding to a group I CD1 molecule.

9. The agent of claim 1, wherein one or more viral T cell epitope is one to which a number of T cells in the subject are already sensitized to.

10. The agent of claim 1, wherein one or more viral T cell epitope is one that elicits an existing immune response, wherein the existing immune response has been generated by prior vaccination against an infectious agent.

11. The agent of claim 1, wherein one or more viral T cell epitope is one that elicits an existing immune response, wherein the existing immune response has been generated by exposing the human subject's T cells to the epitope in vitro.

12. The agent of claim 1, wherein the solid tumor is chosen from an epithelial tumor, prostate tumor, ovarian tumor, renal cell tumor, gastrointestinal tract tumor, hepatic tumor, colorectal tumor, tumor with vasculature, mesothelioma tumor, pancreatic tumor, breast tumor, sarcoma tumor, lung tumor, brain tumor, melanoma tumor, small cell lung tumor, neuroblastoma tumor, testicular tumor, carcinoma tumor, adenocarcinoma tumor, glioma tumor, seminoma tumor, or osteosarcoma tumor.

13. The agent according to claim 1, wherein selective cleavage of each cleavage site enables release of each T cell epitope at or near to the cell surface of the solid tumor cells.

14. The agent according to claim 1, wherein the antibody or antigen binding fragment thereof is specific for EpCAM (CD326).

15. The agent according to claim 1, wherein the antibody or antigen binding fragment thereof is an anti-EpCAM antibody.

16. The agent according to claim 15, wherein the antibody or antigen binding fragment thereof is an anti-CEA antibody.

17. The agent according to claim 1, wherein the antibody or antigen binding fragment thereof is specific for CEACAM.

18. The agent according to claim 1, wherein the antibody is Cetuximab.

19. A pharmaceutical composition, comprising an agent according to claim 1, and a pharmaceutically acceptable carrier, diluent or excipient.

20. A composition comprising (i) an agent according to claim 1 and (ii) a therapeutic agent suitable for treating a solid tumor.

21. The agent according to claim 1, wherein the antibody or antigen binding fragment thereof is specific for any of Her2; EGFR; PSMA; CD30; CD33; CD2; CA125; Carbonic Anhydrase IX; CD70; CD74; CD56; CD40; c met/HGFR; TRAIL R1; DR5; PD-1; PDL1; IGF-1R; VEGF-R2; Prostate stem cell antigen (PSCA); MUC1; CanAg; Mesothelin; P-cadherin; Myostatin (GDF8); Cripto (TDGF1); ACVRL1/ALK1; MUC5AC; CEACAM; SLC44A4; CD137; CXCR4; Neuropilin 1; Glypican; PDGFRa, EphA2, E-cadherin, FGFR3, EpCAM, and CD138.

22. The agent according to claim 1, wherein the antibody or antigen binding fragment thereof is an anti-epidermal growth factor receptor antibody, an anti-Her2 antibody, an anti-MUC1 antibody, an anti-P-cadherin antibody, an anti-E-cadherin antibody, an anti-CEA antibody, or an anti-FGFR3 antibody.

* * * * *

SEQUENCE LISTING

```
<160> NUMBER OF SEQ ID NOS: 323

<210> SEQ ID NO 1

<400> SEQUENCE: 1

000


<210> SEQ ID NO 2
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 2

Tyr Ile Leu Glu Glu Thr Ser Val Met
1               5


<210> SEQ ID NO 3
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 3

Tyr Val Leu Glu Glu Thr Ser Val Met
1               5


<210> SEQ ID NO 4
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 4

Val Leu Glu Glu Thr Ser Val Met Leu
1               5


<210> SEQ ID NO 5
<211> LENGTH: 9
<212> TYPE: PRT
<213> ORGANISM: Artificial Sequence
<220> FEATURE:
<223> OTHER INFORMATION: T cell epitope from cytomegalovirus
```

<400> SEQUENCE: 5

Val Leu Ala Glu Leu Val Lys Gln Ile
1               5

<210> SEQ ID NO 6
<211> LENGTH: 10
<212> TYPE: PRT
<213> ORGANISM: Artificial Sequence
<220> FEATURE:
<223> OTHER INFORMATION: T cell epitope from cytomegalovirus

<400> SEQUENCE: 6

Ala Thr Thr Phe Leu Gln Thr Met Leu Arg
1               5                   10

<210> SEQ ID NO 7
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 7

Glu Val Ile Ser Val Met Lys Arg Arg
1               5

<210> SEQ ID NO 8
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 8

Cys Arg Val Leu Cys Cys Tyr Val Leu
1               5

<210> SEQ ID NO 9
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 9

Glu Leu Arg Arg Lys Met Met Tyr Met
1               5

<210> SEQ ID NO 10
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 10

Glu Leu Lys Arg Lys Met Ile Tyr Met
1               5

<210> SEQ ID NO 11
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 11

Gln Ile Lys Val Arg Val Asp Met Val
1 5

<210> SEQ ID NO 12
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 12

Cys Val Glu Thr Met Cys Asn Glu Tyr
1 5

<210> SEQ ID NO 13
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 13

Arg Arg Lys Met Met Tyr Met Cys Tyr
1 5

<210> SEQ ID NO 14
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 14

Lys Arg Lys Met Ile Tyr Met Cys Tyr
1 5

<210> SEQ ID NO 15
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 15

Arg Arg Ile Glu Glu Ile Cys Met Lys
1 5

<210> SEQ ID NO 16
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 16

Asp Glu Leu Arg Arg Lys Met Met Tyr
1 5

<210> SEQ ID NO 17
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 17

-continued

Lys Glu Val Asn Ser Gln Leu Ser Leu
1 5

<210> SEQ ID NO 18
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 18

Glu Glu Ala Ile Val Ala Tyr Thr Leu
1 5

<210> SEQ ID NO 19
<211> LENGTH: 11
<212> TYPE: PRT
<213> ORGANISM: Artificial Sequence
<220> FEATURE:
<223> OTHER INFORMATION: T cell epitope from cytomegalovirus

<400> SEQUENCE: 19

Phe Pro Lys Thr Thr Asn Gly Cys Ser Gln Ala
1 5 10

<210> SEQ ID NO 20
<211> LENGTH: 11
<212> TYPE: PRT
<213> ORGANISM: Artificial Sequence
<220> FEATURE:
<223> OTHER INFORMATION: T cell epitope from cytomegalovirus

<400> SEQUENCE: 20

Tyr Ser Glu His Pro Thr Phe Thr Ser Gln Tyr
1 5 10

<210> SEQ ID NO 21
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 21

Asn Leu Val Pro Met Val Ala Thr Val
1 5

<210> SEQ ID NO 22
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 22

Met Leu Asn Ile Pro Ser Ile Asn Val
1 5

<210> SEQ ID NO 23
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 23

Arg Ile Phe Ala Glu Leu Glu Gly Val 1               5

<210> SEQ ID NO 24
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 24

Gln Tyr Asp Val Pro Ala Ala Leu Phe
1               5

<210> SEQ ID NO 25
<211> LENGTH: 11
<212> TYPE: PRT
<213> ORGANISM: Artificial Sequence
<220> FEATURE:
<223> OTHER INFORMATION: T cell epitope from cytomegalovirus

<400> SEQUENCE: 25

Phe Thr Ser Gln Tyr Arg Ile Gln Gly Lys Leu
1               5                   10

<210> SEQ ID NO 26
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 26

Val Tyr Ala Leu Pro Leu Lys Met Leu
1               5

<210> SEQ ID NO 27
<211> LENGTH: 10
<212> TYPE: PRT
<213> ORGANISM: Artificial Sequence
<220> FEATURE:
<223> OTHER INFORMATION: T cell epitope from cytomegalovirus

<400> SEQUENCE: 27

Gln Tyr Val Lys Val Tyr Leu Glu Ser Phe
1               5                   10

<210> SEQ ID NO 28
<211> LENGTH: 11
<212> TYPE: PRT
<213> ORGANISM: Artificial Sequence
<220> FEATURE:
<223> OTHER INFORMATION: T cell epitope from cytomegalovirus

<400> SEQUENCE: 28

Phe Val Phe Pro Thr Lys Asp Val Ala Leu Arg
1               5                   10

<210> SEQ ID NO 29
<211> LENGTH: 10
<212> TYPE: PRT
<213> ORGANISM: Artificial Sequence
<220> FEATURE:
<223> OTHER INFORMATION: T cell epitope from cytomegalovirus

<400> SEQUENCE: 29

Tyr Thr Pro Asp Ser Thr Pro Cys His Arg
1               5                   10

<210> SEQ ID NO 30
<211> LENGTH: 10
<212> TYPE: PRT
<213> ORGANISM: Artificial Sequence
<220> FEATURE:
<223> OTHER INFORMATION: T cell epitope from cytomegalovirus

<400> SEQUENCE: 30

Asp Thr Pro Val Leu Pro His Glu Thr Arg
1               5                   10

<210> SEQ ID NO 31
<211> LENGTH: 10
<212> TYPE: PRT
<213> ORGANISM: Artificial Sequence
<220> FEATURE:
<223> OTHER INFORMATION: T cell epitope from cytomegalovirus

<400> SEQUENCE: 31

Thr Pro Arg Val Thr Gly Gly Gly Ala Met
1               5                   10

<210> SEQ ID NO 32
<211> LENGTH: 11
<212> TYPE: PRT
<213> ORGANISM: Artificial Sequence
<220> FEATURE:
<223> OTHER INFORMATION: T cell epitope from cytomegalovirus

<400> SEQUENCE: 32

Arg Pro His Glu Arg Asn Gly Phe Thr Val Leu
1               5                   10

<210> SEQ ID NO 33
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 33

Ile Pro Ser Ile Asn Val His His Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: T cell epitope from cytomegalovirus

<400> SEQUENCE: 34

Phe Pro Thr Lys Asp Val Ala Leu
1               5

<210> SEQ ID NO 35
<211> LENGTH: 12
<212> TYPE: PRT
<213> ORGANISM: Artificial Sequence
<220> FEATURE:
<223> OTHER INFORMATION: T cell epitope from cytomegalovirus

<400> SEQUENCE: 35

Cys Pro Ser Gln Glu Pro Met Ser Ile Tyr Val Tyr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: T cell epitope from cytomegalovirus

<400> SEQUENCE: 36

Gln Pro Ser Leu Ile Leu Val Ser Gln Tyr
1 5 10

<210> SEQ ID NO 37
<211> LENGTH: 10
<212> TYPE: PRT
<213> ORGANISM: Artificial Sequence
<220> FEATURE:
<223> OTHER INFORMATION: T cell epitope from cytomegalovirus

<400> SEQUENCE: 37

Ser Glu His Pro Thr Phe Thr Ser Gln Tyr
1 5 10

<210> SEQ ID NO 38
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 38

Glu Phe Phe Asp Ala Asn Asp Ile Tyr
1 5

<210> SEQ ID NO 39
<211> LENGTH: 11
<212> TYPE: PRT
<213> ORGANISM: Artificial Sequence
<220> FEATURE:
<223> OTHER INFORMATION: T cell epitope from cytomegalovirus

<400> SEQUENCE: 39

Thr Thr Val Tyr Pro Pro Ser Ser Thr Ala Lys
1 5 10

<210> SEQ ID NO 40
<211> LENGTH: 11
<212> TYPE: PRT
<213> ORGANISM: Artificial Sequence
<220> FEATURE:
<223> OTHER INFORMATION: T cell epitope from cytomegalovirus

<400> SEQUENCE: 40

Gln Thr Val Thr Ser Thr Pro Val Gln Gly Arg
1 5 10

<210> SEQ ID NO 41
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 41

Asn Val Arg Arg Ser Trp Glu Glu Leu
1 5

<210> SEQ ID NO 42
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 42

Lys Ala Arg Asp His Leu Ala Val Leu
1 5

<210> SEQ ID NO 43
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 43

Arg Ile Trp Cys Leu Val Val Cys Val
1 5

<210> SEQ ID NO 44
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 44

Val Thr Glu His Asp Thr Leu Leu Tyr
1 5

<210> SEQ ID NO 45
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 45

Arg Gly Asp Pro Phe Asp Lys Asn Tyr
1 5

<210> SEQ ID NO 46
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 46

Thr Val Arg Ser His Cys Val Ser Lys
1 5

<210> SEQ ID NO 47
<211> LENGTH: 16
<212> TYPE: PRT
<213> ORGANISM: Artificial Sequence
<220> FEATURE:
<223> OTHER INFORMATION: T cell epitope from cytomegalovirus

<400> SEQUENCE: 47

Pro Gln Tyr Ser Glu His Pro Thr Phe Thr Ser Gln Tyr Arg Ile Gln
1 5 10 15

<210> SEQ ID NO 48

-continued

<211> LENGTH: 16
<212> TYPE: PRT
<213> ORGANISM: Artificial Sequence
<220> FEATURE:
<223> OTHER INFORMATION: T cell epitope from cytomegalovirus

<400> SEQUENCE: 48

Phe Thr Ser Gln Tyr Arg Ile Gln Gly Lys Leu Glu Tyr Arg His Thr
1 5 10 15

<210> SEQ ID NO 49
<211> LENGTH: 15
<212> TYPE: PRT
<213> ORGANISM: Artificial Sequence
<220> FEATURE:
<223> OTHER INFORMATION: T cell epitope from cytomegalovirus

<400> SEQUENCE: 49

Leu Leu Gln Thr Gly Ile His Val Arg Val Ser Gln Pro Ser Leu
1 5 10 15

<210> SEQ ID NO 50
<211> LENGTH: 15
<212> TYPE: PRT
<213> ORGANISM: Artificial Sequence
<220> FEATURE:
<223> OTHER INFORMATION: T cell epitope from cytomegalovirus

<400> SEQUENCE: 50

Asn Pro Gln Pro Phe Met Arg Pro His Glu Arg Asn Gly Phe Thr
1 5 10 15

<210> SEQ ID NO 51
<211> LENGTH: 15
<212> TYPE: PRT
<213> ORGANISM: Artificial Sequence
<220> FEATURE:
<223> OTHER INFORMATION: T cell epitope from cytomegalovirus

<400> SEQUENCE: 51

Glu Pro Asp Val Tyr Tyr Thr Ser Ala Phe Val Phe Pro Thr Lys
1 5 10 15

<210> SEQ ID NO 52
<211> LENGTH: 15
<212> TYPE: PRT
<213> ORGANISM: Artificial Sequence
<220> FEATURE:
<223> OTHER INFORMATION: T cell epitope from cytomegalovirus

<400> SEQUENCE: 52

Ile Ile Lys Pro Gly Lys Ile Ser His Ile Met Leu Asp Val Ala
1 5 10 15

<210> SEQ ID NO 53
<211> LENGTH: 15
<212> TYPE: PRT
<213> ORGANISM: Artificial Sequence
<220> FEATURE:
<223> OTHER INFORMATION: T cell epitope from cytomegalovirus

<400> SEQUENCE: 53

Ala Gly Ile Leu Ala Arg Asn Leu Val Pro Met Val Ala Thr Val
1 5 10 15

<210> SEQ ID NO 54
<211> LENGTH: 15

<212> TYPE: PRT
<213> ORGANISM: Artificial Sequence
<220> FEATURE:
<223> OTHER INFORMATION: T cell epitope from cytomegalovirus

<400> SEQUENCE: 54

Lys Tyr Gln Glu Phe Phe Trp Asp Ala Asn Asp Ile Tyr Arg Ile
1               5                   10                  15

<210> SEQ ID NO 55
<211> LENGTH: 11
<212> TYPE: PRT
<213> ORGANISM: Artificial Sequence
<220> FEATURE:
<223> OTHER INFORMATION: T cell epitope from cytomegalovirus

<400> SEQUENCE: 55

Asp Tyr Ser Asn Thr His Ser Thr Arg Tyr Val
1               5                   10

<210> SEQ ID NO 56
<211> LENGTH: 15
<212> TYPE: PRT
<213> ORGANISM: Artificial Sequence
<220> FEATURE:
<223> OTHER INFORMATION: T cell epitope from cytomegalovirus

<400> SEQUENCE: 56

Cys Met Leu Thr Ile Thr Thr Ala Arg Ser Lys Tyr Pro Tyr His
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: T cell epitope from cytomegalovirus

<400> SEQUENCE: 57

Val Phe Glu Thr Ser Gly Gly Leu Val Val Phe Trp Gln Gly Ile
1               5                   10                  15

<210> SEQ ID NO 58
<211> LENGTH: 20
<212> TYPE: PRT
<213> ORGANISM: Artificial Sequence
<220> FEATURE:
<223> OTHER INFORMATION: T cell epitope from cytomegalovirus

<400> SEQUENCE: 58

Val Arg Val Asp Met Val Arg His Arg Ile Lys Glu His Met Leu Lys
1               5                   10                  15

Lys Tyr Thr Gln
            20

<210> SEQ ID NO 59
<211> LENGTH: 20
<212> TYPE: PRT
<213> ORGANISM: Artificial Sequence
<220> FEATURE:
<223> OTHER INFORMATION: T cell epitope from cytomegalovirus

<400> SEQUENCE: 59

Asn Tyr Ile Val Pro Glu Asp Lys Arg Glu Met Trp Met Ala Cys Ile
1               5                   10                  15

Lys Glu Leu His

20

<210> SEQ ID NO 60
<211> LENGTH: 12
<212> TYPE: PRT
<213> ORGANISM: Artificial Sequence
<220> FEATURE:
<223> OTHER INFORMATION: T cell epitope from cytomegalovirus

<400> SEQUENCE: 60

His Glu Leu Leu Val Leu Val Lys Lys Ala Gln Leu
1 5 10

<210> SEQ ID NO 61
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 61

Arg Pro Gln Lys Arg Pro Ser Cys Ile
1 5

<210> SEQ ID NO 62
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 62

His Pro Val Gly Glu Ala Asp Tyr Phe
1 5

<210> SEQ ID NO 63
<211> LENGTH: 11
<212> TYPE: PRT
<213> ORGANISM: Artificial Sequence
<220> FEATURE:
<223> OTHER INFORMATION: T cell epitope from Epstein Barr virus

<400> SEQUENCE: 63

His Pro Val Gly Glu Ala Asp Tyr Phe Glu Tyr
1 5 10

<210> SEQ ID NO 64
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 64

Ile Pro Gln Cys Arg Leu Thr Pro Leu
1 5

<210> SEQ ID NO 65
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 65

Val Leu Lys Asp Ala Ile Lys Asp Leu
1 5

<210> SEQ ID NO 66
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 66

Tyr His Leu Ile Val Asp Thr Asp Ser Leu
1 5 10

<210> SEQ ID NO 67
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 67

Asp Thr Pro Leu Ile Pro Leu Thr Ile Phe
1 5 10

<210> SEQ ID NO 68
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 68

Arg Pro Thr Glu Leu Gln Pro Thr Pro
1 5

<210> SEQ ID NO 69
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 69

Gln Ala Lys Trp Arg Leu Gln Thr Leu
1 5

<210> SEQ ID NO 70
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 70

Ala Tyr Ser Ser Trp Met Tyr Ser Tyr
1 5

<210> SEQ ID NO 71
<211> LENGTH: 8
<212> TYPE: PRT
<213> ORGANISM: Artificial Sequence
<220> FEATURE:
<223> OTHER INFORMATION: T cell epitope from Epstein Barr virus

<400> SEQUENCE: 71

Arg Tyr Ser Ile Phe Phe Asp Tyr
1 5

<210> SEQ ID NO 72
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 72

Phe Leu Arg Gly Arg Ala Tyr Gly Leu
1 5

<210> SEQ ID NO 73
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 73

Lys Arg Pro Pro Ile Phe Ile Arg Arg Leu
1 5 10

<210> SEQ ID NO 74
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 74

Arg Pro Pro Ile Phe Ile Arg Arg Leu
1 5

<210> SEQ ID NO 75
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 75

Leu Glu Lys Ala Arg Gly Ser Thr Tyr
1 5

<210> SEQ ID NO 76
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 76

His Leu Ala Ala Gln Gly Met Ala Tyr
1 5

<210> SEQ ID NO 77
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 77

Tyr Pro Leu His Glu Gln His Gly Met
1 5

<210> SEQ ID NO 78
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 78

Val Phe Ser Asp Gly Arg Val Ala Cys
1 5

<210> SEQ ID NO 79
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 79

Val Pro Ala Pro Ala Gly Pro Ile Val
1 5

<210> SEQ ID NO 80
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 80

Ser Val Arg Asp Arg Leu Ala Arg Leu
1 5

<210> SEQ ID NO 81
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 81

Arg Leu Arg Ala Glu Ala Gln Val Lys
1 5

<210> SEQ ID NO 82
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 82

Val Gln Pro Pro Gln Leu Thr Leu Gln Val
1 5 10

<210> SEQ ID NO 83
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 83

His Arg Cys Gln Ala Ile Arg Lys Lys
1 5

<210> SEQ ID NO 84

```
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 84

Thr Tyr Ser Ala Gly Ile Val Gln Ile
1               5


<210> SEQ ID NO 85
<211> LENGTH: 11
<212> TYPE: PRT
<213> ORGANISM: Artificial Sequence
<220> FEATURE:
<223> OTHER INFORMATION: T cell epitope from Epstein Barr virus

<400> SEQUENCE: 85

Arg Arg Ala Arg Ser Leu Ser Ala Glu Arg Tyr
1               5                   10


<210> SEQ ID NO 86
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 86

Val Ser Phe Ile Glu Phe Val Gly Trp
1               5


<210> SEQ ID NO 87
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 87

Ala Val Phe Asp Arg Lys Ser Asp Ala Lys
1               5                   10


<210> SEQ ID NO 88
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 88

Ile Val Thr Asp Phe Ser Val Ile Lys
1               5


<210> SEQ ID NO 89
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 89

Ala Val Leu Leu His Glu Glu Ser Met
1               5


<210> SEQ ID NO 90
<211> LENGTH: 10
```

```
<212> TYPE: PRT
<213> ORGANISM: Artificial Sequence
<220> FEATURE:
<223> OTHER INFORMATION: T cell epitope from Epstein Barr virus

<400> SEQUENCE: 90

Val Glu Ile Thr Pro Tyr Lys Pro Thr Trp
1               5                   10


<210> SEQ ID NO 91
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 91

Glu Gly Gly Val Gly Trp Arg His Trp
1               5


<210> SEQ ID NO 92
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 92

Gln Asn Gly Ala Leu Ala Ile Asn Thr Phe
1               5                   10


<210> SEQ ID NO 93
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 93

Leu Arg Gly Lys Trp Gln Arg Arg Tyr Arg
1               5                   10


<210> SEQ ID NO 94
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 94

Arg Arg Ile Tyr Asp Leu Ile Glu Leu
1               5


<210> SEQ ID NO 95
<211> LENGTH: 8
<212> TYPE: PRT
<213> ORGANISM: Artificial Sequence
<220> FEATURE:
<223> OTHER INFORMATION: T cell epitope from Epstein Barr virus

<400> SEQUENCE: 95

His His Ile Trp Gln Asn Leu Leu
1               5


<210> SEQ ID NO 96
<211> LENGTH: 10
<212> TYPE: PRT
```

<213> ORGANISM: Artificial Sequence
<220> FEATURE:
<223> OTHER INFORMATION: T cell epitope from Epstein Barr virus

<400> SEQUENCE: 96

Glu Glu Asn Leu Leu Asp Phe Val Arg Phe
1               5                   10

<210> SEQ ID NO 97
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 97

Leu Leu Asp Phe Val Arg Phe Met Gly Val
1               5                   10

<210> SEQ ID NO 98
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 98

Leu Asp Phe Val Arg Phe Met Gly Val
1               5

<210> SEQ ID NO 99
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 99

Lys Glu His Val Ile Gln Asn Ala Phe
1               5

<210> SEQ ID NO 100
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 100

Phe Arg Lys Ala Gln Ile Gln Gly Leu
1               5

<210> SEQ ID NO 101
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 101

Gln Pro Arg Ala Pro Ile Arg Pro Ile
1               5

<210> SEQ ID NO 102
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 102

Ser Leu Arg Glu Trp Leu Leu Arg Ile
1 5

<210> SEQ ID NO 103
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 103

Phe Trp Leu Tyr Ile Val Met Ser Asp
1 5

<210> SEQ ID NO 104
<211> LENGTH: 11
<212> TYPE: PRT
<213> ORGANISM: Artificial Sequence
<220> FEATURE:
<223> OTHER INFORMATION: T cell epitope from Epstein Barr virus

<400> SEQUENCE: 104

Phe Arg Arg Asp Leu Leu Cys Pro Leu Gly Ala
1 5 10

<210> SEQ ID NO 105
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 105

Tyr Leu Leu Glu Met Leu Trp Arg Leu
1 5

<210> SEQ ID NO 106
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 106

Tyr Leu Gln Gln Asn Trp Trp Thr Leu
1 5

<210> SEQ ID NO 107
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 107

Thr Leu Leu Val Asp Leu Leu Trp Leu
1 5

<210> SEQ ID NO 108
<211> LENGTH: 12
<212> TYPE: PRT
<213> ORGANISM: Artificial Sequence
<220> FEATURE:

<223> OTHER INFORMATION: T cell epitope from Epstein Barr virus

<400> SEQUENCE: 108

Asp Pro His Gly Pro Val Gln Leu Ser Tyr Tyr Asp
1 5 10

<210> SEQ ID NO 109
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 109

Met Gly Ser Leu Glu Met Val Pro Met
1 5

<210> SEQ ID NO 110
<211> LENGTH: 12
<212> TYPE: PRT
<213> ORGANISM: Artificial Sequence
<220> FEATURE:
<223> OTHER INFORMATION: T cell epitope from Epstein Barr virus

<400> SEQUENCE: 110

Asp Tyr Trp Gly Asn Gly Asp Arg His Ser Asp Tyr
1 5 10

<210> SEQ ID NO 111
<211> LENGTH: 14
<212> TYPE: PRT
<213> ORGANISM: Artificial Sequence
<220> FEATURE:
<223> OTHER INFORMATION: T cell epitope from Epstein Barr virus

<400> SEQUENCE: 111

Asn Pro Val Cys Leu Pro Val Ile Val Ala Pro Tyr Leu Phe
1 5 10

<210> SEQ ID NO 112
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 112

Leu Pro Val Ile Val Ala Pro Tyr Leu
1 5

<210> SEQ ID NO 113
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 113

Pro Tyr Leu Phe Trp Leu Ala Ala Ile
1 5

<210> SEQ ID NO 114
<211> LENGTH: 14
<212> TYPE: PRT
<213> ORGANISM: Artificial Sequence
<220> FEATURE:
<223> OTHER INFORMATION: T cell epitope from Epstein Barr virus

<400> SEQUENCE: 114

Ala Ser Cys Phe Thr Ala Ser Val Ser Thr Val Val Thr Ala
1 5 10

<210> SEQ ID NO 115
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 115

Phe Thr Ala Ser Val Ser Thr Val Val
1 5

<210> SEQ ID NO 116
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 116

Ile Glu Asp Pro Pro Phe Asn Ser Leu
1 5

<210> SEQ ID NO 117
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 117

Arg Arg Arg Trp Arg Arg Leu Thr Val
1 5

<210> SEQ ID NO 118
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 118

Arg Arg Trp Arg Arg Leu Thr Val Cys
1 5

<210> SEQ ID NO 119
<211> LENGTH: 11
<212> TYPE: PRT
<213> ORGANISM: Artificial Sequence
<220> FEATURE:
<223> OTHER INFORMATION: T cell epitope from Epstein Barr virus

<400> SEQUENCE: 119

Arg Arg Leu Thr Val Cys Gly Gly Ile Met Phe
1 5 10

<210> SEQ ID NO 120
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 120

Thr Val Cys Gly Gly Ile Met Phe Leu
1 5

<210> SEQ ID NO 121
<211> LENGTH: 14
<212> TYPE: PRT
<213> ORGANISM: Artificial Sequence
<220> FEATURE:
<223> OTHER INFORMATION: T cell epitope from Epstein Barr virus

<400> SEQUENCE: 121

Met Phe Leu Ala Cys Val Leu Val Leu Ile Val Asp Ala Val
1 5 10

<210> SEQ ID NO 122
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 122

Leu Ile Val Asp Ala Val Leu Gln Leu
1 5

<210> SEQ ID NO 123
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 123

Gly Leu Gly Thr Leu Gly Ala Ala Ile
1 5

<210> SEQ ID NO 124
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 124

Leu Leu Trp Thr Leu Val Val Leu Leu
1 5

<210> SEQ ID NO 125
<211> LENGTH: 11
<212> TYPE: PRT
<213> ORGANISM: Artificial Sequence
<220> FEATURE:
<223> OTHER INFORMATION: T cell epitope from Epstein Barr virus

<400> SEQUENCE: 125

Ser Ser Cys Ser Ser Cys Pro Leu Ser Lys Ile
1 5 10

<210> SEQ ID NO 126
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 126

Ile Leu Leu Ala Arg Leu Phe Leu Tyr
1               5

<210> SEQ ID NO 127
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 127

Phe Leu Tyr Ala Leu Ala Leu Leu Leu
1               5

<210> SEQ ID NO 128
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 128

Thr Tyr Gly Pro Val Phe Met Cys Leu
1               5

<210> SEQ ID NO 129
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 129

Cys Leu Gly Gly Leu Leu Thr Met Val
1               5

<210> SEQ ID NO 130
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 130

Val Met Ser Asn Thr Leu Leu Ser Ala Trp
1               5                   10

<210> SEQ ID NO 131
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 131

Leu Thr Ala Gly Phe Leu Ile Phe Leu
1               5

<210> SEQ ID NO 132
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 132

-continued

Leu Leu Ser Ala Trp Ile Leu Thr Ala
1 5

<210> SEQ ID NO 133
<211> LENGTH: 14
<212> TYPE: PRT
<213> ORGANISM: Artificial Sequence
<220> FEATURE:
<223> OTHER INFORMATION: T cell epitope from Epstein Barr virus

<400> SEQUENCE: 133

Leu Val Ser Asp Tyr Cys Asn Val Leu Asn Lys Glu Phe Thr
1 5 10

<210> SEQ ID NO 134
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 134

Leu Val Ser Asp Tyr Cys Asn Val Leu
1 5

<210> SEQ ID NO 135
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 135

Asp Tyr Cys Asn Val Leu Asn Lys Glu Phe
1 5 10

<210> SEQ ID NO 136
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 136

Ala Glu Asn Ala Gly Asn Asp Ala Cys
1 5

<210> SEQ ID NO 137
<211> LENGTH: 16
<212> TYPE: PRT
<213> ORGANISM: Artificial Sequence
<220> FEATURE:
<223> OTHER INFORMATION: T cell epitope from Epstein Barr virus

<400> SEQUENCE: 137

Ile Ala Cys Pro Ile Val Met Arg Tyr Tyr Val Leu Asp His Leu Ile
1 5 10 15

<210> SEQ ID NO 138
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 138

Tyr Val Leu Asp His Leu Ile Val Val 1 5

<210> SEQ ID NO 139
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 139

Phe Phe Ile Gln Ala Pro Ser Asn Arg Val Met Ile Pro Ala Thr
1 5 10 15

<210> SEQ ID NO 140
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 140

Ala Thr Ile Gly Thr Ala Met Tyr Lys
1 5

<210> SEQ ID NO 141
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 141

Lys His Ser Arg Val Arg Ala Tyr Thr Tyr Ser Lys Val Leu Gly
1 5 10 15

<210> SEQ ID NO 142
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 142

Arg Ala Leu Ile Lys Thr Leu Pro Arg Ala Ser Tyr Ser Ser His
1 5 10 15

<210> SEQ ID NO 143
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 143

Glu Arg Pro Ile Phe Pro His Pro Ser Lys Pro Thr Phe Leu Pro
1 5 10 15

<210> SEQ ID NO 144
<211> LENGTH: 14
<212> TYPE: PRT
<213> ORGANISM: Artificial Sequence
<220> FEATURE:
<223> OTHER INFORMATION: T cell epitope from Epstein Barr virus

<400> SEQUENCE: 144

Gln Lys Glu Glu Ala Ala Ile Cys Gly Gln Met Asp Leu Ser
1 5 10

<210> SEQ ID NO 145
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 145

Glu Val Cys Gln Pro Lys Arg Ile Arg Pro Phe His Pro Pro Gly
1 5 10 15

<210> SEQ ID NO 146
<211> LENGTH: 13
<212> TYPE: PRT
<213> ORGANISM: Artificial Sequence
<220> FEATURE:
<223> OTHER INFORMATION: T cell epitope from Epstein Barr virus

<400> SEQUENCE: 146

Leu Pro Glu Pro Leu Pro Gln Gly Gln Leu Thr Ala Tyr
1 5 10

<210> SEQ ID NO 147
<211> LENGTH: 11
<212> TYPE: PRT
<213> ORGANISM: Artificial Sequence
<220> FEATURE:
<223> OTHER INFORMATION: T cell epitope from Epstein Barr virus

<400> SEQUENCE: 147

Glu Pro Leu Pro Gln Gly Gln Leu Thr Ala Tyr
1 5 10

<210> SEQ ID NO 148
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 148

Ala Pro Glu Asn Ala Tyr Gln Ala Tyr
1 5

<210> SEQ ID NO 149
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 149

Leu Gln His Tyr Arg Glu Val Ala Ala
1 5

<210> SEQ ID NO 150
<211> LENGTH: 12
<212> TYPE: PRT
<213> ORGANISM: Artificial Sequence
<220> FEATURE:
<223> OTHER INFORMATION: T cell epitope from Epstein Barr virus

<400> SEQUENCE: 150

Asp Ser Glu Leu Glu Ile Lys Arg Tyr Lys Asn Arg
1 5 10

<210> SEQ ID NO 151
<211> LENGTH: 16
<212> TYPE: PRT
<213> ORGANISM: Artificial Sequence
<220> FEATURE:
<223> OTHER INFORMATION: T cell epitope from Epstein Barr virus

<400> SEQUENCE: 151

Arg Lys Cys Cys Arg Ala Lys Phe Lys Gln Leu Leu Gln His Tyr Arg
1 5 10 15

<210> SEQ ID NO 152
<211> LENGTH: 8
<212> TYPE: PRT
<213> ORGANISM: Artificial Sequence
<220> FEATURE:
<223> OTHER INFORMATION: T cell epitope from Epstein Barr virus

<400> SEQUENCE: 152

Arg Ala Lys Phe Lys Gln Leu Leu
1 5

<210> SEQ ID NO 153
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 153

Ser Glu Asn Asp Arg Leu Arg Leu Leu
1 5

<210> SEQ ID NO 154
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 154

Lys Asp Thr Trp Leu Asp Ala Arg Met
1 5

<210> SEQ ID NO 155
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 155

Gly Leu Cys Thr Leu Val Ala Met Leu
1 5

<210> SEQ ID NO 156
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 156

Asp Glu Val Glu Phe Leu Gly His Tyr
1 5

<210> SEQ ID NO 157
<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 157

Ser Arg Leu Val Arg Ala Ile Leu Ser Pro
1               5                   10

<210> SEQ ID NO 158
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 158

Cys Tyr Asp His Ala Gln Thr His Leu
1               5

<210> SEQ ID NO 159
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 159

Phe Arg Asn Leu Ala Tyr Gly Arg Thr Cys Val Leu Gly Lys Glu
1               5                   10                  15

<210> SEQ ID NO 160
<211> LENGTH: 13
<212> TYPE: PRT
<213> ORGANISM: Artificial Sequence
<220> FEATURE:
<223> OTHER INFORMATION: T cell epitope from Epstein Barr virus

<400> SEQUENCE: 160

Arg Pro Gln Gly Gly Ser Arg Pro Glu Phe Val Lys Leu
1               5                   10

<210> SEQ ID NO 161
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 161

Thr Leu Asp Tyr Lys Pro Leu Ser Val
1               5

<210> SEQ ID NO 162
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 162

Tyr Arg Ser Gly Ile Ile Ala Val Val
1               5

<210> SEQ ID NO 163

-continued

<211> LENGTH: 10
<212> TYPE: PRT
<213> ORGANISM: Artificial Sequence
<220> FEATURE:
<223> OTHER INFORMATION: T cell epitope from Epstein Barr virus

<400> SEQUENCE: 163

Leu Pro Leu Asp Leu Ser Val Ile Leu Phe
1 5 10

<210> SEQ ID NO 164
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 164

Leu Leu Trp Ala Ala Arg Pro Arg Leu
1 5

<210> SEQ ID NO 165
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 165

Arg Arg Leu Val Val Thr Leu Gln Cys
1 5

<210> SEQ ID NO 166
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 166

Ala Arg Tyr Ala Tyr Tyr Leu Gln Phe
1 5

<210> SEQ ID NO 167
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 167

Arg Arg Arg Lys Gly Trp Ile Pro Leu
1 5

<210> SEQ ID NO 168
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 168

Val Leu Gln Trp Ala Ser Leu Ala Val
1 5

<210> SEQ ID NO 169
<211> LENGTH: 9

<212> TYPE: PRT
<213> ORGANISM: Artificial Sequence
<220> FEATURE:
<223> OTHER INFORMATION: T cell epitope from Epstein Barr virus

<400> SEQUENCE: 169

Phe Leu Asp Lys Gly Thr Tyr Thr Leu
1 5

<210> SEQ ID NO 170
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 170

Ile Leu Ile Tyr Asn Gly Trp Tyr Ala
1 5

<210> SEQ ID NO 171
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 171

Val Pro Gly Ser Glu Thr Met Cys Tyr
1 5

<210> SEQ ID NO 172
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 172

Ala Pro Gly Trp Leu Ile Trp Thr Tyr
1 5

<210> SEQ ID NO 173
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 173

Thr Leu Phe Ile Gly Ser His Val Val
1 5

<210> SEQ ID NO 174
<211> LENGTH: 9
<212> TYPE: PRT
<213> ORGANISM: Artificial Sequence
<220> FEATURE:
<223> OTHER INFORMATION: T cell epitope from Epstein Barr virus

<400> SEQUENCE: 174

Ser Leu Val Ile Val Thr Thr Phe Val
1 5

<210> SEQ ID NO 175
<211> LENGTH: 9
<212> TYPE: PRT

<213> ORGANISM: Artificial Sequence
<220> FEATURE:
<223> OTHER INFORMATION: T cell epitope from Epstein Barr virus

<400> SEQUENCE: 175

Leu Met Ile Ile Pro Leu Ile Asn Val
1               5

<210> SEQ ID NO 176
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 176

Arg Arg Pro Gln Lys Arg Pro Ser Cys Ile Gly Cys Lys Gly Thr
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 177

Arg Pro Phe Phe His Pro Val Gly Glu Ala Asp Tyr Phe Glu Tyr
1               5                   10                  15

<210> SEQ ID NO 178
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 178

Val Pro Pro Gly Ala Ile Glu Gln Gly Pro Ala Asp Asp Pro Gly Glu
1               5                   10                  15

Gly Pro Ser Thr
            20

<210> SEQ ID NO 179
<211> LENGTH: 25
<212> TYPE: PRT
<213> ORGANISM: Artificial Sequence
<220> FEATURE:
<223> OTHER INFORMATION: T cell epitope from Epstein Barr virus

<400> SEQUENCE: 179

Ile Glu Gln Gly Pro Thr Asp Asp Pro Gly Glu Gly Pro Ser Thr Gly
1               5                   10                  15

Pro Arg Gly Gln Gly Asp Gly Gly Arg
            20                  25

<210> SEQ ID NO 180
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 180

Asp Gly Gly Arg Arg Lys Lys Gly Gly Trp Phe Gly Arg His Arg
1               5                   10                  15

<210> SEQ ID NO 181
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 181

Ser Asn Pro Lys Phe Glu Asn Ile Ala Glu Gly Leu Arg Val Leu Leu
1 5 10 15

Ala Arg Ser His
20

<210> SEQ ID NO 182
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 182

Asn Pro Lys Phe Glu Asn Ile Ala Glu Gly Leu Arg Ala Leu Leu
1 5 10 15

<210> SEQ ID NO 183
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 183

Glu Asn Ile Ala Glu Gly Leu Arg Val Leu Leu Ala Arg Ser His Val
1 5 10 15

Glu Arg Thr Thr
20

<210> SEQ ID NO 184
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 184

Ile Ala Glu Gly Leu Arg Ala Leu Leu Ala Arg Ser His Val Glu Arg
1 5 10 15

Thr Thr Asp Glu
20

<210> SEQ ID NO 185
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 185

Leu Arg Ala Leu Leu Ala Arg Ser His Val Glu Arg Thr Thr Asp
1 5 10 15

<210> SEQ ID NO 186
<211> LENGTH: 25
<212> TYPE: PRT

<213> ORGANISM: Artificial Sequence
<220> FEATURE:
<223> OTHER INFORMATION: T cell epitope from Epstein Barr virus

<400> SEQUENCE: 186

Glu Glu Gly Asn Trp Val Ala Gly Val Phe Val Tyr Gly Gly Ser Lys
1 5 10 15

Thr Ser Leu Tyr Asn Leu Arg Arg Gly
20 25

<210> SEQ ID NO 187
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 187

Val Tyr Gly Gly Ser Lys Thr Ser Leu Tyr Asn Leu Arg Arg Gly Thr
1 5 10 15

Ala Leu Ala Ile
20

<210> SEQ ID NO 188
<211> LENGTH: 14
<212> TYPE: PRT
<213> ORGANISM: Artificial Sequence
<220> FEATURE:
<223> OTHER INFORMATION: T cell epitope from Epstein Barr virus

<400> SEQUENCE: 188

Thr Ser Leu Tyr Asn Leu Arg Arg Gly Thr Ala Leu Ala Ile
1 5 10

<210> SEQ ID NO 189
<211> LENGTH: 13
<212> TYPE: PRT
<213> ORGANISM: Artificial Sequence
<220> FEATURE:
<223> OTHER INFORMATION: T cell epitope from Epstein Barr virus

<400> SEQUENCE: 189

Tyr Asn Leu Arg Arg Gly Thr Ala Leu Ala Ile Pro Gln
1 5 10

<210> SEQ ID NO 190
<211> LENGTH: 16
<212> TYPE: PRT
<213> ORGANISM: Artificial Sequence
<220> FEATURE:
<223> OTHER INFORMATION: T cell epitope from Epstein Barr virus

<400> SEQUENCE: 190

Asn Leu Arg Arg Gly Arg Thr Ala Leu Ala Ile Pro Gln Cys Arg Leu
1 5 10 15

<210> SEQ ID NO 191
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 191

Ala Ile Pro Gln Cys Arg Leu Thr Pro Leu Ser Arg Leu Pro Phe
1 5 10 15

<210> SEQ ID NO 192
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 192

```
Pro Gln Cys Arg Leu Thr Pro Leu Ser Arg Leu Pro Phe Gly Met
1               5                   10                  15
```

<210> SEQ ID NO 193
<211> LENGTH: 18
<212> TYPE: PRT
<213> ORGANISM: Artificial Sequence
<220> FEATURE:
<223> OTHER INFORMATION: T cell epitope from Epstein Barr virus

<400> SEQUENCE: 193

```
Ala Pro Gly Pro Gly Pro Gln Pro Leu Arg Glu Ser Ile Val Cys Tyr
1               5                   10                  15

Phe Met
```

<210> SEQ ID NO 194
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 194

```
Pro Gln Pro Gly Pro Leu Arg Glu Ser Ile Val Cys Tyr Phe Met Val
1               5                   10                  15

Phe Leu Gln Thr
            20
```

<210> SEQ ID NO 195
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 195

```
Pro Gly Pro Leu Arg Glu Ser Ile Val Cys Tyr Phe Met Val Phe Leu
1               5                   10                  15

Gln Thr His Ile
            20
```

<210> SEQ ID NO 196
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 196

```
Leu Arg Glu Ser Ile Val Cys Tyr Phe Met Val Phe Leu Gln Thr His
1               5                   10                  15

Ile Phe Ala Glu
            20
```

<210> SEQ ID NO 197

<211> LENGTH: 25
<212> TYPE: PRT
<213> ORGANISM: Artificial Sequence
<220> FEATURE:
<223> OTHER INFORMATION: T cell epitope from Epstein Barr virus

<400> SEQUENCE: 197

Leu Arg Glu Ser Ile Val Cys Tyr Phe Met Val Phe Leu Gln Thr His
1               5                   10                  15

Ile Phe Ala Glu Val Leu Lys Asp Ala
            20                  25

<210> SEQ ID NO 198
<211> LENGTH: 13
<212> TYPE: PRT
<213> ORGANISM: Artificial Sequence
<220> FEATURE:
<223> OTHER INFORMATION: T cell epitope from Epstein Barr virus

<400> SEQUENCE: 198

Tyr Phe Met Val Phe Leu Gln Thr His Ile Phe Ala Glu
1               5                   10

<210> SEQ ID NO 199
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 199

Met Val Phe Leu Gln Thr His Ile Phe Ala Glu Val Leu Lys Asp
1               5                   10                  15

<210> SEQ ID NO 200
<211> LENGTH: 19
<212> TYPE: PRT
<213> ORGANISM: Artificial Sequence
<220> FEATURE:
<223> OTHER INFORMATION: T cell epitope from Epstein Barr virus

<400> SEQUENCE: 200

Val Phe Leu Gln Thr His Ile Phe Ala Glu Val Leu Lys Asp Ala Ile
1               5                   10                  15

Lys Asp Leu

<210> SEQ ID NO 201
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 201

Val Leu Lys Asp Ala Ile Lys Asp Leu Val Met Thr Lys Pro Ala Pro
1               5                   10                  15

Thr Cys Asn Ile
            20

<210> SEQ ID NO 202
<211> LENGTH: 25
<212> TYPE: PRT
<213> ORGANISM: Artificial Sequence
<220> FEATURE:
<223> OTHER INFORMATION: T cell epitope from Epstein Barr virus

<400> SEQUENCE: 202

Pro Thr Cys Asn Ile Lys Val Thr Val Cys Ser Phe Asp Asp Gly Val
1 5 10 15

Asp Leu Pro Pro Trp Phe Pro Pro Met
20 25

<210> SEQ ID NO 203
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 203

Arg Val Thr Val Cys Ser Phe Asp Asp Gly Val Asp Leu Pro Pro Trp
1 5 10 15

Phe Pro Pro Met
20

<210> SEQ ID NO 204
<211> LENGTH: 13
<212> TYPE: PRT
<213> ORGANISM: Artificial Sequence
<220> FEATURE:
<223> OTHER INFORMATION: T cell epitope from Epstein Barr virus

<400> SEQUENCE: 204

Pro Pro Trp Phe Pro Pro Met Val Glu Gly Ala Ala Ala
1 5 10

<210> SEQ ID NO 205
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 205

Gly Gln Thr Tyr His Leu Ile Val Asp Thr Leu Ala Leu His Gly Gly
1 5 10 15

Gln Thr Tyr His
20

<210> SEQ ID NO 206
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 206

Ile Pro Leu Thr Ile Phe Val Gly Glu Asn Thr Gly Val Pro Pro Pro
1 5 10 15

Leu Pro Pro Pro
20

<210> SEQ ID NO 207
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 207

Met Arg Met Leu Trp Met Ala Asn Tyr Ile Val Arg Gln Ser Arg Gly
1 5 10 15

Asp Arg Gly Leu
20

<210> SEQ ID NO 208
<211> LENGTH: 19
<212> TYPE: PRT
<213> ORGANISM: Artificial Sequence
<220> FEATURE:
<223> OTHER INFORMATION: T cell epitope from Epstein Barr virus

<400> SEQUENCE: 208

Leu Pro Pro Ala Thr Leu Val Pro Pro Arg Pro Thr Arg Pro Thr Thr
1 5 10 15

Leu Pro Pro

<210> SEQ ID NO 209
<211> LENGTH: 19
<212> TYPE: PRT
<213> ORGANISM: Artificial Sequence
<220> FEATURE:
<223> OTHER INFORMATION: T cell epitope from Epstein Barr virus

<400> SEQUENCE: 209

Pro Arg Ser Thr Val Phe Tyr Asn Ile Pro Pro Met Pro Leu Pro Pro
1 5 10 15

Ser Gln Leu

<210> SEQ ID NO 210
<211> LENGTH: 11
<212> TYPE: PRT
<213> ORGANISM: Artificial Sequence
<220> FEATURE:
<223> OTHER INFORMATION: T cell epitope from Epstein Barr virus

<400> SEQUENCE: 210

Thr Val Phe Tyr Asn Ile Pro Pro Met Pro Leu
1 5 10

<210> SEQ ID NO 211
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 211

Pro Ala Gln Pro Pro Pro Gly Val Ile Asn Asp Gln Gln Leu His His
1 5 10 15

Leu Pro Ser Gly
20

<210> SEQ ID NO 212
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 212

Glu Asp Leu Pro Cys Ile Val Ser Arg Gly Gly Pro Lys Val Lys Arg
1 5 10 15

Pro Pro Ile Phe

20

<210> SEQ ID NO 213
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 213

Gly Pro Trp Val Pro Glu Gln Trp Met Phe Gln Gly Ala Pro Pro Ser
1 5 10 15

Gln Gly Thr Pro
20

<210> SEQ ID NO 214
<211> LENGTH: 19
<212> TYPE: PRT
<213> ORGANISM: Artificial Sequence
<220> FEATURE:
<223> OTHER INFORMATION: T cell epitope from Epstein Barr virus

<400> SEQUENCE: 214

Gln Val Ala Asp Val Val Arg Ala Pro Gly Val Pro Ala Met Gln Pro
1 5 10 15

Gln Tyr Phe

<210> SEQ ID NO 215
<211> LENGTH: 14
<212> TYPE: PRT
<213> ORGANISM: Artificial Sequence
<220> FEATURE:
<223> OTHER INFORMATION: T cell epitope from Epstein Barr virus

<400> SEQUENCE: 215

Asn Arg Gly Trp Met Gln Arg Ile Arg Arg Arg Arg Arg Arg
1 5 10

<210> SEQ ID NO 216
<211> LENGTH: 21
<212> TYPE: PRT
<213> ORGANISM: Artificial Sequence
<220> FEATURE:
<223> OTHER INFORMATION: T cell epitope from Epstein Barr virus

<400> SEQUENCE: 216

Pro His Asp Ile Thr Tyr Pro Tyr Thr Ala Arg Asn Ile Arg Asp Ala
1 5 10 15

Ala Cys Arg Ala Val
20

<210> SEQ ID NO 217
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 217

Ile Leu Cys Phe Val Met Ala Ala Arg Gln Arg Leu Gln Asp Ile
1 5 10 15

<210> SEQ ID NO 218
<211> LENGTH: 15
<212> TYPE: PRT

<213> ORGANISM: Artificial Sequence
<220> FEATURE:
<223> OTHER INFORMATION: T cell epitope from Epstein Barr virus

<400> SEQUENCE: 218

Ser Asp Asp Glu Leu Pro Tyr Ile Asp Pro Asn Met Glu Pro Val
1 5 10 15

<210> SEQ ID NO 219
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 219

Gln Gln Arg Pro Val Met Phe Val Ser Arg Val Pro Ala Lys Lys
1 5 10 15

<210> SEQ ID NO 220
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 220

Gln Lys Arg Ala Ala Pro Pro Thr Val Ser Pro Ser Asp Thr Gly
1 5 10 15

<210> SEQ ID NO 221
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 221

Pro Pro Ala Ala Gly Pro Pro Ala Ala Gly Pro Arg Ile Leu Ala
1 5 10 15

<210> SEQ ID NO 222
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 222

Pro Pro Val Val Arg Met Phe Met Arg Glu Arg Gln Leu Pro Gln
1 5 10 15

<210> SEQ ID NO 223
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 223

Pro Gln Cys Phe Trp Glu Met Arg Ala Gly Arg Glu Ile Thr Gln
1 5 10 15

<210> SEQ ID NO 224
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 224

Pro Ala Pro Gln Ala Pro Tyr Gln Gly Tyr Gln Glu Pro Pro Ala Pro
1 5 10 15

Gln Ala Pro Tyr
20

<210> SEQ ID NO 225
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 225

Pro Ser Met Pro Phe Ala Ser Asp Tyr Ser Gln Gly Ala Phe Thr
1 5 10 15

<210> SEQ ID NO 226
<211> LENGTH: 16
<212> TYPE: PRT
<213> ORGANISM: Artificial Sequence
<220> FEATURE:
<223> OTHER INFORMATION: T cell epitope from Epstein Barr virus

<400> SEQUENCE: 226

Ala Gln Glu Ile Leu Ser Asp Asn Ser Glu Ile Ser Val Phe Pro Lys
1 5 10 15

<210> SEQ ID NO 227
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 227

Gly Pro Pro Arg Pro Pro Leu Gly Pro Pro Leu Ser Ser Ser Ile Gly
1 5 10 15

Leu Ala Leu Leu
20

<210> SEQ ID NO 228
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 228

Leu Trp Arg Leu Gly Ala Thr Ile Trp Gln Leu Leu Ala Phe Phe
1 5 10 15

<210> SEQ ID NO 229
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 229

Leu Ile Trp Met Tyr Tyr His Gly Pro Arg His Thr Asp Glu His His
1 5 10 15

```
His Asp Asp Ser
            20


<210> SEQ ID NO 230
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 230

Gln Ala Thr Asp Asp Ser Ser His Glu Ser Asp Ser Asn Ser Asn Glu
1               5                   10                  15

Gly Arg His His
            20


<210> SEQ ID NO 231
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 231

Ser Ser His Glu Ser Asp Ser Asn Ser Asn Glu Gly Arg His His Leu
1               5                   10                  15

Leu Val Ser Gly
            20


<210> SEQ ID NO 232
<211> LENGTH: 16
<212> TYPE: PRT
<213> ORGANISM: Artificial Sequence
<220> FEATURE:
<223> OTHER INFORMATION: T cell epitope from Epstein Barr virus

<400> SEQUENCE: 232

Ser Gly His Glu Ser Asp Ser Asn Ser Asn Glu Gly Arg His His His
1               5                   10                  15


<210> SEQ ID NO 233
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 233

Thr Asp Gly Gly Gly Gly His Ser His Asp Ser Gly His Gly Gly
1               5                   10                  15


<210> SEQ ID NO 234
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 234

Asp Tyr Gln Pro Leu Gly Thr Gln Asp Gln Ser Leu Tyr Leu Gly
1               5                   10                  15


<210> SEQ ID NO 235
<211> LENGTH: 15
<212> TYPE: PRT
<213> ORGANISM: Artificial Sequence
```

<220> FEATURE:
<223> OTHER INFORMATION: T cell epitope from Epstein Barr virus

<400> SEQUENCE: 235

Ser Thr Val Val Thr Ala Thr Gly Leu Ala Leu Ser Leu Leu Leu
1 5 10 15

<210> SEQ ID NO 236
<211> LENGTH: 14
<212> TYPE: PRT
<213> ORGANISM: Artificial Sequence
<220> FEATURE:
<223> OTHER INFORMATION: T cell epitope from Epstein Barr virus

<400> SEQUENCE: 236

Ser Ser Tyr Ala Ala Ala Gln Arg Lys Leu Leu Thr Pro Val
1 5 10

<210> SEQ ID NO 237
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 237

Val Thr Phe Phe Ala Ile Cys Leu Thr Trp Arg Ile Glu Asp Pro Pro
1 5 10 15

Phe Asn Ser Ile
20

<210> SEQ ID NO 238
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 238

Ile Cys Leu Thr Trp Arg Ile Glu Asp Pro Pro Phe Asn Ser Ile Leu
1 5 10 15

Phe Ala Leu Leu
20

<210> SEQ ID NO 239
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 239

Val Leu Val Met Leu Val Leu Leu Ile Leu Ala Tyr Arg Arg Arg Trp
1 5 10 15

Arg Arg Leu Thr
20

<210> SEQ ID NO 240
<211> LENGTH: 14
<212> TYPE: PRT
<213> ORGANISM: Artificial Sequence
<220> FEATURE:
<223> OTHER INFORMATION: T cell epitope from Epstein Barr virus

<400> SEQUENCE: 240

-continued

Ser Thr Glu Phe Ile Pro Asn Leu Phe Cys Met Leu Leu Leu
1 5 10

<210> SEQ ID NO 241
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 241

Thr Tyr Gly Pro Val Phe Met Ser Leu Gly Gly Leu Leu Thr Met Val
1 5 10 15

Ala Gly Ala Val
20

<210> SEQ ID NO 242
<211> LENGTH: 19
<212> TYPE: PRT
<213> ORGANISM: Artificial Sequence
<220> FEATURE:
<223> OTHER INFORMATION: T cell epitope from Epstein Barr virus

<400> SEQUENCE: 242

Ala Gly Leu Thr Leu Ser Leu Leu Val Ile Cys Ser Tyr Leu Phe Ile
1 5 10 15

Ser Arg Gly

<210> SEQ ID NO 243
<211> LENGTH: 12
<212> TYPE: PRT
<213> ORGANISM: Artificial Sequence
<220> FEATURE:
<223> OTHER INFORMATION: T cell epitope from Epstein Barr virus

<400> SEQUENCE: 243

Pro Tyr Tyr Val Val Asp Leu Ser Val Arg Gly Met
1 5 10

<210> SEQ ID NO 244
<211> LENGTH: 13
<212> TYPE: PRT
<213> ORGANISM: Artificial Sequence
<220> FEATURE:
<223> OTHER INFORMATION: T cell epitope from Epstein Barr virus

<400> SEQUENCE: 244

Thr Val Val Leu Arg Tyr His Val Leu Leu Glu Glu Ile
1 5 10

<210> SEQ ID NO 245
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 245

Glu Leu Glu Ile Lys Arg Tyr Lys Asn Arg Val Ala Ser Arg Lys
1 5 10 15

<210> SEQ ID NO 246
<211> LENGTH: 15
<212> TYPE: PRT
<213> ORGANISM: Artificial Sequence
<220> FEATURE:

<223> OTHER INFORMATION: T cell epitope from Epstein Barr virus

<400> SEQUENCE: 246

```
Lys Ser Ser Glu Asn Asp Arg Leu Arg Leu Leu Leu Lys Gln Met
1               5                   10                  15
```

<210> SEQ ID NO 247
<211> LENGTH: 20
<212> TYPE: PRT
<213> ORGANISM: Artificial Sequence
<220> FEATURE:
<223> OTHER INFORMATION: T cell epitope from Epstein Barr virus

<400> SEQUENCE: 247

```
Leu Asp Leu Phe Gly Gln Leu Thr Pro His Thr Lys Ala Val Tyr Gln
1               5                   10                  15

Pro Arg Gly Ala
            20
```

<210> SEQ ID NO 248
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 248

```
Phe Gly Gln Leu Thr Pro His Thr Lys Ala Val Tyr Gln Pro Arg
1               5                   10                  15
```

<210> SEQ ID NO 249
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 249

```
Val Tyr Phe Gln Asp Val Phe Gly Thr Met Trp Cys His His Ala
1               5                   10                  15
```

<210> SEQ ID NO 250
<211> LENGTH: 21
<212> TYPE: PRT
<213> ORGANISM: Artificial Sequence
<220> FEATURE:
<223> OTHER INFORMATION: T cell epitope from Epstein Barr virus

<400> SEQUENCE: 250

```
Asp Asn Cys Asn Ser Thr Asn Ile Thr Ala Val Val Arg Ala Gln Gly
1               5                   10                  15

Leu Asp Val Thr Leu
            20
```

<210> SEQ ID NO 251
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 251

```
Ala Trp Cys Leu Glu Gln Lys Arg Gln Asn Met Val Leu Arg Glu
1               5                   10                  15
```

<210> SEQ ID NO 252
<211> LENGTH: 15
<212> TYPE: PRT
<213> ORGANISM: Artificial Sequence
<220> FEATURE:
<223> OTHER INFORMATION: T cell epitope from Epstein Barr virus

<400> SEQUENCE: 252

Asp Asn Glu Ile Phe Leu Thr Lys Lys Met Thr Glu Val Cys Gln
1               5                   10                  15

<210> SEQ ID NO 253
<211> LENGTH: 9
<212> TYPE: PRT
<213> ORGANISM: Artificial Sequence
<220> FEATURE:
<223> OTHER INFORMATION: T cell epitope from cytomegalovirus

<400> SEQUENCE: 253

Glu Leu Lys Arg Lys Met Met Tyr Met
1               5

<210> SEQ ID NO 254
<211> LENGTH: 8
<212> TYPE: PRT
<213> ORGANISM: Artificial Sequence
<220> FEATURE:
<223> OTHER INFORMATION: Protease cleavage site

<400> SEQUENCE: 254

Cys Pro Gly Arg Val Val Gly Gly
1               5

<210> SEQ ID NO 255

<400> SEQUENCE: 255

000

<210> SEQ ID NO 256
<211> LENGTH: 4
<212> TYPE: PRT
<213> ORGANISM: Artificial Sequence
<220> FEATURE:
<223> OTHER INFORMATION: Protease cleavage site
<220> FEATURE:
<221> NAME/KEY: SITE
<222> LOCATION: 4
<223> OTHER INFORMATION: Xaa is any amino acid

<400> SEQUENCE: 256

Gly Gly Arg Xaa
1

<210> SEQ ID NO 257
<211> LENGTH: 8
<212> TYPE: PRT
<213> ORGANISM: Artificial Sequence
<220> FEATURE:
<223> OTHER INFORMATION: Protease cleavage site

<400> SEQUENCE: 257

Tyr Leu Gly Arg Ser Tyr Lys Val
1               5

<210> SEQ ID NO 258
<211> LENGTH: 6
<212> TYPE: PRT

<213> ORGANISM: Artificial Sequence
<220> FEATURE:
<223> OTHER INFORMATION: Protease cleavage site
<220> FEATURE:
<221> NAME/KEY: SITE
<222> LOCATION: 6
<223> OTHER INFORMATION: Xaa is any amino acid

<400> SEQUENCE: 258

Met Gln Leu Gly Arg Xaa
1               5

<210> SEQ ID NO 259
<211> LENGTH: 8
<212> TYPE: PRT
<213> ORGANISM: Artificial Sequence
<220> FEATURE:
<223> OTHER INFORMATION: Protease cleavage site

<400> SEQUENCE: 259

Ser Leu Gly Arg Lys Ile Gln Ile
1               5

<210> SEQ ID NO 260
<211> LENGTH: 6
<212> TYPE: PRT
<213> ORGANISM: Artificial Sequence
<220> FEATURE:
<223> OTHER INFORMATION: Protease cleavage site

<400> SEQUENCE: 260

Leu Val Pro Arg Gly Ser
1               5

<210> SEQ ID NO 261
<211> LENGTH: 5
<212> TYPE: PRT
<213> ORGANISM: Artificial Sequence
<220> FEATURE:
<223> OTHER INFORMATION: Protease cleavage site
<220> FEATURE:
<221> NAME/KEY: SITE
<222> LOCATION: 1, 2, 3 and 5
<223> OTHER INFORMATION: Xaa is any amino acid

<400> SEQUENCE: 261

Xaa Xaa Xaa Arg Xaa
1               5

<210> SEQ ID NO 262
<211> LENGTH: 5
<212> TYPE: PRT
<213> ORGANISM: Artificial Sequence
<220> FEATURE:
<223> OTHER INFORMATION: Protease cleavage site
<220> FEATURE:
<221> NAME/KEY: SITE
<222> LOCATION: 5
<223> OTHER INFORMATION: Xaa is any amino acid

<400> SEQUENCE: 262

Ala Ala Pro Val Xaa
1               5

<210> SEQ ID NO 263
<211> LENGTH: 8
<212> TYPE: PRT
<213> ORGANISM: Artificial Sequence
<220> FEATURE:

<223> OTHER INFORMATION: Protease cleavage site

<400> SEQUENCE: 263

Lys Gln Leu Arg Val Val Asn Gly
1 5

<210> SEQ ID NO 264
<211> LENGTH: 8
<212> TYPE: PRT
<213> ORGANISM: Artificial Sequence
<220> FEATURE:
<223> OTHER INFORMATION: Protease cleavage site

<400> SEQUENCE: 264

Lys Gln Ser Arg Lys Phe Val Pro
1 5

<210> SEQ ID NO 265
<211> LENGTH: 5
<212> TYPE: PRT
<213> ORGANISM: Artificial Sequence
<220> FEATURE:
<223> OTHER INFORMATION: Protease cleavage site

<400> SEQUENCE: 265

Ser Ser Lys Tyr Gln
1 5

<210> SEQ ID NO 266
<211> LENGTH: 7
<212> TYPE: PRT
<213> ORGANISM: Artificial Sequence
<220> FEATURE:
<223> OTHER INFORMATION: Protease cleavage site

<400> SEQUENCE: 266

His Ser Ser Lys Leu Gln Leu
1 5

<210> SEQ ID NO 267
<211> LENGTH: 5
<212> TYPE: PRT
<213> ORGANISM: Artificial Sequence
<220> FEATURE:
<223> OTHER INFORMATION: Protease cleavage site

<400> SEQUENCE: 267

Gly Gly Gly Gly Phe
1 5

<210> SEQ ID NO 268
<211> LENGTH: 6
<212> TYPE: PRT
<213> ORGANISM: Artificial Sequence
<220> FEATURE:
<223> OTHER INFORMATION: Protease cleavage site

<400> SEQUENCE: 268

Pro Leu Gly Leu Leu Gly
1 5

<210> SEQ ID NO 269
<211> LENGTH: 7
<212> TYPE: PRT
<213> ORGANISM: Artificial Sequence
<220> FEATURE:
<223> OTHER INFORMATION: Protease cleavage site

<400> SEQUENCE: 269

Pro Gln Gly Ile Ala Gly Gln
1 5

<210> SEQ ID NO 270
<211> LENGTH: 6
<212> TYPE: PRT
<213> ORGANISM: Artificial Sequence
<220> FEATURE:
<223> OTHER INFORMATION: Protease cleavage site

<400> SEQUENCE: 270

Pro Val Gly Leu Ile Gly
1 5

<210> SEQ ID NO 271
<211> LENGTH: 5
<212> TYPE: PRT
<213> ORGANISM: Artificial Sequence
<220> FEATURE:
<223> OTHER INFORMATION: Protease cleavage site

<400> SEQUENCE: 271

Pro Arg Ala Leu Tyr
1 5

<210> SEQ ID NO 272
<211> LENGTH: 5
<212> TYPE: PRT
<213> ORGANISM: Artificial Sequence
<220> FEATURE:
<223> OTHER INFORMATION: Protease cleavage site

<400> SEQUENCE: 272

Pro Arg His Leu Arg
1 5

<210> SEQ ID NO 273
<211> LENGTH: 30
<212> TYPE: PRT
<213> ORGANISM: Artificial Sequence
<220> FEATURE:
<223> OTHER INFORMATION: Peptide containing T antigen and protease cleavage site

<400> SEQUENCE: 273

Lys Thr Pro Arg Val Thr Gly Gly Gly Ala Met Ala Ile Pro Val Ser
1 5 10 15

Leu Arg Ser Gly Gly Gly Gly Ser Gly Gly Gly Gly Ser Cys
20 25 30

<210> SEQ ID NO 274
<211> LENGTH: 31
<212> TYPE: PRT
<213> ORGANISM: Artificial Sequence
<220> FEATURE:
<223> OTHER INFORMATION: Peptide containing T antigen and protease cleavage site

<400> SEQUENCE: 274

Asp Asp Tyr Ser Asn Thr His Ser Thr Arg Tyr Val Thr Ile Pro Val
1 5 10 15

Ser Leu Arg Ser Gly Gly Gly Gly Ser Gly Gly Gly Gly Ser Cys
20 25 30

```
<210> SEQ ID NO 275
<211> LENGTH: 29
<212> TYPE: PRT
<213> ORGANISM: Artificial Sequence
<220> FEATURE:
<223> OTHER INFORMATION: Peptide containing T antigen and protease
      cleavage site

<400> SEQUENCE: 275

Arg Asn Leu Val Pro Met Val Ala Thr Val Gln Ile Pro Val Ser Leu
1               5                   10                  15

Arg Ser Gly Gly Gly Gly Ser Gly Gly Gly Gly Ser Cys
            20                  25


<210> SEQ ID NO 276
<211> LENGTH: 28
<212> TYPE: PRT
<213> ORGANISM: Artificial Sequence
<220> FEATURE:
<223> OTHER INFORMATION: Peptide containing T antigen and protease
      cleavage site

<400> SEQUENCE: 276

Cys Ser Gly Gly Gly Gly Ser Gly Gly Gly Gly Ala Ile Pro Val Ser
1               5                   10                  15

Leu Arg Ala Asn Leu Val Pro Met Val Ala Thr Val
            20                  25


<210> SEQ ID NO 277
<211> LENGTH: 28
<212> TYPE: PRT
<213> ORGANISM: Artificial Sequence
<220> FEATURE:
<223> OTHER INFORMATION: Peptide containing T antigen and protease
      cleavage site

<400> SEQUENCE: 277

Tyr Val Leu Glu Glu Thr Ser Val Met Leu Ile Pro Val Ser Leu Arg
1               5                   10                  15

Ser Gly Gly Gly Gly Ser Gly Gly Gly Gly Ser Cys
            20                  25


<210> SEQ ID NO 278
<211> LENGTH: 20
<212> TYPE: PRT
<213> ORGANISM: Artificial Sequence
<220> FEATURE:
<223> OTHER INFORMATION: Peptide containing T antigen and protease
      cleavage site

<400> SEQUENCE: 278

Asn Leu Val Pro Met Val Ala Thr Val Gln Gly Ala Leu Ala Leu Ala
1               5                   10                  15

Leu Ala Leu Cys
            20


<210> SEQ ID NO 279
<211> LENGTH: 37
<212> TYPE: PRT
<213> ORGANISM: Artificial Sequence
<220> FEATURE:
<223> OTHER INFORMATION: Peptide containing T antigen and protease
      cleavage site

<400> SEQUENCE: 279
```

```
Asn Leu Val Pro Met Val Ala Thr Val Gln Gly Pro Leu Gly Ala Leu
1               5                   10                  15

Ala Leu Ala Leu Ala Leu Ala Leu Ala Leu Ala Leu Ala Leu Ala Leu
            20                  25                  30

Ala Leu Ala Leu Cys
        35


<210> SEQ ID NO 280
<211> LENGTH: 19
<212> TYPE: PRT
<213> ORGANISM: Artificial Sequence
<220> FEATURE:
<223> OTHER INFORMATION: Peptide containing T antigen and protease
      cleavage site

<400> SEQUENCE: 280

Asn Leu Val Pro Met Val Ala Thr Val Leu Pro Arg Ser Ala Lys Glu
1               5                   10                  15

Leu Arg Cys


<210> SEQ ID NO 281
<211> LENGTH: 9
<212> TYPE: PRT
<213> ORGANISM: Artificial Sequence
<220> FEATURE:
<223> OTHER INFORMATION: Protease cleavage site

<400> SEQUENCE: 281

Lys Trp Asn Lys Trp Ala Leu Ser Arg
1               5


<210> SEQ ID NO 282
<211> LENGTH: 8
<212> TYPE: PRT
<213> ORGANISM: Artificial Sequence
<220> FEATURE:
<223> OTHER INFORMATION: Spacer peptide

<400> SEQUENCE: 282

Ala Ser Ala Leu Ala Ser Ala Leu
1               5


<210> SEQ ID NO 283
<211> LENGTH: 28
<212> TYPE: PRT
<213> ORGANISM: Artificial Sequence
<220> FEATURE:
<223> OTHER INFORMATION: Peptide construct comprising T cell epitope and
      cleavage site

<400> SEQUENCE: 283

Asn Leu Val Pro Met Val Ala Thr Val Gln Lys Trp Asn Lys Trp Ala
1               5                   10                  15

Leu Ser Arg Ala Ser Ala Leu Ala Ser Ala Leu Cys
            20                  25


<210> SEQ ID NO 284
<211> LENGTH: 9
<212> TYPE: PRT
<213> ORGANISM: Artificial Sequence
<220> FEATURE:
<223> OTHER INFORMATION: Spacer peptide

<400> SEQUENCE: 284

Gly Gly Gly Ser Gly Gly Gly Gly Ser
```

1 5

<210> SEQ ID NO 285
<211> LENGTH: 27
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 285

Asn Leu Val Pro Met Val Ala Thr Val Gln His Ser Ser Lys Leu Gln
1 5 10 15

Leu Gly Gly Gly Ser Gly Gly Gly Gly Ser Cys
20 25

<210> SEQ ID NO 286
<211> LENGTH: 10
<212> TYPE: PRT
<213> ORGANISM: Artificial Sequence
<220> FEATURE:
<223> OTHER INFORMATION: Spacer peptide

<400> SEQUENCE: 286

Gly Gly Gly Gly Phe Gly Gly Gly Gly Phe
1 5 10

<210> SEQ ID NO 287
<211> LENGTH: 26
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 287

Asn Leu Val Pro Met Val Ala Thr Val Gln Gly Gly Gly Gly Phe Gly
1 5 10 15

Gly Gly Gly Phe Gly Gly Gly Gly Phe Cys
20 25

<210> SEQ ID NO 288
<211> LENGTH: 28
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 288

Asn Leu Val Pro Met Val Ala Thr Val Gln Lys Gln Ser Arg Lys Phe
1 5 10 15

Val Pro Gly Gly Gly Ser Gly Gly Gly Gly Ser Cys
20 25

<210> SEQ ID NO 289
<211> LENGTH: 28
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 289

Asn Leu Val Pro Met Val Ala Thr Val Gln Cys Pro Gly Arg Val Val
1 5 10 15

Gly Gly Gly Gly Gly Ser Gly Gly Gly Gly Ser Cys
20 25

<210> SEQ ID NO 290
<211> LENGTH: 28
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 290

Asn Leu Val Pro Met Val Ala Thr Val Gln Tyr Leu Gly Arg Ser Tyr
1 5 10 15

Lys Val Gly Gly Gly Ser Gly Gly Gly Gly Ser Cys
20 25

<210> SEQ ID NO 291
<211> LENGTH: 8
<212> TYPE: PRT
<213> ORGANISM: Artificial Sequence
<220> FEATURE:
<223> OTHER INFORMATION: Protease cleavage site

<400> SEQUENCE: 291

Gly Pro Gln Gly Ile Ala Ser Gln
1 5

<210> SEQ ID NO 292
<211> LENGTH: 28
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 292

Asn Leu Val Pro Met Val Ala Thr Val Gln Gly Pro Gln Gly Ile Ala
1 5 10 15

Ser Gln Gly Gly Gly Ser Gly Gly Gly Gly Ser Cys
20 25

<210> SEQ ID NO 293
<211> LENGTH: 27
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 293

Asn Leu Val Pro Met Val Ala Thr Val Gln Pro Gln Gly Ile Ala Gly
1 5 10 15

Gln Gly Gly Gly Ser Gly Gly Gly Gly Ser Cys
20 25

<210> SEQ ID NO 294
<211> LENGTH: 9
<212> TYPE: PRT
<213> ORGANISM: Artificial Sequence
<220> FEATURE:
<223> OTHER INFORMATION: Protease cleavage site

<400> SEQUENCE: 294

Val Leu Lys Val Leu Lys Val Leu Lys 1 5

<210> SEQ ID NO 295
<211> LENGTH: 29
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 295

Asn Leu Val Pro Met Val Ala Thr Val Gln Val Leu Lys Val Leu Lys
1 5 10 15

Val Leu Lys Gly Gly Gly Ser Gly Gly Gly Gly Ser Cys
20 25

<210> SEQ ID NO 296
<211> LENGTH: 10
<212> TYPE: PRT
<213> ORGANISM: Artificial Sequence
<220> FEATURE:
<223> OTHER INFORMATION: Spacer peptide

<400> SEQUENCE: 296

Ser Gly Gly Gly Gly Ser Gly Gly Gly Gly
1 5 10

<210> SEQ ID NO 297
<211> LENGTH: 29
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 297

Cys Ser Gly Gly Gly Gly Ser Gly Gly Gly Gly Cys Pro Gly Arg Val
1 5 10 15

Val Gly Gly Ala Asn Leu Val Pro Met Val Ala Thr Val
20 25

<210> SEQ ID NO 298
<211> LENGTH: 24
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 298

Cys Ser Gly Gly Gly Gly Ser Gly Gly Gly Gly Gly Gly Arg Ala Asn
1 5 10 15

Leu Val Pro Met Val Ala Thr Val
20

<210> SEQ ID NO 299
<211> LENGTH: 29
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 299

Cys Ser Gly Gly Gly Gly Ser Gly Gly Gly Gly Tyr Leu Gly Arg Ser
1 5 10 15

Tyr Lys Val Ala Asn Leu Val Pro Met Val Ala Thr Val
20 25

<210> SEQ ID NO 300
<211> LENGTH: 29
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 300

Cys Ser Gly Gly Gly Gly Ser Gly Gly Gly Gly Ser Leu Gly Arg Lys
1 5 10 15

Ile Gln Ile Ala Asn Leu Val Pro Met Val Ala Thr Val
20 25

<210> SEQ ID NO 301
<211> LENGTH: 27
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 301

Cys Ser Gly Gly Gly Gly Ser Gly Gly Gly Gly Leu Val Pro Arg Gly
1 5 10 15

Ser Ala Asn Leu Val Pro Met Val Ala Thr Val
20 25

<210> SEQ ID NO 302
<211> LENGTH: 7
<212> TYPE: PRT
<213> ORGANISM: Artificial Sequence
<220> FEATURE:
<223> OTHER INFORMATION: Spacer peptide

<400> SEQUENCE: 302

Ser Gly Gly Gly Gly Ser Gly
1 5

<210> SEQ ID NO 303
<211> LENGTH: 4
<212> TYPE: PRT
<213> ORGANISM: Artificial Sequence
<220> FEATURE:
<223> OTHER INFORMATION: Protease cleavage site

<400> SEQUENCE: 303

Gly Gly Gly Arg
1

<210> SEQ ID NO 304
<211> LENGTH: 22
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 304

Cys Ser Gly Gly Gly Gly Ser Gly Gly Gly Gly Arg Ala Asn Leu Val
1 5 10 15

Pro Met Val Ala Thr Val

20

<210> SEQ ID NO 305
<211> LENGTH: 25
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 305

Cys Ser Gly Gly Gly Gly Ser Gly Gly Gly Gly Ala Ala Pro Val Ala
1 5 10 15

Asn Leu Val Pro Met Val Ala Thr Val
20 25

<210> SEQ ID NO 306
<211> LENGTH: 29
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 306

Cys Ser Gly Gly Gly Gly Ser Gly Gly Gly Gly Lys Gln Leu Arg Val
1 5 10 15

Val Asn Gly Ala Asn Leu Val Pro Met Val Ala Thr Val
20 25

<210> SEQ ID NO 307
<211> LENGTH: 26
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 307

Cys Ser Gly Gly Gly Gly Ser Gly Gly Gly Gly Ser Ser Lys Tyr Gln
1 5 10 15

Ala Asn Leu Val Pro Met Val Ala Thr Val
20 25

<210> SEQ ID NO 308
<211> LENGTH: 26
<212> TYPE: PRT
<213> ORGANISM: Artificial Sequence
<220> FEATURE:
<223> OTHER INFORMATION: Peptide construct comprising T cell epitope and cleavage site

<400> SEQUENCE: 308

Cys Ser Gly Gly Gly Gly Ser Gly Gly Gly Gly Gly Gly Gly Gly Phe
1 5 10 15

Ala Asn Leu Val Pro Met Val Ala Thr Val
20 25

<210> SEQ ID NO 309
<211> LENGTH: 15
<212> TYPE: PRT
<213> ORGANISM: Artificial Sequence
<220> FEATURE:
<223> OTHER INFORMATION: Peptide without cleavage site

<400> SEQUENCE: 309

-continued

```
Ile Pro Asp Asp Tyr Ser Asn Thr His Ser Thr Arg Tyr Val Cys
1               5                   10                  15


<210> SEQ ID NO 310
<211> LENGTH: 7
<212> TYPE: PRT
<213> ORGANISM: Artificial Sequence
<220> FEATURE:
<223> OTHER INFORMATION: Protease recognition site

<400> SEQUENCE: 310

Ile Pro Val Ser Leu Arg Ser
1               5


<210> SEQ ID NO 311
<211> LENGTH: 32
<212> TYPE: PRT
<213> ORGANISM: Artificial Sequence
<220> FEATURE:
<223> OTHER INFORMATION: Receptor peptide construct

<400> SEQUENCE: 311

Asn Leu Val Pro Met Val Ala Thr Val Ala Ile Pro Val Ser Leu Arg
1               5                   10                  15

Ser Ala Ala Ala Phe Cys Asp Gly Phe Tyr Ala Cys Tyr Met Asp Val
            20                  25                  30


<210> SEQ ID NO 312
<211> LENGTH: 12
<212> TYPE: PRT
<213> ORGANISM: Artificial Sequence
<220> FEATURE:
<223> OTHER INFORMATION: Her2 receptor peptide agonist

<400> SEQUENCE: 312

Phe Cys Asp Gly Phe Tyr Ala Cys Tyr Met Asp Val
1               5                   10


<210> SEQ ID NO 313
<211> LENGTH: 7
<212> TYPE: PRT
<213> ORGANISM: Artificial Sequence
<220> FEATURE:
<223> OTHER INFORMATION: Protease cleavage site

<400> SEQUENCE: 313

Ala Ile Pro Val Ser Leu Arg
1               5


<210> SEQ ID NO 314
<211> LENGTH: 35
<212> TYPE: PRT
<213> ORGANISM: Artificial Sequence
<220> FEATURE:
<223> OTHER INFORMATION: Receptor peptide construct

<400> SEQUENCE: 314

Asn Leu Val Pro Met Val Ala Thr Val Ala Ile Pro Val Ser Leu Arg
1               5                   10                  15

Ser Ala Ala Ala Tyr Cys Arg Asp Tyr Asp Tyr Asp Gly Arg Tyr Phe
            20                  25                  30

Asp Cys Tyr
        35
```

<210> SEQ ID NO 315
<211> LENGTH: 21
<212> TYPE: PRT
<213> ORGANISM: Artificial Sequence
<220> FEATURE:
<223> OTHER INFORMATION: T cell epitope peptide construct

<400> SEQUENCE: 315

```
Cys Ser Gly Gly Gly Gly Ser Gly Gly Gly Gly Ala Asn Leu Val Pro
1               5                   10                  15

Met Val Ala Thr Val
            20
```

<210> SEQ ID NO 316
<211> LENGTH: 10
<212> TYPE: PRT
<213> ORGANISM: Artificial Sequence
<220> FEATURE:
<223> OTHER INFORMATION: HLA Class I peptide

<400> SEQUENCE: 316

```
Val Leu Glu Glu Glu Thr Ser Val Met Leu
1               5                   10
```

<210> SEQ ID NO 317
<211> LENGTH: 8
<212> TYPE: PRT
<213> ORGANISM: Artificial Sequence
<220> FEATURE:
<223> OTHER INFORMATION: Protease cleavage site

<400> SEQUENCE: 317

```
Thr Ile Pro Val Ser Leu Arg Ser
1               5
```

<210> SEQ ID NO 318
<211> LENGTH: 561
<212> TYPE: PRT
<213> ORGANISM: Artificial Sequence
<220> FEATURE:
<223> OTHER INFORMATION: cytomegalovirus pp65 protein

<400> SEQUENCE: 318

```
Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
```

-continued

```
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
            420                 425                 430

Ala Gly Arg Lys Arg Lys Ser Ala Ser Ser Ala Thr Ala Cys Thr Ser
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly
```

<210> SEQ ID NO 319
<211> LENGTH: 15
<212> TYPE: PRT
<213> ORGANISM: Artificial Sequence
<220> FEATURE:
<223> OTHER INFORMATION: EGFR receptor peptide agonist

<400> SEQUENCE: 319

Tyr Cys Arg Asp Tyr Asp Tyr Asp Gly Arg Tyr Phe Asp Cys Tyr
1 5 10 15

<210> SEQ ID NO 320
<211> LENGTH: 15
<212> TYPE: PRT
<213> ORGANISM: Artificial Sequence
<220> FEATURE:
<223> OTHER INFORMATION: Biotin-RPH peptide

<400> SEQUENCE: 320

Pro Phe Met Arg Pro His Glu Arg Asn Gly Phe Thr Val Leu Cys
1 5 10 15

<210> SEQ ID NO 321
<211> LENGTH: 8
<212> TYPE: PRT
<213> ORGANISM: Artificial Sequence
<220> FEATURE:
<223> OTHER INFORMATION: Protease cleavage site

<400> SEQUENCE: 321

Pro Arg Ser Ala Lys Glu Leu Arg
1 5

<210> SEQ ID NO 322
<211> LENGTH: 29
<212> TYPE: PRT
<213> ORGANISM: Artificial Sequence
<220> FEATURE:
<223> OTHER INFORMATION: Peptide construct

<400> SEQUENCE: 322

Arg Asn Leu Val Pro Met Val Ala Thr Val Thr Ile Pro Val Ser Leu
1 5 10 15

Arg Ser Gly Gly Gly Gly Ser Gly Gly Gly Gly Ser Cys
20 25

<210> SEQ ID NO 323
<211> LENGTH: 28
<212> TYPE: PRT
<213> ORGANISM: Artificial Sequence
<220> FEATURE:
<223> OTHER INFORMATION: Peptide construct

<400> SEQUENCE: 323

Asn Leu Val Pro Met Val Ala Thr Val Ala Ile Pro Val Ser Leu Arg
1 5 10 15

Ser Gly Gly Gly Gly Ser Gly Gly Gly Gly Ser Cys
20 25